United States Patent
Zhang et al.

(10) Patent No.: US 11,918,600 B2
(45) Date of Patent: *Mar. 5, 2024

(54) NUCLEIC ACID, PHARMACEUTICAL COMPOSITION AND CONJUGATE CONTAINING NUCLEIC ACID, AND USE THEREOF

(71) Applicant: SUZHOU RIBO LIFE SCIENCE CO., LTD., Kunshan (CN)

(72) Inventors: Hongyan Zhang, Kunshan (CN); Shan Gao, Kunshan (CN); Daiwu Kang, Kunshan (CN); Gengrong Chen, Kunshan (CN)

(73) Assignee: SUZHOU RIBO LIFE SCIENCE CO., LTD., Kunshan (CN)

( * ) Notice: Subject to any disclaimer, the term of this patent is extended or adjusted under 35 U.S.C. 154(b) by 225 days.

This patent is subject to a terminal disclaimer.

(21) Appl. No.: 17/269,039

(22) PCT Filed: Aug. 20, 2019

(86) PCT No.: PCT/CN2019/101656
§ 371 (c)(1),
(2) Date: Feb. 17, 2021

(87) PCT Pub. No.: WO2020/038377
PCT Pub. Date: Feb. 27, 2020

(65) Prior Publication Data
US 2021/0275564 A1 Sep. 9, 2021

(30) Foreign Application Priority Data

Aug. 21, 2018 (CN) .......................... 201810951752.4
Sep. 30, 2018 (CN) .......................... 201811165363.5

(51) Int. Cl.
*C12N 15/113* (2010.01)
*A61K 31/7088* (2006.01)
(Continued)

(52) U.S. Cl.
CPC ........ *A61K 31/7088* (2013.01); *A61K 31/712* (2013.01); *A61K 31/713* (2013.01);
(Continued)

(58) Field of Classification Search
None
See application file for complete search history.

(56) References Cited

U.S. PATENT DOCUMENTS 8,030,474 B2 10/2011 Khvorova et al.
8,106,022 B2 1/2012 Manoharan et al.
(Continued)

FOREIGN PATENT DOCUMENTS

AU 2014208251 A1 8/2014
CA 2 930 393 A1 6/2009
(Continued)

OTHER PUBLICATIONS

U.S. Appl. No. 18/181,057 filed Mar. 2023, Zhang, Hongyan et al.*
(Continued)

*Primary Examiner* — Eric Olson
(74) *Attorney, Agent, or Firm* — BUCHANAN INGERSOLL & ROONEY PC

(57) ABSTRACT

Provided is a siRNA for inhibiting HBV gene expression, including a sense strand and an antisense strand. The sense strand includes a nucleotide sequence 1, and the antisense strand includes a nucleotide sequence 2; the nucleotide sequence 1 and the nucleotide sequence 2 are at least partially reversely complementary to form a double-stranded region; the nucleotide sequence 1 and the nucleotide sequence shown in SEQ ID NO: 1 are equal in length,
(Continued)

and no more than 3 nucleotide differences are generated; the nucleotide sequence 2 and the nucleotide sequence shown in SEQ ID NO: 2 are equal in length, and no more than 3 nucleotide differences are generated; nucleotides of the 7th, 8th, and 9th bits of the nucleotide sequence 1 and the 2nd, 6th, 14th, and 16th of the nucleotide sequence 2 are fluoro-modified nucleotides. Also provided are a pharmaceutical composition and a conjugate containing the siRNA.

40 Claims, 4 Drawing Sheets

Specification includes a Sequence Listing.

(51) Int. Cl.
A61K 31/712 (2006.01)
A61K 31/713 (2006.01)
A61K 47/18 (2017.01)
A61K 47/54 (2017.01)

(52) U.S. Cl.
CPC .......... A61K 47/18 (2013.01); A61K 47/543 (2017.08); C12N 15/113 (2013.01); C12N 15/1131 (2013.01); C12N 2310/11 (2013.01); C12N 2310/14 (2013.01); C12N 2310/322 (2013.01); C12N 2320/32 (2013.01)

(56) References Cited

U.S. PATENT DOCUMENTS

| | | | |
|---|---|---|---|
| 8,334,372 B2 | 12/2012 | Freier et al. | |
| 8,344,125 B2 | 1/2013 | Manoharan et al. | |
| 9,428,751 B2 | 8/2016 | Macdonald et al. | |
| 9,670,492 B2 | 6/2017 | Freier et al. | |
| 10,130,651 B2 | 11/2018 | Wooddell et al. | |
| 10,246,708 B2 | 4/2019 | Kasperkovitz et al. | |
| 10,294,477 B2 | 5/2019 | Swayze | |
| 10,370,453 B2 | 8/2019 | Sexton et al. | |
| 10,934,544 B2 | 3/2021 | Akinc et al. | |
| 11,084,884 B2 | 8/2021 | Sexton et al. | |
| 11,414,661 B2 | 8/2022 | Zhang et al. | |
| 11,414,665 B2 | 8/2022 | Zhang et al. | |
| 11,492,620 B2 | 11/2022 | Zhang et al. | |
| 2003/0206887 A1 | 11/2003 | Morrissey et al. | |
| 2005/0020525 A1* | 1/2005 | McSwiggen ......... | A61K 47/551 536/23.1 |
| 2005/0245475 A1 | 11/2005 | Khvorova et al. | |
| 2005/0246794 A1 | 11/2005 | Khvorova et al. | |
| 2005/0255487 A1 | 11/2005 | Khvorova et al. | |
| 2008/0113351 A1 | 5/2008 | Naito et al. | |
| 2008/0146788 A1 | 6/2008 | Bhat et al. | |
| 2010/0063132 A1 | 3/2010 | Kim et al. | |
| 2010/0137414 A1 | 6/2010 | Freier et al. | |
| 2011/0015252 A1 | 1/2011 | Fitzgerald et al. | |
| 2011/0039914 A1 | 2/2011 | Pavco et al. | |
| 2011/0054005 A1 | 3/2011 | Naito et al. | |
| 2012/0052487 A9 | 3/2012 | Khvorova et al. | |
| 2012/0108803 A1 | 5/2012 | Han et al. | |
| 2012/0172412 A1 | 7/2012 | Rozema et al. | |
| 2012/0184595 A1 | 7/2012 | Macdonald et al. | |
| 2012/0201756 A1 | 8/2012 | Sexton | |
| 2012/0227119 A1 | 9/2012 | Doran et al. | |
| 2013/0005793 A1 | 1/2013 | Chin et al. | |
| 2013/0023579 A1 | 1/2013 | Crooke et al. | |
| 2013/0041133 A1* | 2/2013 | Aaronson ............ | A61K 47/645 530/324 |
| 2013/0096288 A1 | 4/2013 | Han et al. | |
| 2013/0123482 A1 | 5/2013 | Xi et al. | |
| 2013/0158021 A1 | 6/2013 | Dong et al. | |
| 2013/0190484 A1 | 7/2013 | Rozema et al. | |
| 2014/0099666 A1 | 4/2014 | Rossomando et al. | |
| 2014/0128453 A1 | 5/2014 | Mullick et al. | |
| 2014/0179768 A1 | 6/2014 | Bettencourt et al. | |
| 2014/0194489 A1 | 7/2014 | Bumcrot et al. | |
| 2014/0343123 A1 | 11/2014 | Prakash et al. | |
| 2015/0093444 A1 | 4/2015 | Zhang et al. | |
| 2015/0152436 A1 | 6/2015 | Musunuru et al. | |
| 2015/0174260 A1 | 6/2015 | Yang et al. | |
| 2015/0191726 A1 | 7/2015 | Manoharan et al. | |
| 2015/0247143 A1 | 9/2015 | Fitzgerald et al. | |
| 2015/0263948 A1 | 9/2015 | Jan et al. | |
| 2015/0291958 A1 | 10/2015 | Albaek et al. | |
| 2015/0315584 A1 | 11/2015 | Macdonald et al. | |
| 2015/0315594 A1 | 11/2015 | Prakash et al. | |
| 2016/0017335 A1 | 1/2016 | Borodovsky et al. | |
| 2016/0186180 A1 | 6/2016 | Bettencourt et al. | |
| 2016/0237438 A1 | 8/2016 | Brown et al. | |
| 2016/0283653 A1 | 9/2016 | Staudt et al. | |
| 2016/0354404 A1 | 12/2016 | Hinkle et al. | |
| 2017/0000815 A1 | 1/2017 | Fitzgerald et al. | |
| 2017/0002094 A1 | 1/2017 | Sexton et al. | |
| 2017/0114341 A1 | 4/2017 | Bradshaw et al. | |
| 2018/0087054 A1 | 3/2018 | Querbes et al. | |
| 2018/0148722 A1 | 5/2018 | Fitzgerald et al. | |
| 2018/0216114 A1 | 8/2018 | Fitzgerald et al. | |
| 2018/0245077 A1 | 8/2018 | Chiu et al. | |
| 2019/0062749 A1 | 2/2019 | Zhang | |
| 2019/0202855 A1 | 7/2019 | Sakamuri et al. | |
| 2019/0255091 A1 | 8/2019 | Li et al. | |
| 2019/0292547 A1 | 9/2019 | Li et al. | |
| 2020/0199591 A1 | 6/2020 | Fitzgerald et al. | |
| 2020/0338201 A1 | 10/2020 | Zhang et al. | |
| 2020/0360522 A1 | 11/2020 | Zhang et al. | |
| 2021/0032623 A1 | 2/2021 | Zhang et al. | |
| 2021/0277400 A1 | 9/2021 | Zhang et al. | |
| 2021/0401994 A1 | 12/2021 | Zhang et al. | |
| 2022/0049249 A1 | 2/2022 | Zhang et al. | |
| 2022/0062427 A1 | 3/2022 | Zhang et al. | |
| 2022/0186221 A1 | 6/2022 | Zhang et al. | |
| 2022/0235359 A1 | 7/2022 | Zhang et al. | |
| 2022/0315929 A1 | 10/2022 | Zhang et al. | |
| 2022/0356474 A1 | 11/2022 | Zhang et al. | |
| 2022/0389428 A1 | 12/2022 | Zhang et al. | |
| 2022/0395526 A1 | 12/2022 | Zhang et al. | |

FOREIGN PATENT DOCUMENTS

| | | |
|---|---|---|
| CA | 2 677 068 A1 | 3/2011 |
| CN | 101603042 A | 12/2009 |
| CN | 102006890 A | 4/2011 |
| CN | 102016036 A | 4/2011 |
| CN | 102124107 A | 7/2011 |
| CN | 102140459 A | 8/2011 |
| CN | 102140460 A | 8/2011 |
| CN | 102344477 A | 2/2012 |
| CN | 102439148 A | 5/2012 |
| CN | 102719434 A | 10/2012 |
| CN | 102753186 A | 10/2012 |
| CN | 102140461 B | 12/2012 |
| CN | 102869774 A | 1/2013 |
| CN | 102140458 B | 5/2013 |
| CN | 103380113 A | 10/2013 |
| CN | 102083983 B | 4/2014 |
| CN | 103890000 A | 6/2014 |
| CN | 104107437 A | 10/2014 |
| CN | 104232644 A | 12/2014 |
| CN | 104328121 A | 2/2015 |
| CN | 104717982 A | 6/2015 |
| CN | 104854242 A | 8/2015 |
| CN | 104922141 A | 9/2015 |
| CN | 105324485 A | 2/2016 |
| CN | 105378082 A | 3/2016 |
| CN | 105392488 A | 3/2016 |
| CN | 105452465 A | 3/2016 |
| CN | 105517556 A | 4/2016 |
| CN | 105713092 A | 6/2016 |
| CN | 105814204 A | 7/2016 |
| CN | 106132442 A | 11/2016 |
| CN | 106146591 A | 11/2016 |
| CN | 106232831 A | 12/2016 |
| CN | 106255755 A | 12/2016 |
| CN | 106460025 A | 2/2017 |

(56) References Cited

FOREIGN PATENT DOCUMENTS

| | | |
|---|---|---|
| CN | 107075516 A | 8/2017 |
| CN | 107109405 A | 8/2017 |
| CN | 107250362 A | 10/2017 |
| CN | 107854478 A | 3/2018 |
| CN | 108271386 A | 3/2018 |
| CN | 108064294 A | 5/2018 |
| CN | 108064313 A | 5/2018 |
| CN | 108220293 A | 6/2018 |
| CN | 108239644 A | 7/2018 |
| CN | 108265052 A | 7/2018 |
| CN | 108348541 A | 7/2018 |
| CN | 110945131 A | 3/2020 |
| CN | 110959011 A | 4/2020 |
| CN | 111050807 A | 4/2020 |
| CN | 111973617 A | 11/2020 |
| CN | 111973618 A | 11/2020 |
| CN | 111973619 A | 11/2020 |
| CN | 111979237 A | 11/2020 |
| CN | 112423795 A | 2/2021 |
| CN | 113330117 A | 8/2021 |
| EP | 1 752 536 A1 | 2/2007 |
| EP | 2 194 128 A1 | 6/2010 |
| EP | 2 213 738 A2 | 8/2010 |
| EP | 2 376 641 A0 | 10/2011 |
| EP | 2 669 377 A2 | 12/2013 |
| EP | 2 990 410 A1 | 3/2016 |
| EP | 3 312 281 A2 | 4/2018 |
| EP | 3 315 608 A1 | 5/2018 |
| EP | 3 335 715 A2 | 6/2018 |
| EP | 3409780 A1 | 12/2018 |
| EP | 3 719 128 A1 | 10/2020 |
| EP | 3 862 024 A1 | 8/2021 |
| JP | 2013523149 A | 6/2013 |
| JP | 2013537423 A | 10/2013 |
| JP | 2016501195 A | 1/2016 |
| JP | 2016523087 A | 8/2016 |
| JP | 2017521045 A | 8/2017 |
| JP | 2017534290 A | 11/2017 |
| RU | 2013 134 745 A | 2/2015 |
| RU | 2 558 258 C2 | 7/2015 |
| RU | 2015 133 167 A | 3/2017 |
| TW | 201925471 A | 7/2019 |
| TW | 201929905 A | 8/2019 |
| WO | 00/27795 A1 | 5/2000 |
| WO | 2004/045543 A2 | 6/2004 |
| WO | 2004/078181 A1 | 9/2004 |
| WO | 2005/116204 A1 | 12/2005 |
| WO | 2006/006948 A2 | 1/2006 |
| WO | 2006096018 A1 | 9/2006 |
| WO | 2007/134161 A2 | 11/2007 |
| WO | 2008/011431 A2 | 1/2008 |
| WO | 2008/109472 A2 | 9/2008 |
| WO | 2009/073809 A2 | 6/2009 |
| WO | 2009/082607 A2 | 7/2009 |
| WO | 2009/134487 A2 | 11/2009 |
| WO | 2010012244 A1 | 2/2010 |
| WO | 2010/045509 A2 | 4/2010 |
| WO | 2010/068978 A1 | 6/2010 |
| WO | 2010/083615 A1 | 7/2010 |
| WO | 2010/101951 A1 | 9/2010 |
| WO | 2010/121074 A1 | 10/2010 |
| WO | 2010/131916 A2 | 11/2010 |
| WO | 2010/147992 A1 | 12/2010 |
| WO | 2011/028938 A1 | 3/2011 |
| WO | 2011/085271 A2 | 7/2011 |
| WO | 2011/104169 A1 | 9/2011 |
| WO | 2011126974 A1 | 10/2011 |
| WO | 2011/139702 A2 | 11/2011 |
| WO | 2011/154331 A1 | 12/2011 |
| WO | 2012/013127 A1 | 2/2012 |
| WO | 2012024170 A2 | 2/2012 |
| WO | 2012/037254 A1 | 3/2012 |
| WO | 2012/068176 A1 | 5/2012 |
| WO | 2012/083185 A2 | 6/2012 |
| WO | 2012/089352 A1 | 7/2012 |
| WO | 2012/130086 A1 | 10/2012 |
| WO | 2012/139081 A2 | 10/2012 |
| WO | 2012/139469 A1 | 10/2012 |
| WO | 2012/177784 A2 | 12/2012 |
| WO | 2013/060261 A1 | 5/2013 |
| WO | 2013/070771 A1 | 5/2013 |
| WO | 2013/166155 A1 | 11/2013 |
| WO | 2014025805 A1 | 2/2014 |
| WO | 2014076195 A1 | 5/2014 |
| WO | 2014/089313 A1 | 6/2014 |
| WO | 2014/118267 A2 | 11/2014 |
| WO | 2014/179626 A2 | 11/2014 |
| WO | 2014/179627 A2 | 11/2014 |
| WO | 2014/179629 A2 | 11/2014 |
| WO | 2014205451 A1 | 12/2014 |
| WO | 2015/006498 A1 | 1/2015 |
| WO | 2015006740 A2 | 1/2015 |
| WO | 2015/015496 A1 | 2/2015 |
| WO | 2015/031679 A2 | 3/2015 |
| WO | 2015/051366 A2 | 4/2015 |
| WO | 2015/100394 A1 | 7/2015 |
| WO | 2015/113922 A1 | 8/2015 |
| WO | 2015/148580 A2 | 10/2015 |
| WO | 2015/168532 A2 | 11/2015 |
| WO | 2015168589 A1 | 11/2015 |
| WO | 2015/188197 A2 | 12/2015 |
| WO | 2016/011123 A1 | 2/2016 |
| WO | 2016/028649 A1 | 2/2016 |
| WO | 2016/077321 A1 | 5/2016 |
| WO | 2016/081444 A1 | 5/2016 |
| WO | 2016077349 A1 | 5/2016 |
| WO | 2016/099982 A2 | 6/2016 |
| WO | 2016/149331 A2 | 9/2016 |
| WO | 2016/154127 A2 | 9/2016 |
| WO | 2016/168286 A1 | 10/2016 |
| WO | 2016/179342 A2 | 11/2016 |
| WO | 2016/188473 A1 | 12/2016 |
| WO | 2016/201301 A1 | 12/2016 |
| WO | 2016/206626 A1 | 12/2016 |
| WO | 2017015175 A1 | 1/2017 |
| WO | 2017/019660 A1 | 2/2017 |
| WO | 2017019891 A2 | 2/2017 |
| WO | 2017/035340 A1 | 3/2017 |
| WO | 2017/055627 A1 | 4/2017 |
| WO | 2017/100542 A1 | 6/2017 |
| WO | 2017/120397 A1 | 7/2017 |
| WO | 2017131236 A1 | 8/2017 |
| WO | 2017/184689 A1 | 10/2017 |
| WO | 2017/189813 A1 | 11/2017 |
| WO | 2018/027106 A2 | 2/2018 |
| WO | 2018/035380 A1 | 2/2018 |
| WO | 2018/044350 A1 | 3/2018 |
| WO | 2018/075658 A1 | 4/2018 |
| WO | 2018/140920 A1 | 8/2018 |
| WO | 2018/191278 A2 | 10/2018 |
| WO | 2018/209848 A1 | 11/2018 |
| WO | 2018/223073 A1 | 12/2018 |
| WO | 2019/105403 A1 | 6/2019 |
| WO | 2019/105404 A1 | 6/2019 |
| WO | 2019/105418 A1 | 6/2019 |
| WO | 2019/105419 A1 | 6/2019 |
| WO | 2019/105435 A1 | 6/2019 |
| WO | 2019/105437 A1 | 6/2019 |
| WO | 2019/128611 A1 | 7/2019 |
| WO | 2020/063198 A1 | 4/2020 |
| WO | 2020/093053 A1 | 5/2020 |
| WO | 2020/135581 A1 | 7/2020 |
| WO | 2020/147847 A1 | 7/2020 |

OTHER PUBLICATIONS

English machine translation of CN102140458, downloaded from Worldwide.espacenet.com (Year: 2011).*

Durnov, et al., "Children's Oncology", Paediatric Oncology, Second Edition, Moscow Publishing House Medicine, 2002, p. 139 and its English translation. Cited in Office Action dated Oct. 10, 2022 in Russian Application No. 2020121741). (4 pages).

(56) References Cited

OTHER PUBLICATIONS

Dysop, "Chemistry of Synthetic Drugs", Publishing House MIR, 1964, pp. 12-19 and its English translation. Cited in Office Action dated Oct. 10, 2022 in Russian Application No. 2020121741). (18 pages).

Belikov, V.G., "Pharmaceutical Chemistry", textbook, Moscow, 11th Edition, MEDpress-inform, 2007, pp. 27-29 and its English translation. (Cited in Office Action dated Oct. 10, 2022 in Russian Application No. 2020121741). (8 pages).

The First Office Action dated Jan. 30, 2022, by the State Intellectual Property Office of the People's Republic of China in Chinese Patent Application No. 201880049520.8 and an English translation of the Action (11 pages).

Decision of Rejection dated Mar. 3, 2022, by the State Intellectual Property Office of the People's Republic of China in Chinese Patent Application No. 202010426194.7 and an English translation of the Action. (20 pages).

The Second Office Action dated Mar. 16, 2022, by the State Intellectual Property Office of the People's Republic of China in Chinese Patent Application No. 201980046892.X and an English translation of the Action. (24 pages).

The Second Office Action dated Mar. 21, 2022, by the State Intellectual Property Office of the People's Republic of China in Chinese Patent Application No. 201980046893.4 and an English translation of the Action. (19 pages).

The First Office Action dted May 7, 2022, by the State Intellectual Property Office of the People's Republic of China in Chinese Patent Application No. 201980010095.6 and an English translation of the Action. (27 pages).

The First Office Action dated May 7, 2022, by the State Intellectual Property Office of the People's Republic of China in Chinese Patent Application No. 201980010175.1 and an English translation of the Action. (30 pages).

The First Office Action dated May 7, 2022, by the State Intellectual Property Office of the People's Republic of China in Chinese Patent Application No. 201880049190.2 and an English translation of the Action. (31 pages).

The First Office Action dated May 7, 2022, by the State Intellectual Property Office of the People's Republic of China in Chinese Patent Application No. 201880049191.7 and an English translation of the Action. (30 pages).

The First Office Action dated May 7, 2022, by the State Intellectual Property Office of the People's Republic of China in Chinese Patent Application No. 202080007282.1 and an English translation of the Action. (33 pages).

The First Office Action dated May 7, 2022, by the State Intellectual Property Office of the People's Republic of China in Chinese Patent Application No. 201880049564.0 and an English translation of the Action. (29 pages).

The First Office Action dated May 7, 2022, by the State Intellectual Property Office of the People's Republic of China in Chinese Patent Application No. 201880049586.7 and an English translation of the Action. (33 pages).

The First Office Action dated May 7, 2022, by the State Intellectual Property Office of the People's Republic of China in Chinese Patent Application No. 201880048597.3 and an English translation of the Action. (34 pages).

The First Office Action dated May 7, 2022, by the State Intellectual Property Office of the People's Republic of China in Chinese Patent Application No. 201880048600.1 and an English translation of the Action. (34 pages).

The First Office Action dated May 7, 2022, by the State Intellectual Property Office of the People's Republic of China in Chinese Patent Application No. 202080009787.1 and an English translation of the Action. (50 pages).

The First Office Action dated May 7, 2022, by the State Intellectual Property Office of the People's Republic of China in Chinese Patent Application No. 201880048949.5 and an English translation of the Action. (33 pages).

The First Office Action dated May 20, 2021, by the State Intellectual Property Office of the People's Republic of China in Chinese Patent Application No. 202010426194.7 and an English translation of the Action. (20 pages).

The First Office Action dated Jun. 23, 2021, by the State Intellectual Property Office of the People's Republic of China in Chinese Patent Application No. 201980046892.X and an English translation of the Action. (13 pages).

The First Office Action dated Jun. 23, 2021, by the State Intellectual Property Office of the People's Republic of China in Chinese Patent Application No. 201980046893.4 and an English translation of the Action. (12 pages).

The First Office Action dated Oct. 25, 2021, by the State Intellectual Property Office of the People's Republic of China in Chinese Patent Application No. 202010426196.6 and an English translation of the Action. (16 pages).

The Second Office Action dated Nov. 12, 2021, by the State Intellectual Property Office of the People's Republic of China in Chinese Patent Application No. 202010426194.7 and an English translation of the Action. (16 pages).

The Extended European Search Report dated Jun. 9, 2022, by the European Patent Office in European Patent Application Publication No. 19851738.5. (64 pages).

The Extended European Search Report and Supplementary European Search Report dated Aug. 9, 2021, by the European Patent Office in European Patent Application Publication No. 18883362.8. (9 pages).

Extended European Search Report dated Sep. 17, 2021, issued by the European Patent Office in corresponding European Application No. 18883982.3. (9 pages).

Extended European Search Report dated Sep. 29, 2021, issued by the European Patent Office in corresponding European Application No. 18884492.2. (45 pages).

The Extended European Search Report daated Oct. 7, 2021, by the European Patent Office in European Patent Application Publication No. 18896766.5. (19 pages).

The Extended European Search Report dated Sep. 16, 2021, by the European Patent Office in European Patent Application No. 18883803.1. (10 pages).

Invitation to remedy deficiencies pursuant to Rule 30(3) EPC / Rule 163(3) EPC dated Feb. 22, 2022, by the European Patent Office in European Patent Application No. 20809029.0. (2 pages).

Communication pursuant to Rule 159 and Rule 58 EPC Invitation to remedy deficiencies in the application documents dated Jan. 24, 2022, by the European Patent Office in European Patent Application No. 20815633.1 (2 pages).

Supplementary European Search Report dated Jul. 27, 2022, by the European Patent Office in European Patent Application No. 18883153. (7 pages).

Notification of Substantive Examination Result dated Dec. 2, 2021, by the Intellectual Property Office of the Republic of Indonesia in Indonesian Patent Application No. P00202003125 and an English translation of the Notification. (6 pages).

Notification of Substantive Examination Result dated Aug. 24, 2021, by the Intellectual Property Office of the Republic of Indonesia in Indonesian Patent Application No. P00202003131 and an English translation of the Notification. (6 pages).

Examination report under sections 12 & 13 of the Patents Act, 1970 and the Patents Rules, 2003 dated Nov. 24, 2021, by the Intellectual Property Office of India in Indian Patent Application No. 202047017398 and English translation of the Report. (7 pages).

International Preliminary Report on Patentability dated Jun. 2, 2020, by the International Bureau of WIPO in International Patent Application No. PCT/CN2018/118191. (6 pages).

International Preliminary Report on Patentability dated Jun. 16, 2021, by the International Bureau of WIPO in International Patent Application No. PCT/CN2019/128686 and English translation of the Report. (16 pages).

International Preliminary Report on Patentability dated Jun. 23, 2020, by the International Bureau of WIPO in International Patent Application No. PCT/CN2018/118232 and English translation of the Report. (13 pages).

(56) References Cited

OTHER PUBLICATIONS

International Preliminary Report on Patentability dated Sep. 3, 2021, by the State Intellectual Property Office of the People's Republic of China in International Patent Application No. PCT/CN2020/091489 and English translation of the Report. (12 pages).
Written Opinion of the International Searching Authority and International Search Report dated Feb. 20, 2019, by the State Intellectual Property Office of the People's Republic of China in International Patent Application No. PCT/CN2018/118107 and English translation. (22 pages).
Written Opinion of the International Searching Authority and International Search Report dated Feb. 25, 2019, by the State Intellectual Property Office of the People's Republic of China in International Patent Application No. PCT/CN2018/118212 and English translation. (23 pages).
English translation of the Written Opinion of the International Searching Authority and International Search Report dated Feb. 27, 2019, by the State Intellectual Property Office of the People's Republic of China in International Patent Application No. PCT/CN2018/118224. (13 pages).
Written Opinion of the International Searching Authority and International Search Report dated Feb. 28, 2019, by the State Intellectual Property Office of the People's Republic of China in International Patent Application No. PCT/CN2018/118300 and English translation. (20 pages).
Written Opinion of the International Searching Authority and International Search Report dated Mar. 6, 2019, by the State Intellectual Property Office of the People's Republic of China in International Patent Application No. PCT/CN2018/118106 and English translation. (20 pages).
Written Opinion of the International Searching Authority and International Search Report dated Mar. 6, 2019, by the State Intellectual Property Office of the People's Republic of China in International Application No. PCT/CN2018/118191 and English translation. (17 pages).
Written Opinion of the International Searching Authority and International Search Report dated Mar. 7, 2019, by the State Intellectual Property Office of the People's Republic of China in International Patent Application No. PCT/CN2018/118303 and English translation. (22 pages).
Written Opinion of the International Searching Authority and International Search Report dated Mar. 7, 2019, by the State Intellectual Property Office of the People's Republic of China in International Patent Application No. PCT/CN2018/118232 and English translation. (24 pages).
Written Opinion of the International Searching Authority and International Search Report dated Mar. 26, 2020, by the State Intellectual Property Office of the People's Republic of China in International Patent Application No. PCT/CN2019/129016 and English translation. (27 pages).
Written Opinion of the International Searching Authority and International Search Report dated Mar. 26, 2020, by the State Intellectual Property Office of the People's Republic of China in International Patent Application No. PCT/CN2019/128686 and English translation. (27 pages).
Written Opinion of the International Searching Authority and International Search Report dated Aug. 19, 2020, by the State Intellectual Property Office of the People's Republic of China in International Patent Application No. PCT/CN2020/091489 and English translation. (26 pages).
Written Opinion of the International Searching Authority and International Search Report dated Aug. 21, 2020, by the State Intellectual Property Office of the People's Republic of China in International Patent Application No. PCT/CN2020/091484 and English translation. (29 pages).
Written Opinion of the International Searching Authority and International Search Report dated Aug. 21, 2020, by the State Intellectual Property Office of the People's Republic of China in International Patent Application No. PCT/CN2020/091614 and English translation. (24 pages).
Written Opinion of the International Searching Authority and International Search Report dated Aug. 24, 2020, by the State Intellectual Property Office of the People's Republic of China in International Patent Application No. PCT/CN2020/091624 and English translation. (26 pages).
Written Opinion of the International Searching Authority and International Search Report dated Aug. 25, 2020, by the State Intellectual Property Office of the People's Republic of China in International Patent Application No. PCT/CN2020/091485 and English translation. (30 pages).
Written Opinion of the International Searching Authority and International Search Report dated Aug. 28, 2020, by the State Intellectual Property Office of the People's Republic of China in International Patent Application No. PCT/CN2020/091649 and English translation. (25 pages).
Written Opinion of the International Searching Authority and International Search Report dated Sep. 2, 2020, by the State Intellectual Property Office of the People's Republic of China in International Patent Application No. PCT/CN2020/091606 and English translation. (22 pages).
Written Opinion of the International Searching Authority and International Search Report dated Nov. 21, 2019, by the State Intellectual Property Office of the People's Republic of China in International Patent Application No. PCT/CN2019/101653 and English translation. (23 pages).
Written Opinion of the International Searching Authority and International Search Report dated Apr. 17, 2020, by the State Intellectual Property Office of the People's Republic of China in International Patent Application No. PCT/CN2020/072813 and English translation. (32 pages).
Office Action dated Mar. 9, 2022, by the Russian Agency for Patents and Trademarks in Russian Patent Application No. 2020118025/10(030488) and English translation of the Action. (14 pages).
Office Action dated May 11, 2022, by the Russian Agency for Patents and Trademarks in Russian Patent Application No. 2020121741/04(037329) and English translation of the Action. (18 pages).
Office Action dated Jan. 28, 2022, by the U.S. Patent and Trademark Office in U.S. Appl. No. 16/758,532. (28 pages).
Office Action dated Mar. 11, 2022, by the U.S. Patent and Trademark Office in U.S. Appl. No. 16/758,720. (21 pages).
Notice of Allowance dated Mar. 31, 2022, by the U.S. Patent and Trademark Office in U.S. Appl. No. 16/764,307. (7 pages).
Notice of Allowance dated Apr. 5, 2022, by the U.S. Patent and Trademark Office in U.S. Appl. No. 16/763,058. (7 pages).
Office Action dated May 27, 2022, by the U.S. Patent and Trademark Office in U.S. Appl. No. 16/758,532. (8 pages).
Notice of Allowance dated Jul. 25, 2022, by the U.S. Patent and Trademark Office in U.S. Appl. No. 16/758,720. (5 pages).
Office Action dated Oct. 29, 2021, by the U.S. Patent and Trademark Office in U.S. Appl. No. 16/764,307. (17 pages).
Office Action dated Nov. 16, 2021, by the U.S. Patent and Trademark Office in U.S. Appl. No. 16/763,058. (26 pages).
Office Action dated Aug. 14, 2020, by the Intellectual Property Office of Vietnam in Vietnamese Patent Application No. 1-2020-03065 and an English translation of the Action. (3 pages).
Office Action dated Aug. 28, 2020, by the Intellectual Property Office of Vietnam in Vietnamese Patent Application No. 1-2020-03777 and an English translation of the Action. (3 pages).
Payment and Certificate of Renewal issued on May 30, 2022 by the Patent Office of South Africa in South African Patent Application No. 2020/03833. (1 page).
Ahmad Dar et al., "siRNAmod: a database of experimentally validated chemically modified SiRNAs," Scientific Reports, Jan. 28, 2016, vol. 6, No. 1. (8 pages).
Beaucage et al., "Advances in the Synthesis of Oligonucleotides by the Phosphoramidite Approach", Tetrahedron, 1992, vol. 48, No. 12, pp. 2223-2311.
Behlke, Mark A., "Chemical Modification of siRNAs for In Vivo Use," Oligonucleotides, 2008, vol. 18, pp. 305-320.
Berthold et al., "Cellular Delivery and Antisense Effects of Peptide Nucleic Acid Conjugated to Polyethyleneimine via Disulfide Linkers," Bioconjugate Chemistry, 2010, vol. 21, No. 10, pp. 1933-1938.

(56) References Cited

OTHER PUBLICATIONS

Chen et al., "Research progress on factor XI as a novel target for antithrombotic therapy," Chinese Pharmacological Bulletin, Apr. 15, 2015, vol. 31, No. 5, with English abstract, pp. 619-622.
Dai et al., "A vital role for AngpII3 in the PAN-induced podocyte loss by affecting detachment and apoptosis in vitro," BMC Nephrology, 2015, vol. 16, No. 1. (10 pages).
Ding al., "Limited role of kininogen in the host response during gram-negative pneumonia derived sepsis," American Journal of Physiology Lung Cellular and Molecular Physiology, Nov. 9, 2017. (33 pages).
Dong et al., "A novel packaging system of recombinant AAV5/5 vector," Chinese Journal of Biotechnology, May 25, 2010, vol. 26, No. 5, pp. 679-686.
Common knowledge "RNAi technology" with English translation. (5 pages).
Foster et al., "Advanced siRNA Designs Further Improve In Vivo Performance of GalNAc—SiRNA Conjugates," Molecular Therapy, vol. 26, No. 3, pp. 708-717.
Greene et al., "Protection for the Hydroxyl Group, Including 1,2- and 1,3-DIOLS", Protective Groups in Organic Synthesis, Third Edition, 1999 John Wiley & Sons, Inc. pp. 17-245, (229 pages).
"*Homo sapiens* Kininogen 1 (KNG1), Transcript Variant 1, mRNA" GenBank, May 2, 2018, NM 00102416.2. (8 pages).
Khaitmetova et al., "Synthesis and Study of the Properties of Polymer Complexes of Ethacizin with Carboxymethylcellulose," Chemistry of Plant Raw Materials, No. 4, with English translation. (18 pages).
Khan et al., "High-Molecular-Weight Kininogen Fragments Stimulate the Secretion of Cytokines and Chemokines Through uPAR, Mac-1, and gC1qR in Monocytes," Arteriosclerosis, Thrombosis, and Vascular Biology, Oct. 2006, vol. 26, No. 10, pp. 2260-2266.
Kim et al., "Bifunctional compounds for targeted hepatic gene delivery," Gene Therapy, 2007, vol. 14, pp. 704-708.
Liu et al., "Determination of Human Plasma Pre-Kallikrein," Journal of China Medical University, 1988, vol. 17, No. 6, with English abstract, pp. 432-436.
Liu et al., "Coagulation factor XI induces Ca2+ response and accelerates cell migration in vascular smooth muscle cells via proteinase-activated receptor 1," American Journal of Physiology, Cell Physiology, Mar. 1, 2019, vol. 316, No. 3, pp. C377-C392.
Montagne et al., "Pericyte degeneration causes white matter dysfunction in the mouse CNS," Nature Medicine, 2018, vol. 24, vol. 3, pp. 326-337.
Nakagawa et al., "The RNAi-Mediated Silencing of Xanthine Dehydrogenase Impairs Growth and Fertility and Accelerates Leaf Senescence in Transgenic *Arabidopsis* Plants," Plant & Cell Physiology, 2007, vol. 48, No. 10, pp. 1484-1495.
Norata et al., "Gene silencing approaches for the management of dyslipidaemia," Trends in Pharmacological Sciences, Apr. 13, 2013, vol. 34, No. 4, pp. 198-205.
Nordestgaard et al., "Advances in lipid-lowering therapy through gene-silencing technologies," Nature Reviews, Feb. 8, 2018, vol. 15. (12 pages).
Papulov, Yu. G., "Relationship between Properties of Compounds with Their Structures: Math Modeling," Advances in Modern Natural Sciences, 2006, with English translation, pp. 75-76.
Paris et al., "Conjugating Phosphospermines to siRNAs for Improved Stability in Serum, Intracellular Delivery and RNAi-Mediated Gene Silencing," Molecular Pharmaceutics, 2012, vol. 9, No. 12, pp. 3464-3475.
Peña-Altamira, et al., "Release of soluble and vesicular purine nucleoside phosphorylase from rat astrocytes and microglia induced by pro-inflammatory stimulation with extracellular ATP via P2X7 receptors," Neurochemistry International, May 31, 2018, vol. 115, pp. 37-49.
Pessentheiner et al., "ANGPTL3 targeting: The power of versatile lipid-lowering," Atherosclerosis, Jan. 2018, vol. 268, pp. 185-187.
Prakash et al., "Comprehensive Structure-Activity Relationship of Triantennary N-Acetylgalactosamine Conjugated Antisense Oligo-nucleotides for Targeted Delivery to Hepatocytes," Journal of Medicinal Chemistry, 2016, vol. 59, pp. 2718-2733.
Ren et al., "Synthesis of bifunctional cationic compound for gene delivery," Tetrahedron Letters, 2001, vol. 42, pp. 1007-1010.
Ren et al., "Gene Expression Profile of Transgenic Mouse Kidney Reveals Pathogenesis of Hepatitis B Virus Associated Nephropathy," Journal of Medical Virology, 2006, vol. 78, pp. 551-560.
Ren et al., "Stable Inhibition of Hepatitis B Virus Expression and Replication by Expressed siRNA", Biochemical and Biophysical Research Communications, Oct. 7, 2005, vol. 335, No. 4, with English abstract, pp. 1051-1058.
Springer et al., "GalNAc-siRNA Conjugates: Leading the Way for Delivery of RNAi Therapeutics," Nucleic Acid Therapeutics, May 2018, vol. 28, No. 3, pp. 109-118.
Su et al., "Progress on the Inhibition of Hepatitis B virus by siRNA Strategy," China Biotechnology, 2014, vol. 34, No. 9, with English abstract, pp. 102-107.
Tangkijvanich et al., "Low pretreatment serum HBsAg level and viral mutations as predictors of response to PEG-interferon alpha-2b therapy in chronic hepatitis B," Journal of Clinical Virology, vol. 46, 2009, pp. 117-123.
Wu et al., "Cleaved high molecular weight kininogen inhibits tube formation of endothelial progenitor cells via suppression of matrix metalloproteinase 2," Journal of Thrombosis and Haemostasis, 2010, vol. 8, pp. 185-193.
Wu et al., "Contact pathway of coagulation and inflammation," Thrombosis Journal, 2015, pp. 13-17.
Xu et al., "Role of angiopoielin-like 3 (ANGPTL3) in regulating plasma level of low-density lipoprotein cholesterol," Atherosclerosis, 2018, vol. 268, pp. 196-206.
Yang et al., "A critical role for plasma kallikrein in the pathogenesis of autoantibody-induced arthritis," Federation of American Societies for Experimental Biology, Nov. 2017, vol. 31, No. 12, pp. 5419-5431.
Yang et al., "An essential role of high-molecular-weight kininogen in endotoxemia," Journal of Experimental Medicine, Sep. 4, 2017, vol. 214, No. 9, pp. 2649-2670.
Dong et al., "Lipopeptide nanoparticles for potent and selective siRNA delivery in rodents and nonhuman primates," Proceedings of the National Academy of Sciences of the United States of America, Mar. 18, 2014, vol. 111, No. 11, pp. 3955-3960.
Khvorova et al., "The chemical evolution of oligonucleotide therapies of clinical utility," Nature Biotechnology, Advanced online publication, Feb. 27, 2017. (11 pages).
Love et al., "Lipid-like materials for low-doe in vivo gene silencing," Proceedings of the National Academy of Sciences of the United States of America, Feb. 2, 2010, vol. 107, No. 5, pp. 1864-1869 with correction.
Matsuda et al., "siRNA Conjugates Carrying Sequentially Assembled Trivalent N-Acetylgalactosamine Linked Through Nucleosides Elicit Robust Gene Silencing In Vivo in Hepatocytes," ACS Chemical Biology, May 15, 2015, vol. 10, No. 5, pp. 1181-1187.
Nair et al., "Multivalent N-Acetylgalactosamine-Conjugated siRNA Localizes in Hepatocytes and Elicits Robust RNAi-Mediated Gene Silencing," Journal of the American Chemical Society, 2014, vol. 136, No. 49, pp. 16958-16961.
Rajeev et al., "Hepatocyte-Specific Delivery of siRNAs Conjugated to Novel Non-nucleosidic Trivalent N-Acetylgalactosamine Elicits Robust Gene Silencing in Vivo," ChemBioChem: a European Journal of Chemical Biology, 2015, vol. 16, pp. 903-908.
Ui-Tei et al., "Functional dissection of siRNA sequence by systematic DNA substitution: modified siRNA with a DNA seed arm is a powerful tool for mammalian gene silencing with significantly reduced off-target effect," Nucleic Acids Research, 2008, vol. 36, No. 7, pp. 2136-2151.
Watts et al., "Chemical modified siRNA: tools and applications," Drug Discovery Today, Oct. 2008. vol. 13, No. 19-20, pp. 842-855.
Wooddell et al., "Hepatocyte-targeted RNAi Therapeutics for the Treatment of Chronic Hepatitis B Virus Infection," Molecular Therapy, May 2013, vol. 21, No. 5 , pp. 973-985.

(56) References Cited

OTHER PUBLICATIONS

Decision of Rejection dated Jun. 29, 2022, by the State Intellectual Property Office of the People's Republic of China in Chinese Patent Application No. 201980046892.X and an English translation of the Decision. (8 pages).
Decision of Rejection dated Jun. 29, 2022, by the State Intellectual Property Office of the People's Republic of China in Chinese Patent Application No. 201980046893.4 and an English translation of the Decision. (8 pages).
Office Action dated Aug. 24, 2022, by the U.S. Patent and Trademark Office in U.S. Appl. No. 16/758,532. (13 pages).
Extended European Search Report dated Jul. 19, 2022, by the European Patent Office in European Patent Application No. 19867686.8. (12 pages).
Nakamoto et al., "Enhanced Intercellular Delivery of cRGD—siRNA Conjugates by an Additional Oligospermine Modification," ACS Omega, 2018, vol. 3, pp. 8226-8232. (7 pages).
Nothisen et al., "Cationic siRNAs Provide Carrier-Free Gene Silencing in Animal Cells," Journal of the American Chemical Society, 2009, vol. 131, No. 29, pp. 17730-17731. (2 pages).
International Search Report (PCT/ISA/210) dated Nov. 28, 2019, by the Chinese Patent Office as the International Searching Authority for International Application No. PCT/CN2019/101656, and an English translation of the Report.
Written Opinion (PCT/ISA/237) dated Nov. 28, 2019, by the Chinese Patent Office as the International Searching Authority for International Application No. PCT/CN2019/101656.
Chen et al., "Proof-of-concept Studies for siRNA-mediated Gene Silencing for Coagulation Factors in Rat and Rabbit", Molecular Therapy—Nucleic Acids, Jan. 27, 2015, vol. 4, No. 1, p. e224.
Ferrone et al., "IONIS-PKK Rx a Novel Antisense Inhibitor of Prekallikrein and Bradykinin Production", Nucleic Acid Therapeutics, Apr. 1, 2019, vol. 29, No. 2, pp. 82-91.
Ghosh et al., "Effectiveness and Safety of Inclisiran, a Novel Long-Acting RNA Therapeutic Inhibitor of Proprotein Convertase Subtilisin/Kexin 9", American Journal of Cardiology, Cahners Publishing Co., Newton, MA, US, Jul. 3, 2018, vol. 122, No. 7, pp. 1272-1277.
Joshi et al., "siRNA: novel therapeutics from functional genomics", Biotechnology and Genetic Engineering Reviews, Jan. 2, 2014, vol. 30, No. 1, pp. 1-30.
Pawluczyk et al., "Kallikrein gene 'knock-down' by small interfering RNA transfection induces a profibrotic phenotype in rat mesangial cells", Journal of Hypertension, Lippincott Williams & Wilkens, Ltd., Jan. 1, 2008, vol. 26, No. 1, pp. 93-101.
Revenko et al., "Selective depletion of plasma prekallikrein or coagulation factor XII inhibits thrombosis in mice without increased risk of bleeding", Blood, American Society of Hematology, Nov. 10, 2011, vol. 118, No. 19, pp. 5302-5311.
Yamasaki et al., "Novel molecular targets regulated by tumor suppressors microRNA-1 and microRNA-133a in bladder cancer", International Journal of Oncology, Feb. 29, 2012, vol. 40, pp. 1821-1830.
Supplementary European Search Report dated Jun. 14, 2023, by the European Patent Office in European Patent Application No. 20809702.2 (12 pages).
Supplementary European Search Report dated Jun. 16, 2023, by the European Patent Office in European Patent Application No. 20814338.8 (10 pages).
Partial Supplementary European Search Report dated Jul. 5, 2023, by the European Patent Office in European Patent Application No. 20810635.1 (13 pages).
Partial Supplementary European Search Report dated Jul. 10, 2023, by the European Patent Office in European Patent Application No. 20815633.1 (17 pages).
Examination Report No. 2 dated Feb. 3, 2023, by the Australian Government IP Australia in Australian Patent Application No. 2018394875 (4 pages).
Ren et al., "Synthesis of Galactosyl Compounds for Targeted Gene Delivery", Bioorganic & Medicinal Chemistry, 2001, 9(11), pp. 2969-2978.
Extended European Search Report dated Mar. 27, 2023, by the European Patent Office in European Patent Application No. 19902173.4 (11 pages).
Li et al., "The silencing of ApoC3 suppresses oxidative stress and inflammatory responses in placenta cells from mice with preeclampsia via inhibition of the Nf—B signaling pathway", Biomedicine & Pharmacotherapy, Aug. 31, 2018, vol. 107, pp. 1377-1384.
Notice of Reasons for Refusal dated Jun. 1, 2023, by the Japanese Patent Office in Japanese Patent Application No. 2021-537877, with an English translation of the Notice (6 pages).
Kanasty et al., "Delivery materials for siRNA therapeutics", Nature Materials, Nov. 2023, vol. 12, pp. 967-977.
Notice of Reasons for Refusal dated Jun. 6, 2023, by the Japanese Patent Office in Japanese Patent Application No. 2021-509880, with an English translation of the Notice (6 pages).

* cited by examiner

NUCLEIC ACID, PHARMACEUTICAL COMPOSITION AND CONJUGATE CONTAINING NUCLEIC ACID, AND USE THEREOF

SEQUENCE LISTING

Incorporated by reference herein in its entirety is a computer-readable sequence listing submitted via EFS-Web and identified as follows: One (15,919 byte ASCII (Text)) file named "2021_04_13_sequence_listing.txt" created on Apr. 13, 2021.

TECHNICAL FIELD

The present disclosure relates to a siRNA, a pharmaceutical composition and a conjugate comprising the siRNA and use thereof. In particular, the present disclosure relates to a siRNA suitable for inhibiting the expression of hepatitis B virus (HBV) gene, a pharmaceutical composition and a conjugate comprising the siRNA as an active ingredient, and use of the siRNA, the pharmaceutical composition and the conjugate in the manufacture of a medicament for preventing and/or treating hepatitis type B.

BACKGROUND OF THE INVENTION

Viral hepatitis type B (also known as hepatitis type B or hepatitis B) is an infectious disease, which is a serious threat to the world, especially to China. At present, interferons and nucleoside analogues are two major kinds of globally recognized drugs for the prevention/treatment of hepatitis B; however, these two kinds of drugs have various drawbacks, e.g., being prone to development of drug resistance after use or having limited uses. For example, interferons are susceptible to cause adverse reactions; and nucleoside analogues have the problems of drug resistance and disease recurrence after drug withdrawal. Therefore, the most ideal means for treatment of hepatitis B should undoubtedly be to silence the gene expression of the virus at gene level to block the generation and replication of HBV, thereby fundamentally reducing the virus metabolism and the infection of hepatic cells. Based on the mechanism of RNA interference (RNAi), small interfering RNA (siRNA) can inhibit or block the expression of any target gene of interest, e.g., a gene triggering a disease such as cancer, in a sequence-specific manner, thereby achieving the purpose of treating diseases.

Stabilization modification of siRNA and its delivery system are two key technologies in the development of small RNA drugs.

SUMMARY OF THE INVENTION

The present disclosure provides a siRNA capable of specifically targeting the P gene region, which is one of the four open reading frames of HBV gene, thereby significantly inhibiting the expression of HBV gene.

The siRNA provided by the present disclosure comprises a sense strand and an antisense strand, and each nucleotide in the sense strand and the antisense strand is a modified nucleotide, wherein the sense strand and the antisense strand both comprise fluoro modified nucleotides and non-fluoro modified nucleotides; a "fluoro modified nucleotide" refers to a nucleotide formed by substituting the 2'-hydroxy of the ribose group of the nucleotide with a fluoro group, and a "non-fluoro modified nucleotide" refers to a nucleotide formed by substituting the 2'-hydroxy of the ribose group of the nucleotide with a non-fluoro group, or a nucleotide analogue; the sense strand comprises a nucleotide sequence 1; the antisense strand comprises a nucleotide sequence 2; the nucleotide sequence 1 and the nucleotide sequence 2 are at least partly reverse complementary to form a double-stranded region; wherein the nucleotide sequence 1 and the nucleotide sequence shown in SEQ ID NO: 1 have an equal length and no more than 3 nucleotide differences; and the nucleotide sequence 2 and the nucleotide sequence shown in SEQ ID NO: 2 have an equal length and no more than 3 nucleotide differences:

(SEQ ID NO: 1)
5'-GAAAGUAUGUCAACGAAUZ -3', (SEQ ID NO: 2)
5'-Z'AUUCGUUGACAUACUUUC -3', wherein,
Z is U, Z' is A;
the nucleotide sequence 1 comprises a nucleotide $Z_A$ at the position corresponding to Z, the nucleotide sequence 2 comprises a nucleotide $Z'_B$ at the position corresponding to Z', wherein the nucleotide $Z'_B$ is the first nucleotide from 5' terminal of the antisense strand; and the fluoro modified nucleotides are located within the nucleotide sequence 1 and the nucleotide sequence 2; the nucleotide sequence 1 comprises no more than 5 fluoro modified nucleotides, and in the direction from 5' terminal to 3' terminal, the nucleotides at positions 7, 8 and 9 of the nucleotide sequence 1 are fluoro modified nucleotides; the nucleotide sequence 2 comprises no more than 7 fluoro modified nucleotides and the nucleotides at positions 2, 6, 14 and 16 of the nucleotide sequence 2 are fluoro modified nucleotides.

The nucleotide sequence 1 has no more than 1 nucleotide difference from the nucleotide sequence shown in SEQ ID NO: 1; and/or the nucleotide sequence 2 has no more than 1 nucleotide difference from the nucleotide sequence shown in SEQ ID NO: 2.

The nucleotide difference between the nucleotide sequence 2 and the nucleotide sequence shown in SEQ ID NO: 2 includes a difference at the position of $Z'_B$, wherein $Z'_B$ is selected from U, C and G.

Wherein $Z_A$ is a nucleotide complementary to $Z'_B$.

The nucleotide sequence 1 and the nucleotide sequence 2 are basically reverse complementary, substantially reverse complementary, or completely reverse complementary to each other. "basically reverse complementary" means that there are no more than 3 base mispairings between two nucleotide sequences. "Substantially reverse complementary" means that there is no more than 1 base mispairing between two nucleotide sequences. "Completely reverse complementary" means that there is no mispairing between two nucleotide sequences.

The sense strand further comprises a nucleotide sequence 3, and the antisense strand further comprises a nucleotide sequence 4; the nucleotide sequence 3 and the nucleotide sequence 4 have a length of 1-4 nucleotides, respectively; the nucleotide sequence 3 is linked to 5' terminal of the nucleotide sequence 1; and the nucleotide sequence 4 is linked to 3' terminal of the nucleotide sequence 2; the nucleotide sequence 3 and the nucleotide sequence 4 have equal length and are substantially reverse complementary or completely reverse complementary to each other. "Substantially reverse complementary" means that there is no more than 1 base mispairing between two nucleotide sequences.

"Completely reverse complementary" means that there is no mispairing between two nucleotide sequences.

The nucleotide sequence 3 and the nucleotide sequence 4 both have a length of 1 nucleotide and the base of the nucleotide sequence 3 is G.

Alternatively, the nucleotide sequence 3 and the nucleotide sequence 4 both have a length of 2 nucleotides; in the direction from 5' terminal to 3' terminal, the bases of the nucleotide sequence 3 are U and G in succession.

Alternatively, the nucleotide sequence 3 and the nucleotide sequence 4 both have a length of 3 nucleotides; in the direction from 5' terminal to 3' terminal, the bases of the nucleotide sequence 3 are U, U and G in succession.

Alternatively, the nucleotide sequence 3 and the nucleotide sequence 4 both have a length of 4 nucleotides; in the direction from 5' terminal to 3' terminal, the bases of the nucleotide sequence 3 are A, U, U, and G in succession.

The siRNA further comprises a nucleotide sequence 5, which has a length of 1-3 nucleotides and is linked to 3' terminal of the antisense strand, thereby constituting a 3' overhang of the antisense strand.

The nucleotide sequence 5 has a length of 2 nucleotides; and in the direction from 5' terminal to 3' terminal, the nucleotide sequence 5 is 2 consecutive thymidine deoxyribonucleotides, 2 consecutive uridine ribonucleotides or 2 nucleotides complementary to the target mRNA.

The nucleotide sequence 1 comprises the nucleotide sequence shown in SEQ ID NO: 3 or SEQ ID NO: 4; and the nucleotide sequence 2 comprises any one of the nucleotide sequences selected from the group consisting of the nucleotide sequences shown in SEQ ID NO: 5, SEQ ID NO: 6, SEQ ID NO: 7 and SEQ ID NO: 8:

```
                                          (SEQ ID NO: 3)
5'-GAAAGUAUGUCAACGAAUU-3', (SEQ ID NO: 4)
5'-GAAAGUAUGUCAACGAAUA-3', (SEQ ID NO: 5)
5'-AAUUCGUUGACAUACUUUCUU-3', (SEQ ID NO: 6)
5'-AAUUCGUUGACAUACUUUCCA-3', (SEQ ID NO: 7)
5'-UAUUCGUUGACAUACUUUCUU-3', (SEQ ID NO: 8)
5'-UAUUCGUUGACAUACUUUCCA-3'.
```

In some embodiments, the siRNA is any one of the following siP1 to siP4:

```
siP1
Sense strand:
                                          (SEQ ID NO: 3)
5'- GAAAGUAUGUCAACGAAUU -3', Antisense strand:
                                          (SEQ ID NO: 5)
5'- AAUUCGUUGACAUACUUUCUU -3', siP2
Sense strand:
                                          (SEQ ID NO: 3)
5'- GAAAGUAUGUCAACGAAUU -3', Antisense strand:
                                          (SEQ ID NO: 6)
5'- AAUUCGUUGACAUACUUUCCA -3', siP3
Sense strand:
                                          (SEQ ID NO: 4)
5'- GAAAGUAUGUCAACGAAUA -3', Antisense strand:
                                          (SEQ ID NO: 7)
5'- UAUUCGUUGACAUACUUUCUU -3', siP4
Sense strand:
                                          (SEQ ID NO: 4)
5'- GAAAGUAUGUCAACGAAUA -3', Antisense strand:
                                          (SEQ ID NO: 8)
5'- UAUUCGUUGACAUACUUUCCA -3'.
```

In addition, in the direction from 5' terminal to 3' terminal, the nucleotides at positions 7, 8 and 9 in the sense strand of the nucleotide sequence 1 are fluoro modified nucleotides, and the nucleotides at the other positions in the sense strand are non-fluoro modified nucleotides; and the nucleotides at positions 2, 6, 14 and 16 in the antisense strand of the nucleotide sequence 2 are fluoro modified nucleotides, and the nucleotides at the other positions in the antisense strand are non-fluoro modified nucleotides.

Alternatively, in the direction from 5' terminal to 3' terminal, the nucleotides at positions 5, 7, 8 and 9 in the sense strand of the nucleotide sequence 1 are fluoro modified nucleotides, and the nucleotides at the other positions in the sense strand are non-fluoro modified nucleotides; and the nucleotides at positions 2, 6, 8, 9, 14 and 16 in the antisense strand of the nucleotide sequence 2 are fluoro modified nucleotides, and the nucleotides at the other positions in the antisense strand are non-fluoro modified nucleotides.

Alternatively, in the direction from 5' terminal to 3' terminal, the nucleotides at positions 5, 7, 8 and 9 in the sense strand of the nucleotide sequence 1 are fluoro modified nucleotides, and the nucleotides at the other positions in the sense strand are non-fluoro modified nucleotides; and the nucleotides at positions 2, 6, 14 and 16 in the antisense strand of the nucleotide sequence 2 are fluoro modified nucleotides, and the nucleotides at the other positions in the antisense strand are non-fluoro modified nucleotides.

Each non-fluoro modified nucleotide is independently a nucleotide formed by substituting the 2'-hydroxy of the ribose group of the nucleotide with a non-fluoro group, or a nucleotide analogue.

The nucleotide formed by substituting the 2'-hydroxy of the ribose group of the nucleotide with a non-fluoro group is one selected from the group consisting of 2'-alkoxy modified nucleotide, 2'-substituted alkoxy modified nucleotide, 2'-alkyl modified nucleotide, 2'-substituted alkyl modified nucleotide, 2'-amino modified nucleotide, 2'-substituted amino modified nucleotide and 2'-deoxy nucleotide. The nucleotide analogue is one selected from the group consisting of an isonucleotide, LNA, ENA, cET, UNA, and GNA.

Each non-fluoro modified nucleotide is a methoxy modified nucleotide, wherein the methoxy modified nucleotide refers to a nucleotide formed by substituting the 2'-hydroxy of the ribose group with a methoxy group.

In some embodiments, at least one of the phosphate groups in the phosphate-ribose backbone of at least one single strand of the sense strand and the antisense strand of the siRNA of the present disclosure is a phosphate group with modified group(s).

In some embodiments, the phosphate group with modified group(s) is a phosphorothioate group formed by substituting at least one oxygen atom in the phosphodiester bond in a phosphate group with a sulfur atom. In some embodiments, the phosphate group with modified group(s) is a phosphorothioate group having a structure as shown by Formula (1):

Formula (1)

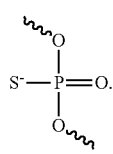

In the siRNA, at least one linkage selected from the group consisting of the following inter-nucleotide linkages is a phosphorothioate linkage:
- the linkage between the first and second nucleotides at 5' terminal of the sense strand;
- the linkage between the second and third nucleotides at 5' terminal of the sense strand;
- the linkage between the first and second nucleotides at 3' terminal of the sense strand;
- the linkage between the second and third nucleotides at 3' terminal of the sense strand;
- the linkage between the first and second nucleotides at 5' terminal of the antisense strand;
- the linkage between the second and third nucleotides at 5' terminal of the antisense strand;
- the linkage between the first and second nucleotides at 3' terminal of the antisense strand; and
- the linkage between the second and third nucleotides at 3' terminal of the antisense strand.

In some embodiments, the nucleotide at 5'-terminal of the antisense strand of the siRNA of the present disclosure is a 5'-phosphate nucleotide or a 5'-phosphate analogue modified nucleotide. In some embodiments, the nucleotide at 5'-terminal is a nucleotide as shown by any one of Formulae (2) to (6):

Formula (2)

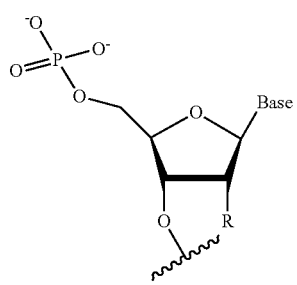

Formula (3)

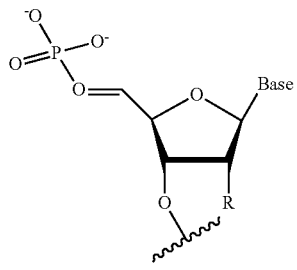

Formula (4)

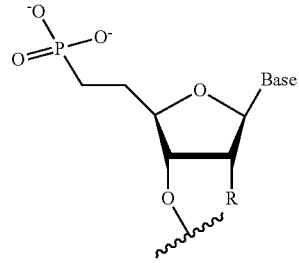

Formula (5)

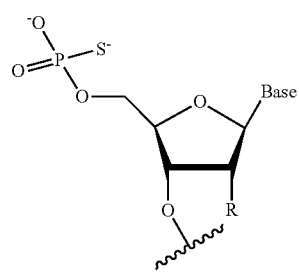

Formula (6)

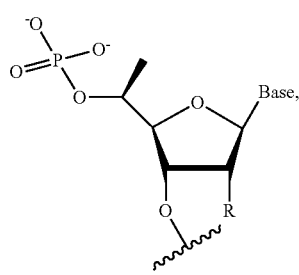

wherein,

R represents a group selected from the group consisting of H, OH, F and methoxy;

"Base" represents a base selected from A, U, C, G, and T.

In some specific embodiments, the siRNA of the present disclosure is any one of the siRNAs listed in Tables 1A-1D.

In some embodiments, the present disclosure provides a pharmaceutical composition comprising the siRNA of the disclosure as an active ingredient and a pharmaceutically acceptable carrier. In one embodiment, the weight ratio of the siRNA and the pharmaceutically acceptable carrier is 1:(1-500), such as 1:(1-50).

In some embodiments, the pharmaceutically acceptable carrier comprises an organic amine, a helper lipid and a PEGylated lipid; wherein the organic amine is a compound as shown by Formula (201) and/or a pharmaceutically acceptable salt thereof:

Formula (201)

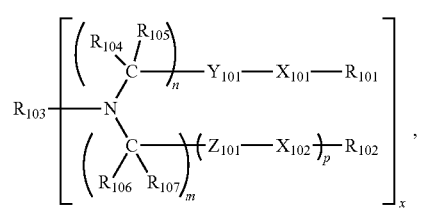

wherein:

$X_{101}$ and $X_{102}$ independently of one another are selected from O, S, N-A and C-A, wherein A is hydrogen or a $C_1$-$C_{20}$ hydrocarbon chain;

$Y_{101}$ and $Z_{101}$ independently of one another are selected from C=O, C=S, S=O, CH—OH and $SO_2$;

$R_{101}$, $R_{102}$, $R_{103}$, $R_{104}$, $R_{105}$, $R_{106}$ and $R_{107}$ independently of one another are selected from hydrogen; a cyclic or an acyclic, substituted or unsubstituted, branched or unbranched aliphatic group; a cyclic or an acyclic, substituted or unsubstituted, branched or unbranched heteroaliphatic group; a substituted or unsubstituted, branched or unbranched acyl group; a substituted or unsubstituted, branched or unbranched aryl group; and a substituted or unsubstituted, branched or unbranched heteroaryl group;

x is an integer of 1-10;

n is an integer of 1-3, m is an integer of 0-20, p is an integer of 0 or 1, wherein if m and p are 0, then $R_{102}$ is hydrogen; and if at least one of n and m is 2, then $R_{103}$ and nitrogen in Formula (201) form a structure as shown by Formula (202) or (203):

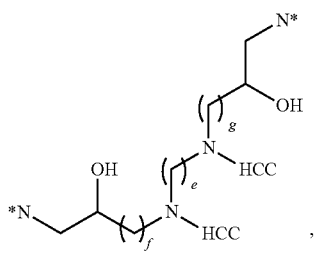

Formula (202)

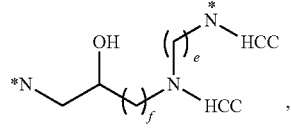

Formula (203)

wherein g, e and f independently of one another are an integer of 1-6; "HCC" represents a hydrocarbon chain; and each *N indicates a nitrogen atom shown in Formula (201).

The organic amine is an organic amine as shown by Formula (214) and/or an organic amine as shown by Formula (215):

Formula (214)
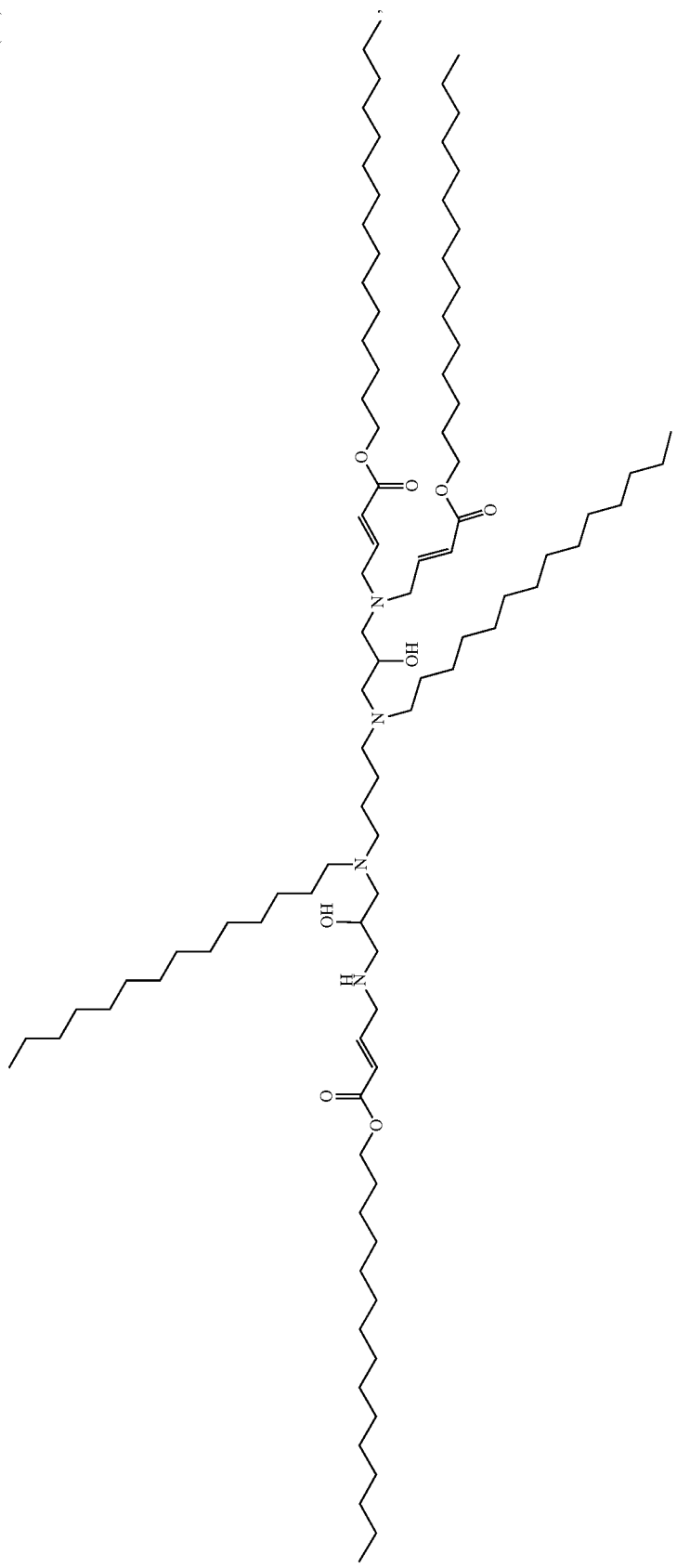

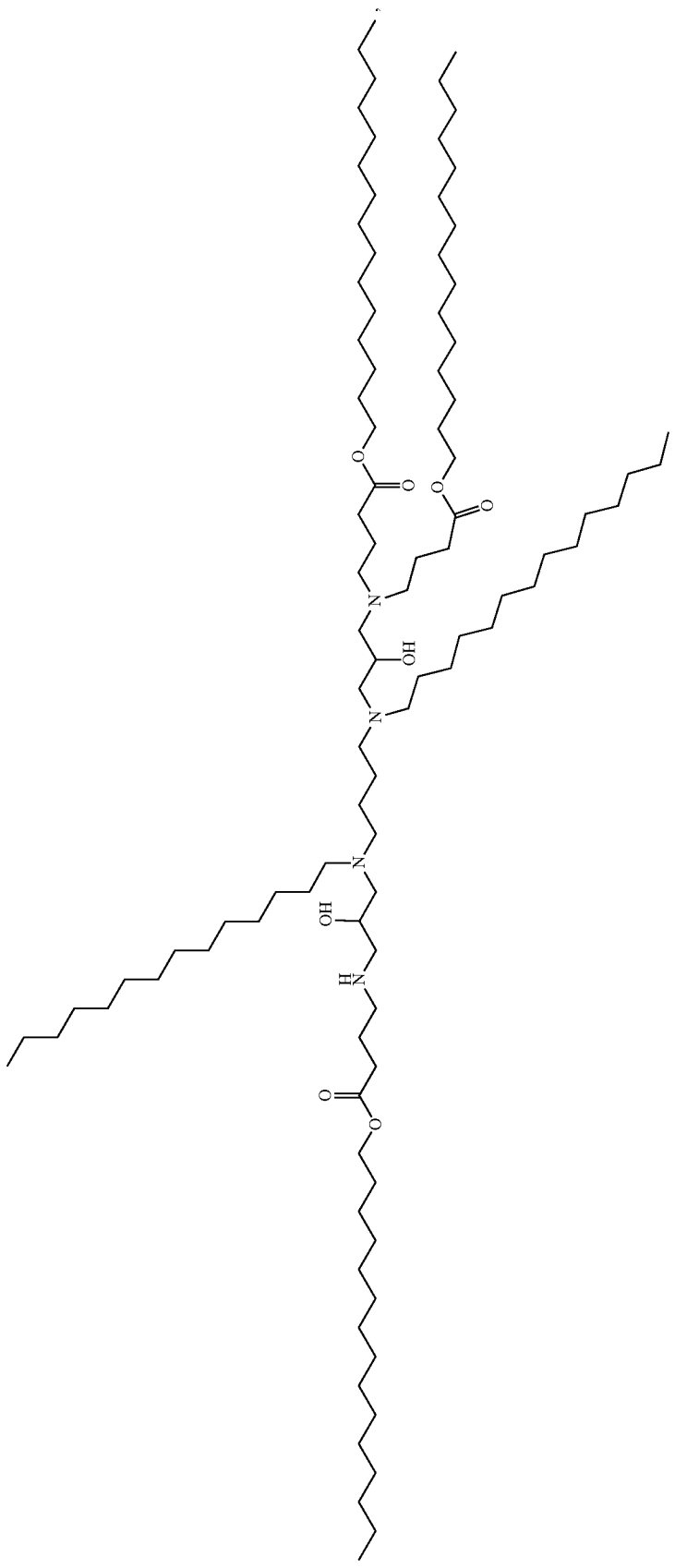
Formula (215)

the helper lipid is cholesterol, cholesterol analog and/or cholesterol derivative; and the PEGylated lipid is 1,2-dipalmitoyl-sn-glycero-3-phosphoethanolamine-N-[methoxy(polyethylene glycol)]-2000.

The molar ratio among the organic amine, the helper lipid, and the PEGylated lipid is (19.7-80):(19.7-80):(0.3-50).

In the pharmaceutical composition, the molar ratio among the organic amine, the helper lipid, and the PEGylated lipid is (50-70):(20-40):(3-20).

In some embodiments, the present disclosure provides a siRNA conjugate comprising the siRNA of the present disclosure as an active ingredient and a ligand conjugated to the siRNA. In some embodiments, the ligand is a pharmaceutically acceptable conjugation group which comprises a pharmaceutically acceptable targeting group and a linker; and the siRNA, the linker and the targeting group are covalently or non-covalently linked in succession.

The linker may have a structure as shown by Formula (301):

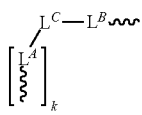

Formula (301)

wherein, k is an integer of 1-3;

$L^A$ is an amide bond-comprising chain moiety that has a structure as shown by Formula (302), two terminals of which are respectively linked to the targeting group and the $L^C$ moiety each via an ether bond:

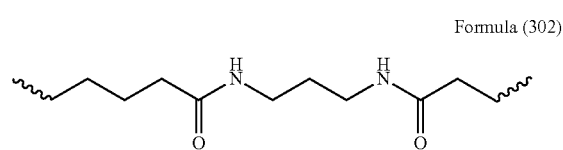

Formula (302)

$L^B$ is an N-acylpyrrolidine-comprising chain moiety that has a structure as shown by Formula (303), which has a carbonyl group and is linked to the $L^C$ moiety via an amide bond at one end, and has an oxygen atom and is linked to the siRNA via a phosphoester bond at the other end thereof:

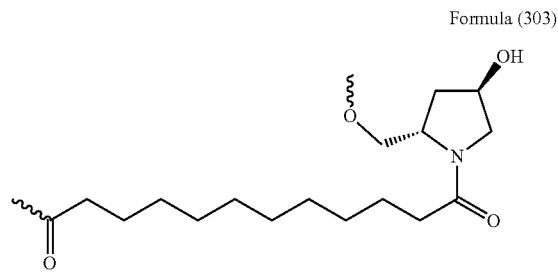

Formula (303)

$L^C$ is a bivalent to tetravalent linking group based on hydroxymethyl aminomethane, dihydroxymethyl aminomethane or trihydroxymethyl aminomethane, $L^C$ being linked to each of the $L^A$ moieties through an ether bond via an oxygen atom, and being linked to the $L^B$ moiety through an amide bond via the nitrogen atom.

The linker is linked to 3'-terminal of the sense strand of the siRNA.

The targeting group is a ligand of an asialoglycoprotein receptor.

The targeting group is galactose or N-acetylgalactosamine.

The siRNA conjugate has a structure as shown by Formula (305):

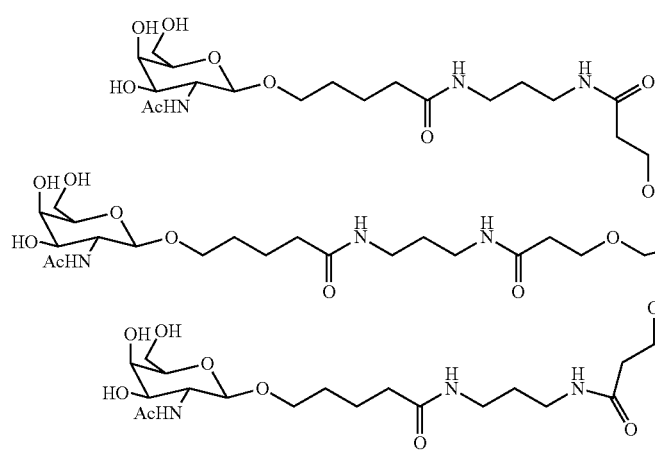
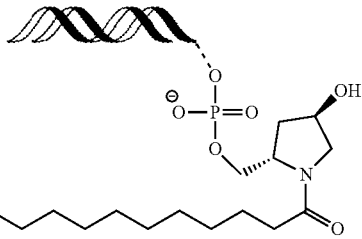

Formula (305)

wherein the double helix structure represents the siRNA; and the linker is linked to 3'-terminal of the sense strand of the siRNA.

The linker may have a structure as shown by Formula (306):

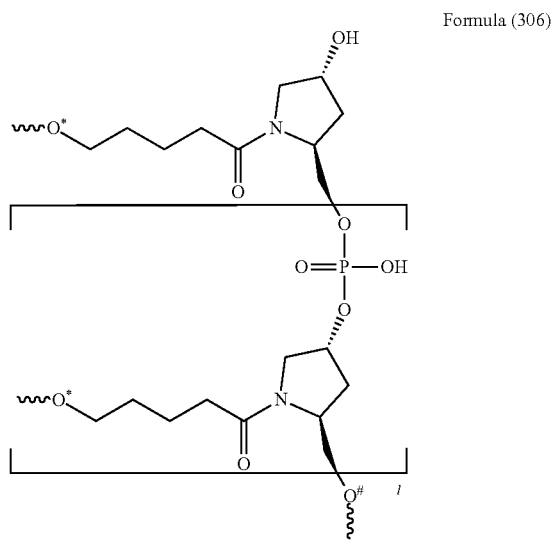

Formula (306)

wherein, l is an integer of 0-3;

represents the site on the linker linked to the targeting group via ether bond; and \# represents the site on the linker linked to the siRNA via phosphoester bond.

The linker is linked to 3'-terminal of the sense strand of the siRNA.

The targeting group is a ligand of an asialoglycoprotein receptor.

The targeting group is galactose or N-acetylgalactosamine.

The siRNA conjugate has a structure as shown by Formula (307):

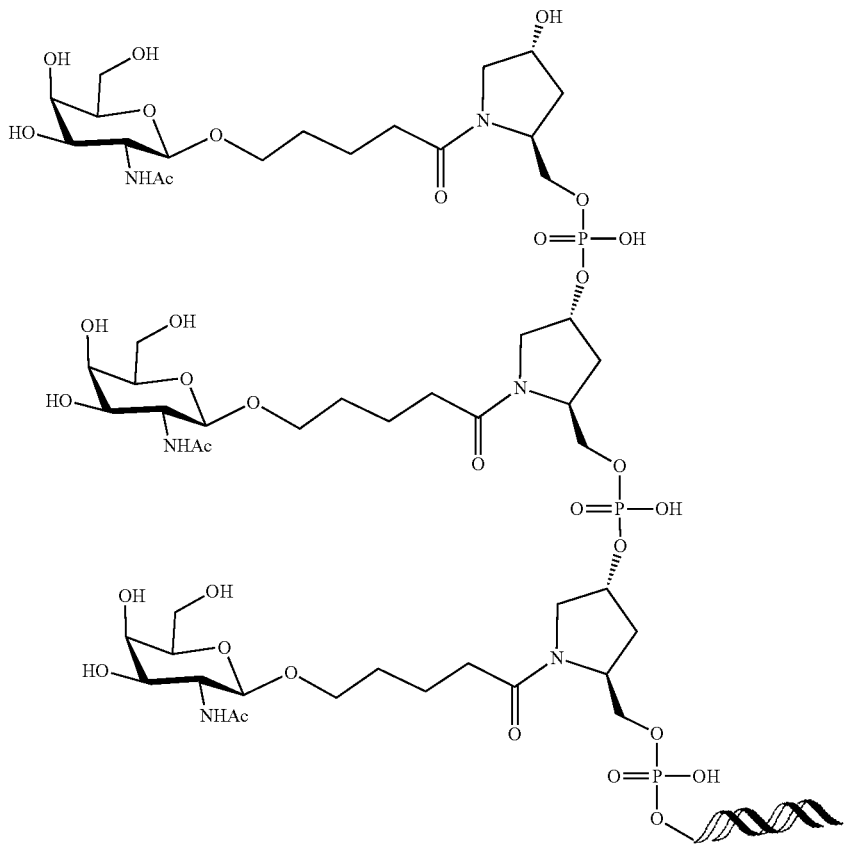

Formula (307)

wherein, the double helix structure represents the siRNA; and the linker is linked to 3'-terminal of the sense strand of the siRNA.

In some embodiments, the present disclosure provides a siRNA conjugate as shown by Formula (401):

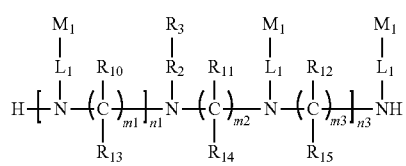

Formula (401)

wherein,
n1 is an integer of 1-3, and n3 is an integer of 0-4;
m1, m2, and m3 independently of one another are an integer of 2-10;
$R_{10}$, $R_{11}$, $R_{12}$, $R_{13}$, $R_{14}$ and $R_{15}$ independently of one another are one of H, methyl and ethyl;
$R_3$ is a group having a structure as shown by Formula (A59):

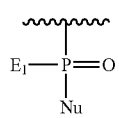

Formula (A59)

wherein $E_1$ is OH, SH or $BH_2$; and Nu is the above siRNA provided by the present disclosure;
$R_2$ is any group capable of linking to the N atom on the nitrogenous backbone and linking to A59;
each $L_1$ is independently selected from the linkage combinations of one or more of Formulae A1-A26:

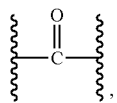 (A1)

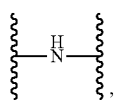 (A2)

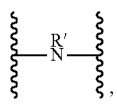 (A3)

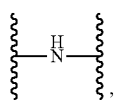 (A4)

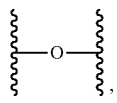 (A5)

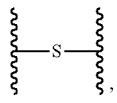 (A6)

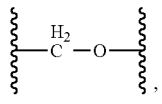 (A6)

-continued

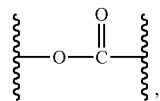 (A7)

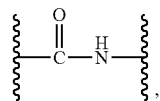 (A8)

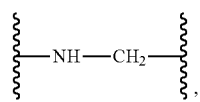 (A9)

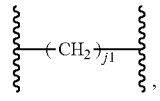 (A10)

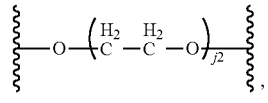 (A11)

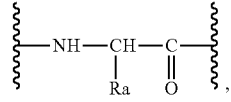 (A12)

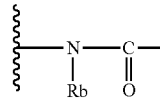 (A13)

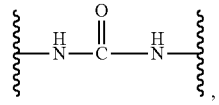 (A14)

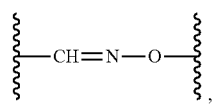 (A15)

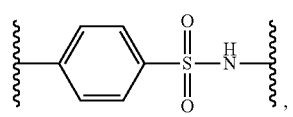 (A16)

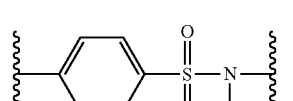 (A17)

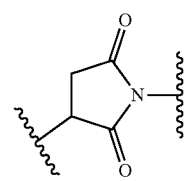 (A18)

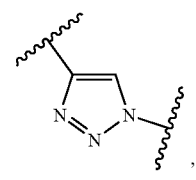 (A19)

-continued (A20)

(A21)

(A22)

(A23)

(A24)

(A25)

, and (A26)

wherein j1 is an integer of 1-20;
j2 is an integer of 1-20;
R' is a $C_1$-$C_{10}$ alkyl;
Ra is selected from one of Formulae A27-A45:

(A27)

(A28)

(A29)

(A30)

-continued (A31)

(A32)

(A33)

(A34)

(A35)

(A36)

(A37)

(A38)

(A39)

(A40)
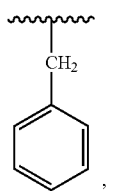

(A41)
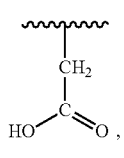

(A42)
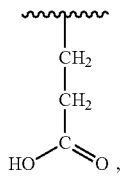

(A43)
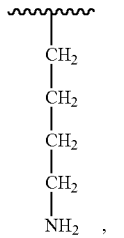

(A44)
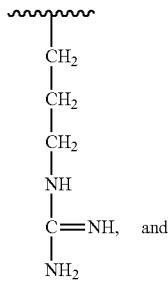

(A45)
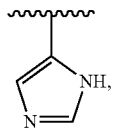

Rb is a $C_1$-$C_{10}$ alkyl; and

~~~ represents the site where a group is covalently linked;

each $M_1$ is selected from one of the ligands that have affinity to the asialoglycoprotein receptors (ASGP-R) on the surface of mammalian hepatocytes.

In some embodiments, in the siRNA conjugate above, $L_1$ is selected from the linkage combinations of one or more of Formulae A1, A4, A5, A6, A8, A10, A11, and A13.

Alternatively, $L_1$ is selected from the linkage combinations of at least two of Formulae A1, A4, A8, A10, and A11.

Alternatively, $L_1$ is selected from the linkage combinations of at least two of Formulae A1, A8, and A10.

In some embodiments, in the siRNA conjugate above, $L_1$ has a length of 3 to 25 atoms. The length of $L_1$ refers to the number of the chain-forming atoms on the longest atom chain formed from the atom linked to the N atom on the nitrogenous backbone to the atom linked to the M1 group.

Alternatively, $L_1$ has a length of 4 to 15 atoms.

In some embodiments, in the siRNA conjugate above, j1 is an integer of 2-10; j2 is an integer of 2-10; R' is a $C_1$-$C_4$ alkyl; Ra is one of A27, A28, A29, A30, and A31; and Rb is a $C_1$-$C_5$ alkyl.

Alternatively, j1 is an integer of 3-5; j2 is an integer of 3-5; R' is one of methyl, ethyl, and isopropyl; Ra is A27 or A28; and Rb is one of methyl, ethyl, isopropyl, and butyl.

In some embodiments, in the siRNA conjugate above, n1 is an integer of 1-2; n3 is an integer of 0-1; and n1+n3=2-3.

In some embodiments, in the siRNA conjugate above, m1, m2 and m3 independently of one another are an integer of 2-5. In some embodiments, m1=m2=m3.

In some embodiments, in the siRNA conjugate above, each $M_1$ is independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose, and L-4-thioribose.

In some embodiments, each $M_1$ is N-acetylgalactosamine.

In some embodiments, in the siRNA conjugate above, $R_{10}$, $R_{11}$, $R_{12}$, $R_{13}$, $R_{14}$, and $R_{15}$ are H.

In some embodiments, in the siRNA conjugate above, $R_2$ comprises both a site linking to the N atom on the nitrogenous backbone and a site linking to the P atom in $R_3$.

In some embodiments, in $R_2$, the site linking to the N atom on the nitrogenous backbone forms an amide bond with the N atom, and the site linking to the P atom in $R_3$ forms a phosphoester bond with the P atom.

In some embodiments, $R_2$ may be selected from B5, B6, B5', or B6':

(B5)

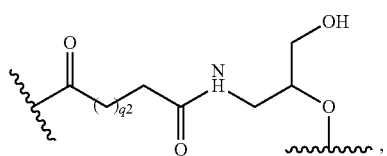
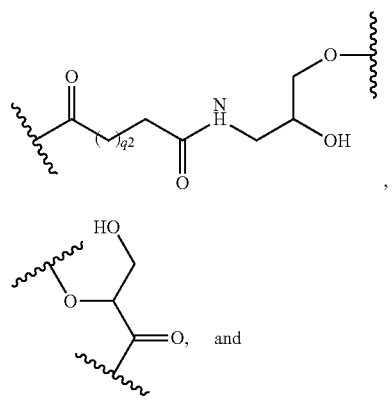
wherein, ⌇ represents the site where a group is covalently linked; and $q_2$ is an integer of 1-10. In some embodiments, $q_2$ may be an integer of 1-5.
In some embodiments, the siRNA conjugate above has a structure as shown by Formula (403), (404), (405), (406), (407), (408), (409), (410), (411), (412), (413), (414), (415), (416), (417), (418), (419), (420), (421), or (422):
Formula (403)
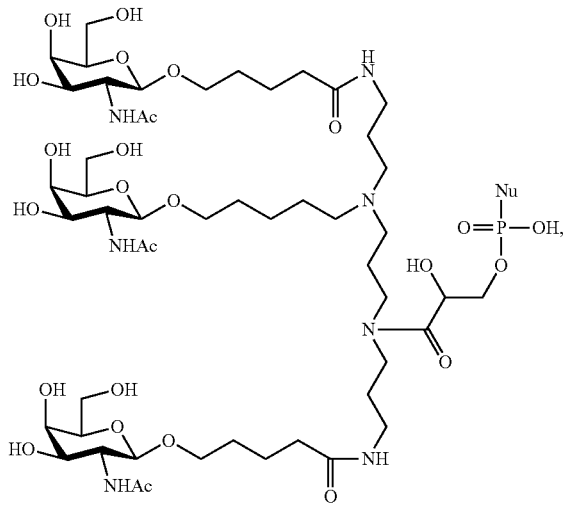
Formula (404)
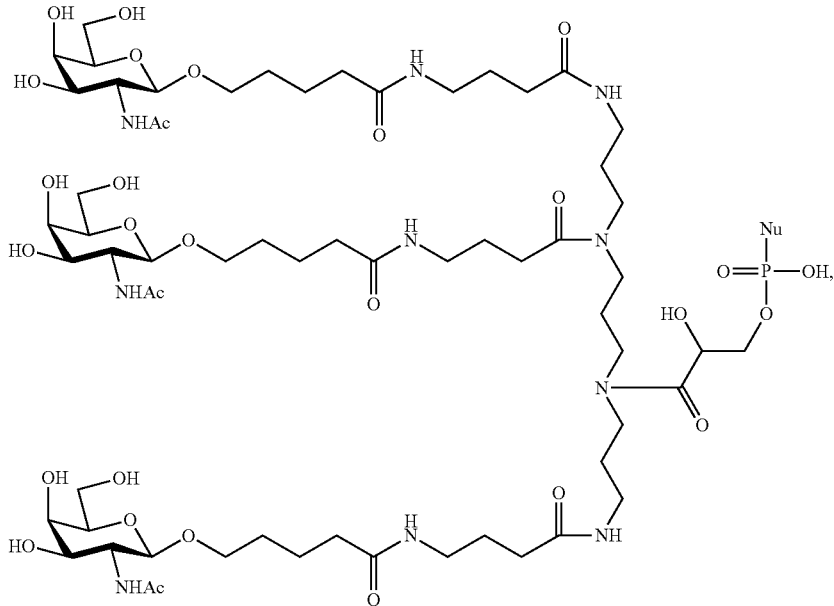

Formula (405)
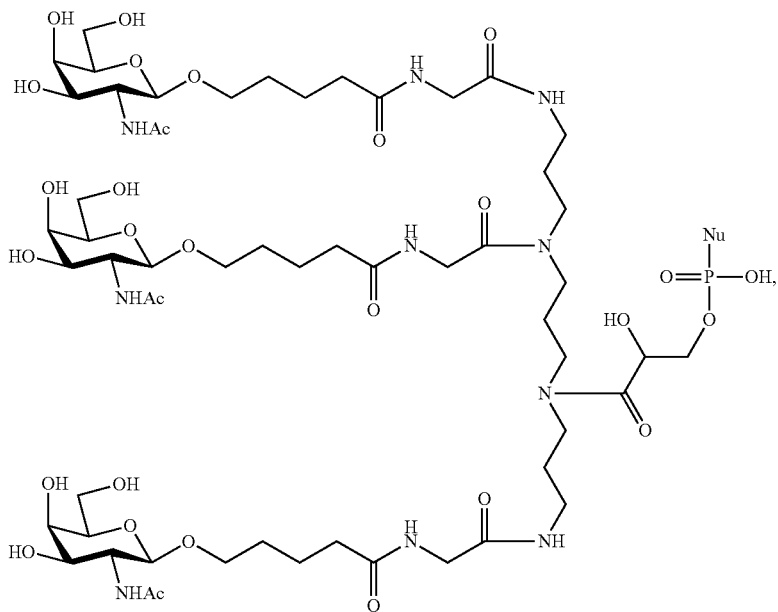
Formula (406)
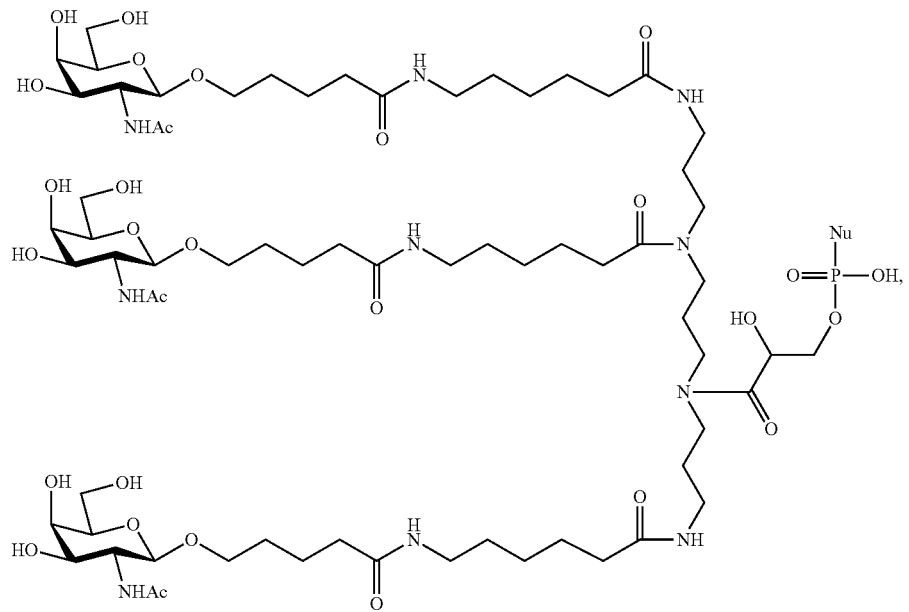

Formula (407)
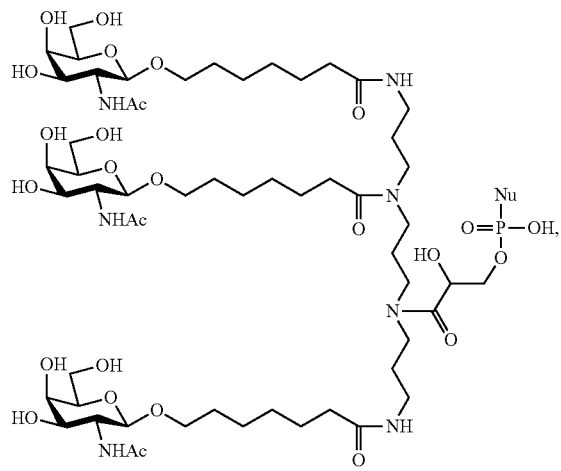
Formula (408)
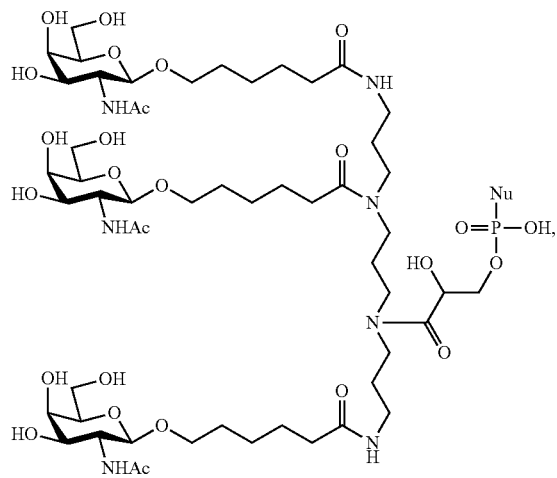
Formula (409)
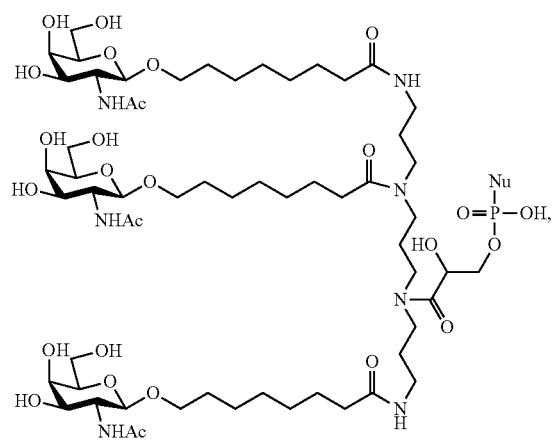
Formula (410)
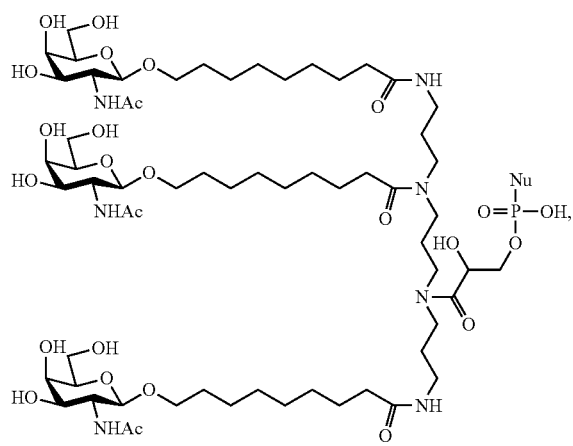
Formula (411)
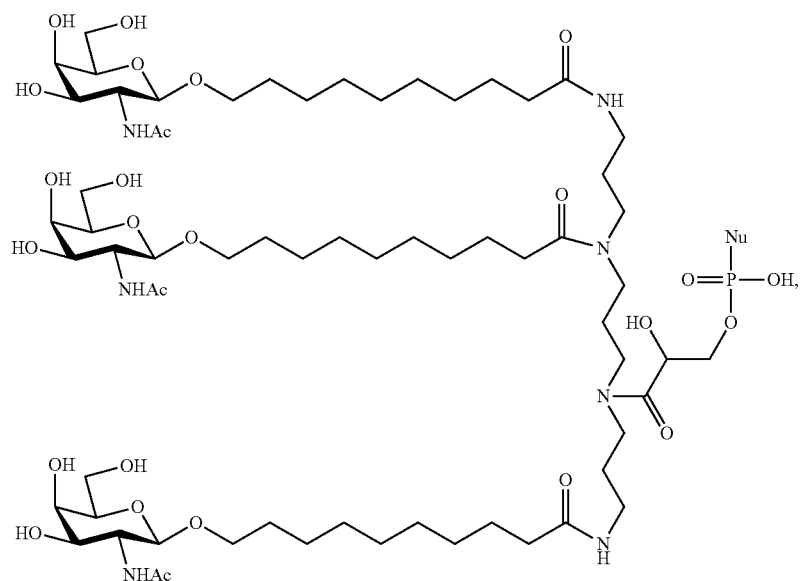

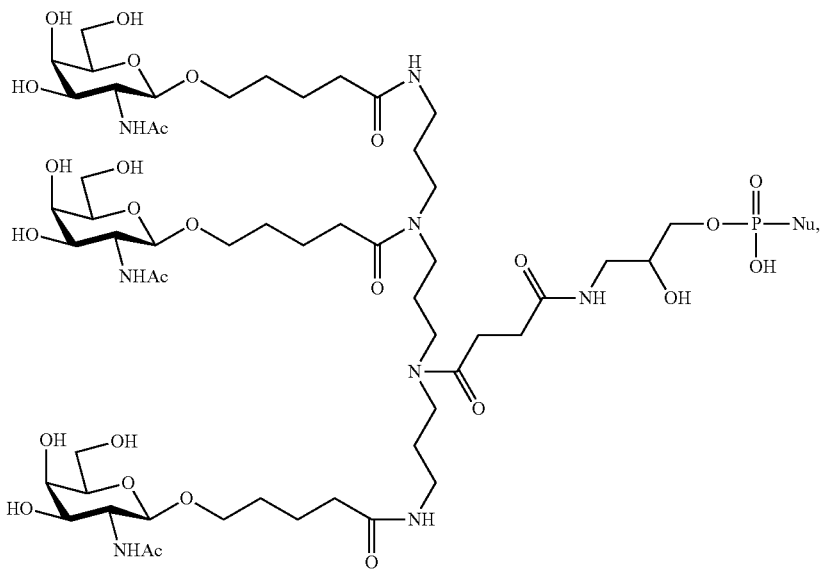
Formula (412)
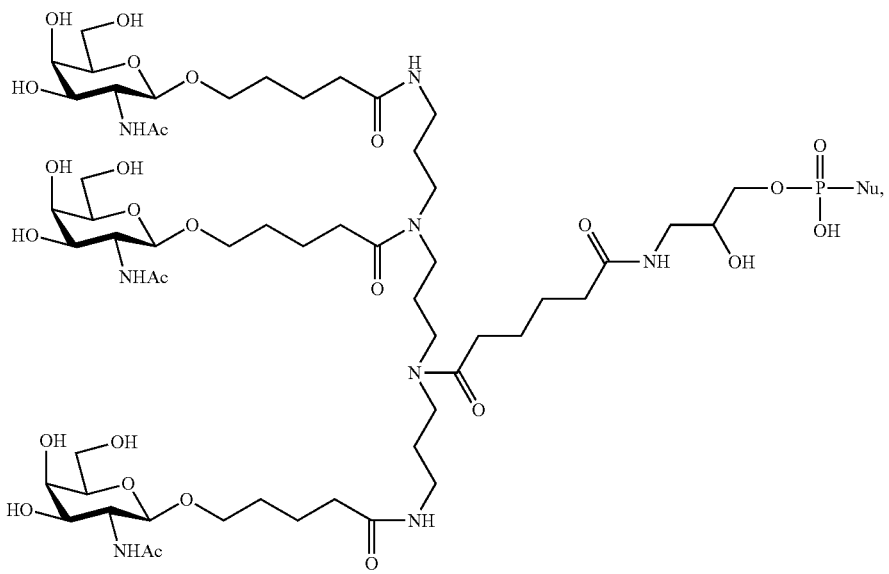
Formula (413)
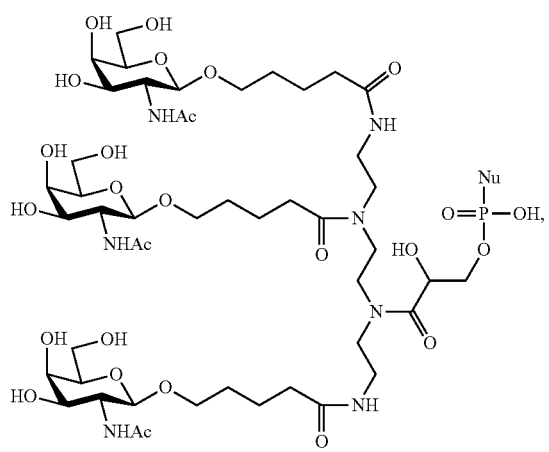
Formula (414)
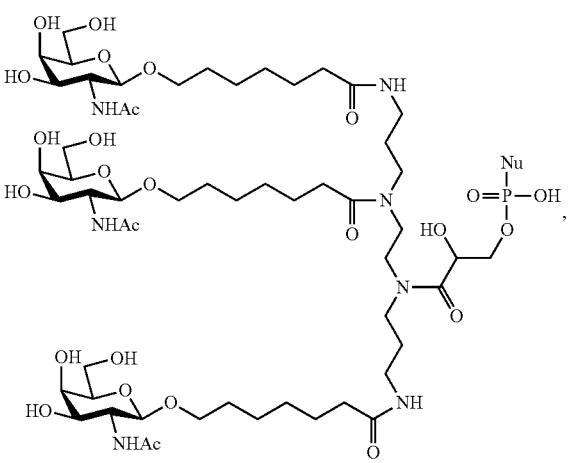
Formula (415)

-continued
Formula (416)
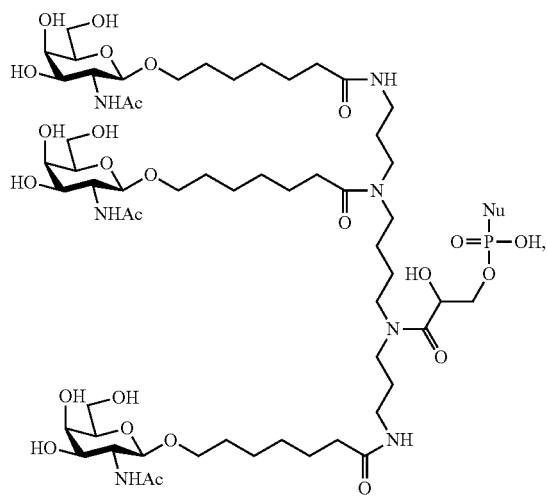
Formula (417)
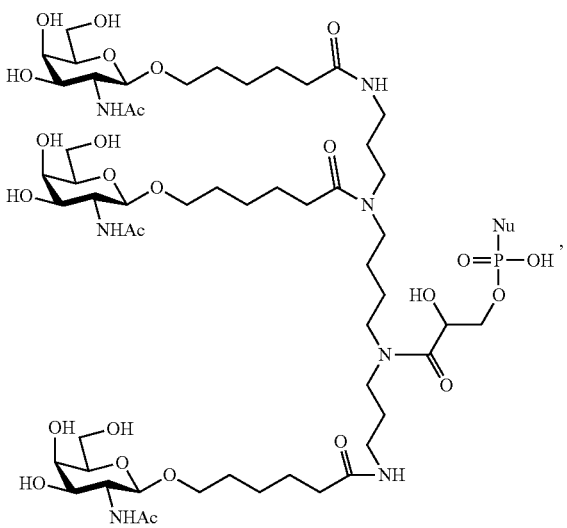
Formula (418)
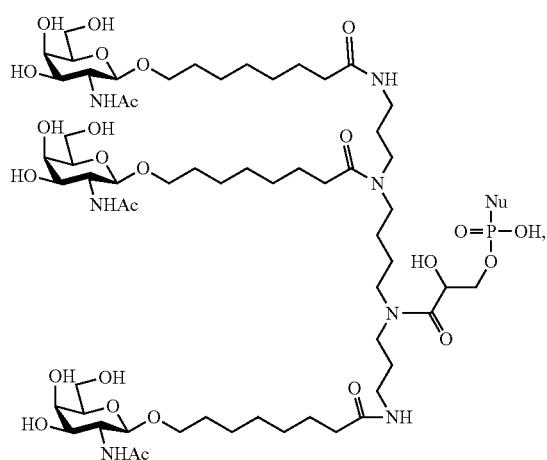
Formula (419)
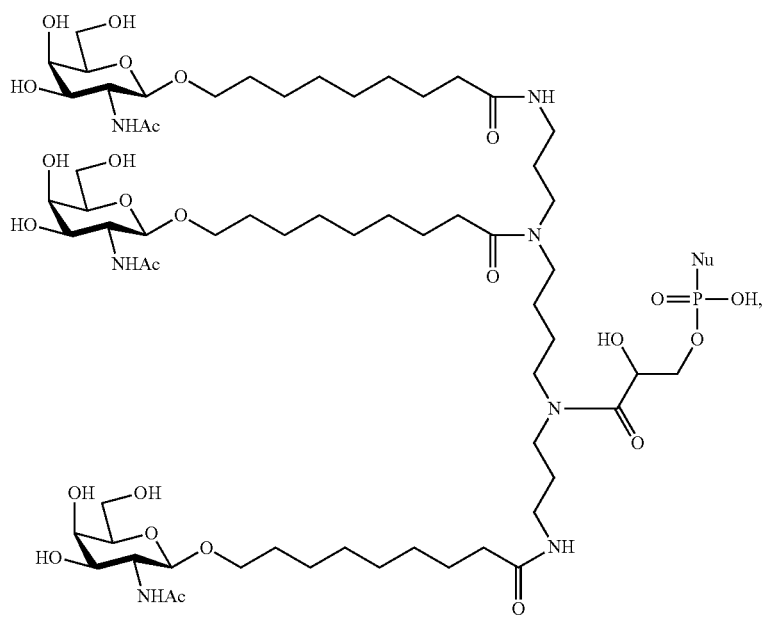

-continued

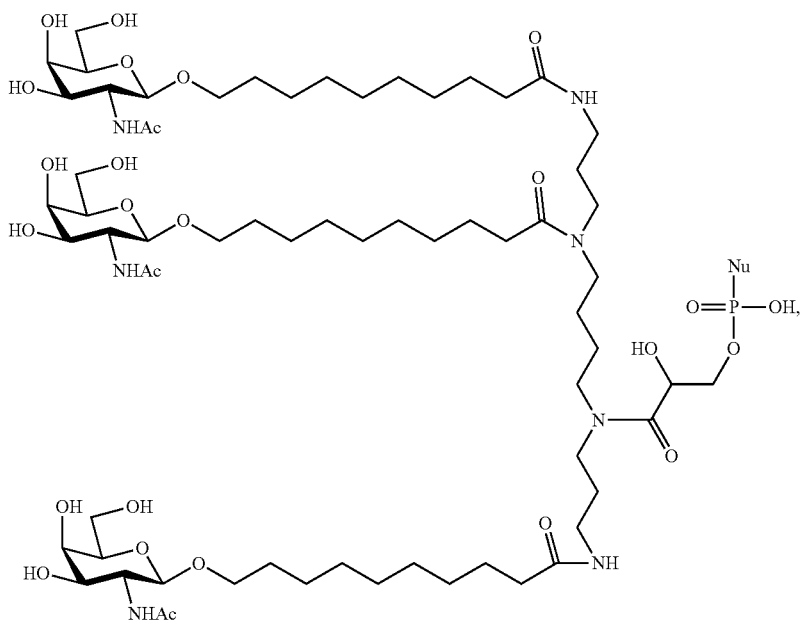

Formula (420)

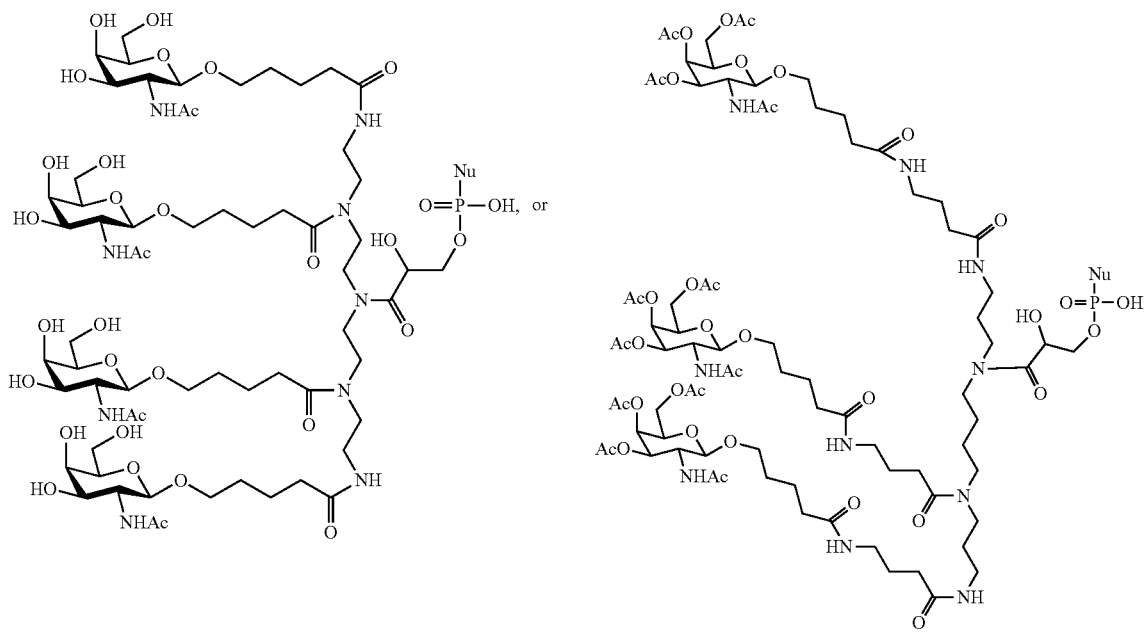

Formula (421)

Formula (422)

In some embodiments, in the siRNA conjugate above, the P atom in Formula A59 is linked to a terminal region of the sense strand or antisense strand of the siRNA, wherein the terminal region refers to the first 4 nucleotides counted from one terminal of the sense strand or antisense strand. In some embodiments, the P atom in Formula A59 is linked to one terminal of the sense strand or antisense strand or linked to 3' terminal of the sense strand.

In some embodiments, in the siRNA conjugate above, the P atom in Formula A59 is linked to position 2', 3', or 5' of a nucleotide in the siRNA by forming a phosphodiester bond.

In some embodiments, the present disclosure provides use of the siRNA, the pharmaceutical composition and/or the siRNA conjugate above in the manufacture of a medicament for treating and/or preventing pathological condition or disease caused by hepatitis B virus (HBV) infection.

In some embodiments, the pathological condition or disease caused by HBV infection is selected from chronic liver diseases, hepatitis, hepatic fibrosis, and liver proliferative diseases.

In some embodiments, the present disclosure provides a method for treating and/or preventing pathological condition or disease caused by HBV infection, comprising administering to a patient an effective amount of the siRNA, the pharmaceutical composition, and/or the siRNA conjugate above.

In some embodiments, the present disclosure provides a method for inhibiting the expression of HBV gene in hepatitis cells, comprising contacting an effective amount of the siRNA, the pharmaceutical composition, and/or the siRNA conjugate above with hepatitis cells infected with HBV.

In some embodiments, the present disclosure provides a kit, comprising the siRNA, the pharmaceutical composition, and/or the siRNA conjugate above.

Advantageous Effects

In some embodiments, the siRNA provided by the present disclosure exhibits higher plasma stability and better inhibitory activity. In some embodiments, the siRNA provided by the present disclosure can be stably present in human plasma in vitro over a period of up to 72 hours. In some embodiments, the siRNA provided by the present disclosure shows an inhibitory activity in vitro of 80% or higher at the concentration of 0.1 nM.

In some embodiments, the conjugate comprising the siRNA provided by the present disclosure exhibits lower off-target effect and better stability in lysosome and/or inhibitory activity. In some embodiments, the conjugate comprising the siRNA provided by the present disclosure can effectively target the liver and exhibit excellent inhibitory activity against the expression of HBV genes: the conjugate could achieve an inhibition percentage of 77.4% to 88.3% of HBV mRNA in the liver of hepatitis B model mice at a single dose of 1 mg/kg, while maintaining a low off-target effect. Meanwhile, the conjugate comprising the siRNA provided by the present disclosure can further effectively reduce the expression of HBV surface antigen in hepatitis B model mice, achieving an inhibition efficiency of 90% or higher against HBV surface antigen and HBV DNA at a single dose of 3 mg/kg over a period of up to 84 days. Even at the end of observation, day 154, the two indicators did not return to the levels before administration. In particular, the conjugate still shows an inhibition percentage of 77.0% against HBsAg and an inhibition percentage of 80.1% against HBV DNA. This suggests that the conjugate comprising the siRNA provided by the present disclosure could effectively deliver the siRNA as an active ingredient to the liver and remain active in vivo over a prolonged period, and thus can efficiently treat and/or prevent pathological conditions and diseases caused by hepatitis B virus (HBV) infection, having a promising application prospect.

Additional features and advantages of the present disclosure will be illustrated in detail in the following part "DETAILED DESCRIPTION OF THE INVENTION".

DETAILED DESCRIPTION OF THE INVENTION

Figure 1:
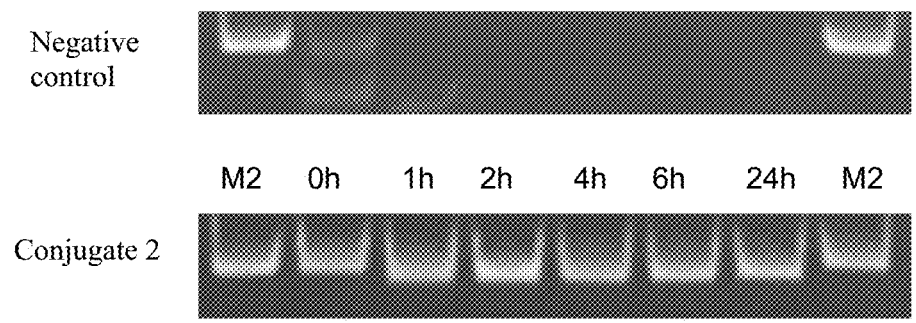
FIG. 1 shows PAGE electrophoretogram of Conjugate 2 after incubation with mouse lysosome lysate over different periods of time.

The specific embodiments of the present disclosure are described in detail as below. It should be understood that the specific embodiments described herein are only for the purpose of illustration and explanation of the present disclosure and are not intended to limit the present disclosure.

In the context of the present disclosure, HBV gene refers to the gene having a DNA sequence as shown in Genbank Accession No. NC_003977.2. Accordingly, the target mRNA refers to the mRNA obtained by the transcription of HBV genes.

In the context of the present disclosure, unless otherwise specified, C, G, U, A, and T represent the base composition of a nucleotide; d represents that the nucleotide adjacent to the right side of the letter d is a deoxyribonucleotide; m represents that the nucleotide adjacent to the left side of the letter m is a methoxy modified nucleotide; f represents that the nucleotide adjacent to the left side of the letter f is a fluoro modified nucleotide; s represents that the two nucleotides adjacent to both sides of the letter s are linked by a phosphorothioate linkage; P1 represents that the nucleotide adjacent to the right side of P1 is a 5'-phosphate nucleotide or a 5'-phosphate analogue modified nucleotide; VP represents that the nucleotide adjacent to the right side of VP is a vinyl phosphate modified nucleotide; Ps represents that the nucleotide adjacent to the right side of Ps is a thiophosphate modified nucleotide; and P represents that the nucleotide adjacent to the right side of the letter P is a 5'-phosphate nucleotide.

In the context of the present disclosure, expressions "complementary" and "reverse complementary" can be interchangeably used, and have a well-known meaning in the art, namely, the bases in one strand are complementarily paired with those in the other strand of a double-stranded nucleic acid molecule. In DNA, a purine base adenine (A) is always paired with a pyrimidine base thymine (T) (or uracil (U) in RNAs); and a purine base guanine (G) is always paired with a pyrimidine base cytosine (C). Each base pair comprises a purine and a pyrimidine. While adenines in one strand are always paired with thymines (or uracils) in another strand, and guanines are always paired with cytosines, the two strands are considered as being complementary to each other; and the sequence of a strand may be deduced from the sequence of its complementary strand. Correspondingly, a "mispairing" means that in a double-stranded nucleic acid, the bases at corresponding positions are not presented in a manner of being complementarily paired.

In the context of the present disclosure, unless otherwise specified, "basically reverse complementary" means that there are no more than 3 base mispairings between two nucleotide sequences. "Substantially reverse complementary" means that there is no more than 1 base mispairing between two nucleotide sequences. "Completely reverse complementary" means that there is no based mispairing between two nucleotide sequences.

In the context of the present disclosure, when a nucleotide sequence has "nucleotide difference" from another nucleotide sequence, the bases of the nucleotides at the same position therebetween are changed. For example, if a nucleotide base in the second sequence is A and the nucleotide base at the same position in the first sequence is U, C, G or T, the two nucleotide sequences are considered as having a nucleotide difference at this position. In some embodiments, if a nucleotide at a position is replaced with an abasic nucleotide or a nucleotide analogue, it is also considered that there is a nucleotide difference at the position.

In the context of the present disclosure, a "fluoro modified nucleotide" refers to a nucleotide formed by substituting the 2'-hydroxy of the ribose group of the nucleotide with a fluoro. A "non-fluoro modified nucleotide" refers to a nucleotide formed by substituting the 2'-hydroxy of the ribose group of the nucleotide with a non-fluoro group, or a nucleotide analogue. A "nucleotide analogue" refers to a group that can replace a nucleotide in a nucleic acid, while structurally differs from an adenine ribonucleotide, a guanine ribonucleotide, a cytosine ribonucleotide, a uracil ribonucleotide or thymine deoxyribonucleotide, such as an isonucleotide, a bridged nucleic acid (BNA) nucleotide or an acyclic nucleotide. The methoxy modified nucleotide refers to a nucleotide formed by substituting the 2'-hydroxy of the ribose group with a methoxy group.

In the context of the present disclosure, the term "modified nucleotide" used herein refers to a nucleotide formed by substituting the 2'-hydroxy of the ribose group of the nucleotide with other groups, a nucleotide analogue, or a nucleotide in which the base is a modified base.

In the context of the present disclosure, particularly in the description of the method for preparing the siRNA conjugate of the present disclosure, unless otherwise specified, the "nucleoside monomer" refers to, according to the type and sequence of the nucleotides in the siRNA or siRNA conjugate to be prepared, "unmodified or modified RNA phosphoramidites" used in a phosphoramidite solid phase synthesis (the RNA phosphoramidites are also referred to as "nucleoside phosphoramidites" sometimes). The phosphoramidite solid phase synthesis is a well-known method for RNA synthesis. Nucleoside monomers used in the present disclosure are all commercially available.

In the context of the present disclosure, unless otherwise specified, "conjugation" refers to two or more chemical moieties each with specific function being linked to each other via a covalent linkage. Correspondingly, a "conjugate" refers to the compound formed by covalent linkage of individual chemical moieties. Further, a "siRNA conjugate" represents a compound formed by covalently attaching a siRNA and one or more chemical moieties each with specific functions.

In this context, the siRNA conjugate of the present disclosure is sometimes abbreviated as "conjugate". More specifically, in the context of the present disclosure, a "conjugation molecule" should be understood as a compound capable of being conjugated to a siRNA via a reaction, thereby finally forming the siRNA conjugate of the present disclosure. Unless otherwise stated, in the specific embodiments of the present disclosure, the siRNA conjugate or conjugate is the generic term of the first siRNA conjugate and the second siRNA conjugate (which will be further described in detail below).

siRNA

The present disclosure provides a siRNA capable of selectively and effectively reducing the expression of HBV gene.

The siRNA of the present disclosure comprises nucleotide groups as basic building units. It is well-known to those skilled in the art that the nucleotide comprises a phosphate group, a ribose group and a base. Detailed illustrations relating to such groups are omitted here.

The siRNA of the present disclosure comprises a sense strand and an antisense strand, and each nucleotide in the sense strand and antisense strand is a modified nucleotide, wherein the sense strand and antisense strand both comprise fluoro modified nucleotides and non-fluoro modified nucleotides; the sense strand comprises a nucleotide sequence 1, and the antisense strand comprises a nucleotide sequence 2; the nucleotide sequence 1 and the nucleotide sequence 2 are at least partly reverse complementary to form a double-stranded region; wherein the nucleotide sequence 1 and the nucleotide sequence shown in SEQ ID NO: 1 have an equal length and no more than 3 nucleotide differences; and the nucleotide sequence 2 and the nucleotide sequence shown in SEQ ID NO: 2 have an equal length and no more than 3 nucleotide differences:

```
                                       (SEQ ID NO: 1)
         5'-GAAAGUAUGUCAACGAAUZ-3', (SEQ ID NO: 2)
         5'-Z'AUUCGUUGACAUACUUUC-3',
``` wherein Z is U; Z' is A;

the nucleotide sequence 1 comprises a nucleotide $Z_A$ at the position corresponding to Z; the nucleotide sequence 2 comprises a nucleotide $Z'_B$ at the position corresponding to Z'; the nucleotide $Z'_B$ is the first nucleotide at 5' terminal of the antisense strand; and the fluoro modified nucleotides are located within the nucleotide sequence 1 and the nucleotide sequence 2; the nucleotide sequence 1 comprises no more than 5 fluoro modified nucleotides, and in the direction from 5' terminal to 3' terminal, the nucleotides at positions 7, 8 and 9 of the nucleotide sequence 1 are fluoro modified nucleotides; the nucleotide sequence 2 comprises no more than 7 fluoro modified nucleotides, and the nucleotides at positions 2, 6, 14 and 16 of the nucleotide sequence 2 are fluoro modified nucleotides.

In this context, the term "position correspondence" means being at the same position in the nucleotide sequences when counting from the same terminals of the nucleotide sequences. For example, the first nucleotide at 3' terminal of the nucleotide sequence 1 is a nucleotide at the position corresponding to the first nucleotide at 3' terminal of SEQ ID NO: 1.

The nucleotide difference present between the nucleotide sequence 1 and the nucleotide sequence shown in SEQ ID NO: 1 or between the nucleotide sequence 2 and the nucleotide sequence shown in SEQ ID NO: 2 will not significantly reduce the ability of the siRNA to inhibit the target gene, and thus, the siRNAs comprising the nucleotide differences are also within the protection scope of the present disclosure.

In some embodiments, the nucleotide sequence 1 and the nucleotide sequence shown in SEQ ID NO: 1 have no more than 1 nucleotide difference or no nucleotide difference; and/or the nucleotide sequence 2 and the nucleotide sequence shown in SEQ ID NO: 2 have no more than 1 nucleotide difference or no nucleotide difference.

In some embodiments, the nucleotide difference between the nucleotide sequence 2 and the nucleotide sequence shown in SEQ ID NO: 2 includes a difference at the position of the nucleotide $Z'_B$, and $Z'_B$ is selected from U, C and G. In some embodiments, the nucleotide difference is a difference at the position of the nucleotide $Z'_B$, and $Z'_B$ is selected from U, C and G, and $Z_A$ is a nucleotide complementary to $Z'_B$.

The nucleotide sequence 1 and the nucleotide sequence 2 can be complementary to each other to any suitable extent as long as the double-stranded structure remains stable. Thus, the nucleotide sequence 1 may be partly reverse complementary to the nucleotide sequence 2. In order to make the siRNA more stable, in some embodiments, the nucleotide sequence 1 is basically reverse complementary, substantially reverse complementary, or completely reverse complementary to the nucleotide sequence 2. The "basically reverse complementary" means that there are no more than 3 base mispairings between two nucleotide sequences. The "substantially reverse complementary" means that there is no more than 1 base mispairing between two nucleotide sequences. The "completely reverse complementary" means that there is no mispairing between two nucleotide sequences.

In some embodiments, the sense strand further comprises nucleotide sequence 3, and the antisense strand further comprises nucleotide sequence 4; the nucleotide sequence 3 and the nucleotide sequence 4 have a length of 1-4 nucleotides, respectively. The nucleotide sequence 3 is linked to 5' terminal of the nucleotide sequence 1; and the nucleotide sequence 4 is linked to 3' terminal of the nucleotide sequence 2. The nucleotide sequence 3 and the nucleotide sequence 4 have equal length and are substantially reverse complementary or completely reverse complementary to each other. In some specific embodiments, the nucleotide sequence 3 and the nucleotide sequence 4 are completely reverse complementary to each other.

Therefore, the sense strand and the antisense strand may independently have a length of 19-23 nucleotides.

In some embodiments, the siRNA of the present disclosure may comprise a nucleotide sequence 3 and a nucleotide sequence 4 selected from the groups below, and the nucleotide sequence 3 and the nucleotide sequence 4 are completely complementary to each other:

The nucleotide sequence 3 and the nucleotide sequence 4 both have a length of 1 nucleotide. The base of the nucleotide sequence 3 is G; in this case, the double-stranded region may have a length of 20 nucleotides, i.e., the length ratio of the sense strand to the antisense strand in the siRNA provided by the present disclosure may be 20/20.

Alternatively, the nucleotide sequence 3 and the nucleotide sequence 4 both have a length of 2 nucleotides; in the direction from 5' terminal to 3' terminal, the bases of the nucleotide sequence 3 are U and G in succession; in this case, the double-stranded region may have a length of 21 nucleotides, i.e., the length ratio of the sense strand to the antisense strand in the siRNA provided by the present disclosure is 21/21.

Alternatively, the nucleotide sequence 3 and the nucleotide sequence 4 both have a length of 3 nucleotides; in the direction from 5' terminal to 3' terminal, the bases of the nucleotide sequence 3 are U, U and G in succession; in this case, the double-stranded region may have a length of 22 nucleotides, i.e., the length ratio of the sense strand to the antisense strand in the siRNA provided by the present disclosure is 22/22.

Alternatively, the nucleotide sequence 3 and the nucleotide sequence 4 both have a length of 4 nucleotides; in the direction from 5' terminal to 3' terminal, the bases of the nucleotide sequence 3 are A, U, U, and G in succession; in this case, the double-stranded region may have a length of 23 nucleotides, i.e., the length ratio of the sense strand to the antisense strand in the siRNA provided by the present disclosure is 23/23.

In a specific embodiment, the nucleotide sequence 3 has a length of 2 nucleotides; and in the direction from 5' terminal to 3' terminal, the bases of the nucleotide sequence 3 are U and G in succession.

In the above groups, the nucleotide sequence 3 and the nucleotide sequence 4 have equal length and are complementary to each other. Thus, once the bases of the nucleotide sequence 3 are provided, the bases of the nucleotide sequence 4 are also determined.

In some embodiments, the siRNA of the present disclosure further comprises a nucleotide sequence 5, which has a length of 1-3 nucleotides and is linked to 3' terminal of the antisense strand, thereby constituting a 3' overhang of the antisense strand.

As such, the length ratio of the sense strand to the antisense strand in the siRNA provided by the present disclosure may be 19/19, 19/20, 19/21, 19/22, 20/20, 20/21, 20/22, 20/23, 21/21, 21/22, 21/23, 21/24, 22/22, 22/23, 22/24, 22/25, 23/23, 23/24, 23/25 or 23/26.

In some embodiments, the nucleotide sequence 5 has a length of 2 nucleotides; and in the direction from 5' terminal to 3' terminal, the nucleotide sequence 5 is 2 consecutive thymidine deoxyribonucleotides, 2 consecutive uridine ribonucleotides, or 2 nucleotides complementary to the target mRNA.

Thus, in some embodiments, the length ratio of the sense strand to the antisense strand in the siRNA provided by the present disclosure is 19/21 or 21/23. Here, the siRNA provided by the present disclosure has better silencing activity against HBV mRNA and/or activity of effectively reducing the expression of the surface antigen HBsAg.

In some embodiments, the nucleotide sequence 1 comprises the nucleotide sequence shown in SEQ ID NO: 3 or SEQ ID NO: 4; and the nucleotide sequence 2 comprises any nucleotide sequences selected from the group consisting of the nucleotide sequences shown in SEQ ID NO: 5, SEQ ID NO: 6, SEQ ID NO: 7, and SEQ ID NO: 8:

```
                                        (SEQ ID NO: 3)
5'-GAAAGUAUGUCAACGAAUU-3', (SEQ ID NO: 4)
5'-GAAAGUAUGUCAACGAAUA-3', (SEQ ID NO: 5)
5'-AAUUCGUUGACAUACUUUCUU-3', (SEQ ID NO: 6)
5'-AAUUCGUUGACAUACUUUCCA-3', (SEQ ID NO: 7)
5'-UAUUCGUUGACAUACUUUCUU-3', (SEQ ID NO: 8)
5'-UAUUCGUUGACAUACUUUCCA-3'.
```

In some specific embodiments, the siRNA of the present disclosure is any one of the following siP1 to siP4:

```
siP1
Sense strand:
                                        (SEQ ID NO: 3)
5'-GAAAGUAUGUCAACGAAUU-3',
```

```
Antisense strand:
                            (SEQ ID NO: 5)
5'-AAUUCGUUGACAUACUUUCUU-3', siP2
Sense strand:
                            (SEQ ID NO: 3)
5'-GAAAGUAUGUCAACGAAUU-3', Antisense strand:
                            (SEQ ID NO: 6)
5'-AAUUCGUUGACAUACUUUCA-3', siP3
Sense strand:
                            (SEQ ID NO: 4)
5'-GAAAGUAUGUCAACGAAUA-3', Antisense strand:
                            (SEQ ID NO: 7)
5'-UAUUCGUUGACAUACUUUCUU-3', siP4
Sense strand:
                            (SEQ ID NO: 4)
5'-GAAAGUAUGUCAACGAAUA-3', Antisense strand:
                            (SEQ ID NO: 8)
5'-UAUUCGUUGACAUACUUUCCA-3'.
```

In some embodiments, in the direction from 5' terminal to 3' terminal, the nucleotides at positions 7, 8 and 9 or 5, 7, 8 and 9 in the sense strand of the nucleotide sequence 1 are fluoro modified nucleotides, and each of the nucleotides at the other positions in the sense strand is independently a non-fluoro modified nucleotide; and the nucleotides at positions 2, 6, 14 and 16 or 2, 6, 8, 9, 14 and 16 in the antisense strand of the nucleotide sequence 2 are fluoro modified nucleotides, and each of the nucleotides at the other positions in the antisense strand is independently a non-fluoro modified nucleotide.

In the context of the present disclosure, a "fluoro modified nucleotide" refers to a nucleotide formed by substituting the 2'-hydroxy of the ribose group of the nucleotide with a fluoro group, as shown by Formula (101), in which "Base" represents a base selected from C, G, A and U.

A "non-fluoro modified nucleotide" refers to a nucleotide formed by substituting the 2'-hydroxy of the ribose group of the nucleotide with a non-fluoro group, or a nucleotide analogue. In some embodiments, each non-fluoro modified nucleotide is independently selected from the group consisting of a nucleotide formed by substituting the 2'-hydroxy of the ribose group of the nucleotide with a non-fluoro group, or a nucleotide analogue.

A nucleotide formed by substituting the 2'-hydroxy of the ribose group with a non-fluoro group is well-known to those skilled in the art; for example, the nucleotide can be selected from one of 2'-alkoxy modified nucleotide, 2'-substituted alkoxy modified nucleotide, 2'-alkyl modified nucleotide, 2'-substituted alkyl modified nucleotide, 2'-amino modified nucleotide, 2'-substituted amino modified nucleotide, and 2'-deoxy nucleotide.

In some embodiments, the 2'-alkoxy modified nucleotide can be a methoxy modified nucleotide (2'-OMe), as shown by Formula (102); the 2'-substituted alkoxy modified nucleotide can be a 2'-O-methoxyethyl modified nucleotide (2'-MOE), as shown by Formula (103); the 2'-amino modified nucleotide (2'-NH$_2$) is as shown by Formula (104). The 2'-deoxy nucleotide (DNA) is as shown by Formula (105).

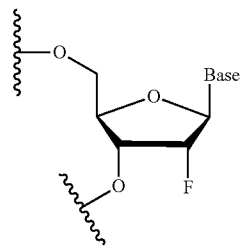

Formula (101)

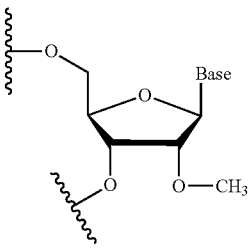

Formula (102)

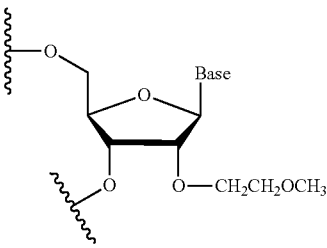

Formula (103)

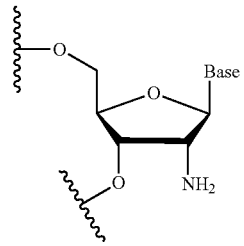

Formula (104)

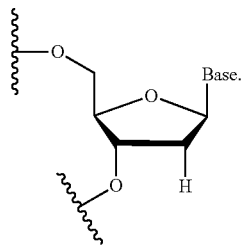

Formula (105)

A "nucleotide analogue" refers to a group that can replace a nucleotide in the nucleic acid, while structurally differs from an adenine ribonucleotide, a guanine ribonucleotide, a cytosine ribonucleotide, a uracil ribonucleotide or thymine deoxyribonucleotide, such as an isonucleotide, a bridged nucleic acid (BNA) nucleotide or an acyclic nucleotide.

A BNA nucleotide is a nucleotide that is constrained or is not accessible. BNA can contain a 5-, 6-membered or even a 7-membered ring bridged structure with a "fixed" C3'-endo sugar puckering. The bridge is typically incorporated at the 2'- and 4'-position of the ribose to afford a 2', 4'-BNA nucleotide, such as LNA, ENA and cET BNA, which are as shown by Formulae (106), (107) and (108), respectively.

Formula (106)

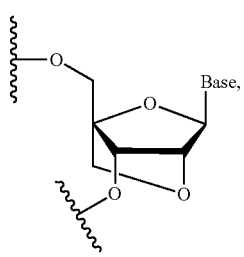

Formula (107)

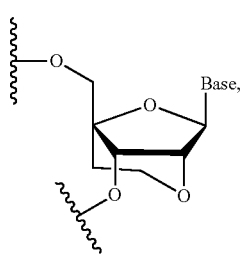

Formula (108)

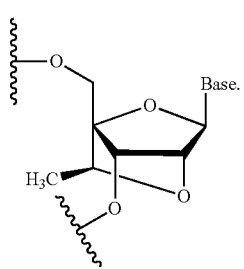

An acyclic nucleotide refers to a class of "ring-opened" nucleotides formed by opening the ribose rings thereof, such as an unlocked nucleic acid (UNA) and a glycerol nucleic acid (GNA), which are as shown by Formulae (109) and (110), respectively.

Formula (109)

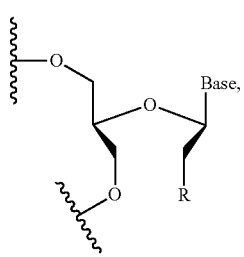

Formula (110)

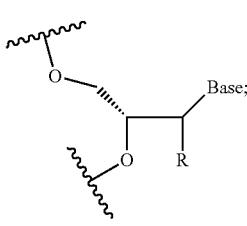

In the above Formulae (109) and (110), R is H, OH or alkoxy (O-alkyl).

An isonucleotide is a compound formed by changing the position of the base on the ribose ring in the nucleotide, such as a compound formed by transposing the base from position-1' to position-2' or 3' on the ribose ring, as shown by Formula (111) or (112):

Formula (111)

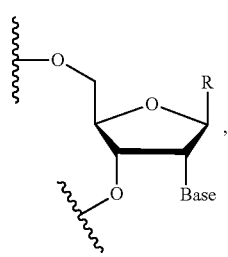

Formula (112)

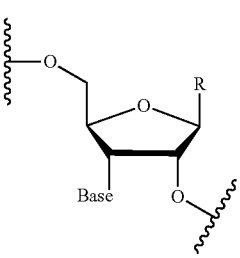

In the compounds of Formulae (111) and (112) above, "Base" represents a base, such as A, U, G, C or T; and R is H, OH, F or a non-fluoro group described above.

In some embodiments, a nucleotide analogue is selected from the group consisting of an isonucleotide, LNA, ENA, cET, UNA, and GNA. In some embodiments, each non-fluoro modified nucleotide is a methoxy modified nucleotide. In the context of the present disclosure, the methoxy modified nucleotide refers to a nucleotide formed by substituting the 2'-hydroxy of the ribose group with a methoxy group.

The siRNA of the present disclosure can resist the cleavage by the ribonucleases in blood, and thus enhance blood stability of the nucleic acid, therefore the nucleic acid has stronger resistance against nuclease hydrolysis, while maintaining higher inhibitory activity against HBV genes.

In some embodiments, the siRNA of the present disclosure has achieved a high degree of balance between the stability in plasma and the gene-silencing efficiency in animal experiments; and some siRNAs also have the advantages of simpler structure and lower cost. Some examples are as follows.

In some embodiments, in the direction from 5' terminal to 3' terminal, the nucleotides at positions 7, 8 and 9 or 5, 7, 8 and 9 of the nucleotide sequence 1 in the sense strand are fluoro modified nucleotides, and the nucleotides at the other positions in the sense strand are methoxy modified nucleotides; and the nucleotides at positions 2, 6, 14 and 16 or 2, 6, 8, 9, 14 and 16 of the nucleotide sequence 2 in the antisense strand are fluoro modified nucleotides, and the nucleotides at the other positions in the antisense strand are methoxy modified nucleotides.

In some embodiments, in the direction from 5' terminal to 3' terminal, the nucleotides at positions 7, 8 and 9 in the sense strand of the nucleotide sequence 1 are fluoro modified nucleotides, and the nucleotides at the other positions in the sense strand are methoxy modified nucleotides; and the nucleotides at positions 2, 6, 14 and 16 in the antisense strand of the nucleotide sequence 2 are fluoro modified nucleotides, and the nucleotides at the other positions in the antisense strand are methoxy modified nucleotides.

Alternatively, in some embodiments, in the direction from 5' terminal to 3' terminal, the nucleotides at positions 5, 7, 8 and 9 in the sense strand of the nucleotide sequence 1 are fluoro modified nucleotides, and the nucleotides at the other positions in the sense strand are methoxy modified nucleotides; and the nucleotides at positions 2, 6, 8, 9, 14, and 16 in the antisense strand of the nucleotide sequence 2 are fluoro modified nucleotides, and the nucleotides at the other positions in the antisense strand are methoxy modified nucleotides.

Alternatively, in some embodiments, in the direction from 5' terminal to 3' terminal, the nucleotides at positions 5, 7, 8 and 9 in the sense strand of the nucleotide sequence 1 are fluoro modified nucleotides, and the nucleotides at the rest of positions in the sense strand are methoxy modified nucleotides; and the nucleotides at positions 2, 6, 14 and 16 in the antisense strand of the nucleotide sequence 2 are fluoro modified nucleotides, and the nucleotides at the rest of positions in the antisense strand are methoxy modified nucleotides.

In some specific embodiments, the siRNA of the present disclosure is any siRNA shown in Table 1A.

TABLE 1A

Some specific siRNA sequences of the present disclosure

| No. | | Sequence direction 5'-3' | SEQ ID NO |
|---|---|---|---|
| siHB1M1 | Sense strand | GmAmAmAmGmUmAfUfGfUmCmAmAmCmGmAmAmUmUm | 11 |
| | Antisense strand | AmAfUmUmCmGfUmUmGmAmCmAmUmAfCmUfUmUmCmUmUm | 13 |
| siHB2M1 | Sense strand | GmAmAmAmGmUmAfUfGfUmCmAmAmCmGmAmAmUmUm | 11 |
| | Antisense strand | AmAfUmUmCmGfUmUmGmAmCmAmUmAfCmUfUmUmCmCmAm | 14 |
| siHB3M1 | Sense strand | GmAmAmAmGmUmAfUfGfUmCmAmAmCmGmAmAmUmAm | 12 |
| | Antisense strand | UmAfUmUmCmGfUmUmGmAmCmAmUmAfCmUfUmUmCmUmUm | 15 |
| siHB4M1 | Sense strand | GmAmAmAmGmUmAfUfGfUmCmAmAmCmGmAmAmUmAm | 12 |
| | Antisense strand | UmAfUmUmCmGfUmUmGmAmCmAmUmAfCmUfUmUmCmCmAm | 16 |
| siHB1M2 | Sense strand | GmAmAmAmGfUmAfUfGfUmCmAmAmCmGmAmAmUmUm | 17 |
| | Antisense strand | AmAfUmUmCmGfUmUfGfAmCmAmUmAfCmUfUmUmCmUmUm | 19 |
| siHB2M2 | Sense strand | GmAmAmAmGfUmAfUfGfUmCmAmAmCmGmAmAmUmUm | 17 |
| | Antisense strand | AmAfUmUmCmGfUmUfGfAmCmAmUmAfCmUfUmUmCmCmAm | 20 |
| siHB3M2 | Sense strand | GmAmAmAmGfUmAfUfGfUmCmAmAmCmGmAmAmUmAm | 18 |
| | Antisense strand | UmAfUmUmCmGfUmUfGfAmCmAmUmAfCmUfUmUmCmUmUm | 21 |
| siHB4M2 | Sense strand | GmAmAmAmGfUmAfUfGfUmCmAmAmCmGmAmAmUmAm | 18 |
| | Antisense strand | UmAfUmUmCmGfUmUfGfAmCmAmUmAfCmUfUmUmCmCmAm | 22 |
| siHB1M3 | Sense strand | GmAmAmAmGfUmAfUfGfUmCmAmAmCmGmAmAmUmUm | 17 |
| | Antisense strand | AmAfUmUmCmGfUmUmGmAmCmAmUmAfCmUfUmUmCmUmUm | 13 |
| siHB2M3 | Sense strand | GmAmAmAmGfUmAfUfGfUmCmAmAmCmGmAmAmUmUm | 17 |
| | Antisense strand | AmAfUmUmCmGfUmUmGmAmCmAmUmAfCmUfUmUmCmCmAm | 14 |
| siHB3M3 | Sense strand | GmAmAmAmGfUmAfUfGfUmCmAmAmCmGmAmAmUmAm | 18 |
| | Antisense strand | UmAfUmUmCmGfUmUmGmAmCmAmUmAfCmUfUmUmCmUmUm | 15 |
| siHB4M3 | Sense strand | GmAmAmAmGfUmAfUfGfUmCmAmAmCmGmAmAmUmAm | 18 |
| | Antisense strand | UmAfUmUmCmGfUmUmGmAmCmAmUmAfCmUfUmUmCmCmAm | 16 |
| siHB5M1 | Sense strand | UmGmGmAmAmAmGmUmAfUfGfUmCmAmAmCmGmAmAmUmAm | 51 |
| | Antisense strand | UmAfUmUmCmGfUmUmGmAmCmAmUmAfCmUfUmUmCmCmAmUmUm | 52 |
| siHB6M2 | Sense strand | UmGmGmAmAmAmGfUmAfUfGfUmCmAmAmCmGmAmAmUmAm | 51 |
| | Antisense strand | UmAfUmUmCmGfUmUfGfAmCmAmUmAfCmUfUmUmCmCmAmAmUm | 53 |
| SiHB7M3 | Sense strand | UmGmGmAmAmAmGfUmAfUfGfUmCmAmAmCmGmAmAmUmUm | 54 |
| | Antisense strand | AmAfUmUmCmGfUmUmGmAmCmAmUmAfCmUfUmUmCmAmUmUm | 55 |

In some specific embodiments, the siRNA of the present disclosure further comprises other modified nucleotides which would not cause significant decrease or loss of the function of the siRNA for inhibiting the expression of HBV gene.

Currently, there are many means in the art that can be used to modify siRNA, including the ribose group modification above, backbone modification (such as phosphate group modification), base modification, and the like (see, for example, J. K. Watts, G. F. Deleavey and M. J. Damha, Chemically Modified siRNA: tools and applications. Drug Discov Today, 2008.13(19-20): p. 842-55, which is incorporated herein by reference in its entirety). In some embodiments of the siRNA of the present disclosure, the modified nucleotide is, but not limited to, a nucleotide in which a ribose group and optionally a phosphate group are modified.

In some embodiments, at least one of the phosphate groups in the phosphate-ribose backbone of at least one single strand of the sense strand and the antisense strand is a phosphate group with modified group(s). The phosphate group with modified group(s) is a phosphorothioate group formed by substituting at least one oxygen atom in the phosphodiester bond in a phosphate group with a sulfur atom, such as the phosphorothioate structure as shown by Formula (1), in which a non-bridging oxygen atom in a phosphodiester bond is substituted with a sulfur atom to change the phosphodiester bond to a phosphorothioate diester bond, such that the linkage between two nucleotides is a phosphorothioate linkage. This modification could stabilize the structure of the siRNA, while maintain high specificity and high affinity of base pairing.

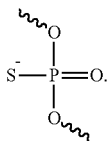

Formula (1)

In some embodiments, in the siRNA, at least one linkage selected from the group consisting of the following internucleotide linkages is a phosphorothioate linkage:
- the linkage between the first and second nucleotides at 5' terminal of the sense strand;
- the linkage between the second and third nucleotides at 5' terminal of the sense strand;
- the linkage between the first and second nucleotides at 3' terminal of the sense strand;
- the linkage between the second and third nucleotides at 3' terminal of the sense strand;
- the linkage between the first and second nucleotides at 5' terminal of the antisense strand;
- the linkage between the second and third nucleotides at 5' terminal of the antisense strand;
- the linkage between the first and second nucleotides at 3' terminal of the antisense strand; and
- the linkage between the second and third nucleotides at 3' terminal of the antisense strand.

In some specific embodiments, the siRNA of the present disclosure is any siRNA shown in Table 11B.

TABLE 1B

Some specific siRNA sequences (comprising phosphorothioate linkage) of the present disclosure

| No. | | Sequence direction 5'-3' | SEQ ID NO |
|---|---|---|---|
| siHB1M1S | Sense strand | GmsAmsAmAmGmUmAfUfGfUmCmAmAmCmGmAmAmUmUm | 23 |
| | Antisense strand | AmsAfsUmUmCmGfUmUmGmAmCmAmUmAfCmUfUmUmCmsUmsUm | 25 |
| siHB2M1S | Sense strand | GmsAmsAmAmGmUmAfUfGfUmCmAmAmCmGmAmAmUmUm | 23 |
| | Antisense strand | AmsAfsUmUmCmGfUmUmGmAmCmAmUmAfCmUfUmUmCmsCmsAm | 26 |
| siHB3M1S | Sense strand | GmsAmsAmAmGmUmAfUfGfUmCmAmAmCmGmAmAmUmAm | 24 |
| | Antisense strand | UmsAfsUmUmCmGfUmUmGmAmCmAmUmAfCmUfUmUmCmsUmsUm | 27 |
| siHB4M1S | Sense strand | GmsAmsAmAmGmUmAfUfGfUmCmAmAmCmGmAmAmUmAm | 24 |
| | Antisense strand | UmsAfsUmUmCmGfUmUmGmAmCmAmUmAfCmUfUmUmCmsCmsAm | 28 |
| siHB1M2S | Sense strand | GmsAmsAmAmGfUmAfUfGfUmCmAmAmCmGmAmAmUmUm | 29 |
| | Antisense strand | AmsAfsUmUmCmGfUmUfGfAmCmAmUmAfCmUfUmUmCmsUmsUm | 31 |
| siHB2M2S | Sense strand | GmsAmsAmAmGfUmAfUfGfUmCmAmAmCmGmAmAmUmUm | 29 |
| | Antisense strand | AmsAfsUmUmCmGfUmUfGfAmCmAmUmAfCmUfUmUmCmsCmsAm | 32 |

TABLE 1B-continued

Some specific siRNA sequences (comprising phosphorothioate linkage) of the present disclosure

| No. | | Sequence direction 5'-3' | SEQ ID NO |
|---|---|---|---|
| siHB3M2S | Sense strand | GmsAmsAmAmGfUmAfUfGfUmCmAmAmCmGmAmAmUmAm | 30 |
| | Antisense strand | UmsAfsUmUmCmGfUmUfGfAmCmAmUmAfCmUfUmUmCmsUmsUm | 33 |
| siHB4M2S | Sense strand | GmsAmsAmAmGfUmAfUfGfUmCmAmAmCmGmAmAmUmAm | 30 |
| | Antisense strand | UmsAfsUmUmCmGfUmUfGfAmCmAmUmAfCmUfUmUmCmsCmsAm | 34 |
| siHB1M3S | Sense strand | GmsAmsAmAmGfUmAfUfGfUmCmAmAmCmGmAmAmUmUm | 29 |
| | Antisense strand | AmsAfsUmUmCmGfUmUmGmAmCmAmUmAfCmUfUmUmCmsUmsUm | 25 |
| siHB2M3S | Sense strand | GmsAmsAmAmGfUmAfUfGfUmCmAmAmCmGmAmAmUmUm | 29 |
| | Antisense strand | AmsAfsUmUmCmGfUmUmGmAmCmAmUmAfCmUfUmUmCmsCmsAm | 26 |
| siHB3M3S | Sense strand | GmsAmsAmAmGfUmAfUfGfUmCmAmAmCmGmAmAmUmAm | 30 |
| | Antisense strand | UmsAfsUmUmCmGfUmUmGmAmCmAmUmAfCmUfUmUmCmsUmsUm | 27 |
| siHB4M3S | Sense strand | GmsAmsAmAmGfUmAfUfGfUmCmAmAmCmGmAmAmUmAm | 30 |
| | Antisense strand | UmsAfsUmUmCmGfUmUmGmAmCmAmUmAfCmUfUmUmCmsCmsAm | 28 |
| siHB5M1S | Sense strand | UmsGmsGmAmAmAmGmUmAfUfGfUmCmAmAmCmGmAmAmUmAm | 56 |
| | Antisense strand | UmsAfsUmUmCmGfUmUmGmAmCmAmUmAfCmUfUmUmCmCmAmUsmsUm | 57 |
| siHB6M2S | Sense strand | UmsGmsGmAmAmAmGfUmAfUfGfUmCmAmAmCmGmAmAmUmAm | 56 |
| | Antisense strand | UmsAfsUmUmCmGfUmUfGfAmCmAmUmAfCmUfUmUmCmCmAmsAmsUm | 58 |
| SiHB7M3S | Sense strand | UmsGmsGmAmAmAmGfUmAfUfGfUmCmAmAmCmGmAmAmUmUm | 59 |
| | Antisense strand | AmsAfsUmUmCmGfUmUmGmAmCmAmUmAfCmUfUmUmCmCmAmsUmsUm | 60 |

In some embodiments, the nucleotide at 5'-terminal of the antisense strand of the siRNA molecule is a 5'-phosphate nucleotide or a 5'-phosphate analogue modified nucleotide.

As well known to those skilled in the art, the 5'-phosphate nucleotide has the structure as shown by Formula (2):

Common types of the 5'-phosphate analogue modified nucleotides are well known to those skilled in the art, such as, the following 5'-phosphate analogue modified nucleotides as shown by Formulae (3)-(6) as disclosed in Anastasia Khvorova and Jonathan K. Watts, The chemical evolution of oligonucleotide therapies of clinical utility. Nature Biotechnology, 2017, 35(3): 238-48:

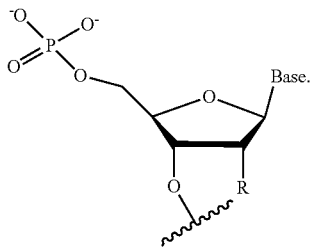

Formula (2)

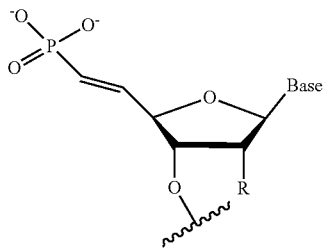

Formula (3)

Formula (4)

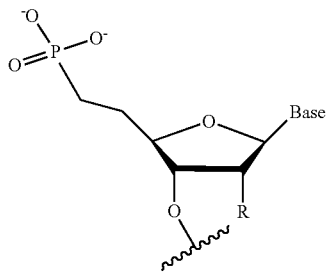

Formula (5)

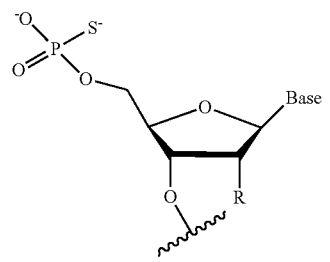

Formula (6)

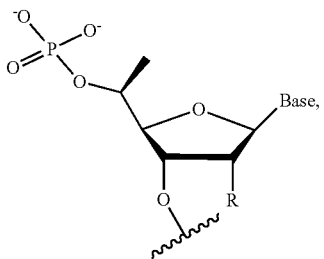

wherein R represents a group selected from the group consisting of H, OH, F and methoxy; and "Base" represents a base selected from A, U, C, G, and T.

In some specific embodiments, the 5'-phosphate analogue modified nucleotide is a nucleotide with E-vinylphosphonate (E-VP) as shown by Formula (3), or a nucleotide with phosphorothioate as shown by Formula (5).

In some specific embodiments, the siRNA of the present disclosure is any siRNA shown in Table 1C or Table 1D.

TABLE 1C

Some specific siRNA sequences (comprising 5'-phosphate nucleotides or 5'-phosphate analogue modified nucleotides) of the present disclosure

| No. | | Sequence direction 5'-3' | SEQ ID NO |
|---|---|---|---|
| siHB1M1P | Sense strand | GmAmAmAmGmUmAfUfGfUmCmAmAmCmGmAmAmUmUm | 11 |
| | Antisense strand | P1-AmAfUmUmCmGfUmUmGmAmCmAmUmAfCmUfUmUmCmUmUm | 35 |
| siHB2M1P | Sense strand | GmAmAmAmGmUmAfUfGfUmCmAmAmCmGmAmAmUmUm | 11 |
| | Antisense strand | P1-AmAfUmUmCmGfUmUmGmAmCmAmUmAfCmUfUmUmCmCmAm | 36 |
| siHB3M1P | Sense strand | GmAmAmAmGmUmAfUfGfUmCmAmAmCmGmAmAmUmAm | 12 |
| | Antisense strand | P1-UmAfUmUmCmGfUmUmGmAmCmAmUmAfCmUfUmUmCmUmUm | 37 |
| siHB4M1P | Sense strand | GmAmAmAmGmUmAfUfGfUmCmAmAmCmGmAmAmUmAm | 12 |
| | Antisense strand | P1-UmAfUmUmCmGfUmUmGmAmCmAmUmAfCmUfUmUmCmCmAm | 38 |
| siHB1M2P | Sense strand | GmAmAmAmGfUmAfUfGfUmCmAmAmCmGmAmAmUmUm | 17 |
| | Antisense strand | P1-AmAfUmUmCmGfUmUfGfAmCmAmUmAfCmUfUmUmCmUmUm | 39 |
| siHB2M2P | Sense strand | GmAmAmAmGfUmAfUfGfUmCmAmAmCmGmAmAmUmUm | 17 |
| | Antisense strand | P1-AmAfUmUmCmGfUmUfGfAmCmAmUmAfCmUfUmUmCmCmAm | 40 |
| siHB3M2P | Sense strand | GmAmAmAmGfUmAfUfGfUmCmAmAmCmGmAmAmUmAm | 18 |
| | Antisense strand | P1-UmAfUmUmCmGfUmUfGfAmCmAmUmAfCmUfUmUmCmUmUm | 41 |
| siHB4M2P | Sense strand | GmAmAmAmGfUmAfUfGfUmCmAmAmCmGmAmAmUmAm | 18 |
| | Antisense strand | P1-UmAfUmUmCmGfUmUfGfAmCmAmUmAfCmUfUmUmCmCmAm | 42 |

TABLE 1C-continued

Some specific siRNA sequences (comprising 5'-phosphate nucleotides or 5'-phosphate analogue modified nucleotides) of the present disclosure

| No. | | Sequence direction 5'-3' | SEQ ID NO |
|---|---|---|---|
| siHB1M3P | Sense strand | GmAmAmAmGfUmAfUfGfUmCmAmAmCmGmAmAmUmUm | 17 |
| | Antisense strand | P1-AmAfUmUmCmGfUmUmGmAmCmAmUmAfCmUfUmUmCmUmUm | 35 |
| siHB2M3P | Sense strand | GmAmAmAmGfUmAfUfGfUmCmAmAmCmGmAmAmUmUm | 17 |
| | Antisense strand | P1-AmAfUmUmCmGfUmUmGmAmCmAmUmAfCmUfUmUmCmCmAm | 36 |
| siHB3M3P | Sense strand | GmAmAmAmGfUmAfUfGfUmCmAmAmCmGmAmAmUmAm | 18 |
| | Antisense strand | P1-UmAfUmUmCmGfUmUmGmAmCmAmUmAfCmUfUmUmCmUmUm | 37 |
| siHB4M3P | Sense strand | GmAmAmAmGfUmAfUfGfUmCmAmAmCmGmAmAmUmAm | 18 |
| | Antisense strand | P1-UmAfUmUmCmGfUmUmGmAmCmAmUmAfCmUfUmUmCmCmAm | 38 |
| siHB5M1P | Sense strand | UmGmGmAmAmAmGfUmAfUfGfUmCmAmAmCmGmAmAmUmAm | 51 |
| | Antisense strand | P1-UmAfUmUmCmGfUmUmGmAmCmAmUmAfCmUfUmUmCmCmAmUmUm | 61 |
| siHB6M2P | Sense strand | UmGmGmAmAmAmGfUmAfUfGfUmCmAmAmCmGmAmAmUmAm | 51 |
| | Antisense strand | P1-UmAfUmUmCmGfUmUfGfAmCmAmAmUmAfCmUfUmUmCmCmAmAmUm | 62 |
| SiHB7M3P | Sense strand | UmGmGmAmAmAmGfUmAfUfGfUmCmAmAmCmGmAmAmUmUm | 54 |
| | Antisense strand | P1-AmAfUmUmCmGfUmUmGmAmCmAmAmUmAfCmUfUmUmCmCmAmUmUm | 63 |

TABLE 1D

Some specific siRNA sequences (comprising both phosphorothioate linkage and 5'-phosphate nucleotide or 5'-phosphate analogue modified nucleotide) of the present disclosure

| No. | | Sequence direction 5'-3' | SEQ ID NO |
|---|---|---|---|
| siHB1M1SP | Sense strand | GmsAmsAmAmGmUmAfUfGfUmCmAmAmCmGmAmAmUmUm | 23 |
| | Antisense strand | P1-AmsAfsUmUmCmGfUmUmGmAmCmAmUmAfCmUfUmUmCmsUmsUm | 43 |
| siHB2M1SP | Sense strand | GmsAmsAmAmGmUmAfUfGfUmCmAmAmCmGmAmAmUmUm | 23 |
| | Antisense strand | P1-AmsAfsUmUmCmGfUmUmGmAmCmAmUmAfCmUfUmUmCmsCmsAm | 44 |
| siHB3M1SP | Sense strand | GmsAmsAmAmGmUmAfUfGfUmCmAmAmCmGmAmAmUmAm | 24 |
| | Antisense strand | P1-UmsAfsUmUmCmGfUmUmGmAmCmAmUmAfCmUfUmUmCmsUmsUm | 45 |
| siHB4M1SP | Sense strand | GmsAmsAmAmGmUmAfUfGfUmCmAmAmCmGmAmAmUmAm | 24 |
| | Antisense strand | P1-UmsAfsUmUmCmGfUmUmGmAmCmAmUmAfCmUfUmUmCmsCmsAm | 46 |
| siHB1M2SP | Sense strand | GmsAmsAmAmGfUmAfUfGfUmCmAmAmCmGmAmAmUmUm | 29 |
| | Antisense strand | P1-AmsAfsUmUmCmGfUmUfGfAmCmAmAmUmAfCmUfUmUmCmsUmsUm | 47 |
| siHB2M2SP | Sense strand | GmsAmsAmAmGfUmAfUfGfUmCmAmAmCmGmAmAmUmUm | 29 |
| | Antisense strand | P1-AmsAfsUmUmCmGfUmUfGfAmCmAmAmUmAfCmUfUmUmCmsCmsAm | 48 |

TABLE 1D-continued

Some specific siRNA sequences
(comprising both phosphorothioate linkage and 5'-phosphate nucleotide or
5'-phosphate analogue modified nucleotide) of the present disclosure

| No. | | Sequence direction 5'-3' | SEQ ID NO |
|---|---|---|---|
| siHB3M2SP | Sense strand | GmsAmsAmAmGfUmAfUfGfUmCmAmAmCmGmAmAmUmAm | 30 |
| | Antisense strand | P1-UmsAfsUmUmCmGfUmUfGfAmCmAmUmAfCmUfUmUmCmsUmsUm | 49 |
| siHB4M2SP | Sense strand | GmsAmsAmAmGfUmAfUfGfUmCmAmAmCmGmAmAmUmAm | 30 |
| | Antisense strand | P1-UmsAfsUmUmCmGfUmUfGfAmCmAmUmAfCmUfUmUmCmsCmsAm | 50 |
| siHB1M3SP | Sense strand | GmsAmsAmAmGfUmAfUfGfUmCmAmAmCmGmAmAmUmUm | 29 |
| | Antisense strand | P1-AmsAfsUmUmCmGfUmUmGmAmCmAmUmAfCmUfUmUmCmsUmsUm | 43 |
| siHB2M3SP | Sense strand | GmsAmsAmAmGfUmAfUfGfUmCmAmAmCmGmAmAmUmUm | 29 |
| | Antisense strand | P1-AmsAfsUmUmCmGfUmUmGmAmCmAmUmAfCmUfUmUmCmsCmsAm | 44 |
| siHB3M3SP | Sense strand | GmsAmsAmAmGfUmAfUfGfUmCmAmAmCmGmAmAmUmAm | 30 |
| | Antisense strand | P1-UmsAfsUmUmCmGfUmUmGmAmCmAmUmAfCmUfUmUmCmsUmsUm | 45 |
| siHB4M3SP | Sense strand | GmsAmsAmAmGfUmAfUfGfUmCmAmAmCmGmAmAmUmAm | 30 |
| | Antisense strand | P1-UmsAfsUmUmCmGfUmUmGmAmCmAmUmAfCmUfUmUmCmsCmsAm | 46 |
| siHB5M1SP | Sense strand | UmsGmsGmAmAmAmGmUmAfUfGfUmCmAmAmCmGmAmAmUmAm | 56 |
| | Antisense strand | P1-UmsAfsUmUmCmGfUmUmGmAmCmAmUmAfCmUfUmUmCmCmAmsUmsUm | 64 |
| siHB6M2SP | Sense strand | UmsGmsGmAmAmAmGfUmAfUfGfUmCmAmAmCmGmAmAmUmAm | 56 |
| | Antisense strand | P1-UmsAfsUmUmCmGfUmUfGfAmCmAmUmAfCmUfUmUmCmCmAmsAmsUm | 65 |
| siHB7M3SP | Sense strand | UmsGmsGmAmAmAmGfUmAfUfGfUmCmAmAmCmGmAmAmUmUm | 59 |
| | Antisense strand | P1-AmsAfsUmUmCmGfUmUmGmAmCmAmUmAfCmUfUmUmCmCmAmsUmsUm | 66 |

The inventors of the present disclosure have surprisingly found that the siRNAs of the present disclosure, such as the siRNAs shown in the above Table 1A to Table 1D, have significantly improved stability in plasma and lysosome and exhibit unexpected silencing activity against HBV mRNA and excellent inhibitory effect on HBsAg.

Those skilled in the art clearly know that the siRNAs of the present disclosure, such as the siRNAs shown in the above Table 1A to Table 1D, can be obtained by conventional methods in the art for preparing siRNAs, e.g., solid phase synthesis and liquid phase synthesis methods. Therein, commercial customization services have already been available for solid phase synthesis. A modified nucleotide can be introduced into the siRNA of the present disclosure by using a nucleotide monomer having a corresponding modification, wherein the methods for preparing a nucleotide monomer having a corresponding modification and the methods for introducing a modified nucleotide into a siRNA are also well-known to those skilled in the art.

Pharmaceutical Composition

The present disclosure provides a pharmaceutical composition comprising the siRNA described above as an active ingredient, and a pharmaceutically acceptable carrier.

The pharmaceutically acceptable carrier may be a carrier conventionally used in the field of siRNA administration, for example, but not limited to, one or more of magnetic nanoparticles (such as $Fe_3O_4$ and $Fe_2O_3$-based nanoparticle), carbon nanotubes, mesoporous silicon, calcium phosphate nanoparticles, polyethylenimine (PEI), polyamidoamine (PAMAM) dendrimer, poly(L-lysine) (PLL), chitosan, 1,2-dioleoyl-3-trimethylammonium-propane (DOTAP), poly(D&L-lactic/glycolic acid) copolymer (PLGA), poly(2-aminoethyl ethylene phosphate) (PPEEA), poly(2-dimethylaminoethyl methacrylate) (PDMAEMA), and derivatives thereof.

In some embodiments, in the pharmaceutical composition, there are no special requirements for the contents of the siRNA and the pharmaceutically acceptable carrier. In some embodiments, the weight ratio of the siRNA to the pharmaceutically acceptable carrier is 1:(1-500), and in some embodiments, the weight ratio is 1:(1-50).

In some embodiments, the pharmaceutical composition may also contain other pharmaceutically acceptable excipients, which may be one or more of various conventional formulations or compounds in the art. For example, said other pharmaceutically acceptable excipients may comprise at least one of a pH buffer, a protective agent and an osmotic pressure regulator.

The pH buffer may be a tris(hydroxymethyl) aminomethane hydrochloride buffer solution with a pH of 7.5-8.5, and/or a phosphate buffer solution with a pH of 5.5-8.5, such as a phosphate buffer solution with a pH of 5.5-8.5.

The protective agent may be at least one of inositol, sorbitol, sucrose, trehalose, mannose, maltose, lactose, and glucose. The content of the protective agent may be from 0.01 wt % to 30 wt % based on the total weight of the pharmaceutical composition.

The osmotic pressure regulator may be sodium chloride and/or potassium chloride. The content of the osmotic pressure regulator allows the osmotic pressure of the pharmaceutical composition to be 200-700 milliosmol/kg. Depending on the desired osmotic pressure, those skilled in the art can readily determine the content of the osmotic pressure regulator.

In some embodiments, the pharmaceutical composition may be a liquid formulation, for example, an injection solution; or a lyophilized powder for injection, which is mixed with a liquid excipient to form a liquid formulation when performing administration. The liquid formulation may, but is not limited to, be used for administration by subcutaneous, intramuscular or intravenous injection, and also may, but is not limited to, be administered to lung by spray, or to other organ tissues (such as liver) via the lung by spray. In some embodiments, the pharmaceutical composition is used for administration by intravenous injection.

In some embodiments, the pharmaceutical composition may be in the form of a liposome formulation. In some embodiments, the pharmaceutically acceptable carrier used in the liposome formulation comprises an amine-containing transfection compound (hereinafter also referred to as an organic amine), a helper lipid and/or a PEGylated lipid. Therein, the organic amine, the helper lipid and the PEGylated lipid may be respectively selected from one or more of the amine-containing transfection compounds or the pharmaceutically acceptable salts or derivatives thereof, the helper lipids and the PEGylated lipids as described in CN103380113A, which is incorporated herein by reference in its entirety.

In some embodiments, the organic amine may be a compound as shown by Formula (201) as described in CN103380113A or a pharmaceutically acceptable salt thereof:

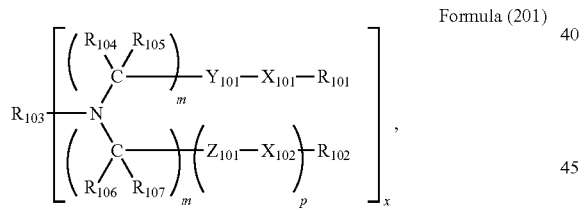

Formula (201)

wherein,
$X_{101}$ and $X_{102}$ independently of one another are selected from O, S, N-A and C-A, wherein A is hydrogen or a $C_1$-$C_{20}$ hydrocarbon chain;
$Y_{101}$ and $Z_{101}$ independently of one another are selected from C=O, C=S, S=O, CH—OH and $SO_2$;
$R_{101}$, $R_{102}$, $R_{103}$, $R_{104}$, $R_{105}$, $R_{106}$ and $R_{107}$ independently of one another are selected from hydrogen; a cyclic or an acyclic, substituted or unsubstituted, branched or linear aliphatic group; a cyclic or an acyclic, substituted or unsubstituted, branched or linear heteroaliphatic group; a substituted or unsubstituted, branched or linear acyl group; a substituted or unsubstituted, branched or linear aryl group; and a substituted or unsubstituted, branched or linear heteroaryl group;
x is an integer of 1-10;
n is an integer of 1-3, m is an integer of 0-20, p is 0 or 1, wherein if m and p are both 0, then $R_{102}$ is hydrogen; and if at least one of n or m has is 2, then $R_{103}$ and nitrogen in Formula (201) form a structure as shown by Formula (202) or (203):

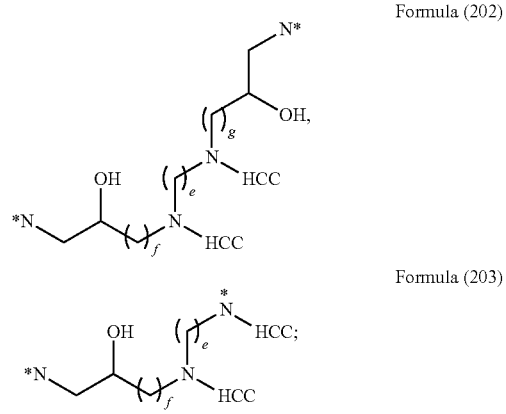

Formula (202)

Formula (203)

wherein g, e and f independently of one another are an integer of 1-6; "HCC" represents a hydrocarbon chain, and each *N represents a nitrogen atom shown in Formula (201).

In some embodiments, $R_{103}$ is a polyamine. In other embodiments, $R_{103}$ is a ketal. In some embodiments, $R_{101}$ and $R_{10}2$ in the Formula (201) independently of one another are any of substituted or unsubstituted, branched or linear alkyl or alkenyl groups which have 3-20 carbon atoms (such as 8-18 carbon atoms) and 0-4 double bonds (such as 0-2 double bonds).

In some embodiments, if n and m independently of one another are 1 or 3, $R_{103}$ is any of the following Formulae (204)-(213):

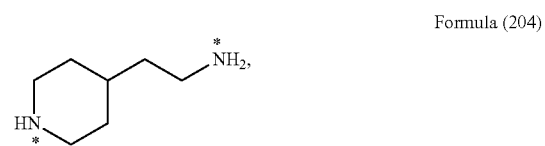

Formula (204)

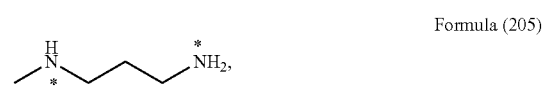

Formula (205)

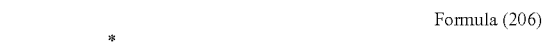

Formula (206)

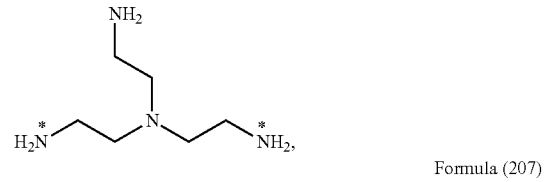

Formula (207)

Formula (208)

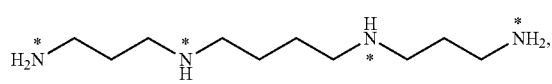

Formula (209)
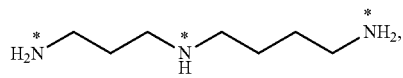

Formula (210)
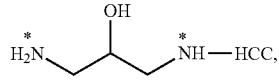

Formula (211)
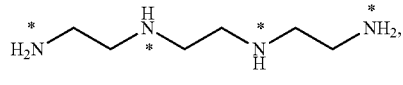

Formula (212)
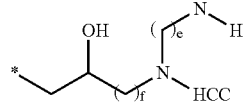

Formula (213)
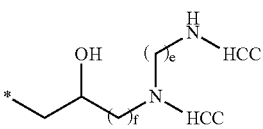

wherein in Formulae (204)-(213), each "HCC" represents a hydrocarbon chain, and each * represents a potential attachment point of $R_{103}$ to the nitrogen atom in Formula (201), where each H at any * position can be replaced to achieve the attachment to the nitrogen atom in Formula (201).

The compound as shown by (201) may be prepared as described in CN103380113A.

In some embodiments, the organic amine may be an organic amine as shown by Formula (214) and/or an organic amine as shown by Formula (215):

Formula (214)
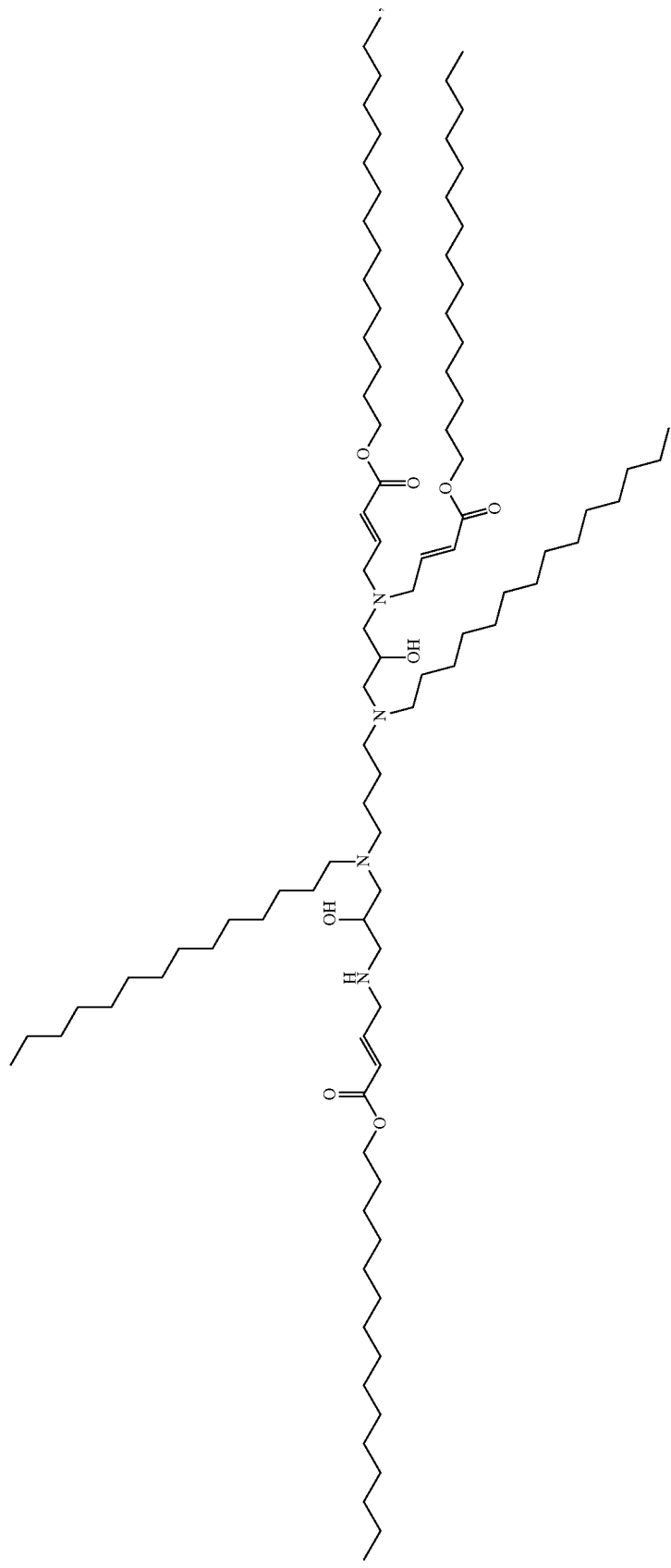

-continued
Formula (215)
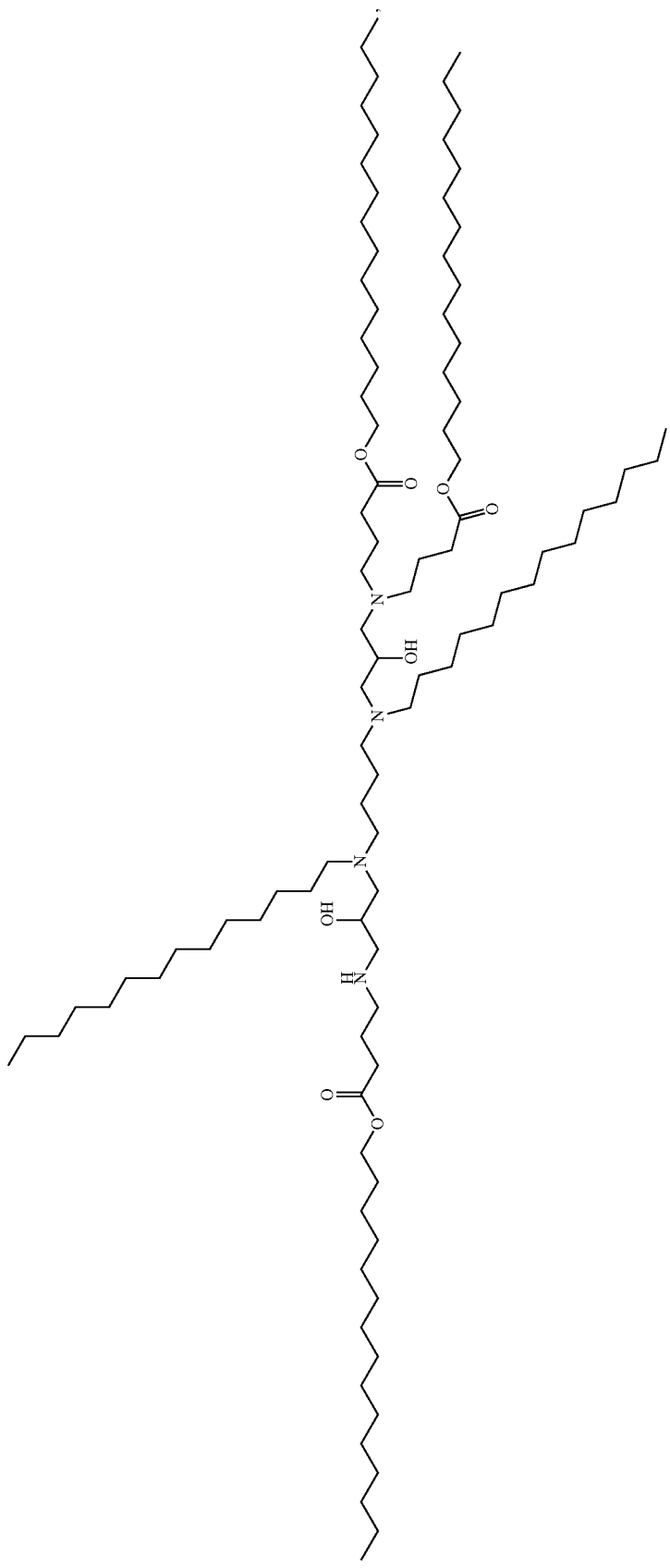

The helper lipid is cholesterol, cholesterol analogs and/or cholesterol derivatives.

The PEGylated lipid is 1,2-dipalmitoyl-sn-glycero-3-phosphatidylethanolamine-N-[methoxy(polyethylene glycol)]-2000.

In some embodiments, the molar ratio among the organic amine, the helper lipid, and the PEGylated lipid in the pharmaceutical composition is (19.7-80):(19.7-80):(0.3-50); for example, the molar ratio may be (50-70):(20-40):(3-20).

In some embodiments, the pharmaceutical composition particles formed by the siRNA of the present disclosure and the above amine-containing transfection reagents have an average diameter from about 30 nm to about 200 nm, typically from about 40 nm to about 135 nm, and more typically, the average diameter of the liposome particles is from about 50 nm to about 120 nm, from about 50 nm to about 100 nm, from about 60 nm to about 90 nm, or from about 70 nm to about 90 nm; for example, the average diameter of the liposome particles is about 30, 40, 50, 60, 70, 75, 80, 85, 90, 100, 110, 120, 130, 140, 150 or 160 nm.

In some embodiments, in the pharmaceutical composition formed by the siRNA of the present disclosure and the above amine-containing transfection reagents, the weight ratio (weight/weight ratio) of the siRNA to total lipids, e.g., the organic amines, the helper lipids and/or the PEGylated lipids, ranges from about 1:1 to about 1:50, from about 1:1 to about 1:30, from about 1:3 to about 1:20, from about 1:4 to about 1:18, from about 1:5 to about 1:17, from about 1:5 to about 1:15, from about 1:5 to about 1:12, from about 1:6 to about 1:12, or from about 1:6 to about 1:10. For example, the ratio of the siRNA of the present disclosure to total lipids is about 1:5, 1:6, 1:7, 1:8, 1:9, 1:10, 1:11, 1:12, 1:13, 1:14, 1:15, 1:16, 1:17 or 1:18.

In some embodiments, the pharmaceutical composition may be marketed with each component being separate, and used in the form of a liquid formulation. In some embodiments, the pharmaceutical composition formed by the siRNA provided by the present disclosure and the above pharmaceutically acceptable carrier may be prepared by various known processes, except for replacing the existing siRNA with the siRNA provided by the present disclosure. In some specific embodiments, the pharmaceutical composition may be prepared according to the following process:

The organic amines, helper lipids and PEGylated lipids are suspended in alcohol at a molar ratio as described above and mixed homogeneously to yield a lipid solution; the alcohol is used in an amount such that the resultant lipid solution is present at a total mass concentration of 2 to 25 mg/mL (e.g., 8 to 18 mg/mL). The alcohol is a pharmaceutically acceptable alcohol, such as an alcohol that is in liquid form at about room temperature, for example, one or more of ethanol, propylene glycol, benzyl alcohol, glycerol, PEG 200, PEG 300, PEG 400, such as ethanol.

The siRNA of the present disclosure is dissolved in a buffered salt solution to produce an aqueous solution of the siRNA. The buffered salt solution has a concentration of 0.05 to 0.5 M, such as 0.1 to 0.2 M. The pH of the buffered salt solution is adjusted to 4.0 to 5.5, such as 5.0 to 5.2. The buffered salt solution is used in an amount such that the siRNA is present at a concentration of less than 0.6 mg/ml, such as 0.2 to 0.4 mg/mL. The buffered salt may be one or more selected from the group consisting of soluble acetate and soluble citrate, such as sodium acetate and/or potassium acetate.

The lipid solution and the aqueous solution of the siRNA are mixed. The product obtained after mixing is incubated at a temperature of 40 to 60° C. for at least 2 minutes (e.g., 5 to 30 minutes) to produce an incubated lipid formulation. The volume ratio of the lipid solution to the aqueous solution of the siRNA is 1:(2-5), such as 1:4.

The incubated lipid formulation is concentrated or diluted, purified to remove impurities, and then sterilized to obtain the pharmaceutical composition of the present disclosure, which has the following physicochemical parameters: a pH of 6.5 to 8, an encapsulation percentage of more than 80%, a particle size of 40 to 200 nm, a polydispersity index of less than 0.30, and an osmotic pressure of 250 to 400 mOsm/kg. For example, the physicochemical parameters may be as follows: a pH of 7.2 to 7.6, an encapsulation percentage of more than 90%, a particle size of 60 to 100 nm, a polydispersity index of less than 0.20, and an osmotic pressure of 300 to 400 mOsm/kg.

Therein, the concentration or dilution step may be performed before, after or simultaneously with removal of the impurities. The method for removing impurities may be any of various existing methods, for example, ultrafiltration with 100 kDa hollow fiber column and PBS at pH 7.4 as ultrafiltration exchange solution using tangential flow system. The method for sterilization may be any of various existing methods, such as filtration sterilization on a 0.22 μm filter.

The First siRNA Conjugate

In one embodiment, the present disclosure provides a siRNA conjugate comprising the above siRNA provided by the present disclosure and a ligand conjugated to the siRNA. Hereinafter, these siRNA conjugates are also referred to as first siRNA conjugates.

The type and linking mode of the ligand is well-known to those skilled in the art, and it typically serves the function of binding to the specific receptors on the surface of the target cell, thereby mediating delivery of the siRNA linked to the ligand into the target cell.

The ligand conjugated to the siRNA is a pharmaceutically acceptable conjugation group. The conjugation group typically comprises a pharmaceutically acceptable targeting molecule and an optional linker. The siRNA molecule may be non-covalently or covalently conjugated to the conjugation group, for example, the siRNA molecule is covalently conjugated to the conjugation group. The conjugation site between the siRNA and the conjugation group can be at 3'-terminal or 5'-terminal of the sense strand of the siRNA, or at 5'-terminal of the antisense strand, or within the internal sequence of the siRNA. In some embodiments, the conjugation site between the siRNA and the conjugation group is at 3'-terminal of the sense strand of the siRNA.

In some embodiments, the conjugation group may be linked to the phosphate group, the 2'-hydroxy group or the base of a nucleotide. The conjugation group may also be linked to a 3'-hydroxy group when the nucleotides are linked via a 2'-5'-phosphodiester bond. When the conjugation group is linked to a terminal of the siRNA, the conjugation group is typically linked to a phosphate group of a nucleotide; when the conjugation group is linked to an internal sequence of the siRNA, the conjugation group is typically linked to a ribose ring or a base. For specific linking modes, reference may be made to: Muthiah Manoharan et. al. siRNA conjugates carrying sequentially assembled trivalent N-acetylgalactosamine linked through nucleosides elicit robust gene silencing in vivo in hepatocytes. ACS Chemical biology, 2015, 10(5): 1181-7.

In some embodiments, the siRNA and the conjugation group can be linked by an acid-labile or reducible chemical bond, and these chemical bonds can be degraded under the acidic environment of cell endosomes, thereby making the siRNA be in free state. For non-degradable conjugation modes, the conjugation group can be linked to the sense strand of the siRNA, thereby minimizing the effect of conjugation on the activity of the siRNA.

The pharmaceutically acceptable targeting group may be a conventional targeting molecule in the field of siRNA administration, such as, but not limited to, one or more of the following targeting molecules or derivatives thereof: lipophilic molecules, such as cholesterol, bile acids, vitamins (such as vitamin E), lipid molecules with different chain lengths; polymers, such as polyethylene glycol; polypeptides, such as cell-penetrating peptide; aptamers; antibodies; quantum dots; saccharides, such as lactose, polylactose, mannose, galactose, N-acetylgalactosamine (GalNAc); folate; or receptor ligands expressed in hepatic parenchymal cells, such as asialoglycoprotein, asialo-sugar residue, lipoproteins (such as high density lipoprotein, low density lipoprotein and the like), glucagon, neurotransmitters (such as adrenaline), growth factors, transferrin and the like.

In some embodiments, the pharmaceutically acceptable targeting group may be one or more selected from the following molecules: asialoglycoprotein, such as asialoorosomucoid (ASOR); and a ligand for asialoglycoprotein receptors (ASGPR).

In some embodiments, the pharmaceutically acceptable targeting group is a ligand for asialoglycoprotein receptors (ASGPR). The ligand may be selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, j3-D-glucopyranose, α-D-glucofuranose, j3-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose and L-4-thioribose. Other ligand selections may be found, for example, in the disclosure of CN105378082A, which is incorporated herein by reference in its entirety.

In some embodiments, the pharmaceutically acceptable targeting group may be galactose or N-acetylgalactosamine, wherein the galactose or N-acetylgalactosamine molecules can be mono-, bi-, tri-, or tetra-valent. It should be understood that the terms mono-, bi-, tri-, or tetra-valent described herein respectively mean that the molar ratio of the siRNA molecule to the galactose or N-acetylgalactosamine molecule in the first siRNA conjugate is 1:1, 1:2, 1:3 or 1:4, wherein the siRNA conjugate is formed from the siRNA molecule and the conjugation group containing galactose or N-acetylgalactosamine molecule as the targeting group. In some embodiments, the pharmaceutically acceptable targeting group is N-acetylgalactosamine. In some embodiments, when the siRNA of the present disclosure is conjugated to a conjugation group comprising N-acetylgalactosamine, the N-acetylgalactosamine molecule is trivalent or tetravalent. In some specific embodiments, when the siRNA of the present disclosure is conjugated to a conjugation group containing N-acetylgalactosamine, the N-acetylgalactosamine molecule is trivalent.

When the siRNA of the present disclosure is conjugated to a conjugation molecule, the conjugation molecule can be linked to the siRNA molecule via an appropriate linker, and the appropriate linker can be selected by those skilled in the art according to the specific type of the targeting group.

The types of exemplary conjugation groups, linkers and targeting molecules and the linking modes with the siRNA may be found in the disclosure of WO2015006740A2, which is incorporated herein by reference in its entirety.

In some embodiments, when the targeting group is N-acetylgalactosamine, a suitable linker may have the following structure as shown by Formula (301):

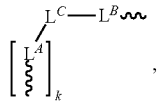

Formula (301)

wherein k is an integer of 1-3;

$L^A$ is an amide bond-comprising chain moiety that has a structure as shown by Formula (302), two terminals of which are respectively linked to the targeting group and the $L^C$ moiety each via an ether bond:

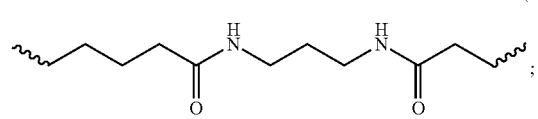

Formula (302)

$L^B$ is an N-acylpyrrolidine-comprising chain moiety that has a structure as shown by Formula (303), which has a carbonyl group and is linked to the $L^C$ moiety via an amide bond at one end, and has an oxygen atom and is linked to the siRNA via a phosphoester bond at the other end thereof:

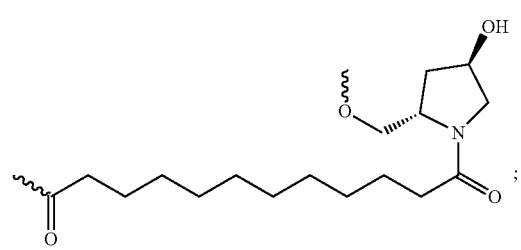

Formula (303)

$L^C$ is a bivalent to tetravalent linking group based on hydroxymethyl aminomethane, dihydroxymethyl aminomethane or trihydroxymethyl aminomethane, one terminal of which is linked to $L^A$ moieties via an ether bond by an oxygen atom, and the other terminal of which is linked to $L^B$ moiety via an amide bond by the nitrogen atom.

In some embodiments, when n=3 and $L^C$ is a tetravalent linking group based on trihydroxymethyl aminomethane, the siRNA conjugate formed by linking N-acetylgalactosamine molecules with a siRNA molecule via -(L$^A$)$_3$-trihydroxymethyl aminomethane-L$^B$- as a linker has a structure as shown by Formula (304):

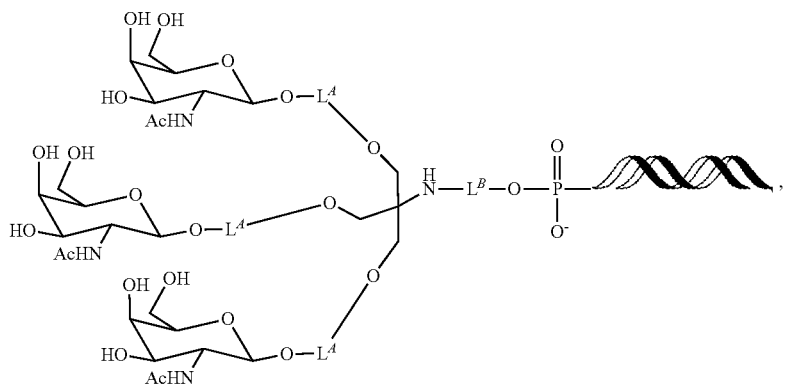

Formula (304)

wherein the double helix structure represents a siRNA.

Likewise, the conjugation site between the siRNA and the conjugation molecule can be at 3'-terminal or 5'-terminal of the sense strand of the siRNA, or at 5'-terminal of the antisense strand, or within the internal sequence of the siRNA.

In some embodiments, the 3'-terminal of the sense strand of the siRNA of the present disclosure is covalently conjugated to three N-acetylgalactosamine (GalNAc) molecules via a linker -(L$^A$)$_3$-trihydroxymethyl aminomethane-L$^B$- to obtain a siRNA conjugate in which the molar ratio of the siRNA molecule to the GalNAc molecule is 1:3 (hereinafter referred to as (GalNAc)$_3$-siRNA), and this conjugate has a structure as shown by Formula (305):

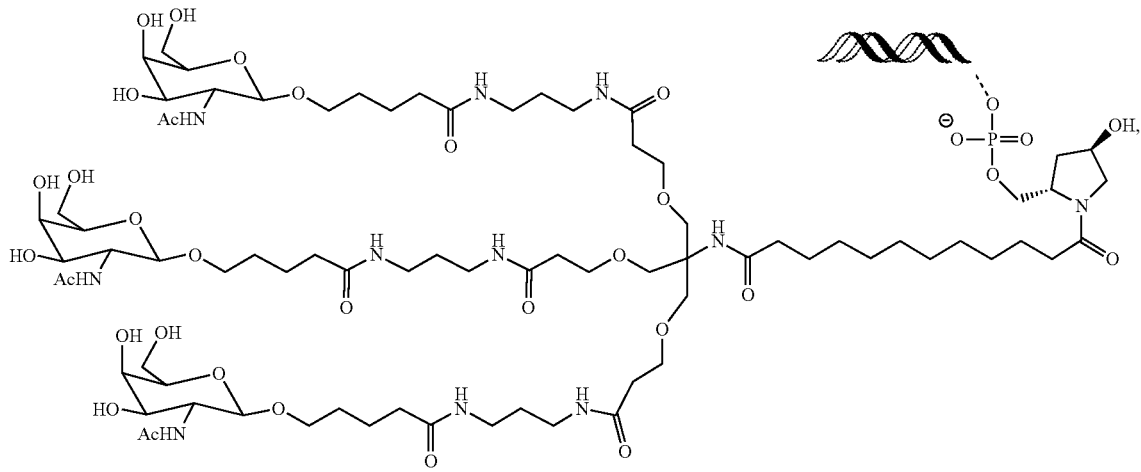

Formula (305)

wherein the double helix structure represents the siRNA; and the linker is linked to 3'-terminal of the sense strand of the siRNA.

In some embodiments, when the targeting group is N-acetylgalactosamine, a suitable linker may have a structure as shown by Formula (306):

Formula (306)

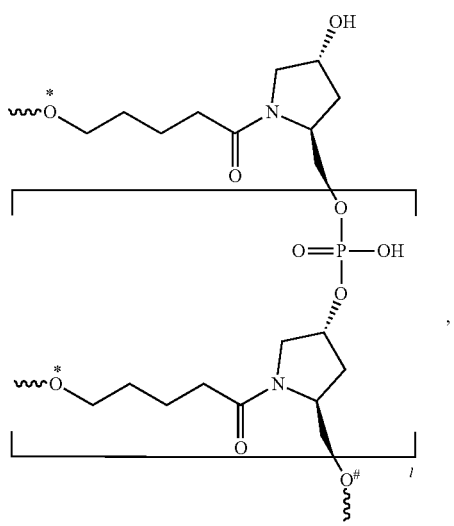

wherein l is an integer of 0-3;
* represents a site on the linker linked to the targeting group via ether bond; and
# represents a site on the linker linked to the siRNA via phosphoester bond.

In some specific embodiments, when l=2, the siRNA conjugate has a structure as shown by Formula (307):

Formula (307)

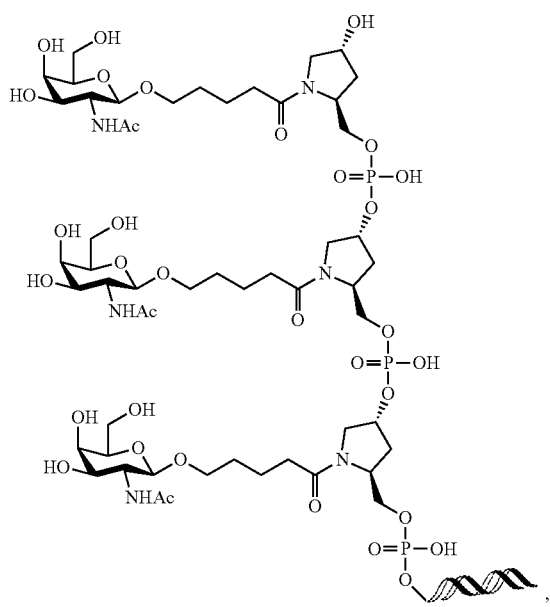

wherein the double helix structure represents the siRNA; and
the linker is linked to 3'-terminal of the sense strand of the siRNA.

The above conjugation molecules can be synthesized according to the method described in detail in the prior art. For example, WO2015006740A2 has described in detail the preparation of various conjugation molecules; for example, in particular, please refer to the description in Examples 14-15 and 21 in this disclosure. WO2014025805A1 has also described the preparation method of the conjugation molecule having the structure as shown by Formula (305); for example, please refer to the synthesis schemes shown in Reaction Schemes 1-8 in the description of the present disclosure, especially the detailed description in Examples 1-5.

The first siRNA conjugate of the present disclosure can be obtained by conjugating the siRNA of the present disclosure to the above conjugation molecules by the methods well known to those skilled in the art.

The Second siRNA Conjugate

In some embodiments, the present disclosure provides another siRNA conjugate (hereinafter also referred to as a second siRNA conjugate; this terminology is only used to distinguish the siRNA conjugate from the above-mentioned first siRNA conjugate for ease of description, and does not mean that there is any inherent mutually exclusive difference between the two siRNA conjugates in terms of scope or meaning), which has a structure as shown by Formula (401):

Formula (401)

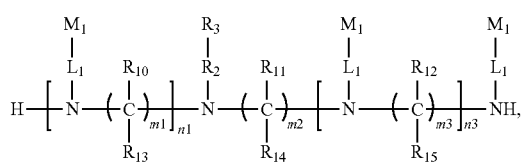

wherein,
$n1$ is an integer of 1-3, and $n3$ is an integer of 0-4;
$m1$, $m2$, and $m3$ independently of one another are an integer of 2-10;
$R_{10}$, $R_{11}$, $R_{12}$, $R_{13}$, $R_{14}$ and $R_{15}$ independently of one another are one of H, methyl and ethyl;
$R_3$ is a group having a structure as shown by Formula (A59):

Formula (A59)

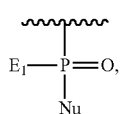

wherein $E_1$ is OH, SH or $BH_2$; Nu is the above siRNA provided by the present disclosure;
$R_2$ is any group capable of linking to the N atom on the nitrogenous backbone and linking to A59;
each $L_1$ is independently selected from the linkage combinations of one or more of Formulae A1-A26:

(A1)

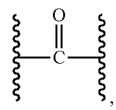

(A2)

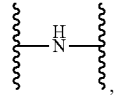

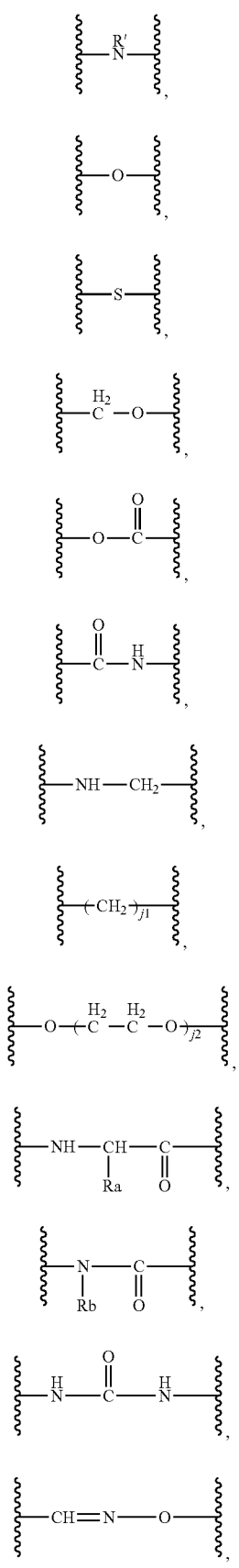
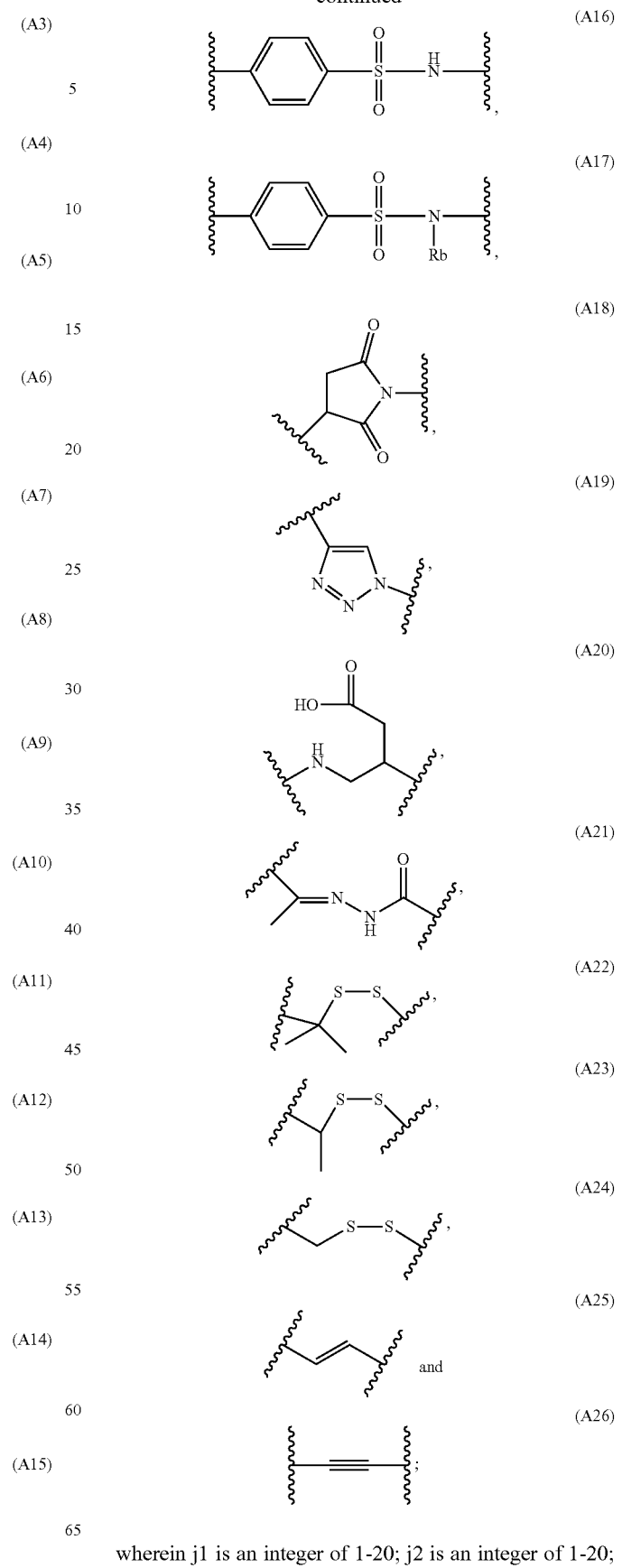
wherein j1 is an integer of 1-20; j2 is an integer of 1-20; R' is a $C_1$-$C_{10}$ alkyl;

Ra is selected from one of Formulae A27-A45:
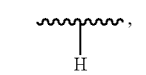 (A27)
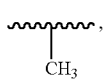 (A28)
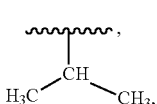 (A29)
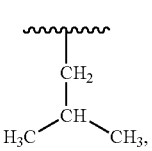 (A30)
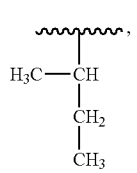 (A31)
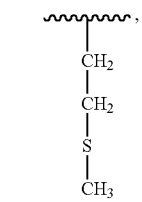 (A32)
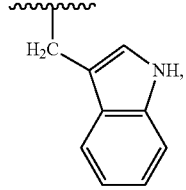 (A33)
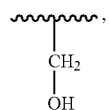 (A34)
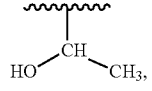 (A35)
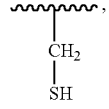 (A36)
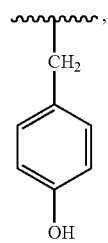 (A37)
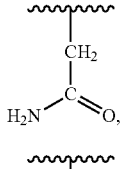 (A38)
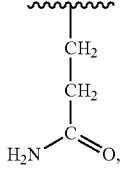 (A39)
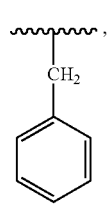 (A40)
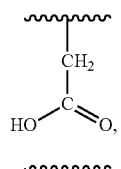 (A41)
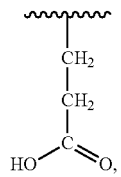 (A42)
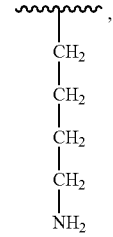 (A43)
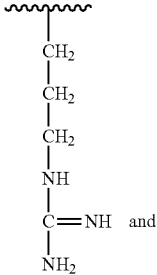 (A44)

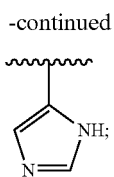

Rb is a $C_1$-$C_{10}$ alkyl; and

~~~ represents the site where the group is covalently linked;

each $M_1$ is independently selected from one of the ligands that have affinity to the asialoglycoprotein receptor (ASGP-R) on the surface of mammalian hepatocytes.

In some embodiments, n1 may be an integer of 1-3, and n3 may be an integer of 0-4 to ensure that the number of the $M_1$ ligand in the conjugate is at least 2. In some embodiments, n1+n3≥2, such that the number of the $M_1$ ligand in the conjugate is at least 3, thereby allowing the $M_1$ ligand to bind to the asialoglycoprotein receptors on the surface of hepatocytes more easily, which may facilitates the endocytosis of the conjugate into cells. Experiments have shown that when the number of the $M_1$ ligand is greater than 3, the ease of binding the $M_1$ ligand to the asialoglycoprotein receptors on the surface of hepatocytes is not significantly increased. Therefore, in view of various aspects such as synthesis convenience, structure/process costs and delivery efficiency, in some embodiments, n1 is an integer of 1-2, n3 is an integer of 0-1, and n1+n3=2-3.

In some embodiments, when m1, m2, and m3 independently of one another are selected from an integer of 2-10, the steric positions among many $M_1$ ligands may be suitable for the binding between the $M_1$ ligands and the asialoglycoprotein receptor on the surface of hepatocytes. In order to make the conjugate provided by the present disclosure have simpler structure, easier synthesis and/or reduced cost, in some embodiments of the disclosure, m1, m2 and m3 independently of one another are an integer of 2-5, and in some embodiments, m1=m2=m3.

Those skilled in the art would understand that when $R_{10}$, $R_{11}$, $R_{12}$, $R_{13}$, $R_{14}$, and $R_{15}$ independently of one another is one of H, methyl or ethyl, they would not change the properties of the conjugate of the present disclosure, while could all achieve the purpose of the present disclosure. Nevertheless, in order to simplify the compounds provided by the present disclosure and facilitate synthesize, in some embodiments, $R_{10}$, $R_{11}$, $R_{12}$, $R_{13}$, $R_{14}$, and $R_{15}$ are all H.

$R_2$ is selected to achieve the linkage between A59 and the N atom on a nitrogenous backbone. In the context of the present disclosure, a "nitrogenous backbone" refers to a chain structure in which N atoms are coadjecently linked to carbon atoms to which $R_{10}$, $R_{11}$, $R_{12}$, $R_{13}$, $R_{14}$, and $R_{15}$ are attached. Therefore, $R_2$ may be any linking group capable of attaching the group as shown by Formula (A59) to the N atom on a nitrogenous backbone by suitable means. In some embodiments, in the case where the second siRNA conjugate of the present disclosure is prepared by a solid phase synthesis process, $R_2$ group needs to comprise both a site linking to the N atom on the nitrogenous backbone and a site linking to the P atom in $R_3$. In some embodiments, in $R_2$, the site linking to the N atom on the nitrogenous backbone forms an amide bond with the N atom, and the site linking to the P atom in $R_3$ forms a phosphoester bond with the P atom. In some embodiments, $R_2$ is selected from B5, B6, B5' or B6':

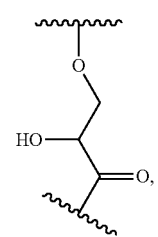

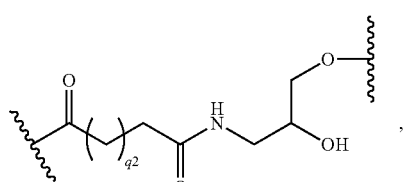

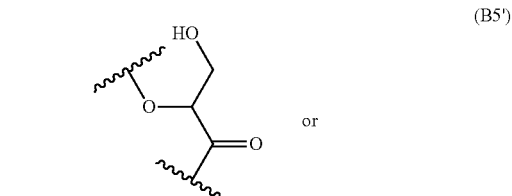

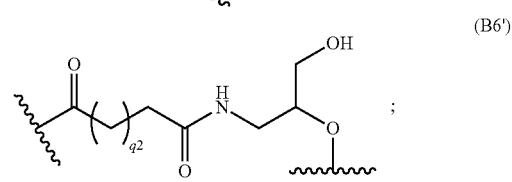

wherein ~~~ represents the site where the group is covalently linked;

$q_2$ is an integer of 1-10; in order to simplify the conjugates provided by the present disclosure, in some embodiments, $q_2$ is an integer of 1-5.

According to the second siRNA conjugate of the present disclosure, considering the availability of starting materials, in some embodiments, $E_1$ is OH or SH.

$L_1$ is used to link the $M_1$ ligand to the N atom on the nitrogenous backbone, thereby providing liver targeting function for the second siRNA conjugate of the present disclosure. When $L_1$ is selected from the linkage combinations of one or more of Formulae A1-A26, they could all achieve the aforementioned purpose. In order to make the steric position among the $M_1$ ligands more suitable for the binding between the $M_1$ ligands and the asialoglycoprotein receptors on the surface of hepatocytes and save costs, in some embodiments, $L_1$ is selected from the linkage combinations of one or more of Formulae A1, A4, A5, A6, A8, A10, A11, and A13; in some embodiments, $L_1$ is selected from the linkage combinations of at least two of Formulae A1, A4, A8, A10, and A11; in some embodiments, $L_1$ is selected from the linkage combinations of at least two of Formulae A1, A8, and A10.

In order to realize the above function of $L_1$, in some embodiments, the length of $L_1$ may be 3 to 25, 3 to 20, 4 to 15 or 5 to 12 atoms. Unless otherwise specified, in the context of the present disclosure, the length of $L_1$ refers to the number of the chain-forming atoms in the longest atomic chain formed from the atom linked to the N atom on the nitrogenous backbone to the atom linked to the $M_1$ in $L_1$.

In Formulae A1-A26, j1, j2, R', Ra, and Rb are respectively selected to achieve the linkage between the $M_1$ ligands and the N atom on the nitrogenous backbone, and to make the steric position among the $M_1$ ligands more suitable for the binding between the $M_1$ ligands and the asialoglycoprotein receptor on the surface of hepatocytes. Therefore, in some embodiments of the present disclosure, j1 is an integer of 2-10, and in one embodiment, is an integer of 3-5. j2 is an integer of 2-10, and in one embodiment, is an integer of 3-5. R' is a $C_1$-$C_4$ alkyl, and in one embodiment, is one of methyl, ethyl and isopropyl. Ra is one of Formulae A27, A28, A29, A30, and A30, and in one embodiment, is A27 or A28. Rb is a $C_1$-$C_5$ alkyl, and in one embodiment, is one of methyl, ethyl, isopropyl, and butyl.

$M_1$ ligand is used to bind to the asialoglycoprotein receptor on the surface of hepatocytes so as to facilitate the endocytosis of the conjugate into cells. Therefore, $M_1$ ligand may be any ligand that has affinity to the asialoglycoprotein receptor (ASGP-R) on the surface of mammalian hepatocytes. The types of these ligands are well-known to those skilled in the art. For example, each $M_1$ ligand may be independently selected from the group consisting of polysaccharides, modified polysaccharides, monosaccharides and monosaccharide derivatives. In some embodiments, each $M_1$ ligand may be independently selected from the group consisting of glucose and its derivatives, mannose and its derivatives, galactose and its derivatives, xylose and its derivatives, ribose and its derivatives, fucose and its derivatives, lactose and its derivatives, maltose and its derivatives, arabinose and its derivatives, fructose and its derivatives, and sialic acid.

In some embodiments, each $M_1$ ligand may be independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, j3-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose and L-4-thioribose. In some embodiments, each $M_1$ ligand is N-acetylgalactosamine (GalNAc). Other ligand selections may be found, for example, in the disclosure of CN105378082A, which is incorporated herein by reference in its entirety.

According to some specific embodiments of the present disclosure, the second conjugate of the present disclosure has a structure as shown by Formula (403), (404), (405), (406), (407), (408), (409), (410), (411), (412), (413), (414), (415), (416), (417), (418), (419), (420), (421) or (422):

Formula (403)

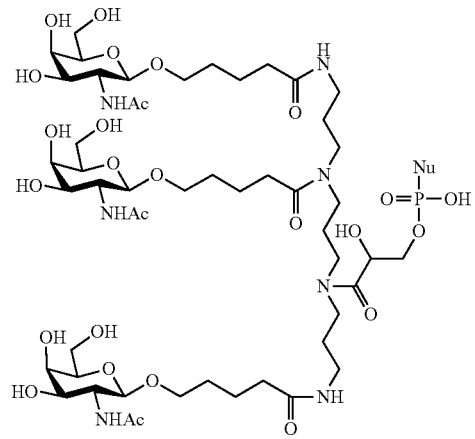

Formula (404)

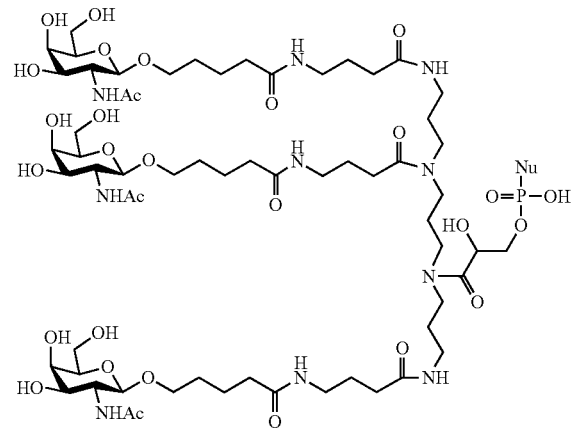

Formula (405)
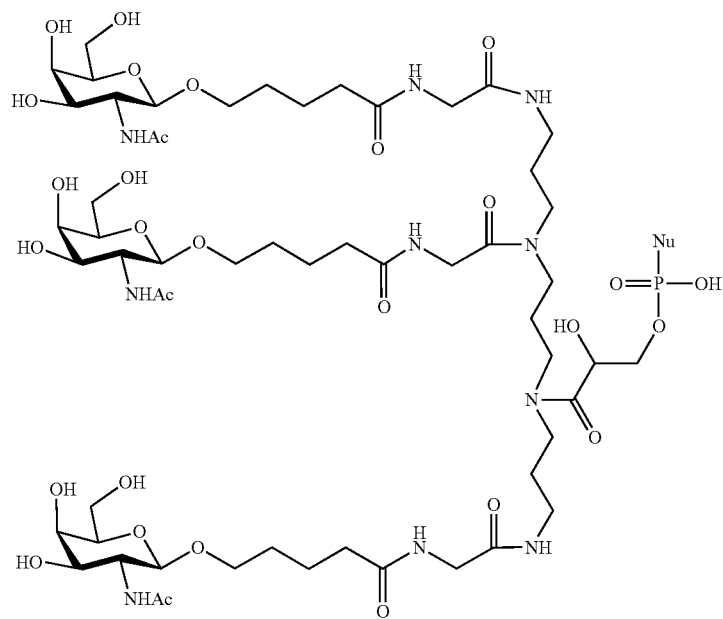
Formula (406)
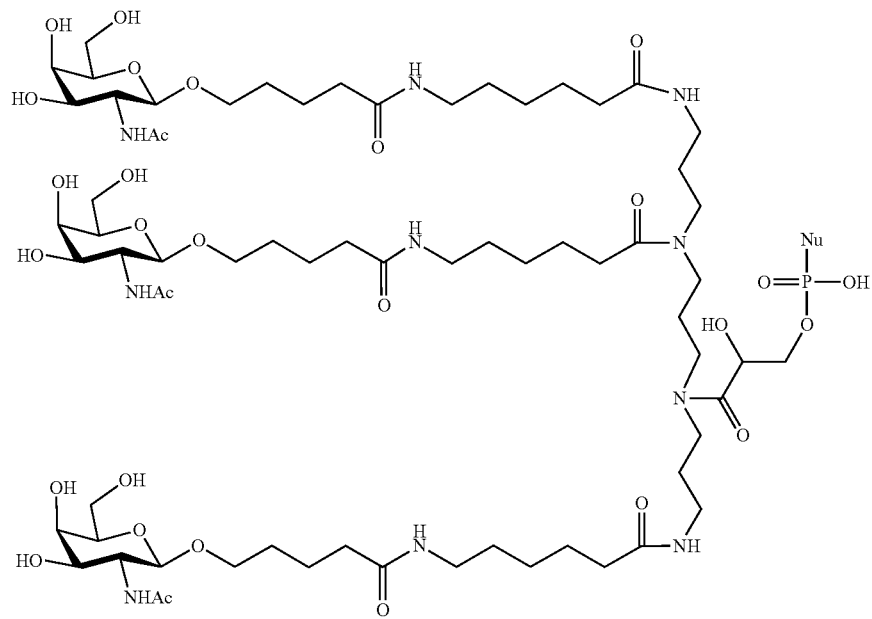

-continued
Formula (407)
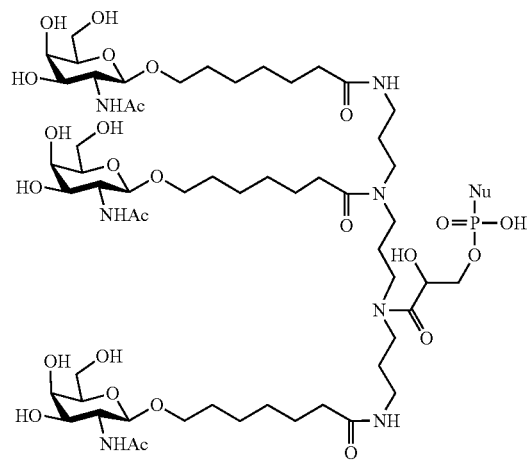
Formula (408)
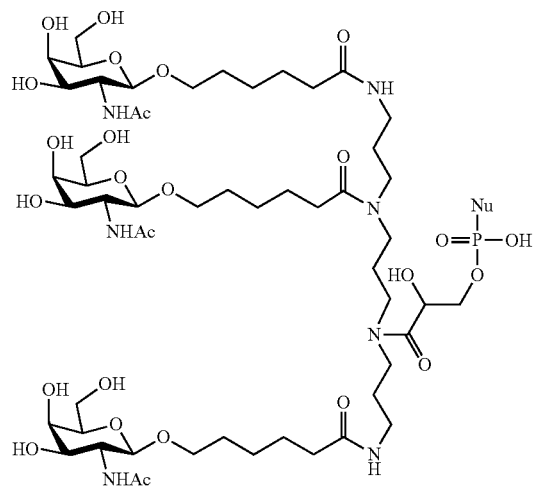
Formula (409)
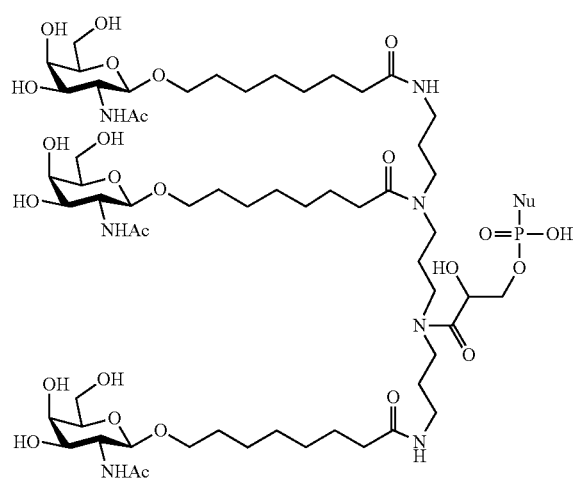
Formula (410)
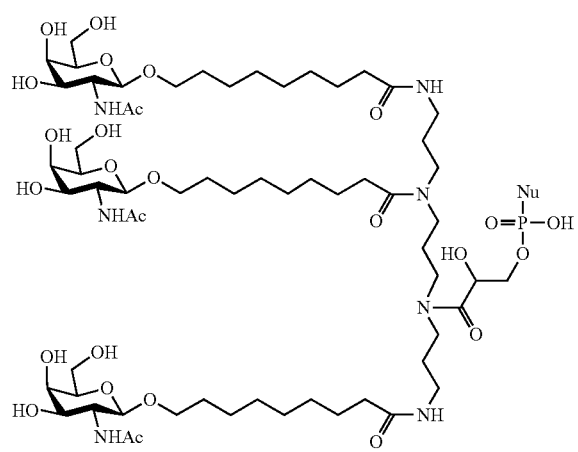
Formula (411)
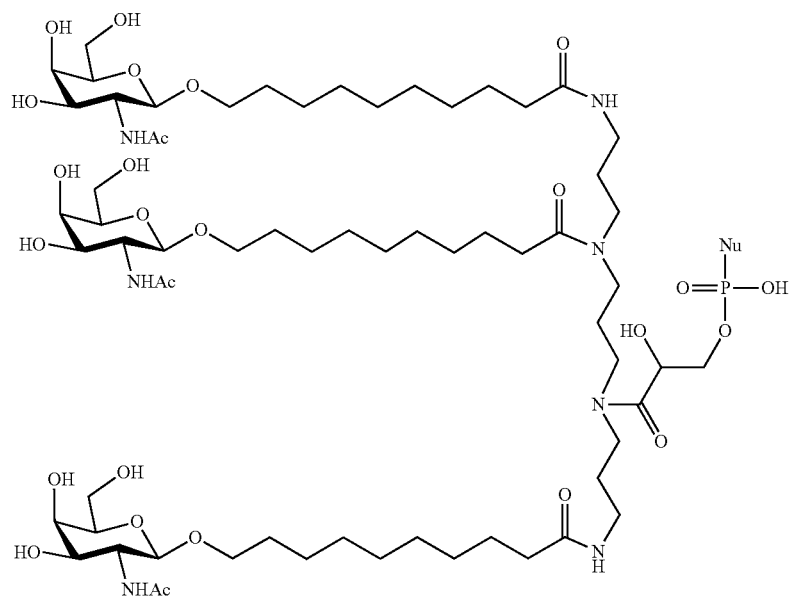

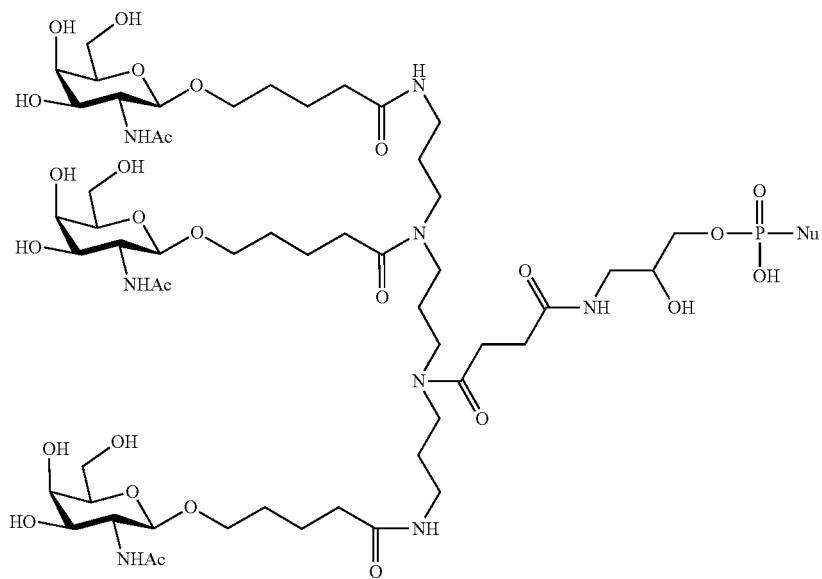
Formula (412)
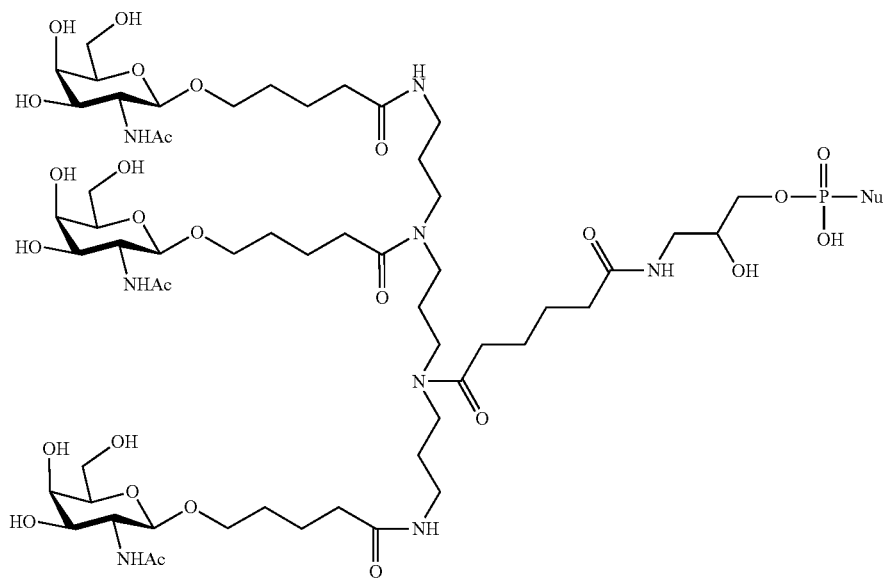
Formula (413)

Formula (414)
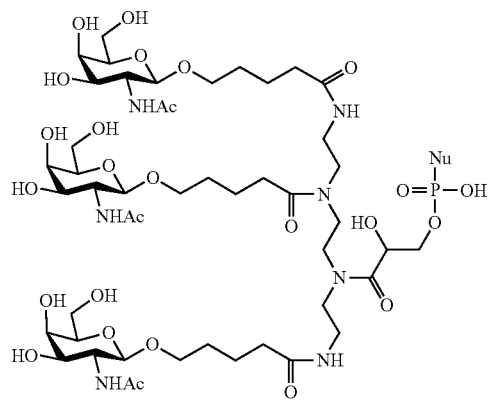
Formula (415)
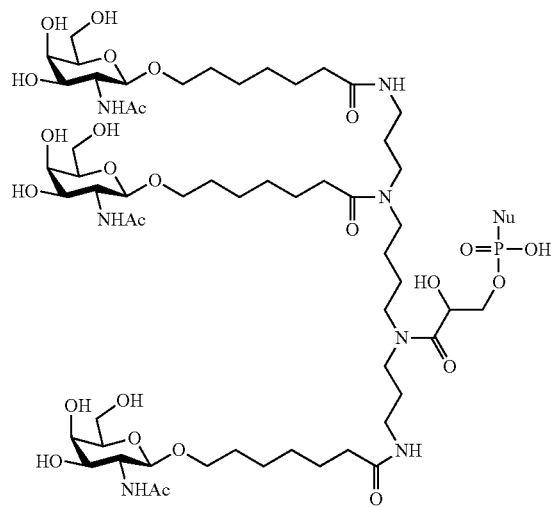
Formula (416)
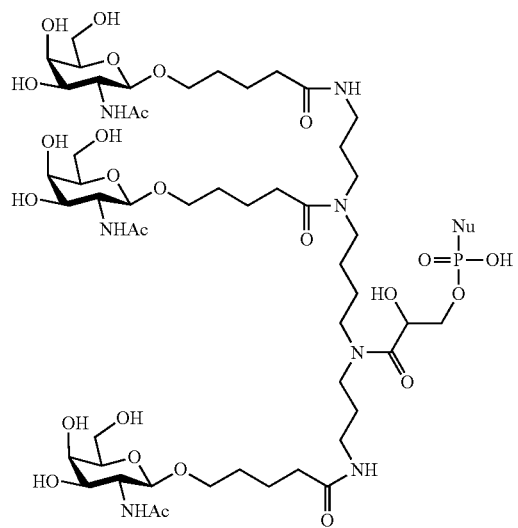
Formula (417)
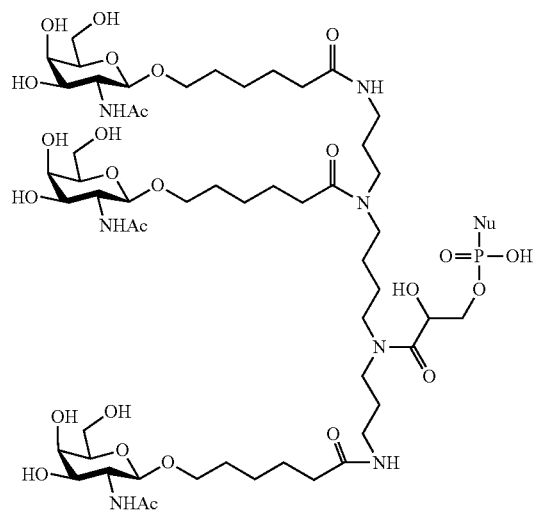

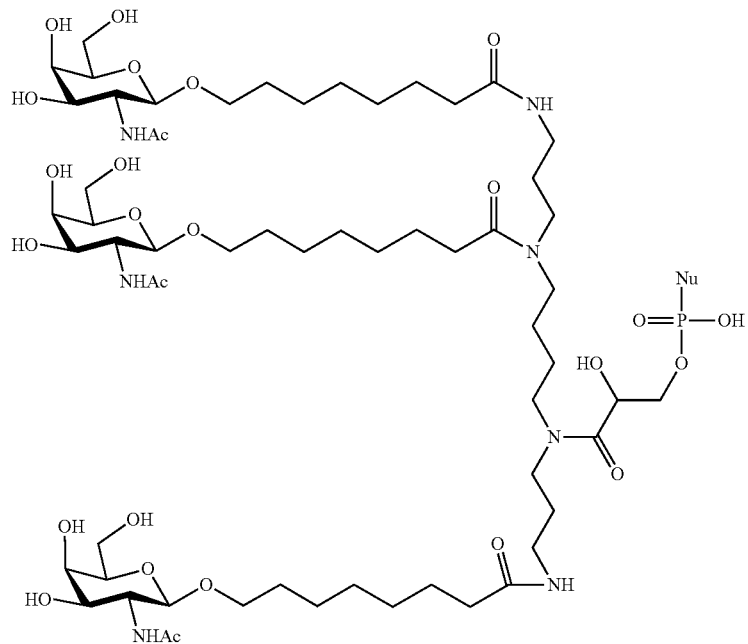
Formula (418)
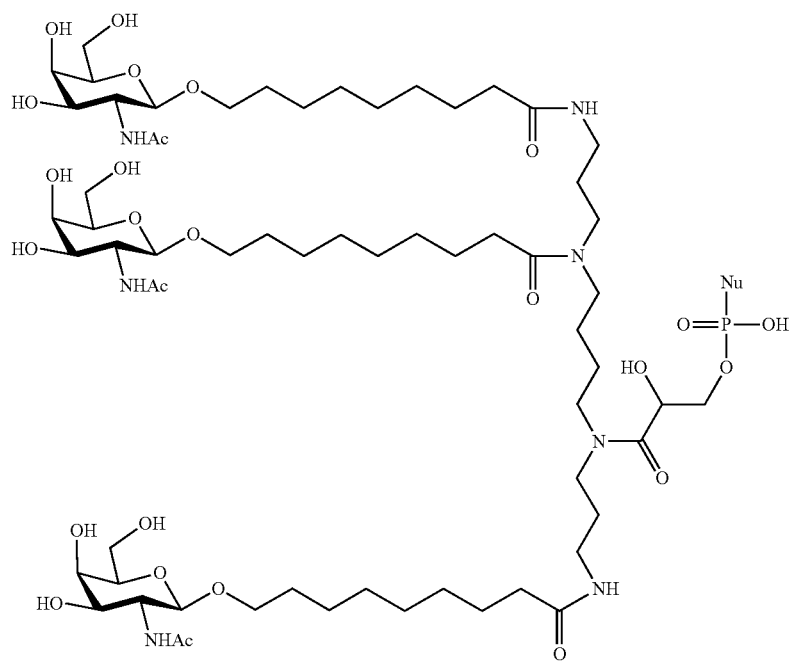
Formula (419)

Formula (420)

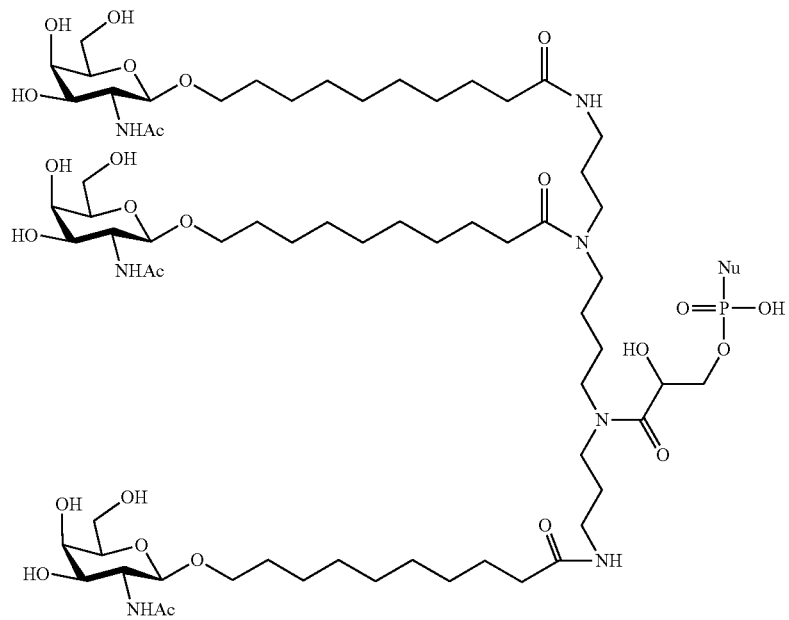

Formula (421)

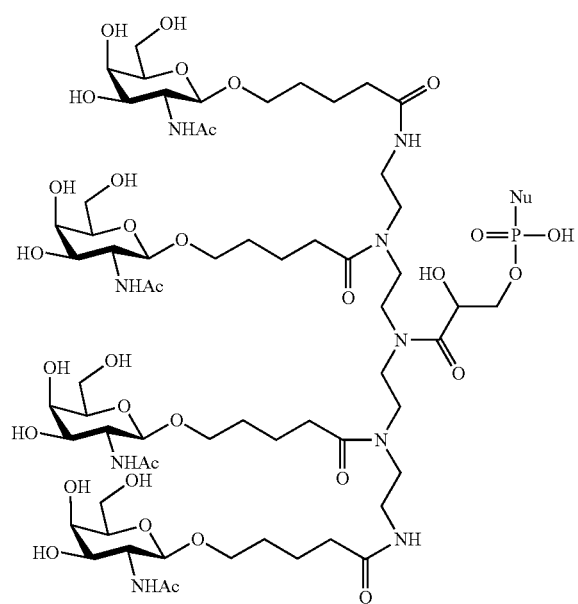

Formula (422)

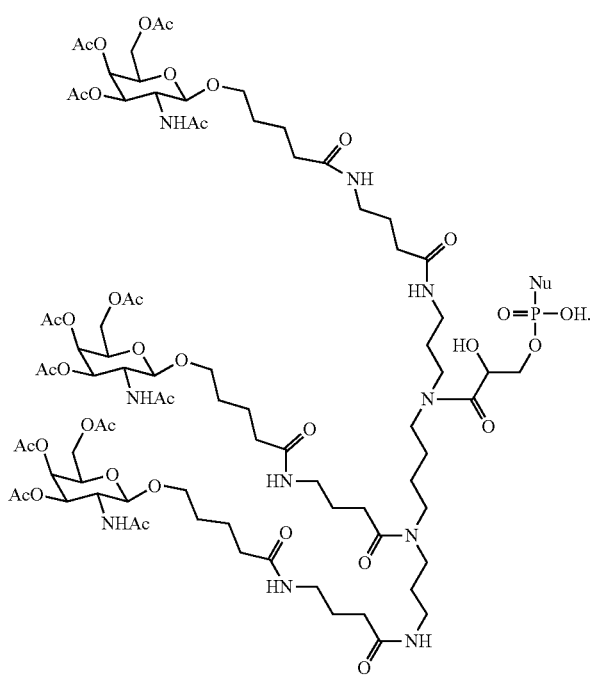

The P atom in Formula A59 may be linked to any possible position in the siRNA sequence. In some embodiments, the P atom in Formula A59 may be linked to any nucleotide in the sense or antisense strand of the siRNA. In some embodiments, the P atom is linked to any nucleotide in the sense strand of the siRNA. In some embodiments, the P atom in Formula A59 may be linked to a terminal region of the sense or antisense strand of the siRNA. In some embodiments, the P atom is linked to a terminal region of the sense strand of the siRNA. Said terminal region refers to the first 4 nucleotides counted from one terminal of the sense or antisense strand. In some embodiments, the P atom in Formula A59 may be linked to either terminal of the sense or antisense strand of the siRNA. In some embodiments, the P atom is linked to 3' terminal of the sense strand of the siRNA. In the case where the P atom in Formula A59 is linked to the above position in the sense strand of the siRNA, after entering into cells, the conjugate provided by the present disclosure can release a separate antisense strand of the siRNA during unwinding, thereby blocking the translation of the HBV mRNA into protein and inhibiting the expression of hepatitis B virus (HBV) gene.

The P atom in Formula A59 may be linked to any possible position of a nucleotide in the siRNA. In some embodiments, the P atom in Formula A59 may be linked to position 5', 2' or 3', or to the base of the nucleotide. In some embodiments, the P atom in Formula A59 may be linked to position 2', 3', or 5' of a nucleotide in the siRNA by forming a phosphodiester bond. In some embodiments, the P atom in Formula A59 is linked to an oxygen atom formed by dehydrogenation of 3'-hydroxy of the nucleotide at 3' terminal of the sense strand in the siRNA (in this case, the P atom and the corresponding phosphate group may be regarded as the P atom and the phosphate group in the nucleotide), or the P atom in Formula A59 is linked to a nucleotide by substituting a hydrogen atom in 2'-hydroxy of a nucleotide of the sense strand in the siRNA, or the P atom in Formula A59 is linked to a nucleotide by substituting a hydrogen atom in 5'-hydroxy of the nucleotide at 5' terminal of the sense strand in the siRNA.

The inventors of the present disclosure have surprisingly found that the second siRNA conjugate of the present disclosure, i.e., the siRNA conjugates comprising the above siRNAs (such as the siRNAs shown in the above Table 1A to Table 1D), exhibits a significantly improved stability in plasma without significantly reduced silencing activity against HBV mRNA, and further shows excellent inhibitory effect on the expression of HBsAg and HBV DNA. In addition, the second siRNA conjugate of the present disclosure exhibits lower off-target effect.

The first siRNA conjugate or the second siRNA conjugate of the present disclosure may also be used in combination with other pharmaceutically acceptable excipients, which may be one or more of the various conventional formulations or compounds in the art. For details, please refer to the above description of the pharmaceutical compositions of the present disclosure.

Preparation of the Second siRNA Conjugate of the Present Disclosure

The second siRNA conjugate of the present disclosure may be prepared by any appropriate synthetic routes.

In one embodiment, the second siRNA conjugate of the present disclosure may be prepared by the following method, comprising successively linking nucleoside monomers in 3' to 5' direction according to the nucleotide type and sequence in the sense strand and antisense strands of the siRNA respectively, under the condition of phosphoramidite solid phase synthesis, wherein the step of linking each nucleoside monomer includes a four-step reaction of deprotection, coupling, capping, and oxidation or sulfurization; isolating the sense strand and the antisense strand of the siRNA; and annealing; wherein the siRNA is the above siRNA provided by the present disclosure. Moreover, the method further comprises: contacting the compound as shown by Formula (321) with a nucleoside monomer or a nucleotide sequence linked to a solid phase support under coupling reaction condition and in the presence of a coupling agent, thereby linking the compound as shown by Formula (321) to the nucleotide sequence through a coupling reaction. Hereinafter, the compound as shown by Formula (321) is also called a conjugation molecule.

Formula (321)

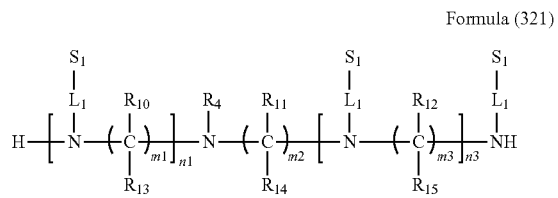

wherein, $R_4$ is a group comprising any functional group that may be conjugated to a siRNA via a phosphodiester bond by reaction;

Each $S_1$ is independently a group formed by substituting all active hydroxyls in $M_1$ with the group YCOO—, wherein each Y is independently selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl;

The definitions and options of n1, n3, m1, m2, m3, $R_{10}$, $R_{11}$, $R_{12}$, $R_{13}$, $R_{14}$, $R_{15}$, $L_1$ and $M_1$ are respectively as described above;

$R_4$ is selected to achieve the linkage to the N atom on a nitrogenous backbone and to provide a suitable reaction site for synthesizing the siRNA conjugate as shown by Formula (401). In some embodiments, $R_4$ comprises a $R_2$ linking group or protected $R_2$ linking group. Moreover, $R_4$ comprises a functional group that can react with a siRNA to form a structure as shown by Formula (A59).

In some embodiments, $R_4$ comprises a group 1 or $R_4$ comprises a group 1 and a group 2, wherein the group 1 comprises a functional group that can react with a group on a siRNA or a nucleoside monomer to form a phosphite ester; and the group 2 comprises a functional group that can form a covalent bond with a hydroxy group or an amino group, or comprises a solid phase support linked via the covalent bond. In some embodiments, the functional group that can react with a group on a siRNA or a nucleoside monomer to form a phosphite ester is a phosphoramidite, a hydroxy or a protected hydroxy which, after removal of the protecting group, can form a hydroxy to participate in the reaction. The functional group that can form a covalent bond with a hydroxy group or an amino group is a phosphoramidite, a carboxyl or a carboxylate salt. The solid phase support linked via the covalent bond is a solid phase support linked via a phosphoester bond, a carboxyl ester bond, or an amide bond. In some embodiments, the solid phase support is a resin.

In some embodiments, the group 1 comprises hydroxy, —$OR_k$ or a group as shown by Formula (C3); the group 2 comprises a structure as shown by Formula (C1), (C2), (C3), (C1'), or (C3'):

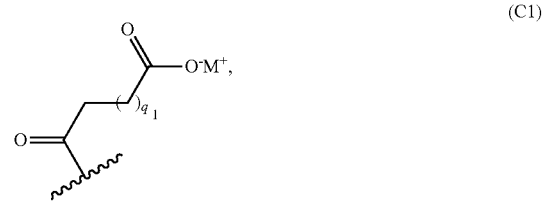
(C1)

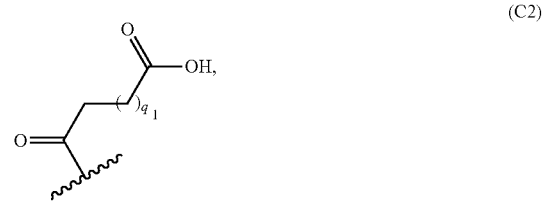
(C2)

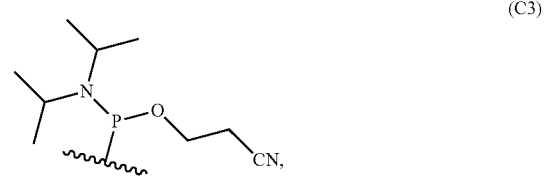
(C3)

-continued

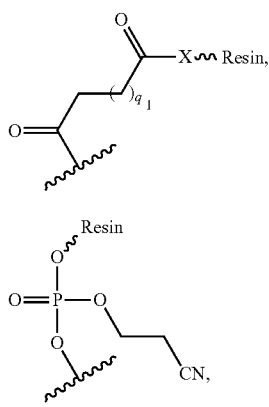

(C1')

(C3')

wherein $q_1$ is an integer of 1-4, X is O or NH, M$^+$ is a cation, $R_k$ is a hydroxy protecting group, Resin represents a solid phase support, and ∿∿∿ represents the site where a group is covalently linked.

In some embodiments, the group 1 comprises a phosphoramidite functional group, such as the group as shown by Formula (C3). The phosphoramidite group can form a phosphite ester with a hydroxy at any position on a nucleotide (such as a 2'- or 3'-hydroxy) by coupling reaction, and the phosphite ester can form a phosphodiester bond or phosphorothioate ester bond as shown by Formula (A59) via oxidation or sulfurization, so as to conjugate the conjugation molecule to a siRNA. Here, whether the group 2 is present will not affect the obtaining of the siRNA conjugate as shown by Formula (401). Under such circumstances, after obtaining a sense or antisense strand of the siRNA by a method such as phosphoramidite solid phase synthesis, the compound as shown by Formula (321) is reacted with a hydroxy on the terminal nucleotide of the nucleotide sequence, and the resultant phosphite ester forms a phosphodiester bond or phosphorothioate bond by a subsequent oxidation or sulfurization, thereby conjugating the compound as shown by Formula (321) to a siRNA.

In some embodiments, the group 1 comprises a protected hydroxy group, and the group 2 comprises a carboxyl functional group, a carboxylate functional group or a phosphoramidite functional group, such as the functional group as shown by Formula (C1), (C2) or (C3). When the group 2 comprises a carboxyl functional group or a carboxylate functional group, the compound as shown by Formula (321) can react via an esterification or an amidation reaction with a hydroxy or an amino group on a solid phase support such as a resin, to form a solid phase support linked via a carboxylate ester bond or a solid phase support linked via an amide bond. When the group 2 comprises a phosphoramidite functional group, the compound as shown by Formula (321) can be coupled with a hydroxy group on a universal solid phase support, such as a resin, and by oxidation, form a solid phase support linked via a phosphodiester bond. Subsequently, starting from the above product linked to a solid phase support, the nucleoside monomers are linked sequentially by a phosphoramidite solid phase synthesis method, thereby obtaining a sense or antisense strand of the siRNA linked to the conjugation molecule. During the phosphoramidite solid phase synthesis, the group 1 is deprotected, and then coupled with a phosphoramidite group on a nucleoside monomer under coupling reaction condition.

In one embodiment, the group 1 comprises a hydroxy or a protected hydroxy group, and the group 2 comprises a solid phase support linked via a carboxylate ester bond, an amide bond or a phosphoester bond as shown by Formula (C1') or (C3'). Under such circumstances, starting from the compound as shown by Formula (321) in place of the solid phase support, the nucleoside monomers are linked sequentially by a phosphoramidite solid phase synthesis method, thereby obtaining a sense or antisense strand of the siRNA linked to a conjugation molecule. In some embodiments, the carboxylate functional group may be expressed as —COO$^-$ M$^+$, wherein M$^+$ is a cation such as one of a metal cation, an ammonium cation NH$_4^+$ and an organic ammonium cation. In one embodiment, the metal cation may be an alkali metal cation, such as K$^+$ or Na$^+$. In order to increase solubility and facilitate the reaction, in some embodiments, the organic ammonium cation is an ammonium cation formed by a tertiary amine, or a quaternary ammonium cation, such as an ammonium cation formed by triethylamine or N,N-diisopropylethylamine. In some embodiments, the carboxylate is a triethylamine carboxylate or an N,N-diisopropylethylamine carboxylate.

In some embodiments, $R_4$ comprises a structure as shown by Formula (B9), (B10), (B9'), (B10'), (B11), (B12), (B11') or (B12'):

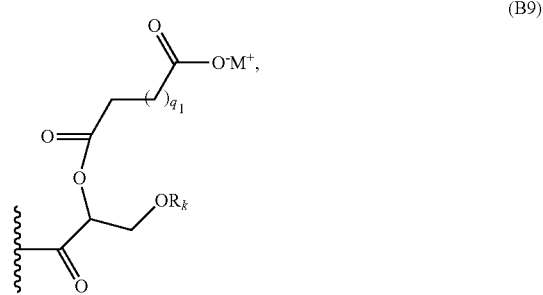

(B9)

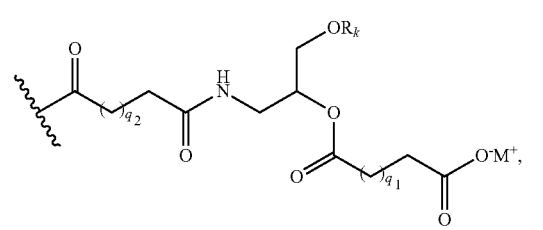

(B10)

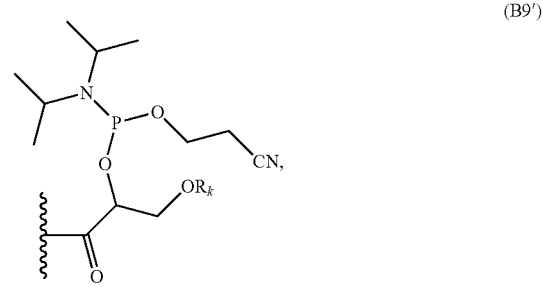

(B9')

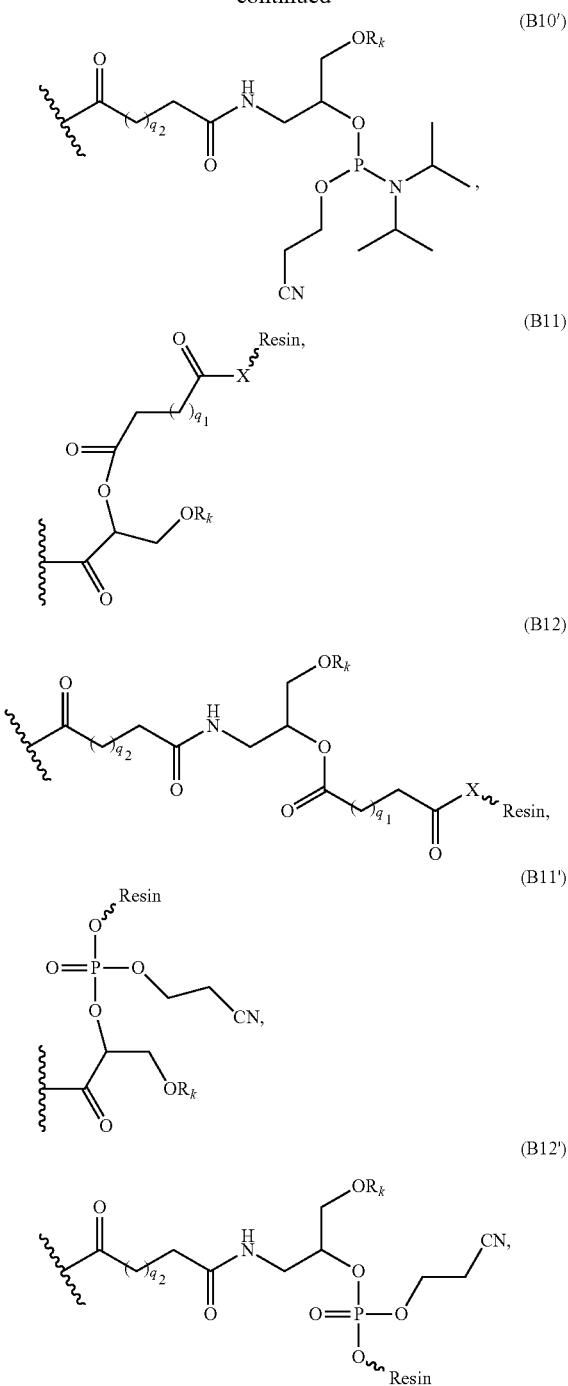

(B10')

(B11)

(B12)

(B11')

(B12')

wherein $q_1$ is an integer of 1-4, $q_2$ is an integer of 1-10, X is O or NH, $M^+$ is a cation, $R_k$ is a hydroxy protecting group, Resin represents a solid phase support, and 〜〜 represents a site where a group is covalently linked. From the viewpoint of synthesis convenience and costs, $q_1$ is 1 or 2, and $q_2$ is an integer of 1-5. In some embodiments, $R_4$ comprises a structure as shown by Formula (B9) or (B10). In some embodiments, $R_4$ comprises a structure as shown by Formula (B11) or (B12).

The hydroxy protecting group $R_k$ is selected to replace the hydrogen on the hydroxyl in $R_4$ to form a non-reactive group. The protecting group $R_k$ can be removed in the subsequent reaction process to release an active hydroxyl again to participate in the subsequent reaction. The types of the protecting group are well-known to those skilled in the art. For example, the protecting group $R_k$ is one or more of Tr (trityl), MMTr (4-methoxytrityl), DMTr (4,4'-dimethoxytrityl), and TMTr (4,4',4''-trimethoxytrityl). In some embodiments, $R_k$ may be DMTr, i.e., 4,4'-dimethoxytrityl.

According to the description above, those skilled in the art would easily understand that as compared with the well-known phosphoramidite solid phase synthesis methods in the art, a siRNA conjugate in which a conjugation molecule is linked to any possible position of the nucleotide sequence can be obtained through the above group 1 and an optional group 2. For example, the conjugation molecule is linked to a terminal region of the nucleotide sequence or to a terminal of the nucleotide sequence. Correspondingly, unless otherwise specified, in the following description regarding conjugate preparation, when referring to the reactions such as "deprotection", "coupling", "capping", "oxidation", "sulfurization", it will be understood that the reaction conditions and agents involved in the well-known phosphoramidite solid phase synthesis methods in the art would also apply to these reactions. Exemplary reaction conditions and agents will be described in detail hereinafter.

Each $S_1$ is independently a group formed by substituting all active hydroxyl groups in $M_1$ with the group YCOO—. During preparation of the siRNA conjugate from the compound as shown by Formula (321), the active hydroxyl in the $M_1$ is protected by the group YCOO—, and the protecting group is removed in the subsequent steps to obtain a $M_1$ ligand.

In some embodiments, each $S_1$ is independently one of Formulae A46-A54:

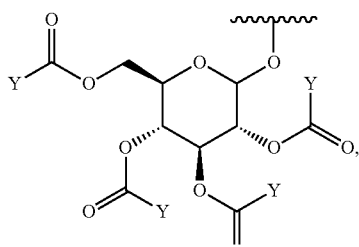

(A46)

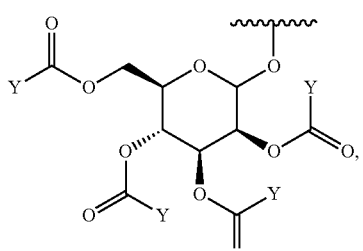

(A47)

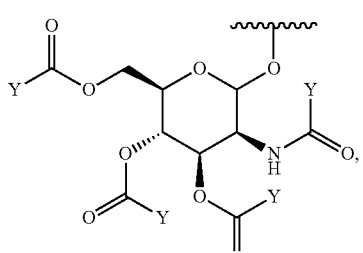

(A48)

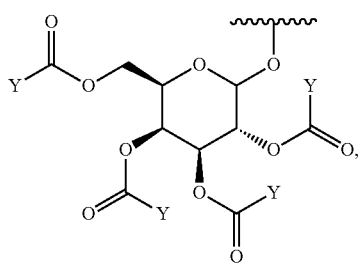
(A49)

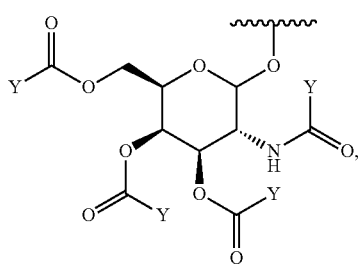
(A50)

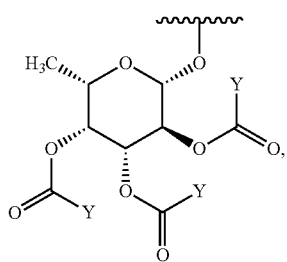
(A51)

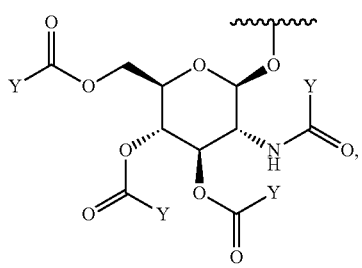
(A52)

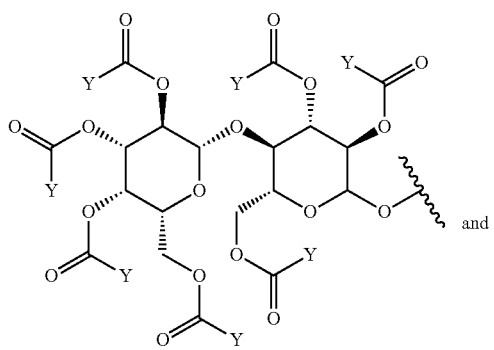
(A53) and

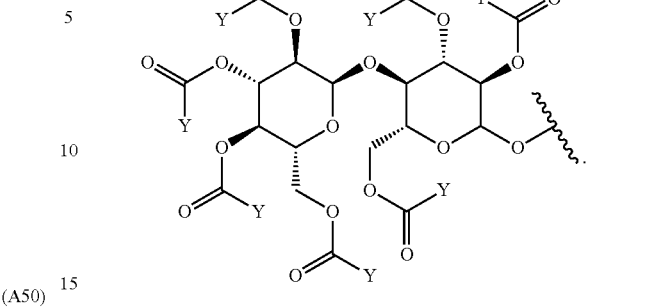
(A54)

In some embodiments, $S_1$ is Formula A49 or A50.

In some embodiments, each Y is independently selected from one of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl. For the purpose of simplifying the conjugation molecule of the present disclosure, in one embodiment, Y is methyl.

As mentioned previously, the method for preparing the second siRNA conjugate of the present disclosure further comprises the following step: synthesizing the other strand of the siRNA (for example, when a sense strand of the siRNA linked to a conjugation molecule is synthesized in the above step, the method further comprises synthesizing an antisense strand of the siRNA by the solid phase synthesis method, and vice versa); isolating the sense strand and the antisense strand; and annealing. In particular, in the isolating step, the solid phase support linked to the nucleotide sequence and/or conjugation molecule is cleaved, and the necessary protecting group is removed (in this case, each $S_1$ group in the compound as shown by Formula (321) is converted to the corresponding $M_1$ ligand), thereby obtaining a sense strand (or antisense strand) of the siRNA linked to the conjugation molecule and the corresponding antisense strand (or sense strand). The sense strand and the antisense strand are annealed to form a double-stranded RNA structure, thereby obtaining a siRNA conjugate as shown by Formula (401).

In some embodiments, the method for preparing the siRNA conjugate comprises the following steps: contacting the compound as shown by Formula (321) with the first nucleoside monomer at 3' terminal of the sense or antisense strand under coupling reaction condition in the presence of a coupling agent, thereby linking the compound as shown by Formula (321) to the first nucleotide in the sequence; successively linking nucleoside monomers in 3' to 5' direction to synthesize the sense or antisense strand of the siRNA according to the desired nucleotide type and sequence of the sense or antisense strand, under the condition of phosphoramidite solid phase synthesis; wherein the compound of Formula (321) is a compound in which $R_4$ comprises a group 1 and a group 2, wherein the group 1 comprises a protected hydroxy and the group 2 has a structure as shown by Formula (C1') or (C3'), and the compound of Formula (321) is deprotected before linked to the first nucleoside monomer; and the linking of each nucleoside monomer comprises a four-step reaction of deprotection, coupling, capping, and oxidation or sulfurization; thus obtaining a sense or antisense strand of nucleic acid linked to the conjugation molecule; successively linking nucleoside monomers in 3' to 5' direction to synthesize the sense or antisense strand of nucleic acid according to the nucleotide type and sequence of the sense or antisense strand, under the condition of phosphoramidite solid phase synthesis; wherein the linking of each nucleoside monomer includes a four-step reaction of deprotection, coupling, capping, and oxidation or sulfurization; removing the protecting groups and cleaving the solid phase support; isolating and purifying the sense strand and the antisense strand of nucleic acid; and annealing.

In some embodiments, the method for preparing the siRNA conjugate comprises the following steps: successively linking nucleoside monomers in 3' to 5' direction to synthesize the sense strand or the antisense strand according to the nucleotide type and sequence of the sense or antisense strand in the double-stranded siRNA; wherein the linking of each nucleoside monomer comprises a four-step reaction of deprotection, coupling, capping, and oxidation or sulfurization, thus obtaining a sense strand linked to the solid phase support and an antisense strand linked to the solid phase support; contacting the compound as shown by Formula (321) with the sense strand linked to the solid phase support or the antisense strand linked to the solid phase support under coupling reaction condition in the presence of a coupling agent, thereby linking the compound as shown by Formula (321) to the sense strand or the antisense strand; wherein the compound of Formula (321) is a compound in which $R_4$ comprises a group 1 which comprises a phosphoramidite group; removing the protecting groups and cleaving the solid phase support; respectively isolating and purifying the sense or antisense strand of the siRNA; and annealing; wherein the sense or antisense strand of the siRNA is linked to a conjugation molecule.

In some embodiments, the nucleoside monomers used are selected according to the siRNA sequence in the second siRNA conjugate desired. For example, when the siRNA sequence comprises a fluoro modified or methoxy modified nucleotide, the corresponding fluoro modified or methoxy modified nucleoside monomer is used in synthesis of the siRNA. As described above, these fluoro modified or methoxy modified nucleoside monomers are well-known in the art and can be readily commercially available.

In one embodiment, the P atom in formula A59 is linked to 3' terminal of the sense strand of the siRNA, and the method for preparing the second siRNA conjugate of the present disclosure comprises:

(1) removing the hydroxyl protecting group $R_k$ in the compound of Formula (321), wherein the compound of Formula (321) is a compound in which $R_4$ comprises a group 1 and a group 2, wherein the group 1 comprises a protected hydroxy $OR_k$, and the group 2 has a structure as shown by Formula (C1') or (C3'); contacting the deprotected product with a nucleoside monomer to obtain a nucleoside monomer linked to a solid phase support via the conjugation molecule, under coupling reaction condition in the presence of a coupling agent;
(2) starting from the nucleoside monomer linked to a solid phase support via the conjugation molecule, synthesizing a sense strand of the siRNA in 3' to 5' direction by a phosphoramidite solid phase synthesis method;
(3) synthesizing an antisense strand of the siRNA by a phosphoramidite solid phase synthesis method; and
(4) isolating the sense strand and the antisense strand of the siRNA and annealing the same to obtain the second siRNA conjugate of the present disclosure;
wherein in step (1), the method for removing the protecting group $R_k$ in the compound of Formula (321) comprises contacting the compound of Formula (321) with a deprotection agent under deprotection condition. The deprotection condition comprises a temperature of 0-50° C., and in one embodiment, 15-35° C., and a reaction time of 30-300 seconds, and in one embodiment, 50-150 seconds. The deprotection agent may be selected from one or more trifluoroacetic acid, trichloroacetic acid, dichloroacetic acid, and monochloroacetic acid, and in one embodiment, the deprotection agent is dichloroacetic acid. The molar ratio of the deprotection agent to the compound as shown by Formula (321) may be 10:1 to 1000:1, and in some embodiments, 50:1 to 500:1.

The coupling reaction condition and the coupling agent may be any conditions and agents suitable for the above coupling reaction. For the purpose of simplifying the process, the same condition and agent as those of the coupling reaction in the solid phase synthesis method can be used.

Typically, the coupling reaction condition comprises a reaction temperature of 0-50° C., and in one embodiment, 15-35° C. The molar ratio of the compound of Formula (321) to the nucleoside monomer may be 1:1 to 1:50, and in one embodiment, 1:2 to 1:5. The molar ratio of the compound of Formula (321) to the coupling agent may be 1:1 to 1:50, and in one embodiment, 1:3 to 1:10. The reaction time may be 200-3000 seconds, and in one embodiment, 500-1500 seconds. The coupling agent may be selected from one or more of 1H-tetrazole, 5-ethylthio-1H-tetrazole and 5-benzylthio-1H-tetrazole, and in one embodiment, is 5-ethylthio-1H-tetrazole. The coupling reaction may be performed in an organic solvent. The organic solvent may be selected from one or more of anhydrous acetonitrile, anhydrous DMF and anhydrous dichloromethane, and in one embodiment, is anhydrous acetonitrile. With respect to the compound as shown by Formula (321), the amount of the organic solvent may be 3-50 L/mol, and in one embodiment, 5-20 L/mol.

In step (2), a sense strand S of the siRNA conjugate is synthesized in 3' to 5' direction by the phosphoramidite solid phase synthesis method, starting from the nucleoside monomer linked to a solid phase support via a conjugation molecule prepared in the above steps. In this case, the conjugation molecule is linked to 3' terminal of the resultant sense strand.

Other conditions for the solid phase synthesis in steps (2) and (3), including the deprotection condition for the nucleoside monomer, the type and amount of the deprotection agent, the coupling reaction condition, the type and amount of the coupling agent, the capping reaction condition, the type and amount of the capping agent, the oxidation reaction condition, the type and amount of the oxidation agent, the sulfurization reaction condition, and the type and amount of the sulfurization agent, adopt various conventional agents, amounts, and conditions in the art.

In one embodiment, for example, the solid phase synthesis in steps (2) and (3) can use the following conditions:

The deprotection condition for the nucleoside monomer comprises a reaction temperature of 0-50° C., and in one embodiment, 15-35° C., and a reaction time of 30-300 seconds, and in one embodiment, 50-150 seconds. The deprotection agent may be selected from one or more of trifluoroacetic acid, trichloroacetic acid, dichloroacetic acid, and monochloroacetic acid, and in one embodiment, is dichloroacetic acid. The molar ratio of the deprotection agent to the protecting group 4,4'-dimethoxytrityl on the solid phase support is 2:1 to 100:1, and in one embodiment, is 3:1 to 50:1.

The coupling reaction condition comprises a reaction temperature of 0-50° C., and in one embodiment, 15-35° C.

The molar ratio of the nucleic acid sequence linked to the solid phase support to the nucleoside monomer is 1:1 to 1:50, and in one embodiment, is 1:5 to 1:15. The molar ratio of the nucleic acid sequence linked to the solid phase support to the coupling agent is 1:1 to 1:100, and in one embodiment, is 1:50 to 1:80. The selection of the reaction time and the coupling agent can be same as above.

The capping reaction condition comprises a reaction temperature of 0-50° C., and in one embodiment, 15-35° C., and a reaction time of 5-500 seconds, and in one embodiment, 10-100 seconds. The selection of the capping agent can be same as above. The molar ratio of the total amount of the capping agent to the nucleic acid sequence linked to the solid phase support may be 1:100 to 100:1, and in one embodiment, is 1:10 to 10:1. In the case where the capping agent uses equimolar acetic anhydride and N-methylimidazole, the molar ratio of acetic anhydride, N-methylimidazole, and the nucleic acid sequence linked to the solid phase support may be 1:1:10-10:10:1, and in one embodiment, is 1:1:2-2:2:1.

The oxidation reaction condition comprises a reaction temperature of 0-50° C., and in one embodiment, 15-35° C., and a reaction time of 1-100 seconds, and in one embodiment, 5-50 seconds. In one embodiment, the oxidation agent is iodine (in one embodiment provided as iodine water). The molar ratio of the oxidation agent to the nucleic acid sequence linked to the solid phase support in the coupling step may be 1:1 to 100:1, and in one embodiment, is 5:1 to 50:1. In some embodiments, the oxidation reaction is performed in a mixed solvent in which the ratio of tetrahydrofuran:water:pyridine is 3:1:1-1:1:3. The sulfurization reaction condition comprises a reaction temperature of 0-50° C., and in one embodiment, 15-35° C., and a reaction time of 50-2000 seconds, and in one embodiment, 100-1000 seconds. In one embodiment, the sulfurization agent is xanthane hydride. The molar ratio of the sulfurization agent to the nucleic acid sequence linked to the solid phase support in the coupling step is 10:1 to 1000:1, and in one embodiment, is 10:1 to 500:1. In some embodiments, the sulfurization reaction is performed in a mixed solvent in which the ratio of acetonitrile:pyridine is 1:3-3:1.

The method further comprises isolating the sense strand and the antisense strand of the siRNA after linking all nucleoside monomers and before the annealing. Methods for isolation are well-known to those skilled in the art and generally comprise cleaving the synthesized nucleotide sequence from the solid phase support, removing protecting groups on the bases, phosphate groups and ligands, purifying and desalting.

The conventional cleavage and deprotection methods in the synthesis of siRNAs can be used to cleave the synthesized nucleotide sequence from the solid phase support, and remove the protecting groups on the bases, phosphate groups and ligands. For example, the resultant nucleotide sequence linked to the solid phase support is contacted with concentrated aqueous ammonia; during deprotection, the protecting group YCO⁻ in groups A46-A54 is converted to a hydroxyl group, and thus the $S_1$ groups are converted to corresponding $M_1$ ligands, providing the conjugate as shown by Formula (401); wherein the concentrated aqueous ammonia may be aqueous ammonia of a concentration of 25-30 wt %. The amount of the concentrated aqueous ammonia may be 0.2 ml/μmol-0.8 ml/μmol with respect to the target siRNA.

When there is at least one 2'-TBDMS protection on the synthesized nucleotide sequence, the method further comprises contacting the nucleotide sequence removed from the solid phase support with triethylamine trihydrofluoride to remove the 2'-TBDMS protection. Here, the resultant target siRNA sequence comprises the corresponding nucleoside having free 2'-hydroxy. The amount of pure triethylamine trihydrofluoride is 0.4 ml/μmol-1.0 ml/μmol with respect to the target siRNA sequence. As such, the second siRNA conjugate of the present disclosure can be obtained.

Methods for purification and desalination are well-known to those skilled in the art. For example, nucleic acid purification may be performed using a preparative ion chromatography purification column with a gradient elution of NaBr or NaCl; after collection and combination of the product, the desalination may be performed using a reverse phase chromatography purification column.

The non-bridging oxygen or sulfur atom in the phosphodiester bond or phosphorothioate diester bond between the nucleotides in the resultant siRNA conjugate substantially binds to a sodium ion, and the siRNA conjugate is substantially present in the form of a sodium salt. The well-known ion-exchange methods may be used, in which the sodium ion may be replaced with hydrogen ion and/or other cations, thereby providing other forms of siRNA conjugates. The cations will be described in detail hereinafter.

During synthesis, the purity and molecular weight of the nucleic acid sequence may be determined at any time, in order to better control the synthesis quality. Such determination methods are well-known to those skilled in the art. For example, the purity of the nucleic acid may be determined by ion exchange chromatography, and the molecular weight may be determined by liquid chromatography-mass spectrometry (LC-MS).

Methods for annealing are also well-known to those skilled in the art. For example, the synthesized sense strand (S strand) and antisense strand (AS strand) may be simply mixed in water for injection at an equimolar ratio, heated to 70-95° C., and then cooled at room temperature to form a double-stranded structure via hydrogen bond. Hence, the second siRNA conjugate of the present disclosure can be obtained.

After obtaining the second siRNA conjugate of the present disclosure, in one embodiment, the synthesized siRNA conjugate can also be characterized by the means such as molecular weight detection using the methods such as LC-MS, to confirm that the synthesized siRNA conjugate is the designed siRNA conjugate of interest, and the sequence of the synthesized siRNA is the sequence of the desired siRNA sequence to be synthesized, for example, is one of the sequences listed in Tables 1A-1D above.

The compound as shown by Formula (321) may be prepared by the following method comprising: contacting a compound as shown by Formula (313) with a cyclic anhydride in an organic solvent under esterification reaction condition in the presence of a base and an esterification catalyst; isolating the compound as shown by Formula (321) by ion exchange:

Formula (313)

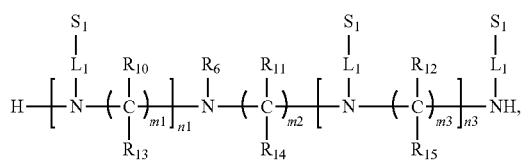

wherein the definitions and options of n1, n3, m1, m2, m3, $R_{10}$, $R_{10}$, $R_{12}$, $R_{13}$, $R_{14}$, $R_{15}$, $L_1$, and $S_1$ are respectively as described above;

$R_6$ has a structure as shown by Formula (A61):

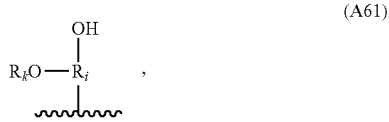

(A61)

wherein $R_i$ is any group capable of linking to the N atom on the nitrogenous backbone, linking to $R_kO$ and linking to a free hydroxy group; $R_k$ is a hydroxy protecting group. In this case, a compound as shown by Formula (321) is obtained, wherein $R_4$ comprises a group 1 which comprises a hydroxy protecting group and a group 2 which comprises a structure as shown by Formula (C1) or (C2).

The esterification reaction condition includes a reaction temperature of 0-100° C. and a reaction time of 8-48 hours. In one embodiment, the esterification reaction condition comprises a reaction temperature of 10-40° C. and a reaction time of 20-30 hours.

The organic solvent is one or more of an epoxy solvent, an ether solvent, an haloalkane solvent, dimethyl sulfoxide, N,N-dimethylformamide, and N,N-diisopropylethylamine. In one embodiment, the epoxy solvent is dioxane and/or tetrahydrofuran, the ether solvent is diethyl ether and/or methyl tertbutyl ether, and the haloalkane solvent is one or more of dichloromethane, trichloromethane and 1,2-dichloroethane. In one embodiment, the organic solvent is dichloromethane. With respect to the compound as shown by Formula (313), the amount of the organic solvent is 3-50 L/mol, and in one embodiment, 5-20 L/mol.

In some embodiments, the cyclic anhydride is one of succinic anhydride, glutaric anhydride, adipic anhydride or pimelic anhydride, and in one embodiment, the cyclic anhydride is succinic anhydride. The molar ratio of the cyclic anhydride to the compound as shown by Formula (313) is 1:1 to 10:1, and in one embodiment, 2:1 to 5:1.

The esterification catalyst may be any catalyst capable of catalyzing esterification, such as 4-dimethylaminopyridine. The molar ratio of the catalyst to the compound as shown by Formula (313) is 1:1 to 10:1, and in one embodiment, is 2:1 to 5:1.

In some embodiments, the base may be any inorganic base, organic base or combination thereof. Considering solubility and product stability, the base may be, for example, an organic base of tertiary amine. In one embodiment, the organic base of tertiary amine is triethylamine or N,N-diisopropylethylamine. The molar ratio of the organic base of tertiary amine to the compound as shown by Formula (313) is 1:1 to 20:1, and in one embodiment, 3:1 to 10:1.

The ion exchange serves the function of converting the compound as shown by Formula (321) into a desired form of carboxylic acid or carboxylic salt and the methods of ion exchange are well-known to those skilled in the art. The above conjugation molecule in which the cation is $M^+$ may be obtained by using suitable ion exchange solution and ion exchange condition, which is not described here in detail. In one embodiment, a triethylamine phosphate solution is used in the ion exchange reaction, and the concentration of the triethylamine phosphate solution is 0.2-0.8 M. In one embodiment, the concentration of the triethylamine phosphate solution is 0.4-0.6 M, and with respect to the compound as shown by Formula (313), the amount of the triethylamine phosphate solution is 3-6 L/mol, and in one embodiment, 4-5 L/mol.

The compound as shown by Formula (321) may be isolated from the reaction mixture using any suitable isolation methods. In some embodiments, the compound as shown by Formula (321) may be isolated by removal of solvent via evaporation followed by chromatography, for example, using the following chromatographic conditions for isolation: normal phase purification: 200-300 mesh silica gel filler, gradient elution of 1 wt ‰ triethylamine in dichloromethane:methanol=100:18-100:20; reverse phase purification: C18 and C8 reverse phase filler, gradient elution of methanol:acetonitrile=0.1:1-1:0.1. In some embodiments, the solvent may be directly removed to obtain a crude product of the compound as shown by Formula (321), which may be directly used in subsequent reactions.

In some embodiments, the method for preparing the compound as shown by Formula (321) further comprises: contacting the product obtained from the above ion exchanging reaction with a solid phase support with amino or hydroxy groups in an organic solvent under condensation reaction condition in the presence of a condensation agent and an organic base of tertiary amine. In this case, a compound as shown by Formula (321) is obtained, wherein $R_4$ comprises a group 1 which comprises a hydroxy protecting group and a group 2 which a structure as shown by Formula (C1').

The solid phase support is one of the supports used in solid phase synthesis of siRNA, some of which are well-known to those skilled in the art. For example, the solid phase support may be selected from the solid phase supports containing an active hydroxy or amino functional group, and in one embodiment, is an amino or hydroxy resin. For the purpose of facilitating subsequent solid phase synthesis of nucleic acid, in one embodiment, the amino or hydroxy resin has the following parameters: particle size of 100-400 mesh, and surface amino or hydroxy loading of 0.2-0.5 mmol/g. The ratio of the compound as shown by Formula (321) to the solid phase support is 10-400 μmol/g. In one embodiment, the ratio of the compound of Formula (321) to the solid phase support is 50 μmol/g to 200 μmol/g.

The organic solvent is one or more of acetonitrile, an epoxy solvent, an ether solvent, an haloalkane solvent, dimethyl sulfoxide, N,N-dimethylformamide, and N,N-diisopropylethylamine. In one embodiment, the epoxy solvent is dioxane and/or tetrahydrofuran; the ether solvent is diethyl ether and/or methyl tertbutyl ether; the haloalkane solvent is one or more of dichloromethane, trichloromethane and 1,2-dichloroethane. In one embodiment, the organic solvent is acetonitrile. With respect to the compound as shown by Formula (321), the amount of the organic solvent is 20-200 L/mol, and in one embodiment, 50-100 L/mol.

The condensation agent may be benzotriazol-1-yl-oxytripyrrolidinophosphonium hexafluorophosphate, 3-diethoxyphosphoryl-1,2,3-benzotrizin-4(3H)-one and/or O-benzotriazol-tetramethyluronium hexafluorophosphate. In one embodiment, the condensation agent is O-benzotriazol-tetramethyluronium hexafluorophosphate. The molar ratio of the condensation agent to the compound as shown by Formula (321) is 1:1 to 20:1, and in one embodiment, 1:1 to 5:1.

In some embodiments, the organic base of tertiary amine is triethylamine and/or N,N-diisopropylethylamine, and in one embodiment, N,N-diisopropylethylamine. The molar ratio of the organic base of tertiary amine to the compound as shown by Formula (321) is 1:1 to 20:1, and in one embodiment, 1:1 to 5:1.

In some embodiments, the method for preparing the compound as shown by Formula (321) further comprises: contacting the resultant condensation product with a capping agent and an acylation catalyst in an organic solvent under capping reaction condition, and isolating the compound as shown by Formula (321). The capping reaction is used to remove any active functional group that does not completely react, so as to avoid producing unnecessary by-products in subsequent reactions. The capping reaction condition comprises a reaction temperature of 0-50° C., and in one embodiment, 15-35° C., and a reaction time of 1-10 hours, and in one embodiment, 3-6 hours. The capping agent may be a capping agent used in solid phase synthesis of siRNA, which are well-known to those skilled in the art.

In some embodiments, the capping agent is composed of capping agent 1 (cap1) and capping agent 2 (cap2). The cap1 is N-methylimidazole, and in one embodiment, provided as a mixed solution of N-methylimidazole in pyridine/acetonitrile, wherein the volume ratio of pyridine to acetonitrile is 1:10 to 1:1, and in one embodiment, 1:3 to 1:1. In one embodiment, the ratio of the total volume of pyridine and acetonitrile to the volume of N-methylimidazole is 1:1 to 10:1, and in one embodiment, 3:1 to 7:1. The cap2 is acetic anhydride. In one embodiment, the cap2 is provided as a solution of acetic anhydride in acetonitrile, wherein the volume ratio of acetic anhydride to acetonitrile is 1:1 to 1:10, and in one embodiment, 1:2 to 1:6.

In some embodiments, the ratio of the volume of the mixed solution of N-methylimidazole in pyridine/acetonitrile to the weight of the compound of Formula (321) is 5 ml/g-50 ml/g, and in one embodiment, 15 ml/g-30 ml/g. The ratio of the volume of the solution of acetic anhydride in acetonitrile to the weight of the compound of Formula (321) is 0.5 ml/g-10 ml/g, and in one embodiment, 1 ml/g-5 ml/g.

In one embodiment, the capping agent comprises equimolar acetic anhydride and N-methylimidazole. The organic solvent is one or more of acetonitrile, an epoxy solvent, an ether solvent, an haloalkane solvent, dimethyl sulfoxide, N,N-dimethylformamide, and N,N-diisopropylethylamine. In one embodiment, the organic solvent is acetonitrile. With respect to the compound as shown by Formula (321), the amount of the organic solvent is 10-50 L/mol, and in one embodiment, 5-30 L/mol.

The acylation catalyst may be selected from any catalyst that may be used for esterification condensation or amidation condensation, such as alkaline heterocyclic compounds. In one embodiment, the acylation catalyst is 4-dimethylaminopyridine. The weight ratio of the catalyst to the compound as shown by Formula (321) may be 0.001:1 to 1:1, and in one embodiment, 0.01:1 to 0.1:1.

The compound as shown by Formula (321) may be isolated from the reaction mixture by any suitable separation methods. In some embodiments, the compound of Formula (321) may be obtained by thoroughly washing with an organic solvent and filtering to remove unreacted reactants, excess capping agent and other impurities, wherein the organic solvent is selected from acetonitrile, dichloromethane, or methanol. In one embodiment, the organic solvent is acetonitrile.

In some embodiments, the preparation of the conjugation molecule as shown by Formula (321) comprises contacting a compound as shown by Formula (313) with a phosphorodiamidite in an organic solvent under coupling reaction condition in the presence of a coupling agent, and isolating the compound as shown by Formula (321). In this case, a compound as shown by Formula (321) is obtained, wherein $R_4$ comprises a group 1 comprising a hydroxy protecting group and a group 2 having a structure as shown by Formula (C3).

The coupling reaction condition comprises a reaction temperature of 0-50° C., such as 15-35° C. The molar ratio of the compound of Formula (313) to the phosphorodiamidite is 1:1 to 1:50, such as 1:5 to 1:15. The molar ratio of the compound of Formula (313) to the coupling agent is 1:1 to 1:100, such as 1:50 to 1:80. The reaction time is 200-3000 seconds, such as 500-1500 seconds. The phosphorodiamidite may be, for example, bis(diisopropylamino)(2-cyanoethoxy)phosphine, which may be commercially available or synthesized according to methods well-known in the art. The coupling agent is selected from one or more of 1H-tetrazole, 5-ethylthio-1H-tetrazole and 5-benzylthio-1H-tetrazole, such as 5-ethylthio-1H-tetrazole. The coupling reaction may be performed in an organic solvent. The organic solvent is selected from one or more of anhydrous acetonitrile, anhydrous DMF and anhydrous dichloromethane, such as anhydrous acetonitrile. With respect to the compound as shown by Formula (313), the amount of the organic solvent is 3-50 L/mol, such as 5-20 L/mol. By performing the coupling reaction, the hydroxy group in the compound (313) reacts with the phosphorodiamidite to form a phosphoramidite group. In some embodiments, the solvent may be directly removed to obtain a crude product of the compound as shown by Formula (321), which may be directly used in subsequent reactions.

In some embodiments, the method for preparing the compound as shown by Formula (321) further comprises: further contacting the isolated product with a solid phase support with hydroxy groups in an organic solvent under coupling reaction condition in the presence of a coupling agent, followed by capping, oxidation, and isolation, to obtain the compound as shown by Formula (321), where $R_4$ comprises a group 1 comprising a hydroxy protecting group and a group 2 having a structure as shown by Formula (C3').

The solid phase support is a support well-known in the art for solid phase synthesis of nucleic acid, such as a deprotected universal solid phase support, which is commercially available (NittoPhase®HL UnyLinker™ 300 Oligonucleotide Synthesis Support, Kinovate Life Sciences, as shown by Formula B80):

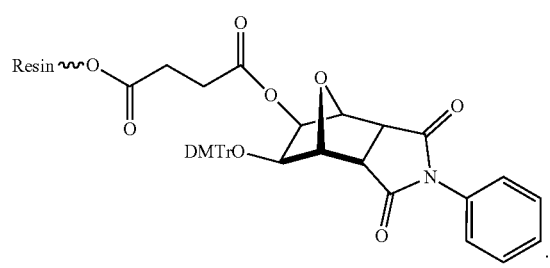

(B80)

A deprotection reaction is well known to those skilled in the art. In one embodiment, the deprotection condition comprises a temperature of 0-50° C., such as 15-35° C., and a reaction time of 30-300 seconds, such as 50-150 seconds. The deprotection agent may be selected from one or more of trifluoroacetic acid, trichloroacetic acid, dichloroacetic acid, and monochloroacetic acid. In some embodiments, the deprotection agent is dichloroacetic acid.

The molar ratio of the deprotection agent to the protecting group -DMTr (4,4'-dimethoxytrityl) on the solid phase support is 2:1 to 100:1, such as 3:1 to 50:1. Through such deprotection, reactive free hydroxy groups are obtained on the surface of the solid phase support, for facilitating the subsequent coupling reaction.

The coupling reaction condition and the coupling agent may be selected as above. Through such a coupling reaction, the free hydroxy groups formed in the deprotection react with the phosphoramidite groups, so as to form a phosphite ester linkage.

The capping reaction condition comprises a temperature of 0-50° C., such as 15-35° C., and a reaction time of 5-500 seconds, such as 10-100 seconds. The capping reaction is carried out in the presence of the capping agent. The selection and amount of the capping agent are as above.

The oxidation reaction condition may comprise a temperature of 0-50° C., such as 15-35° C., and a reaction time of 1-100 seconds, such as 5-50 seconds. The oxidation agent may be, for example, iodine (in some embodiments, provided as iodine water). The molar ratio of the oxidation agent to the phosphite ester group is 1:1 to 100:1, such as 5:1 to 50:1. In some embodiments, the oxidation reaction is performed in a mixed solvent in which the ratio of tetrahydrofuran:water:pyridine=3:1:1-1:1:3.

In one embodiment, $R_6$ is one of the groups as shown by Formula B7 or B8:

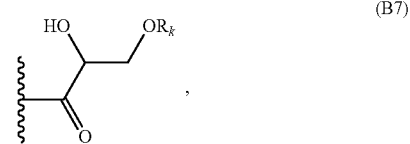

(B7)

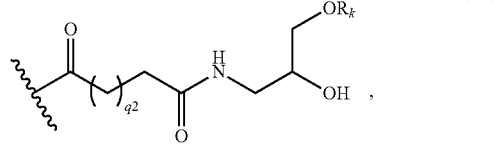

(B8)

wherein the definition of $q_2$ is as described above.

In this case, the compound shown in the Formula (313) may be obtained by the following preparation method comprising: contacting the compound as shown by Formula (314) with a compound as shown by Formula (A-1) or (A-2) in an organic solvent under amidation reaction condition in the presence of a condensation agent for amidation reaction and an organic base of tertiary amine, followed by isolation:

Formula (314)

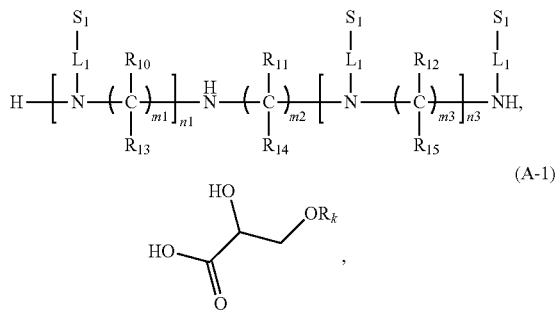

(A-1)

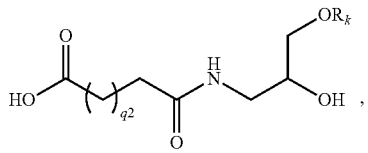

(A-2)

wherein the definitions and options of n1, n3, m1, m2, m3, $R_{10}$, $R_{11}$, $R_{12}$, $R_{13}$, $R_{14}$, $R_{15}$, $L_1$, $S_1$, $q_2$ and $R_k$ are respectively as described above.

The amidation reaction condition comprises a reaction temperature of 0-100° C. and a reaction time of 1-48 hours. In one embodiment, the amidation reaction condition comprises a reaction temperature of 10-40° C. and a reaction time of 2-16 hours.

The organic solvent is one or more of an alcohol solvent, an epoxy solvent, an ether solvent, an haloalkane solvent, dimethyl sulfoxide, N,N-dimethylformamide, and N,N-diisopropylethylamine. In one embodiment, the alcohol solvent is one or more of methanol, ethanol and propanol, and in one embodiment, ethanol. In one embodiment, the epoxy solvent is dioxane and/or tetrahydrofuran. In one embodiment, the ether solvent is diethyl ether and/or methyl tert-butyl ether. In one embodiment, the haloalkane solvent is one or more of dichloromethane, trichloromethane and 1,2-dichloroethane. In one embodiment, the organic solvent is dichloromethane. With respect to the compound as shown by Formula (314), the amount of the organic solvent is 3-50 L/mol, and in one embodiment, 3-20 L/mol.

The condensation agent for amidation reaction is benzotriazol-1-yl-oxytripyrrolidinophosphonium hexafluorophosphate, 3-(diethoxyphosphoryl)-1,2,3-benzotrizin-4(3H)-one, 4-(4,6-dimethoxytriazin-2-yl)-4-methylmorpholine hydrochloride, 2-ethoxy-1-ethoxycarbonyl-1,2-dihydroquinoline (EEDQ) or O-benzotriazol-tetramethyluronium hexafluorophosphate, and in one embodiment, 3-(diethoxyphosphoryl)-1,2,3-benzotrizin-4(3H)-one. The molar ratio of the condensation agent for amidation reaction to the compound as shown by Formula (314) is 1:1 to 10:1, and in one embodiment, 2.5:1 to 5:1.

The organic base of tertiary amine is triethylamine or N,N-diisopropylethylamine, and in one embodiment, N,N-diisopropylethylamine. The molar ratio of the organic base of tertiary amine to the compound as shown by Formula (314) is 3:1 to 20:1, and in one embodiment, 5:1 to 10:1.

The compounds of Formula (A-1) and (A-2) may be prepared by any suitable means. For example, when $R_k$ is a DMTr group, the compound of Formula (A-1) may be prepared by reacting calcium glycerate with DMTrCl. Similarly, the compound of Formula (A-2) may be prepared by firstly contacting 3-amino-1,2-propanediol with a cyclic anhydride and then reacting with DMTrCl, wherein the cyclic anhydride may have 4-13 carbon atoms, and in one embodiment 4-8 carbon atoms. It will be readily understood by those skilled in the art that the selections of different cyclic anhydrides correspond to different values for $q_2$ in the compound of Formula (A-2). For example, when the cyclic anhydride is succinic anhydride, $q_2=1$; when the cyclic anhydride is glutaric anhydride, $q_2=2$, and so on.

In some variations, the compound of Formula (313) can also be prepared by successively reacting the compound as shown by Formula (314) with the cyclic anhydride, 3-amino-1,2-propanediol, and DMTrCl. It will be readily understood by those skilled in the art that these variations would not affect the structure and function of the compound of Formula (313), and these variations are readily achieved by those skilled in the art on the basis of the above methods.

Similarly, the compound as shown by Formula (313) may be isolated from the reaction mixture by any suitable isolation methods. In some embodiments, the compound as shown by Formula (313) may be isolated by removal of solvent via evaporation followed by chromatography. For example, the following chromatographic conditions may be used for isolation: normal phase purification of silica gel: 200-300 mesh silica gel filler, with gradient elution of petroleum ether:ethyl acetate:dichloromethane:N,N-dimethylformamide=1:1:1:0.5-1:1:1:0.6; reverse phase purification: C18 and C8 reverse phase fillers, with gradient elution of methanol:acetonitrile=0.1:1-1:0.1. In some embodiments, the solvent may be directly removed to obtain a crude product of the compound as shown by Formula (313), which may be directly used in subsequent reactions.

The compound as shown by Formula (314) may be obtained by the following preparation method comprising: contacting the compound as shown by Formula (315) with haloacetic acid in an organic solvent under deprotection reaction condition, followed by isolation:

Formula (315)

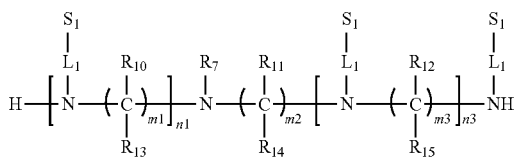

wherein $R_7$ is selected from the groups as shown by Formula (330), (331), (332) or (333), and in one embodiment, $R_7$ has the structure as shown by Formula (330):

Formula (330)

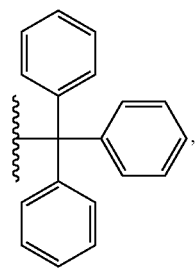

Formula (331)

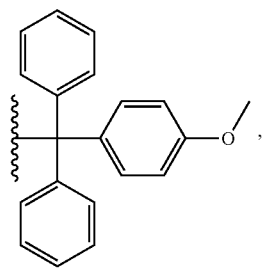

Formula (332)

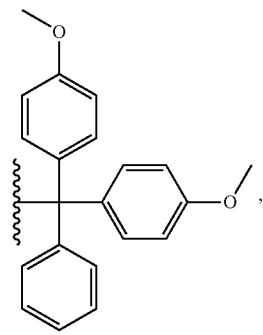

Formula (333)

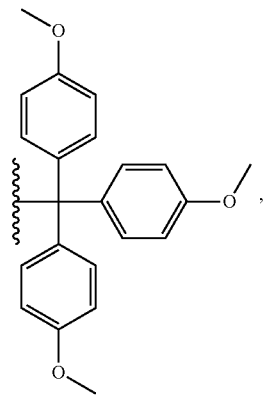

the definitions and options of n1, n3, m1, m2, m3, $R_{10}$, $R_{11}$, $R_{12}$, $R_{13}$, $R_{14}$, $R_{15}$, $L_1$, and $S_1$ are respectively as described above.

The haloacetic acid is selected from one or more of dichloroacetic acid, trichloroacetic acid, monochloroacetic acid and trifluoroacetic acid, and in one embodiment, dichloroacetic acid.

The deprotection reaction condition comprises a reaction temperature of 0-100° C. and a reaction time of 0.1-24 hours, and in one embodiment, a reaction temperature of 10-40° C. and a reaction time of 0.5-16 hours.

The organic solvent is one or more of an epoxy solvent, an ether solvent, an haloalkane solvent, dimethyl sulfoxide, N,N-dimethylformamide, and N,N-diisopropylethylamine. In one embodiment, the epoxy solvent is dioxane and/or tetrahydrofuran. In one embodiment, the ether solvent is diethyl ether and/or methyl tert-butyl ether. In one embodiment, the haloalkane solvent is one or more of dichloromethane, trichloromethane and 1,2-dichloroethane. In one embodiment, the organic solvent is dichloromethane. The amount of the organic solvent is 3-50 L/mol, and in one embodiment, 5-20 L/mol, with respect to the compound as shown by Formula (315).

The molar ratio of the haloacetic acid to the compound as shown by Formula (315) is 5:1 to 100:1, and in one embodiment, 10:1 to 50:1.

Similarly, the compound as shown by Formula (314) may be isolated from the reaction mixture by any suitable isolation methods. In some embodiments, the compound as shown by Formula (314) may be isolated by removal of solvent via evaporation followed by chromatography, for example, using the following chromatographic conditions for isolation: normal phase purification of silica gel: 200-300 mesh silica gel filler, with gradient elution of dichloromethane:methanol=100:30-100:40; reverse phase purification:

C18 and C8 reverse phase fillers, with gradient elution of methanol:acetonitrile=0.1:1-1:0.1. In some embodiments, the solvent may be directly removed to obtain a crude product of the compound as shown by Formula (314), which may be directly used in subsequent reactions.

The compound as shown by Formula (315) may be obtained by the following method comprising: contacting the compound as shown by Formula (317) with the compound as shown by Formula (316) in an organic solvent under condensation reaction condition in the presence of a condensation agent for amidation reaction and an organic base of tertiary amine, followed by isolation:

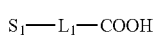

Formula (316)

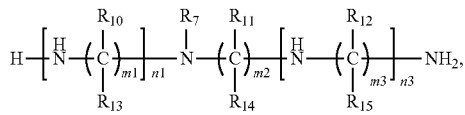

Formula (317)

wherein the definitions and options of n1, n3, m1, m2, m3, $R_7$, $R_{10}$, $R_{11}$, $R_{12}$, $R_{13}$, $R_{14}$, $R_{15}$, $L_1$, and $S_1$ are respectively as described above.

The compound of Formula (316) can be, such as, those disclosed in J. Am. Chem. Soc. 2014, 136, 16958-16961. Alternatively, the compounds of Formula (316) may be prepared by those skilled in the art via various methods. For example, some compounds of Formula (316) may be prepared according to the disclosure in Example 1 of U.S. Pat. No. 8,106,022B2, which is incorporated herein by reference in its entirety.

The condensation reaction condition comprises a reaction temperature of 0-100° C. and a reaction time of 0.1-24 hours, and in one embodiment, a reaction temperature of 10-40° C. and a reaction time of 0.5-16 hours.

The molar ratio of the compound as shown by Formula (316) to the compound as shown by Formula (317) is 2:1 to 10:1, and in one embodiment, 2.5:1 to 5:1.

The organic solvent is one or more of acetonitrile, an epoxy solvent, an ether solvent, an haloalkane solvent, dimethyl sulfoxide, N,N-dimethylformamide and N,N-diisopropylethylamine. In one embodiment, the epoxy solvent is dioxane and/or tetrahydrofuran. In one embodiment, the ether solvent is diethyl ether and/or methyl tert-butyl ether. In one embodiment, the haloalkane solvent is one or more of dichloromethane, trichloromethane and 1,2-dichloroethane. In one embodiment, the organic solvent is acetonitrile. With respect to the compound as shown by Formula (317), the amount of the organic solvent is 3-50 L/mol, and in one embodiment, 5-20 L/mol.

The condensation agent for amidation reaction is benzotriazol-1-yl-oxytripyrrolidinophosphonium hexafluorophosphate, 3-(diethoxyphosphoryl)-1,2,3-benzotrizin-4(3H)-one (DEPBT), O-benzotriazol-tetramethyluronium hexafluorophosphate or 4-(4,6-dimethoxytriazin-2-yl)-4-methylmorpholine hydrochloride, and in one embodiment, 4-(4,6-dimethoxytriazin-2-yl)-4-methylmorpholine hydrochloride. The molar ratio of the condensation agent for amidation reaction to the compound as shown by Formula (317) is 2:1 to 10:1, and in one embodiment, 2.5:1 to 5:1.

The organic base of tertiary amine is N-methylmorpholine, triethylamine or N,N-diisopropylethylamine, and in one embodiment, N-methylmorpholine. The molar ratio of the organic base of tertiary amine to the compound as shown by Formula (317) is 3:1 to 20:1, and in one embodiment, 5:1 to 10:1.

Similarly, the compound as shown by Formula (315) may be isolated from the reaction mixture by any suitable isolation methods. In some embodiments, the compound as shown by Formula (315) is isolated by removal of solvent via evaporation followed by chromatography, for example, using the following chromatographic conditions for isolation: normal phase purification of silica gel: 200-300 mesh silica gel filler, with gradient elution of dichloromethane:methanol=100:5-100:7; reverse phase purification: C18 and C8 reverse phase fillers, with gradient elution of methanol:acetonitrile=0.1:1-1:0.1. In some embodiments, the solvent is directly removed to obtain a crude product of the compound as shown by Formula (315), which may be directly used in subsequent reactions.

In some embodiments, the compound of Formula (317) reacts with a sufficient amount of one compound of Formula (316) in one batch to obtain the desired compound of Formula (315), wherein all $S_1$-$L_1$ moieties are identical. In some embodiments, the compound of Formula (317) is reacted with different compounds of Formula (316) in batches as desired, i.e., the compounds of Formula (316) having different $L_1$ and/or $S_1$, so as to obtain the compound of Formula (315) having more than two types of $S_1$ and/or $L_1$ therein. For example, 1 eq of the compound of Formula (317) may be firstly contacted with 2 eq of the first compound of Formula (316) to attach a first $S_1$-$L_1$ moieties to the two terminal primary amine groups in the compound of Formula (317), and then contacted with the (n3+n1-1) eq of the second compound of Formula (316) to attach a second $S_1$-$L_1$ moieties to the (n3+n1-1) secondary amine groups in the compound of Formula (317), wherein the definition and ranges of n3 and n1 are as described above.

The compound as shown by Formula (317) may be obtained by the following method comprising: contacting the compound as shown by Formula (318) with aqueous methylamine solution under deprotection reaction condition in the presence of an organic solvent, followed by isolation:

Formula (318)

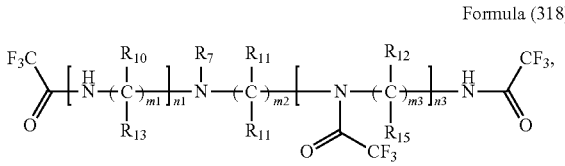

wherein the definitions and options of n1, n3, m1, m2, m3, $R_7$, $R_{10}$, $R_{11}$, $R_{12}$, $R_{13}$, $R_{14}$ and $R_{15}$ are respectively as defined above.

The deprotection reaction condition comprises a reaction temperature of 0-150° C. and a reaction time of 5-72 hours, and in one embodiment, a reaction temperature of 20-80° C. and a reaction time of 10-30 hours.

The organic solvent is selected from alcohols, in one embodiment, is one of methanol, ethanol and isopropanol, and in one embodiment, methanol. The amount of the organic solvent is 1-20 L/mol, and in one embodiment, 1.5-10 L/mol, with respect to the compound as shown by Formula (318).

The concentration of the aqueous methylamine solution is 30-40 wt %, and the molar ratio of methylamine to the compound as shown by Formula (318) is 10:1 to 500:1, and in one embodiment, 50:1 to 200:1.

Similarly, the compound as shown by Formula (317) may be isolated from the reaction mixture using any suitable isolation methods. In some embodiments, the compound as shown by Formula (317) may be isolated by removal of solvent via evaporation followed by chromatography, for example, using the following chromatographic conditions for isolation: normal phase purification of silica gel: 200-300 mesh silica gel filler, with gradient elution of dichloromethane:methanol:aqueous ammonia (25 wt %)=1:1:0.05-1:1:0.25; reverse phase purification: C18 and C8 reverse phase fillers, with gradient elution of methanol:acetonitrile=0.1:1-1:0.1. In some embodiments, the solvent may be directly removed to obtain a crude product of the compound as shown by Formula (317), which may be directly used in subsequent reactions.

The compound as shown by Formula (318) may be obtained by the following method comprising: contacting the compound as shown by Formula (319) with triphenylchloromethane (TrCl), diphenylethylphenylchloromethane, phenyldiethylphenylchloromethane or triethylphenylchloromethane, and in one embodiment, with triphenylchloromethane (TrCl) under substitution reaction condition in the presence of an organic solvent, followed by isolation:

Formula (319)

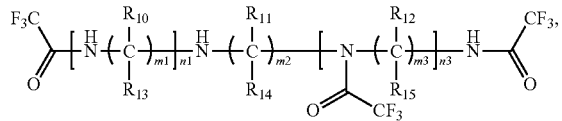

wherein the definitions and options of n1, n3, m1, m2, m3, $R_{10}$, $R_{11}$, $R_{12}$, $R_{13}$, $R_{14}$ and $R_{15}$ are respectively as described above.

The substitution reaction condition comprises a reaction temperature of 0-100° C. and a reaction time of 5-72 hours, and in one embodiment, a reaction temperature of 10-40° C. and a reaction time of 10-30 hours.

Triphenylchloromethane (TrCl), diphenylethylphenylchloromethane, phenyldiethylphenylchloromethane or triethylphenylchloromethane are commercially available. The molar ratio of triphenylchloromethane (TrCl), diphenylethylphenylchloromethane, phenyldiethylphenylchloromethane or triethylphenylchloromethane to the compound as shown by Formula (319) is 1:1 to 10:1, and in one embodiment, 1:1 to 3:1.

The organic solvent is one or more of an epoxy solvent, an ether solvent, an haloalkane solvent, dimethyl sulfoxide, N,N-dimethylformamide, and N,N-diisopropylethylamine. In one embodiment, the epoxy solvent is dioxane and/or tetrahydrofuran. In one embodiment, the ether solvent is diethyl ether and/or methyl tert-butyl ether. In one embodiment, the haloalkane solvent is one or more of dichloromethane, trichloromethane and 1,2-dichloroethane. In one embodiment, the organic solvent is dichloromethane. With respect to the compound as shown by Formula (319), the amount of the organic solvent is 3-50 L/mol, and in one embodiment, 5-20 L/mol.

Similarly, the compound as shown by Formula (318) may be isolated from the reaction mixture by any suitable isolation methods. In some embodiments, the compound as shown by Formula (318) may be isolated by removal of solvent via evaporation followed by chromatography, for example, using the following chromatographic conditions for isolation: normal phase purification of silica gel: 200-300 mesh silica gel filler, with gradient elution of methanol:dichloromethane=0.01:1-0.5:1 or gradient elution of methanol:dichloromethane:ethyl acetate:petroleum ether=0.1:1:1:1-1:1:1:1; reverse phase purification: C18 and C8 reverse phase fillers, with gradient elution of methanol:acetonitrile=0.1:1-1:0.1. In some embodiments, the solvent may be directly removed to obtain a crude product of the compound as shown by Formula (318), which may be directly used in subsequent reactions.

The compound as shown by Formula (319) may be obtained by the following method comprising: contacting the compound as shown by Formula (320) with ethyl trifluoroacetate in an organic solvent under substitution reaction condition, followed by isolation:

Formula (320)

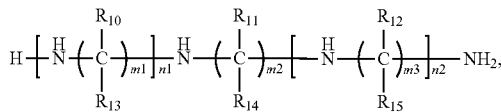

wherein the definitions and options of n1, n3, m1, m2, m3, $R_{10}$, $R_{11}$, $R_{12}$, $R_{13}$, $R_{14}$ and $R_{15}$ are respectively as described above.

The organic solvent is one or more of acetonitrile, an epoxy solvent, an ether solvent, an haloalkane solvent, dimethyl sulfoxide, N,N-dimethylformamide, and N,N-diisopropylethylamine. In one embodiment, the epoxy solvent is dioxane and/or tetrahydrofuran. In one embodiment, the ether solvent is diethyl ether and/or methyl tert-butyl ether. In one embodiment, the haloalkane solvent is one or more of dichloromethane, trichloromethane and 1,2-dichloroethane. In one embodiment, the organic solvent is acetonitrile. With respect to the compound as shown by Formula (320), the amount of the organic solvent is 1-50 L/mol, and in one embodiment, 1-20 L/mol.

The substitution reaction condition comprises a reaction temperature of 0-100° C. and a reaction time of 5-72 hours, and in one embodiment, a reaction temperature of 10-40° C. and a reaction time of 10-30 hours.

The compound as shown by Formula (320) may be commercially available, or obtained by those skilled in the art via the known methods. For example, in the case that m1=m2=m3=3, n1=1, n3=2, and $R_{10}$, $R_{11}$, $R_{12}$, $R_{13}$, $R_{14}$ and $R_{15}$ are all H, the compound as shown by Formula (320) is commercially available from Alfa Aesar Inc.

The molar ratio of ethyl trifluoroacetate to the compound as shown by Formula (320) is 2:1 to 10:1, and in one embodiment, 3:1 to 5:1.

Similarly, the compound as shown by Formula (319) may be isolated from the reaction mixture using any suitable isolation methods. In some embodiments, the compound as shown by Formula (319) may be isolated by removal of solvent via evaporation followed by chromatography, for example, using the following chromatographic conditions for isolation: normal phase purification of silica gel: 200-300 mesh silica gel filler, with gradient elution of methanol:dichloromethane=0.01:1-0.5:1 or gradient elution of methanol:dichloromethane:ethyl acetate:petroleum ether=0.1:1:1:1-1:1:1:1; reverse phase purification: C18 and C8 reverse phase fillers, with gradient elution of methanol:acetonitrile=0.1:1-1:0.1. In some embodiments, the solvent may be directly removed to obtain a crude product of the compound as shown by Formula (319), which may be directly used in subsequent reactions.

In the siRNA and the conjugate comprising the siRNA provided by the present disclosure, each pair of adjacent nucleotides is linked via a phosphodiester bond or phosphorothioate diester bond. The non-bridging oxygen or sulfur atom in the phosphodiester bond or phosphorothioate diester bond is negatively charged, and may be present in the form of hydroxy or sulfhydryl. Moreover, the hydrogen ion in the hydroxy or sulfhydryl may be partially or completely substituted with a cation. The cation may be any cation, such as a metal cation, an ammonium cation $NH_4^+$ or an organic ammonium cation. In order to increase solubility, in one embodiment, the cation is selected from one or more of an alkali metal cation, an ammonium cation formed by a tertiary amine and a quaternary ammonium cation. The alkali metal ion may be $K^+$ and/or $Na^+$, and the cation formed by a tertiary amine may be an ammonium cation formed by triethylamine and/or an ammonium cation formed by N,N-diisopropylethylamine. Thus, the siRNA and conjugate of the present disclosure can be at least partially present in the form of salt. In one embodiment, non-bridging oxygen atom or sulfur atom in the phosphodiester bond or phosphorothioate diester bond at least partly binds to sodium ion, and thus the siRNA and conjugate of the present disclosure is present or partially present in the form of sodium salt.

Those skilled in the art clearly know that a modified nucleotide may be introduced into the siRNA of the conjugate of the present disclosure by a nucleoside monomer with a corresponding modification. The methods for preparing a nucleoside monomer having the corresponding modification and the methods for introducing a modified nucleotide into a siRNA are also well-known to those skilled in the art. All modified nucleoside monomers may be either commercially available or prepared by known methods.

Use of the siRNA, the Pharmaceutical Composition and the siRNA Conjugate of the Present Disclosure In some embodiments, the present disclosure provides use of the siRNA, the pharmaceutical composition and/or the siRNA conjugate provided by the present disclosure in the manufacture of a medicament for treating and/or preventing a pathological condition or disease caused by the infection of hepatitis B virus.

In some embodiments, the present disclosure provides a method for treating a pathological condition or disease caused by the infection of hepatitis B virus, which comprises administering an effective amount of the siRNA, the pharmaceutical composition and/or the siRNA conjugate provided by the present disclosure to a patient.

In some embodiments, the present disclosure provides a method for inhibiting the expression of hepatitis B virus gene, which comprises contacting an effective amount of the siRNA, the pharmaceutical composition and/or the siRNA conjugate provided by the present disclosure with hepatitis cells infected with hepatitis B virus.

The pathological condition or disease caused by the infection of hepatitis B virus is selected from chronic liver disease, hepatitis, hepatic fibrosis disease and liver proliferative disease.

The purpose of treating and/or preventing hepatitis B may be achieved through the mechanism of RNA interference by administering an effective amount of the siRNA and/or the pharmaceutical composition and/or the siRNA conjugate of the present disclosure to a patient in need thereof. Therefore, the siRNA and/or the pharmaceutical composition and/or the siRNA conjugate of the present disclosure may be used for preventing and/or treating hepatitis B, or for preparing a medicament for preventing and/or treating hepatitis B.

In some embodiments, the present disclosure provides use of the siRNA, the pharmaceutical composition and/or the siRNA conjugate provided by the present disclosure in the manufacture of a medicament for treating and/or preventing a pathological condition or disease caused by the overexpression of any gene.

In some embodiments, the present disclosure provides a method for treating a pathological condition or disease caused by the overexpression of any gene, which comprises administering an effective amount of the siRNA, the pharmaceutical composition and/or the siRNA conjugate provided by the present disclosure to a patient.

In some embodiments, the present disclosure provides a method for inhibiting gene expression, which comprises contacting an effective amount of the siRNA, the pharmaceutical composition and/or the siRNA conjugate provided by the present disclosure with the cells expressing the gene.

The pathological condition or disease caused by the overexpression of any gene is selected from various chronic diseases, inflammation, fibrosis diseases, and proliferative diseases, such as cancer.

The purpose of treating the disease can be achieved through the mechanism of RNA interference by administering the siRNA and/or the pharmaceutical composition and/or the siRNA conjugate of the present disclosure to a patient in need thereof. Therefore, the siRNA and/or the pharmaceutical composition and/or the siRNA conjugate of the present disclosure may be used for preventing and/or treating the diseases caused by the overexpression of any gene, or for preparing a medicament for preventing and/or treating the diseases caused by the overexpression of any gene.

As used herein, the term "administration/administer" refers to the delivery of the siRNA or the pharmaceutical composition or the siRNA conjugate into a patient's body by a method or a route that at least partly locates the siRNA or the pharmaceutical composition or the siRNA conjugate at a desired site to produce a desired effect. Suitable administration routes for the methods of the present disclosure include topical administration and systemic administration. In general, topical administration results in the delivery of more siRNA or pharmaceutical composition or siRNA conjugate to a particular site compared with the whole body of the patient; whereas systemic administration results in the delivery of the siRNA or the pharmaceutical composition or the siRNA conjugate to substantially the whole body of the patient. Considering that the present disclosure is intended to provide a means for preventing and/or treating hepatitis B, in some specific embodiments, an administration mode of delivering a drug to the liver is used.

The administration to a patient may be achieved by any suitable routes known in the art, including but not limited to, oral and parenteral route, such as intravenous administration, intramuscular administration, subcutaneous administration, transdermal administration, intratracheal administration (aerosol), pulmonary administration, nasal administration, rectal administration, and topical administration (including buccal administration and sublingual administration). The administration frequency may be once or more times daily, weekly, monthly, or yearly.

The dose of the siRNA or the pharmaceutical composition or the siRNA conjugate of the present disclosure may be a conventional dose in the art, which may be determined according to various parameters, especially age, weight and gender of a patient. Toxicity and efficacy may be measured in cell cultures or experimental animals by standard pharmaceutical procedures, for example, by determining LD50 (the lethal dose that causes 50% population death) and ED50

(the dose that can cause 50% of the maximum response intensity in a graded response, and that causes 50% of the experimental subjects to have a positive response in a qualitative response). The dose range for human may be derived based on data obtained from cell culture assays and animal studies.

When administering the pharmaceutical composition or the siRNA conjugate of the present disclosure, for example, to male or female C57BL/6J mice of 6-12 weeks old and 18-25 g body weight, (i) for the pharmaceutical composition formed by the siRNA and the pharmaceutically acceptable carrier, the amount of the siRNA may be 0.001-50 mg/kg body weight, such as 0.01-10 mg/kg body weight, 0.05-5 mg/kg body weight or 0.1-3 mg/kg body weight; (ii) for the siRNA conjugate formed by the siRNA and the pharmaceutically acceptable conjugation molecule, the amount of the siRNA may be 0.001-100 mg/kg body weight, such as 0.01-50 mg/kg body weight, 0.05-20 mg/kg body weight or 0.1-10 mg/kg body weight, as calculated based on the amount of the siRNA in the pharmaceutical composition or the siRNA conjugate. When administering the siRNA of the present disclosure, the above amounts can be considered for reference.

In addition, the purpose of inhibiting the expression of HBV genes in hepatitis cells infected with chronic HBV may also be achieved through the mechanism of RNA interference by introducing the siRNA and/or the pharmaceutical composition and/or the siRNA conjugate of the present disclosure into hepatitis cells infected with chronic HBV. In some embodiments, the cells are HepG2.2.15 cells.

In the case where the expression of HBV genes in cells is inhibited by using the method provided by the present disclosure, the amount of siRNA in the provided siRNA, the pharmaceutical composition, and/or the siRNA conjugate is typically an amount sufficient to reduce the expression of the target gene and result in an extracellular concentration of 1 pM to 1 μM, or 0.01 nM to 100 nM, or 0.05 nM to 50 nM or 0.05 nM to about 5 nM on the surface of the target cells. The amount required to achieve this local concentration will vary with various factors, including the delivery method, the delivery site, the number of cell layers between the delivery site and the target cells or tissues, the delivery route (topical or systemic), etc. The concentration at the delivery site may be significantly higher than that on the surface of the target cells or tissues.

Kit

The present disclosure provides a kit comprising the siRNA, the pharmaceutical composition and/or the siRNA conjugate as described above.

In some embodiments, one container can be used to provide the siRNA, and at least another container can be used to provide pharmaceutically acceptable carriers and/or excipients. In addition to the siRNA and pharmaceutically acceptable carriers and/or excipients, the kit may further comprise other ingredients, such as stabilizers or preservatives. The other ingredients may be comprised in the kit, but present in a container different from that providing the siRNA and pharmaceutically acceptable carriers and/or excipients. In these embodiments, the kit may comprise an instruction for mixing the siRNA with pharmaceutically acceptable carriers and/or excipients or other ingredients.

In some embodiments, the siRNA conjugate may be kept in one container, while the kit comprises or does not comprise at least another container for providing or not providing pharmaceutically acceptable excipients. In addition to the siRNA conjugate and optional pharmaceutically acceptable excipients, the kit may further comprise additional ingredients, such as stabilizers or preservatives. The additional ingredients may be comprised in the kit, but present in a container other than that for providing the siRNA conjugate and optional pharmaceutically acceptable excipients. In these embodiments, the kit may comprise an instruction for mixing the siRNA conjugate with pharmaceutically acceptable excipients (if any) or other ingredients.

In the kit of the present disclosure, the siRNA and/or the pharmaceutically acceptable carriers and/or excipients as well as the siRNA conjugate and optional pharmaceutically acceptable excipients may be provided in any form, e.g., in a liquid form, a dry form, or a lyophilized form. In some embodiments, the siRNA and/or the pharmaceutically acceptable carriers and/or excipients as well as the siRNA conjugate and optional pharmaceutically acceptable excipients are substantially pure and/or sterile. Sterile water may optionally be provided in the kits of the present disclosure.

Hereinafter, the present disclosure will be further illustrated with reference to Examples, but is not limited thereto in any respect.

EXAMPLES

Hereinafter, the present disclosure will be described with reference to the examples. Unless otherwise specified, the reagents and culture media used in following examples are all commercially available, and the procedures used such as nucleic acid electrophoresis and real-time PCR are all performed according to methods described in Molecular Cloning (Cold Spring Harbor LaBboratory Press (1989)).

Unless otherwise specified, ratios of the reagents provided below are all calculated by volume ratio (v/v).

Preparation Example 1 Preparation of Conjugates 1-3

In this preparation example, Conjugates 1-2 (hereinafter also referred to as L10-siHB3M1SVP conjugate and L10-siHB3M1SP conjugate) were synthesized. Conjugate 3 (hereinafter also referred to as L10-siHB3M1SPs conjugate) is planned to be synthesized. The conjugates were those formed by conjugating the L-9 conjugation molecule to the siRNAs numbered as siHB3M1SVP, siHB3M1SP or siHB3M1SPs, respectively. The conjugated siRNA sequences in the conjugates are shown in Table 3.

(1-1) Synthesis of Compound L-10

Compound L-10 was synthesized according to the following method.

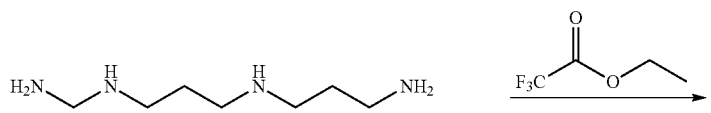

J-0

121
-continued
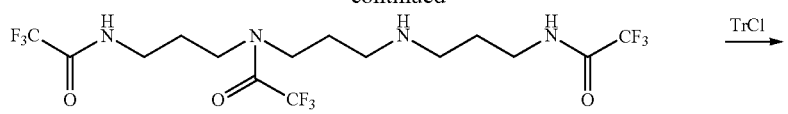
M-11-T3
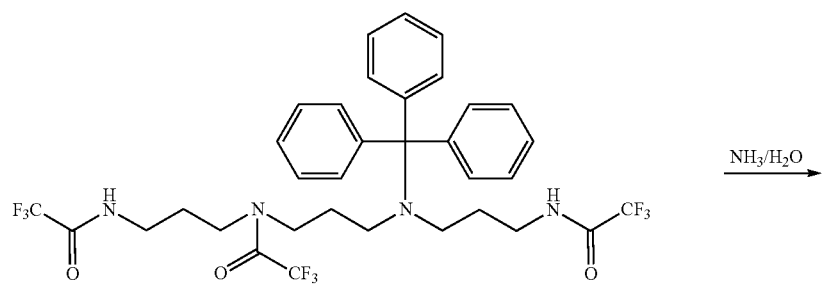
M-11-T3-Tr
122
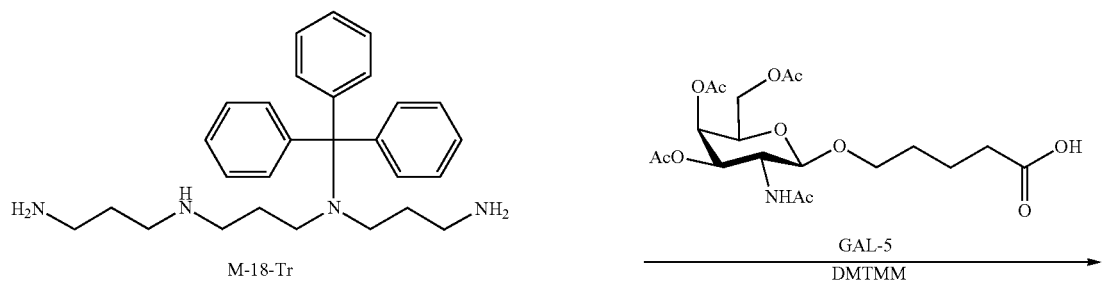
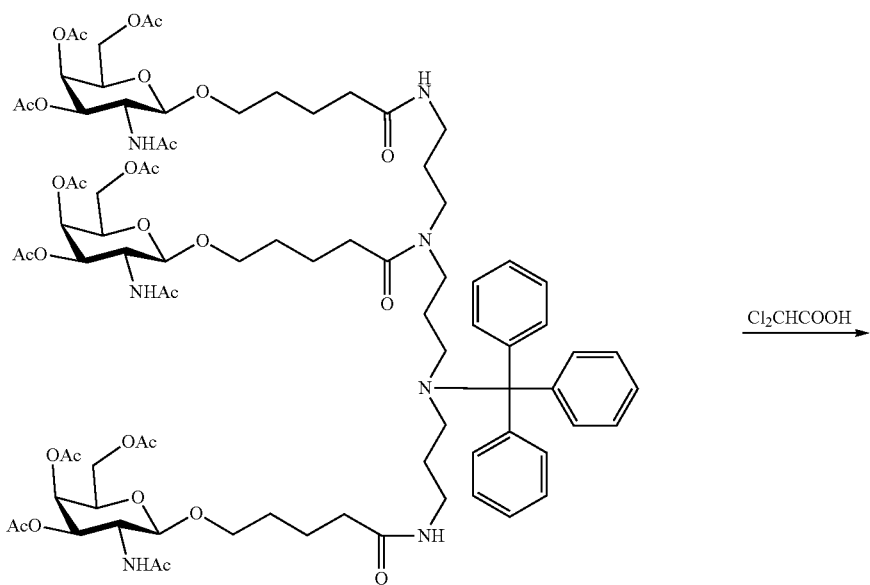
L-5-Tr 123
-continued
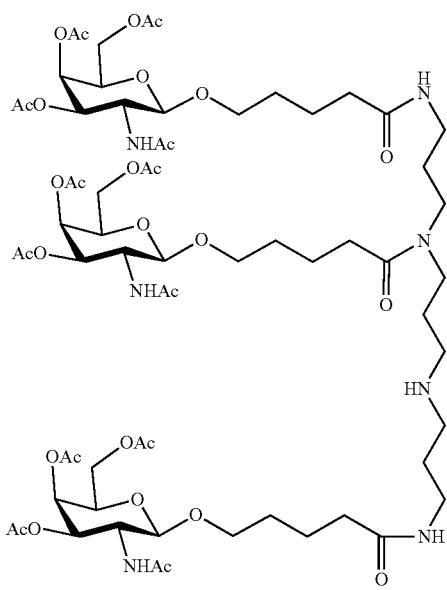
L-8
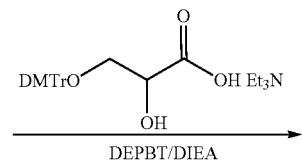
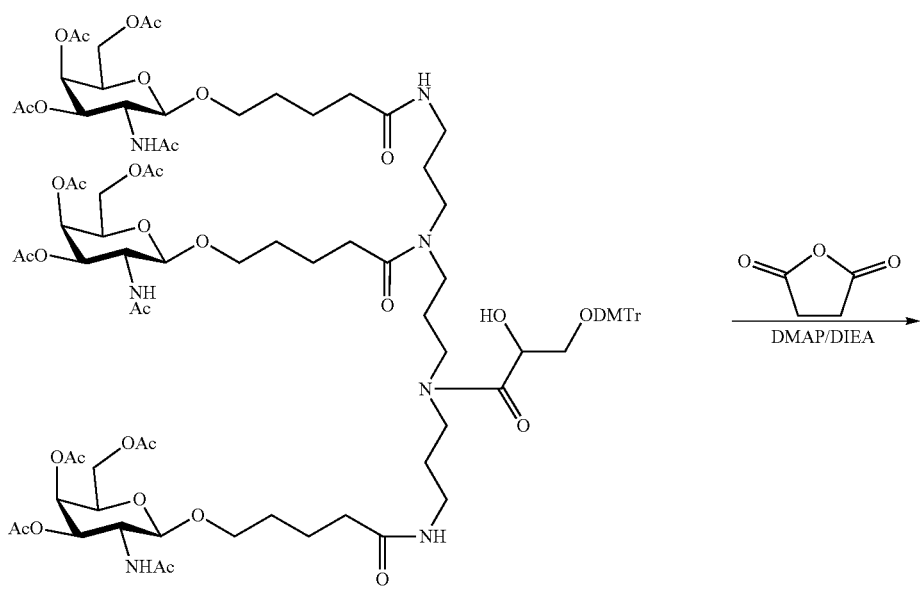
L-7

-continued
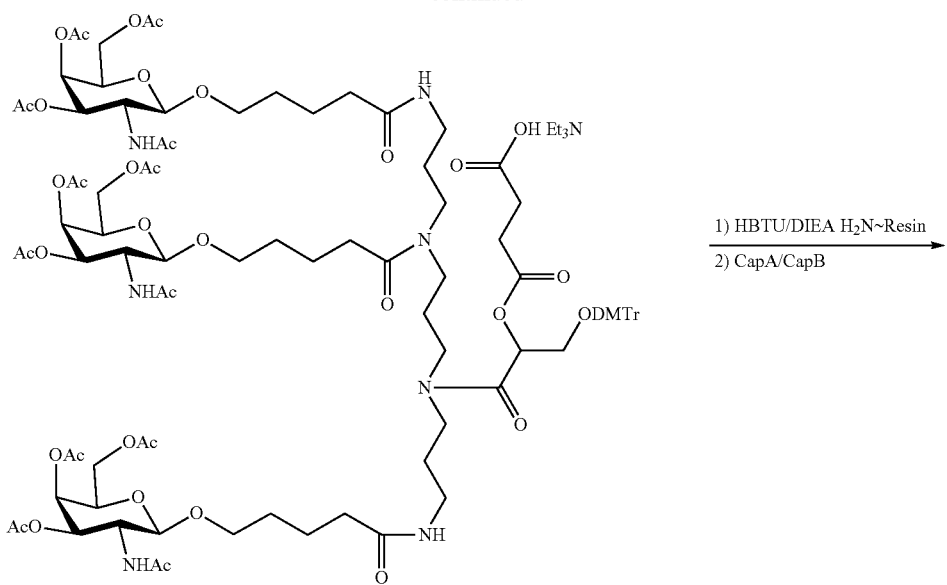
L-9
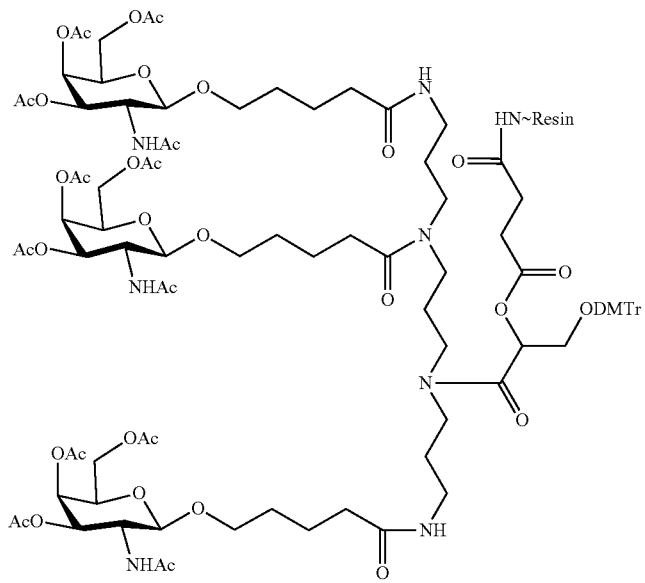
L-10

(1-1-1) Synthesis of GAL-5 (a Terminal Segment of the Conjugation Molecule)

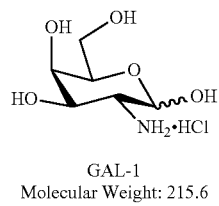

GAL-1
Molecular Weight: 215.6

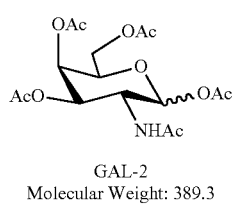

GAL-2
Molecular Weight: 389.3

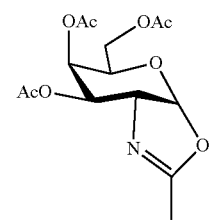

GAL-3
Molecular Weight: 329.3

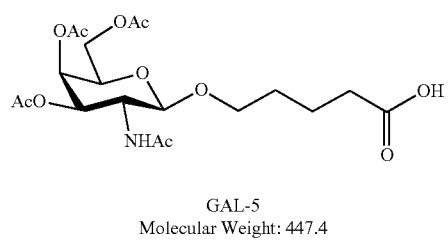

GAL-5
Molecular Weight: 447.4

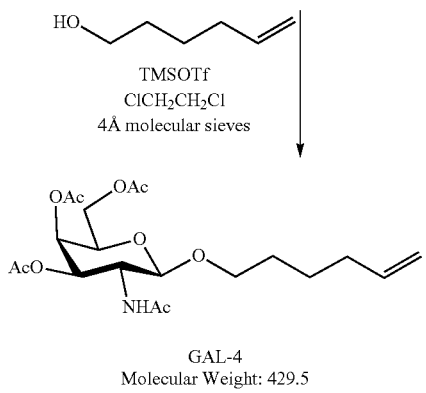

GAL-4
Molecular Weight: 429.5

(1-1-1a) Synthesis of GAL-2

100.0 g of GAL-1 (N-acetyl-D-galactosamine hydrochloride, CAS No.: 1772-03-8, purchased from Ning Bo hongxiang bio-chem Co., Ltd., 463.8 mmol) was dissolved in 1000 ml of anhydrous pyridine, to which 540 ml of acetic anhydride (purchased from Enox Inc., 5565.6 mmol) was added in an ice water bath to react under stirring at room temperature for 1.5 hours. The resultant reaction solution was poured into 10 L of ice water and subjected to suction filtration under reduced pressure. The residue was washed with 2 L of ice water, and then added with a mixed solvent of acetonitrile/toluene (v/v ratio=1:1) until completely dissolved. The solvent was removed by evaporation to give 130.0 g of product GAL-2 as a white solid.

(1-1-1b) Synthesis of GAL-3

GAL-2 (35.1 g, 90.0 mmol) obtained in step (1-1-1a) was dissolved in 213 ml of anhydrous 1,2-dichloroethane, to which 24.0 g of TMSOTf (CAS No.: 27607-77-8, purchased from Macklin Inc., 108.0 mmol) was added in an ice water bath and nitrogen atmosphere to react at room temperature overnight.

The reaction solution was added with 400 ml dichloromethane for dilution, filtered with diatomite, and then added with 1 L saturated aqueous sodium bicarbonate solution and stirred evenly. An organic phase was isolated. The aqueous phase remained was extracted twice, each with 300 ml of dichloroethane, and the phases were combined and washed with 300 ml of saturated aqueous sodium bicarbonate solution and 300 ml of saturated brine, respectively. The organic phase was isolated and dried with anhydrous sodium sulfate. The solvent was removed by evaporation to dryness under reduced pressure to give 26.9 g of product GAL-3 as a light yellow viscous syrup.

(1-1-1c) Synthesis of GAL-4

GAL-3 (26.9 g, 81.7 mmol) obtained in step (1-1-1b) was dissolved in 136 ml of anhydrous 1,2-dichloroethane, added with 30 g of dry 4 Å molecular sieve powder followed by 9.0 g of 5-hexen-1-ol (CAS No.: 821-41-0, purchased from Adamas-beta Inc., 89.9 mmol), and stirred at room temperature for 30 minutes. 9.08 g of TMSOTf (40.9 mmol) was added in an ice bath and nitrogen atmosphere to react under stirring at room temperature overnight. The 4 Å molecular sieve powder was removed by filtration. The filtrate was added with 300 ml dichloroethane for dilution, filtered with diatomite, and then added with 500 ml of saturated aqueous sodium bicarbonate solution and stirred for 10 minutes for washing. An organic phase was isolated. The aqueous phase was extracted once with 300 ml of dichloroethane. The organic phases were combined and washed with 300 ml of saturated aqueous sodium bicarbonate solution and 300 ml of saturated brine, respectively. The organic phase was isolated and dried with anhydrous sodium sulfate. The solvent was removed by evaporation to dryness under reduced pressure to give 41.3 g of product GAL-4 as a yellow syrup, which was directly used in the next oxidation reaction without purification.

(1-1-1d) Synthesis of GAL-5

GAL-4 (14.9 g, 34.7 mmol) obtained according to the method described in step (1-1-1c) was dissolved in a mixed solvent of 77 ml of dichloromethane and 77 ml of acetonitrile, added with 103 ml of deionized water and 29.7 g of sodium periodate (CAS No.: 7790-28-5, purchased from Aladdin Inc., 138.8 mmol) respectively, and stirred in an ice bath for 10 minutes. Ruthenium trichloride (CAS No.: 14898-67-0, available from Energy Chemical, 238 mg, 1.145 mmol) was added to react at room temperature overnight. The resultant reaction solution was diluted by adding 300 ml of water under stirred, and adjusted to a pH of about 7.5 by adding saturated sodium bicarbonate. The organic phase was isolated and discarded. The aqueous phase was extracted three times, each with 200 ml of dichloromethane, and the organic phase was discarded. The aqueous phase was adjusted to a pH of about 3 with citric acid solids and extracted three times, each with 200 ml of dichloromethane, and the resultant organic phases were combined and dried with anhydrous sodium sulfate. The solvent was removed by evaporation to dryness under reduced pressure to give 6.85 g of product GAL-5 as a white foamy solid. $^1$H NMR (400 MHz, DMSO) δ 12.01 (br, 1H), 7.83 (d, J=9.2 Hz, 1H), 5.21 (d, J=3.2 Hz, 1H), 4.96 (dd, J=11.2, 3.2 Hz, 1H), 4.49 (d, J=8.4 Hz, 1H), 4.07-3.95 (m, 3H), 3.92-3.85 (m, 1H), 3.74-3.67 (m, 1H), 3.48-3.39 (m, 1H), 2.20 (t, J=6.8 Hz, 2H), 2.11 (s, 3H), 2.00 (s, 3H), 1.90 (s, 3H), 1.77 (s, 3H), 1.55-1.45 (m, 4H).

(1-1-2) Synthesis of M-11-T3

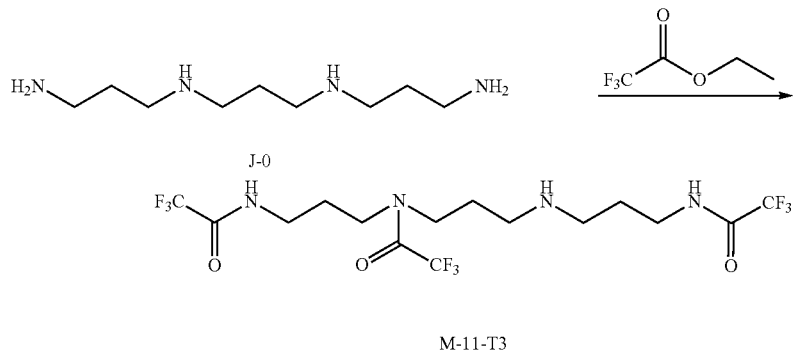

M-11-T3

J-0 (1.883 g, 10 mmol, purchased from Alfa Aesar) was dissolved in 25 ml of acetonitrile, added with triethylamine (4.048 g, 40 mmol), and cooled to 0° C. in an ice water bath. Ethyl trifluoroacetate (5.683 g, 40 mmol) was added to react at room temperature for 22 hours. The solvent was removed by evaporation to dryness under reduced pressure, and the residue was foam-dried in a vacuum oil pump for 18 hours to give 5.342 g of crude solid product M-11-T3, which was directly used in subsequent reaction without further purification. MS m/z: C15H22F9N4O3, [M+H]+, calculated: 477.35, measured: 477.65.

(1-1-3) Synthesis of M-11-T3-Tr

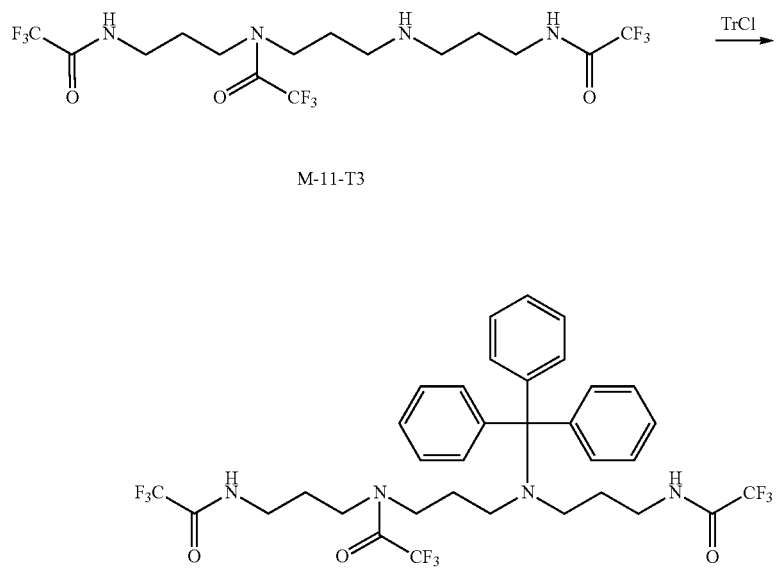

M-11-T3-Tr

The crude product M-11-T3 (5.342 g, 10 mmol) was dissolved in 50 ml of dichloromethane. The resultant reaction solution was added with TrCl (3.345 g, 12 mmol) and triethylamine (1.518 g, 15 mmol) to react under stirring at room temperature for 20 hours. The reaction solution was washed twice, each with 20 ml of saturated sodium bicarbonate and once with 20 ml of saturated brine. An organic phase was dried with anhydrous sodium sulfate and filtered.

The organic solvent was removed by evaporation to dryness under reduced pressure, and the residue was foam-dried in a vacuum oil pump overnight to give 7.763 g of crude solid product M-11-T3-Tr. MS m/z: C34H36F9N4O3, [M+Na]+, calculated: 741.25, measured: 741.53. The crude solid product M-11-T3-Tr was then used in the next step for synthesis of M-18-Tr without purification.

(1-1-4) Synthesis of M-18-Tr reduced pressure, and the residue was added with 200 ml of mixed solvent of dichloromethane:methanol in a volume ratio of 1:1, washed with 50 ml of saturated sodium bicarbonate. The aqueous phase obtained was extracted three times, each with 50 ml of dichloromethane (DCM). The organic phases were combined, dried with anhydrous sodium sulfate and filtered. The solvent was removed by evaporation to dryness under reduced pressure, and the residue was foam-dried in a vacuum oil pump overnight, and purified by using a normal phase silica gel column (200-300 mesh). The column was packed with petroleum ether, added with 1 wt % triethylamine for neutralizing the acidity of silica gel, and eluted with a gradient elution of dichloromethane:methanol:aqueous ammonia (25 wt %)=1:1:0.05-1:1:0.25. The eluate was collected, the solvent was removed by evaporation to dryness under reduced pressure, and the

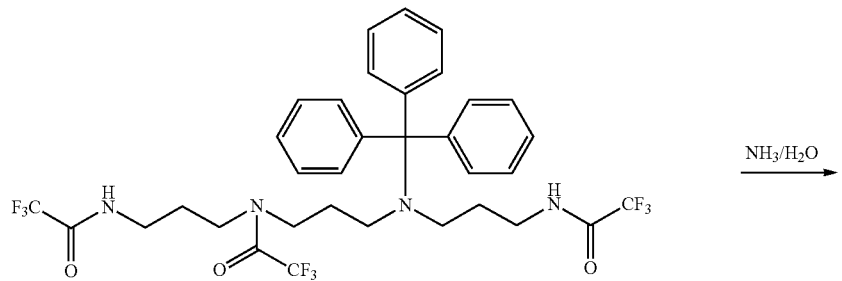

M-11-T3-Tr

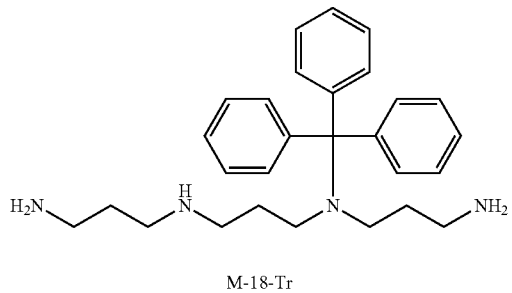

M-18-Tr

The crude product M-11-T3-Tr (7.763 g, 10 mmol) obtained in step (1-1-3) was dissolved in 100 ml of methanol, and added with 100 ml of aqueous methylamine solution (40 weight %) to react under stirring at 50° C. for 23 hours. Insoluble particles were removed by filtration. The solvent was removed by evaporation to dryness under residue was foam-dried in a vacuum oil pump to give 2.887 g of pure product M-18-Tr. $^1$H NMR (400 MHz, DMSO) δ7.47-7.39 (m, 6H), 7.32-7.24 (m, 6H), 7.19-7.12 (m, 3H), 2.60-2.47 (m, 4H), 2.46-2.19 (m, 13H), 1.70-1.55 (m, 4H), 1.40 (p, J=6.8 Hz, 2H). MS m/z: C28H39N4, [M+H]+, calculated: 431.65, measured: 432.61.

(1-1-5) Synthesis of L-5-Tr

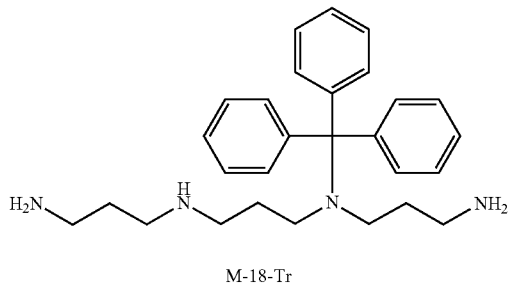

M-18-Tr

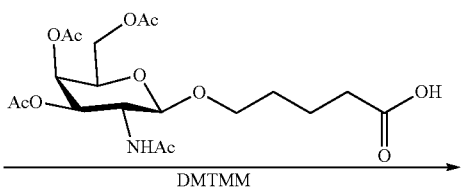

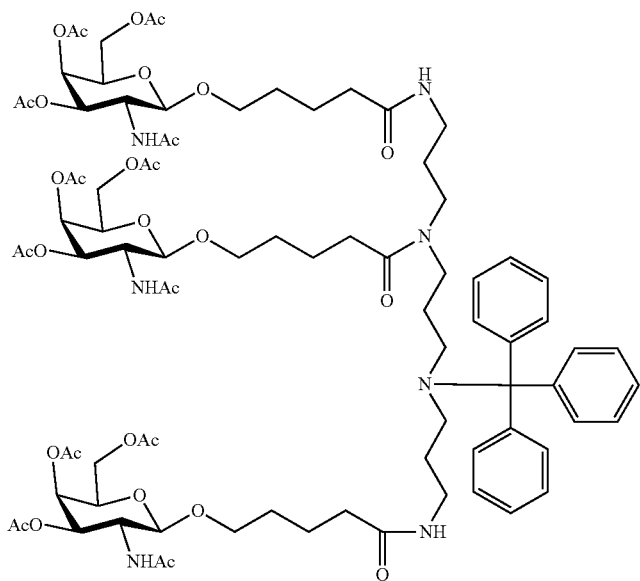

L-5-Tr

M-18-Tr (2.02 g, 4.69 mmol) obtained in step (1-1-4) and GAL-5 (6.93 g, 15.48 mmol) obtained in step (1-1-1) were mixed and dissolved in 47 ml of acetonitrile, and added with N-methylmorpholine (3.13 g, 30.96 mmol) and 4-(4,6-dimethoxytriazin-2-yl)-4-methylmorpholine hydrochloride (DMTMM, 4.28 g, 15.48 mmol) to react under stirring at room temperature for 2 hours. The resultant reaction solution was diluted with 200 ml of dichloromethane for dilution. The organic phase was washed with 100 ml of a saturated sodium bicarbonate solution and 100 ml of saturated brine, dried with anhydrous sodium sulfate, and filtered. Then the solvent was removed by evaporation to dryness under reduced pressure to give a crude product. The crude product was purified by using a normal phase silica gel column (200-300 mesh). The column was packed with petroleum ether, added with 1 wt % triethylamine for neutralizing the acidity of silica gel, and eluted with a gradient elution of dichloromethane:methanol=100:5-100:7. The eluate was collected, and evaporated to dryness under reduced pressure to give 7.49 g of pure product L-5-Tr. $^1$H NMR (400 MHz, DMSO) δ7.83-7.10 (m, 4H), 7.67-7.60 (m, 1H), 7.44-7.34 (m, 6H), 7.33-7.24 (m, 6H), 7.20-7.15 (m, 3H), 5.22 (s, 3H), 4.97 (d, J=11.3 Hz, 3H), 4.49 (d, J=8.4 Hz, 3H), 4.06-3.07 (m, 9H), 3.95-3.83 (m, 3H), 3.77-3.64 (m, 3H), 3.45-3.35 (m, 3H), 3.12-2.87 (m, 8H), 2.30-2.15 (m, 3H), 2.11-1.98 (m, 22H), 1.95-1.84 (m, 11H), 1.81-1.61 (m, 14H), 1.54-1.36 (m, 14H). MS m/z: C85H119N7O30, [M+H]+, calculated: 1718.81, measured: 1718.03.

(1-1-6) Synthesis of L-8

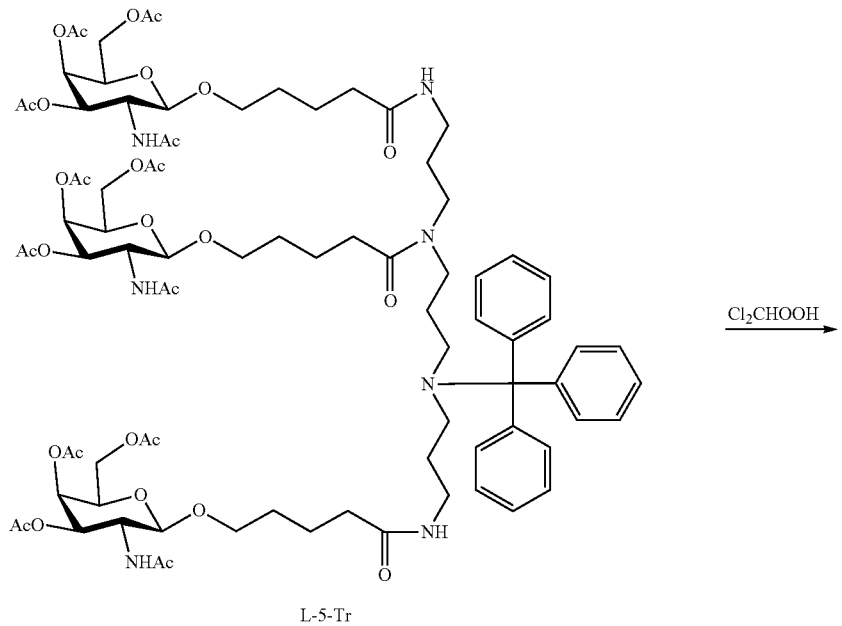

L-5-Tr

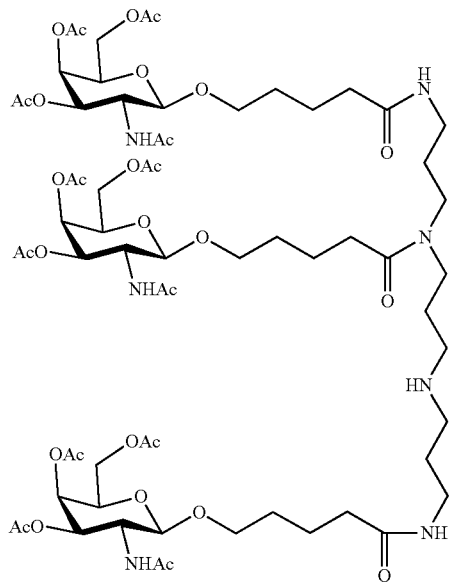

L-8

L-5-Tr (5.94 g, 3.456 mmol) obtained in step (1-1-5) was dissolved in 69 ml of dichloromethane, and added with dichloroacetic acid (13.367 g, 103.67 mmol) to react at room temperature for 2 hours. The resultant reaction solution was diluted by adding 100 ml of dichloromethane, washed and adjusted to pH 7-8 with saturated sodium bicarbonate solution. The aqueous phase was extracted six times, each with 30 ml of dichloromethane. The organic phases were combined, dried with anhydrous sodium sulfate, and filtered. Then the solvent was removed by evaporation to dryness under reduced pressure to give a crude product. The crude product was purified by using a normal phase silica gel (200-300 mesh). The column was adding with 10 wt % triethylamine for neutralizing the acidity of silica gel and equilibrated with 1 wt ‰ triethylamine, and eluted with a gradient elution of dichloromethane:methanol=100:30-100:40. The eluate was collected, and the solvent was removed by evaporation to dryness under reduced pressure to give 4.26 g of pure product L-8. $^1$H NMR (400 MHz, DMSO) δ 7.84 (d, J=9.0 Hz, 3H), 7.27-7.23 (m, 1H), 7.13-7.18 (m, 1H), 5.22 (d, J=3.1 Hz, 3H), 4.97 (dd, J=11.3, 3.1 Hz, 3H), 4.48 (d, J=8.4 Hz, 3H), 4.09-3.98 (m, 9H), 3.88 (dd, J=19.3, 9.3 Hz, 3H), 3.75-3.66 (m, 3H), 3.44-3.38 (m, 3H), 3.17-3.30 (m, 4H), 3.10-2.97 (m, 4H), 2.35-2.20 (m, 6H), 2.15-2.08 (m, 9H), 2.07-1.98 (m, 13H), 1.94-1.87 (m, 9H), 1.81-1.74 (m, 9H), 1.65-1.42 (m, 18H). MS m/z: $C_{85}H_{119}N_7O_{30}$, [M+H]+, calculated: 1477.59, measured: 1477.23.

(1-1-7a) Synthesis of A-1

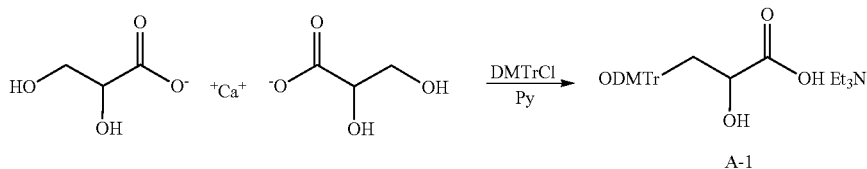

DMTrCl (4,4'-dimethoxytrityl chloride, 38.12 g, 112.5 mmol) was dissolved in 450 ml of anhydrous pyridine, and added with calcium DL-glycerate hydrate (12.88 g, 45.0 mmol) to react at 45° C. for 22 hours. The resultant reaction solution was filtered. The residue was rinsed with 200 ml of DCM, and the filtrate was concentrated to dryness under reduced pressure. The residue was redissolved in 500 ml of dichloromethane and washed twice, each with 200 ml of 0.5 M triethylamine phosphate (pH=7-8). The aqueous phase was extracted twice, each with 200 ml of dichloromethane. The organic phases were combined, dried with anhydrous sodium sulfate, and filtered. The solvent was removed by evaporation to dryness under reduced pressure, and the residue was purified by using a normal phase silica gel column (200-300 mesh) which was eluted with a gradient elution of petroleum ether:ethyl acetate:dichloromethane:methanol=1:1:1:0.35-1:1:1:0.55. The eluate was collected, and the solvent was removed by evaporation to dryness under reduced pressure. The residue was redissolved in 500 ml of dichloromethane, and washed once with 200 ml of 0.5 M triethylamine phosphate. The aqueous phase was extracted twice, each with 200 ml of dichloromethane. The organic phases were combined, dried with anhydrous sodium sulfate, and filtered. The solvent was removed by evaporation to dryness under reduced pressure, and the residue was subjected to suction filtration to dryness in a vacuum oil pump overnight to give 20.7 g of product A-1 as a white solid. $^1$H NMR (400 MHz, DMSO-d6) δ 7.46 (ddd, J=6.5, 2.3, 1.1 Hz, 1H), 7.40-7.28 (m, 7H), 6.89-6.81 (m, 4H), 4.84 (d, J=5.0 Hz, 1H), 4.36-4.24 (m, 1H), 4.29 (s, 6H), 3.92 (dd, J=12.4, 7.0 Hz, 1H), 3.67 (dd, J=12.3, 7.0 Hz, 1H), 2.52 (q, J=6.3 Hz, 6H), 1.03 (t, J=6.3 Hz, 9H). MS m/z: C24H23O6, [M−H]−, calculated: 407.15, measured: 406.92.

(1-1-7b) Synthesis of L-7

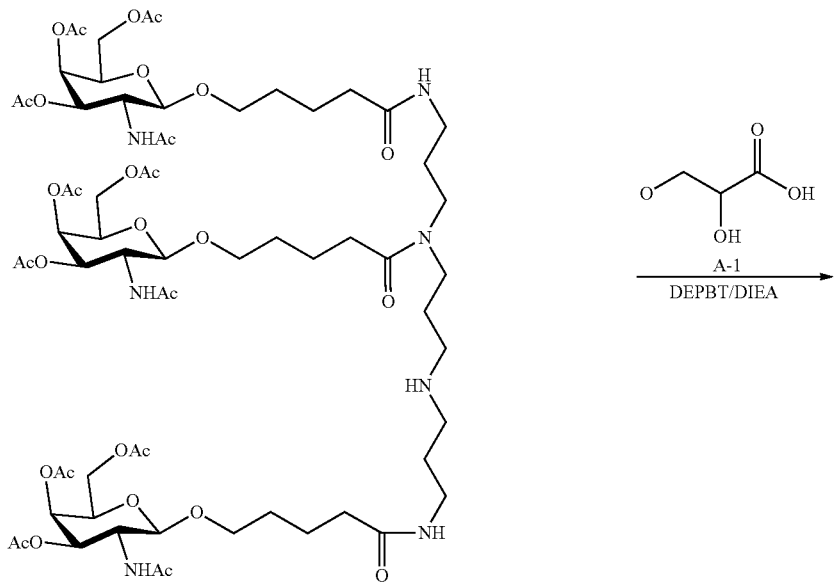

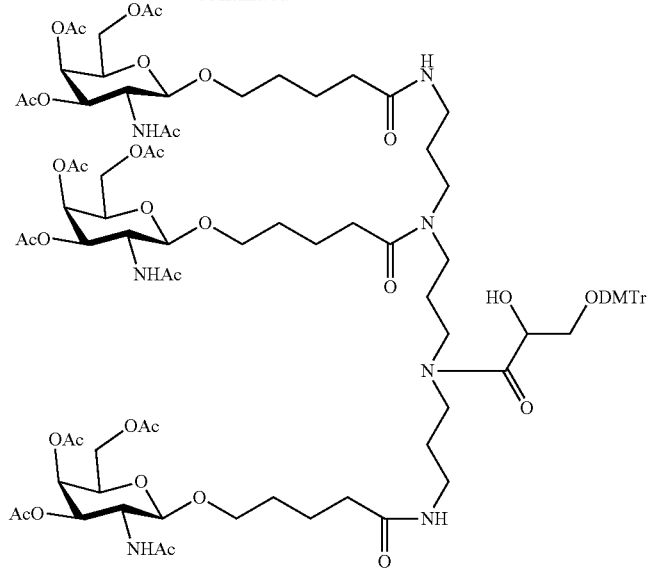

L-7

L-8 (2.262 g, 1.532 mmol) obtained in step (1-1-6) and A-1 (2.342 g, 4.596 mmol) obtained in step (1-1-7a) were mixed and dissolved in 16 ml of dichloromethane, added with 3-(diethoxyphosphoryl)-1,2,3-benzotrizin-4(3H)-one (DEPBT) (1.375 g, 4.596 mmol), and further added with diisopropylethylamine (1.188 g, 9.191 mmol) to react under stirring at 25° C. for 2 hours. The organic phase was washed with 10 ml of saturated sodium bicarbonate. The aqueous phase was extracted three times, each with 10 ml of dichloromethane. The organic phase was washed with 10 ml of saturated brine, and the aqueous phase was extracted twice, each with 10 ml of dichloromethane, and the organic phases were combined, dried with anhydrous sodium sulfate and filtered. The solvent was removed by evaporation to dryness under reduced pressure, and the residue was foam-dried in a vacuum oil pump overnight to give 4.900 g of crude product. The crude product was subjected to a column purification. The column was filled with 120 g normal phase silica gel (200-300 mesh), added with 20 ml triethylamine for neutralizing the acidity of silica gel, equilibrated with petroleum ether containing 1 wt % triethylamine, and eluted with a gradient elution of petroleum ether:ethyl acetate: dichloromethane:N,N-dimethylformamide=1:1:1:0.5-1:1:1: 0.6. The eluate was collected, and the solvent was removed by evaporation to dryness under reduced pressure to give 2.336 g of pure product L-7. $^1$H NMR (400 MHz, DMSO) δ7.90-7.78 (m, 4H), 7.75-7.64 (m, 1H), 7.38-7.18 (m, 9H), 6.91-6.83 (m, 4H), 5.25-5.10 (m, 4H), 4.97 (dd, J=11.2, 3.2 Hz, 3H), 4.48-4.30 (m, 4H), 4.02 (s, 9H), 3.93-3.84 (m, 3H), 3.76-3.66 (m, 9H), 3.45-3.35 (m, 3H), 3.24-2.98 (m, 10H), 2.30-2.20 (m, 2H), 2.11-1.88 (m, 31H), 1.80-1.40 (m, 28H). MS m/z: C90H128N7O35, [M-DMTr]+, calculated: 1564.65, measured: 1564.88.

(1-1-8) Synthesis of L-9 Conjugation Molecule

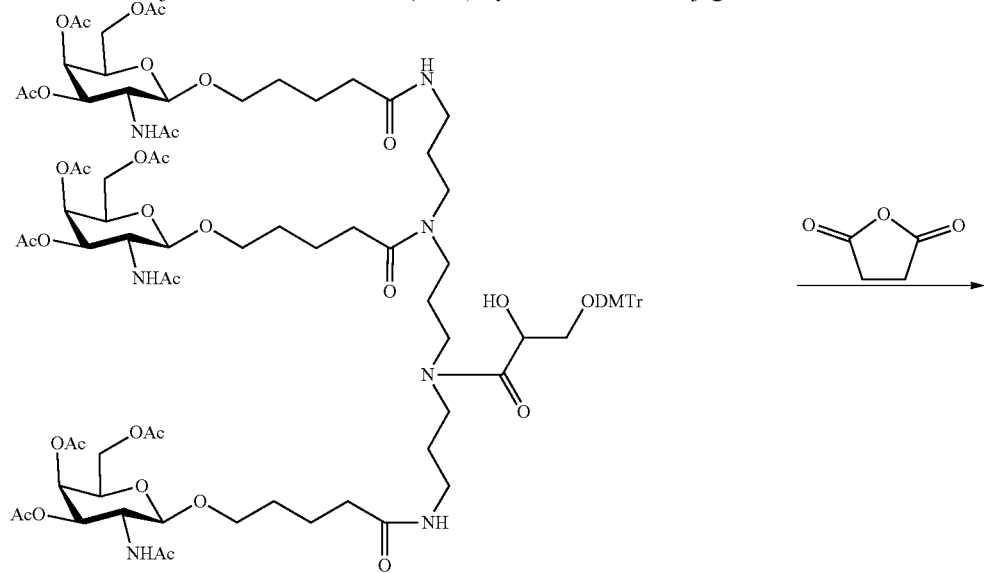

L-7

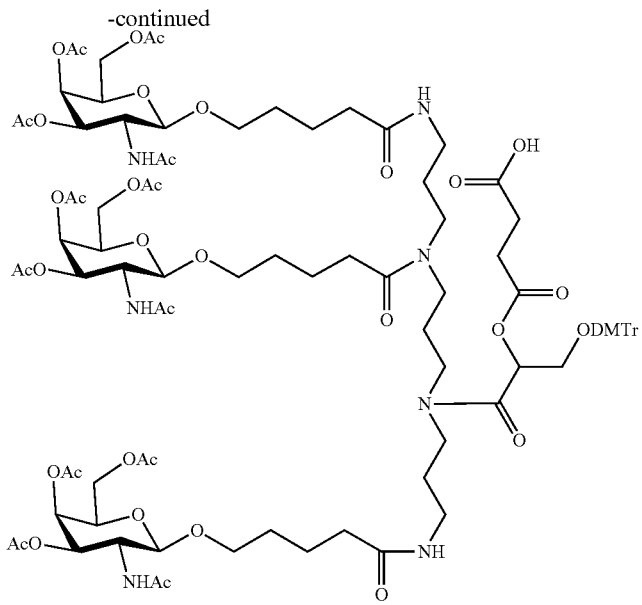

L-9

L-7 (2.300 g, 1.26 mmol) obtained in step (1-1-7), succinic anhydride (0.378 g, 3.78 mmol) and 4-dimethylaminopyridine (DMAP, 0.462 g, 3.78 mmol) were mixed and dissolved in 13 ml of dichloromethane, further added with diisopropylethylamine (DIEA, 0.814 g, 6.30 mmol), and stirred at 25° C. for 24 hours. The resultant reaction solution was washed with 5 ml of 0.5 M triethylamine phosphate. The aqueous phase was extracted three times, each with 5 ml of dichloromethane. The organic phases were combined and removed by evaporation to dryness under reduced pressure to give 2.774 g of crude product. The crude product was subjected to a column purification. The column was filled 60 g normal phase silica gel (200-300 mesh), added with 1 wt % triethylamine for neutralizing the acidity of silica gel, equilibrated with dichloromethane, and eluted with a gradient elution of 1 wt ‰ triethylamine-containing dichloromethane:methanol=100:18-100:20. The eluate was collected, and the solvent was removed by evaporation to dryness under reduced pressure to give 1.874 g of pure product L-9 conjugation molecule. $^1$H NMR (400 MHz, DMSO) δ 8.58 (d, J=4.2 Hz, 1H), 7.94-7.82 (m, 3H), 7.41-7.29 (m, 5H), 7.22 (d, J=8.1 Hz, 5H), 6.89 (d, J=8.3 Hz, 4H), 5.49-5.37 (m, 1H), 5.21 (d, J=3.0 Hz, 3H), 4.97 (d, J=11.1 Hz, 3H), 4.49 (d, J=8.2 Hz, 3H), 4.02 (s, 9H), 3.88 (dd, J=19.4, 9.4 Hz, 3H), 3.77-3.65 (m, 9H), 3.50-3.39 (m, 6H), 3.11-2.90 (m, 5H), 2.61-2.54 (m, 4H), 2.47-2.41 (m, 2H), 2.26-2.17 (m, 2H), 2.15-1.95 (m, 22H), 1.92-1.84 (m, 9H), 1.80-1.70 (m, 10H), 1.65-1.35 (m, 17H), 1.31-1.19 (m, 4H), 0.96 (t, J=7.1 Hz, 9H). MS m/z: C94H132N7O38, [M-DMTr]+, calculated: 1664.72, measured: 1665.03.

(1-1-9) Synthesis of Compound L-10

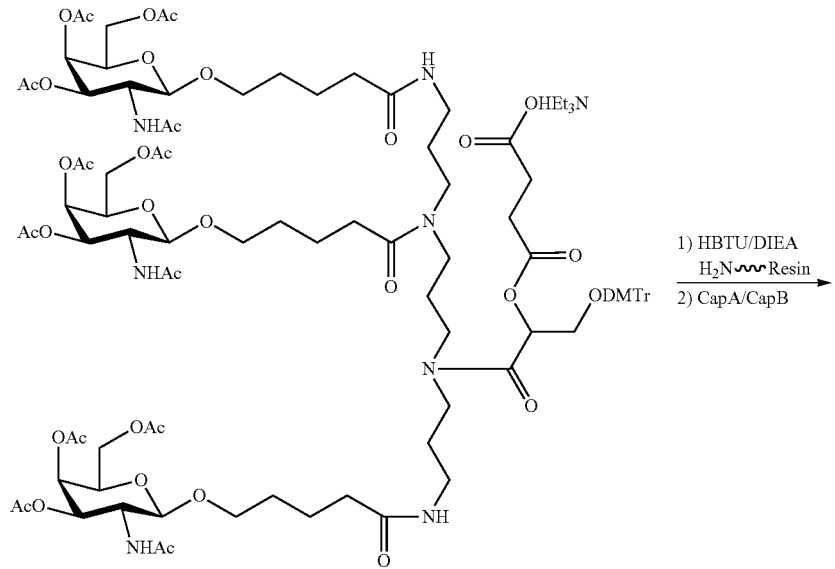

L-9

-continued

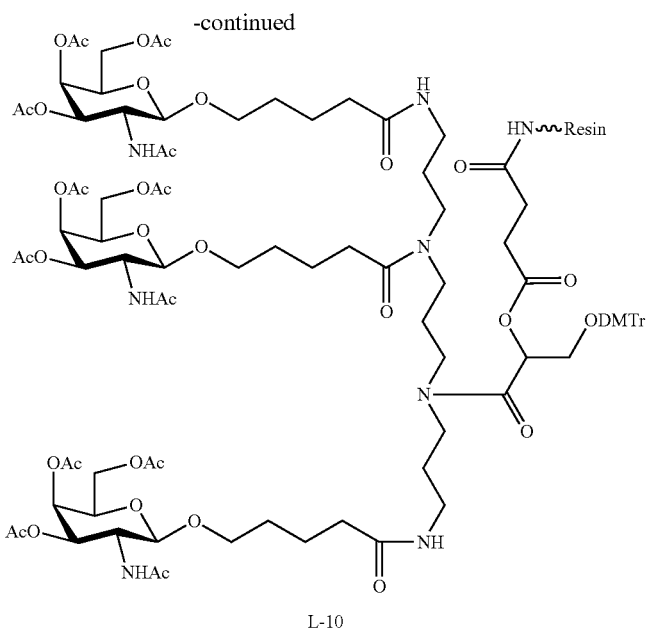

L-10

In this step, Compound L-10 was prepared by linking the L-9 conjugation molecule to a solid phase support.

The L-9 conjugation molecule (0.233 g, 0.1126 mmol) obtained in step (1-1-8), O-benzotriazol-tetramethyluronium hexafluorophosphate (HBTU, 0.064 g, 0.1689 mmol) and diisopropylethylamine (DIEA, 0.029 g, 0.2252 mmol) were mixed and dissolved in 19 ml of acetonitrile, and stirred at room temperature for 5 minutes. The resultant reaction solution was added with Aminomethyl resin ($H_2$NResin, 0.901 g, 100-200 mesh, amino loading: 400 mol/g, purchased from Tianjin Nankai HECHENG S&T Co., Ltd.). A reaction was performed on a shaker at 25° C. and 220 rpm/min for 15 hours, followed by filtration. The residue was rinsed twice (each with 30 ml of DCM), three times (each with 30 ml of acetonitrile), and once (with 30 ml of ethyl ether), and dried in a vacuum oil pump for 2 hours. Then starting materials (CapA, CapB, 4-dimethylaminopyridine (DMAP) and acetonitrile) were added according to the charge ratio shown in Table 2 for a capping reaction. The reaction was performed on a shaker at 25° C. and 200 rpm/min for 5 hours. The reaction liquid was filtered. The residue was rinsed three times, each with 30 ml of acetonitrile, subjected to suction filtration to dryness, and dried overnight in a vacuum oil pump to give 1.100 g of Compound L-10 (i.e., the L-9 conjugation molecule linked to a solid phase support), with a loading of 90.8 μmol/g.

TABLE 2

The charge ratio of capping reaction

| Starting Materials | Amount | Specs | Lot No. | Manufacturer |
|---|---|---|---|---|
| CapA | 20 ml | — | — | — |
| CapB | 2.3 ml | — | — | — |
| DMAP | 0.01 g | analytical pure | I1422139 | Aladdin |
| acetonitrile | 2.3 ml | spectroscopic pure | O15161001 | CINC (Shanghai) Co., Ltd |

In the above table, Cap A and Cap B are solutions of capping agents. Cap A is a mixed solution of 20% by volume of N-methylimidazole in pyridine/acetonitrile, wherein the volume ratio of pyridine to acetonitrile is 3:5. Cap B is a solution of 20% by volume of acetic anhydride in acetonitrile.

(1-2) Synthesis of Sense Strands of the Conjugates 1-3

The sense strands of Conjugates 1-3 have the same sequences, and thus their preparation methods are also the same.

Nucleoside monomers were linked one by one in 3' to 5' direction according to the arrangement sequence of nucleotides in the sense strand by the phosphoramidite solid phase synthesis method, starting the cycles from the Compound L-10 prepared in the above step. The linking of each nucleoside monomer included a four-step reaction of deprotection, coupling, capping, and oxidation or sulfurization. Therein, when two nucleotides is linked via a phosphoester linkage, a four-step reaction of deprotection, coupling, capping, and oxidation was included during linking of the later nucleoside monomer; and when two nucleotides is linked via a phosphorothioate linkage, a four-step reaction of deprotection, coupling, capping, and sulfurization was included during linking of the later nucleoside monomer. The synthesis conditions are as follows.

The nucleoside monomers are provided in a 0.1 M acetonitrile solution. The condition for deprotection reaction in each step is identical, i.e., a temperature of 25° C., a reaction time of 70 seconds, a solution of dichloroacetic acid in dichloromethane (3% v/v) as a deprotection reagent, and a molar ratio of dichloroacetic acid to the protecting group on the solid phase support of 4,4'-dimethoxytrityl of 5:1.

The condition for coupling reaction in each step is identical, including a temperature of 25° C., a molar ratio of the nucleic acid sequence linked to the solid phase support to nucleoside monomers of 1:10, a molar ratio of the nucleic acid sequence linked to the solid phase support to a coupling reagent of 1:65, a reaction time of 600 seconds, and 0.5 M acetonitrile solution of 5-ethylthio-1H-tetrazole as a coupling reagent.

The condition for capping reaction in each step is identical, including a temperature of 25° C. and a reaction time of 15 seconds, a mixed solution of Cap A and Cap B in a molar ratio of 1:1 as a capping agent, and a molar ratio of the capping agent to the nucleic acid sequence linked to the solid phase support of 1:1:1 (acetic anhydride:N-methylimidazole: the nucleic acid sequence linked to the solid phase support).

The condition for oxidation reaction in each step is identical, including a temperature of 25° C., a reaction time of 15 seconds, and 0.05 M iodine water as an oxidation reagent; and a molar ratio of iodine to the nucleic acid sequence linked to the solid phase support in the coupling step of 30:1. The reaction is carried out in a mixed solvent of tetrahydrofuran:water:pyridine (3:1:1).

The condition for sulfurization reaction in each step is identical, including a temperature of 25° C., a reaction time of 300 seconds, and xanthane hydride as a sulfuration reagent; and a molar ratio of the sulfuration reagent to the nucleic acid sequence linked to the solid phase support in the coupling step of 120:1. The reaction is carried out in a mixed solvent of acetonitrile:pyridine (1:1).

The conditions for cleavage and deprotection are as follows: adding the synthesized nucleotide sequence linked to the support into 25 wt % aqueous ammonia to react at 55° C. for 16 hours, and the aqueous ammonia is in an amount of 0.5 ml/μmol. The liquid was removed, and the residue is concentrated in vacuum to dryness.

Purification and desalination: purification of the nucleic acid is achieved by using a preparative ion chromatography purification column (Source 15Q) with a gradient elution of NaCl.

Specifically, eluent A: 20 mM sodium phosphate (pH 8.1), solvent: water/acetonitrile=9:1 (v/v); eluent B: 1.5 M sodium chloride, 20 mM sodium phosphate (pH 8.1), solvent: water/acetonitrile=9:1 (v/v); elution gradient: the ratio of eluent A:eluent B=100:0-50:50.

The eluate is collected, combined and desalted by using a reverse phase chromatography purification column. The specific condition includes: using a Sephadex column for desalination (filler: Sephadex G25) and deionized water for eluting.

Detection: the purity is determined by ion exchange chromatography (IEX-HPLC); and the molecular weight is analyzed by Liquid Chromatography-Mass Spectrometry (LC-MS).

For the sense strand batch of Conjugate 1, the purity is 90.4%; the calculated value and the measured value of the molecular weight are 7627.5 and 7626.6, respectively. For the sense strand batch of Conjugate 2, the purity is 94.1%; the calculated value and the measured value of the molecular weight are 7627.5 and 7625.1, respectively. The fact that the measured values were in conformity with the calculated values indicates that a sense strand S of which 3' terminal is conjugated to the L-9 conjugation molecule was synthesized.

(1-3) Synthesis of Antisense Strands of Conjugates 1-3
(1-3A) Preparation of an Antisense Strand of Conjugate 1

An antisense strand AS of Conjugate 1 is synthesized by starting the cycles using a universal solid phase support (UnyLinker™ loaded NittoPhase®HL Solid Supports, Kinovate Life Sciences Inc.) in the phosphoramidite solid phase synthesis method. The reaction conditions of deprotection, coupling, capping, oxidation or sulfurization, cleavage and deprotection, and purification and desalting in the solid phase synthesis method were the same as those used for the synthesis of the sense strand.

Detection: the purity is detected by ion exchange chromatography (IEX-HPLC), with a purity of 93.1%; and the molecular weight is analyzed by liquid chromatography-mass spectrometry (LC-MS), with a calculated value of 6920.17 and a measured value of 6919.9. The fact that the measured value is in conformity with the calculated value indicates that an antisense strand AS having the target sequence is synthesized.

Therein, the vinyl phosphate and 2'-methoxy modified uridine monomer (VP-Um) is synthesized according to the following method:

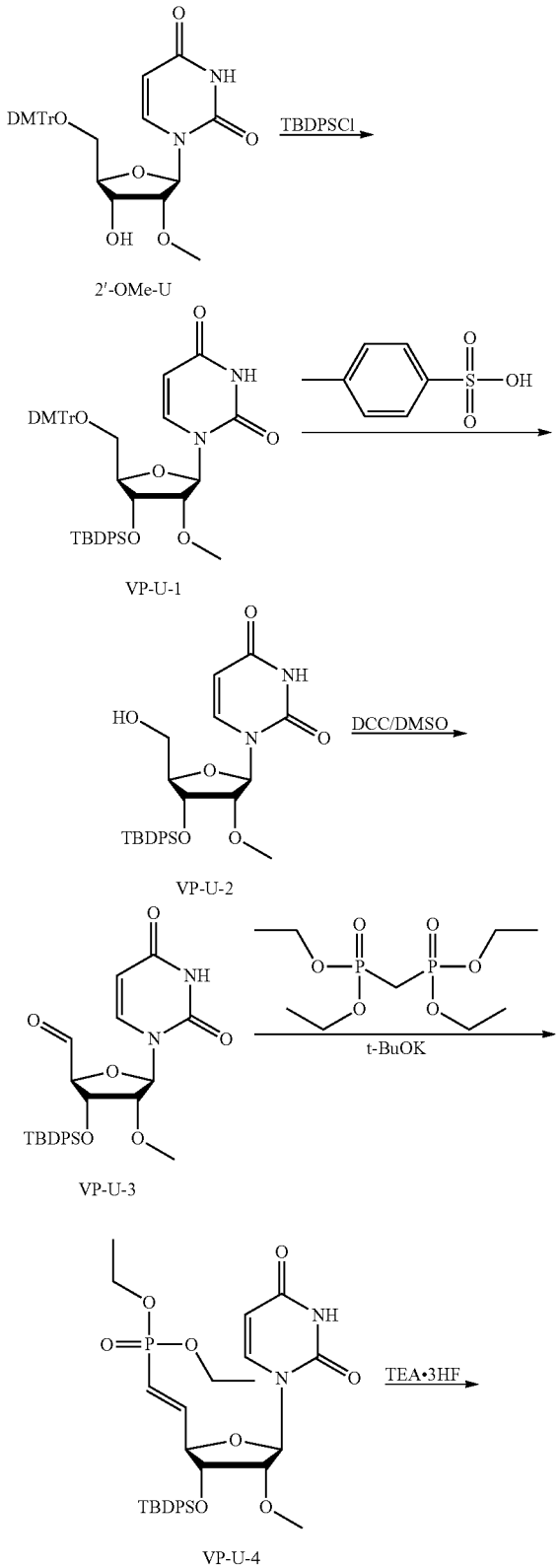

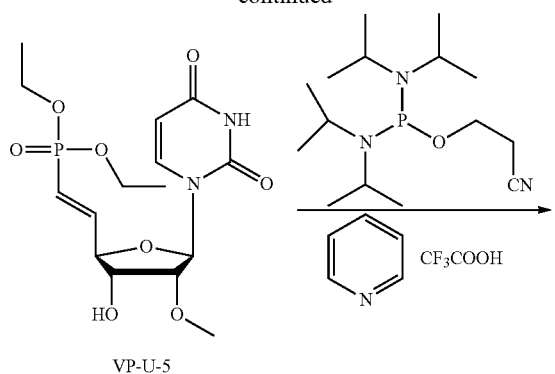

(1-3-1) Synthesis of VP-U-2

A VP-U-2 molecule was synthesized according to the following method:

A 2′-methoxy modified uracil nucleoside (2′-OMe-U, 51.30 g, 91.6 mmol), tert-butyl diphenylchlorosilane (TBDPSCl, 50.35 g, 183.2 mmol), and imidazole (12.47 g, 183.2 mmol) were mixed and dissolved in 450 ml of N,N-dimethylformamide (DMF) to react under stirring at room temperature for 20 hours. DMF was removed by evaporation, and the residue was dissolved with 600 ml of dichloromethane and washed with 300 ml of saturated sodium bicarbonate. The aqueous phase was extracted three times, each with 300 ml of dichloromethane (DCM). The organic phases were combined, washed with 5% oxalic acid until the pH of the aqueous phase is <5. The solvent was evaporated to dryness to give a crude product VP-U-1, which was directly used in the subsequent synthesis of VP-U-2.

The crude product VP-U-1 was dissolved in 100 ml of dichloromethane, and then stirred for 10 minutes in an ice bath. 450 ml of 2% p-toluenesulfonic acid solution (with a mixed solvent of methanol and dichloromethane in a volume ratio of 3:7) pre-cooled in a refrigerator at 4° C. was added to react for 10 minutes. The reaction was quenched by addition of 200 ml of saturated sodium bicarbonate. The organic phase was washed to pH=8 by addition of saturated sodium bicarbonate solution. The aqueous phases were combined and extracted twice, each with 200 ml of dichloromethane. The organic phases were combined and washed once with 200 ml of saturated brine. The solvent was removed by evaporation to dryness, and the residue was purified by using a normal phase silica gel column (200-300 mesh). The column was packed with petroleum ether and eluted with a gradient elution of petroleum ether:ethyl acetate:dichloromethane:methanol=1:1:1:0.05-1:1:1:0.25.

The eluate was collected, the solvent was removed by evaporation to dryness under reduced pressure, and the residue was foam-dried in a vacuum oil pump to give a total of 40.00 g of pure product VP-U-2. 1H NMR (400 MHz, DMSO-d6) δ 7.96 (d, J=7.8 Hz, 1H), 7.64 (dtd, J=5.1, 4.0, 2.2 Hz, 4H), 7.41-7.30 (m, 6H), 6.79 (d, J=4.7 Hz, 1H), 5.73 (d, J=7.6 Hz, 1H), 4.94 (t, J=7.0 Hz, 1H), 4.12 (td, J=4.6, 3.9 Hz, 1H), 4.05 (dd, J=4.8, 4.0 Hz, 1H), 3.96 (t, J=4.7 Hz, 1H), 3.68 (ddd, J=11.8, 7.0, 4.6 Hz, 1H), 3.57-3.46 (m, 1H), 3.39 (s, 3H), 1.05 (s, 8H). MS m/z: C26H33N2O6Si, [M+H]+, calculated: 497.21, measured: 497.45.

(1-3-2) Synthesis of VP-U-4

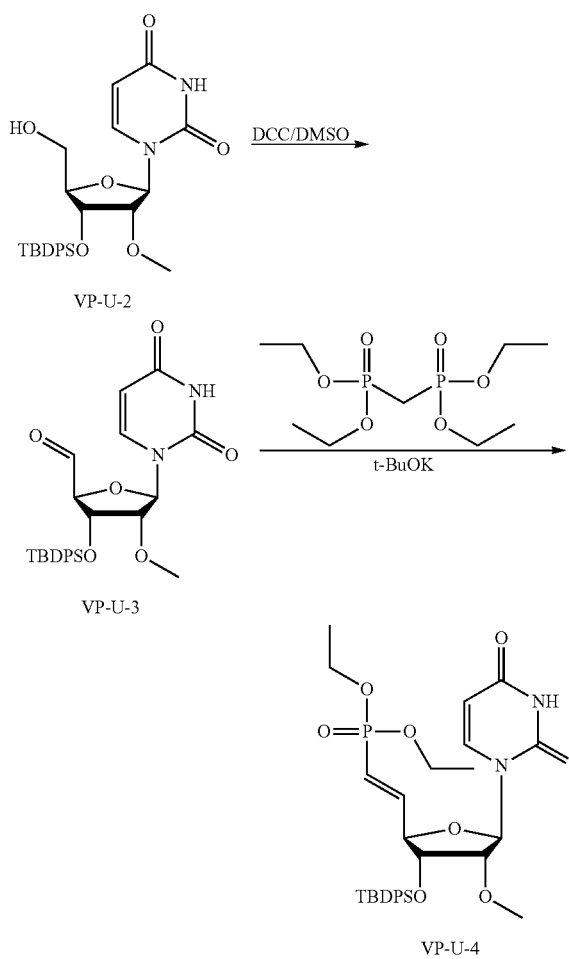

(m, 6H), 6.82-6.71 (m, 2H), 5.90 (ddd, J=25.9, 15.0, 1.0 Hz, 1H), 5.73 (d, J=7.6 Hz, 1H), 4.36-4.21 (m, 3H), 4.18 (t, J=4.9 Hz, 1H), 4.05 (ddq, J=9.7, 8.5, 6.9 Hz, 2H), 3.87 (t, J=4.8 Hz, 1H), 3.39 (s, 3H), 1.32 (td, J=6.9, 0.7 Hz, 6H), 1.05 (s, 8H). MS m/z: C31H42N2O8PSi, [M+H]+, calculated: 629.24, measured: 629.51.

(1-3-3) Synthesis of VP-U-5

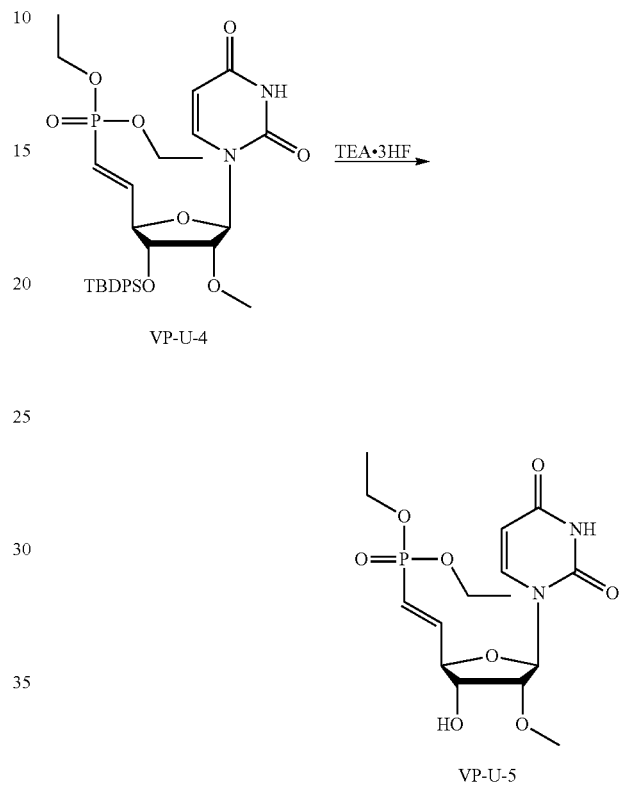

VP-U-2 (19.84 g, 40.0 mmol), dicyclohexylcarbodiimide (DCC, 16.48 g, 80.0 mmol), pyridine (4.20 g, 53.2 mmol), and trifluoroacetic acid (6.61 g, 53.2 mmol) were mixed and dissolved in 200 ml of dimethyl sulfoxide (DMSO) to react under stirring at room temperature for 20 hours. Separately, tetraethyl methylenediphosphate (21.44 g, 74.4 mmol) was dissolved in 120 ml of THF, cooled in an ice bath, added with t-BuOK (11.36 g, 101.2 mmol) at a temperature of the ice bath to react for 10 min, warmed to room temperature to react for 0.5 hour and added into the above reaction liquid over about 1 hour. The reaction was carried out at a temperature of the ice bath for 1 hour and then warmed to room temperature to react for 18 hours. The reaction was quenched by addition of water. The aqueous phase was extracted three times, each with 200 ml of dichloromethane. The organic phases were combined and washed once with 200 ml of saturated brine. The solvent was evaporated to dryness, and the residue was purified by using a normal phase silica gel column (200-300 mesh). The column was packed with petroleum ether and eluted with a gradient elution of petroleum ether:ethyl acetate=1:1-1:4. The eluate was collected. The solvent was removed by evaporation to dryness under reduced pressure, and the residue was foam-dried in a vacuum oil pump to give a total of 14.00 g of pure product VP-U-4. 1H NMR (400 MHz, DMSO-d6) δ 7.96 (d, J=7.8 Hz, 1H), 7.64 (dtd, J=5.1, 4.0, 2.2 Hz, 4H), 7.41-7.30

VP-U-4 (14.00 g, 22.29 mmol) was dissolved in 100 ml of tetrahydrofuran, added with triethylamine trihydrofluoride (17.96 g, 111.45 mmol), and stirred at room temperature for 20 hours to react completely. The solvent was directly evaporated to dryness, the residue was dissolved in dichloromethane, then the solvent was evaporated to dryness again. The above dissolution and evaporation steps were performed twice, each with 50 ml of dichloromethane to give a crude product. The crude product was purified by using a normal phase silica gel column (200-300 mesh). The column was packed with petroleum ether and eluted with a gradient elution of petroleum ether:ethyl acetate:dichloromethane:methanol=1:1:1:0.05-1:1:1:0.25. The eluate was collected, the solvent was removed by evaporation to dryness under reduced pressure, and the residue was foam-dried in a vacuum oil pump to give a total of 6.70 g of pure product VP-U-5. 1H NMR (400 MHz, DMSO-d6) δ 7.96 (d, J=7.8 Hz, 1H), 6.77 (dd, J=15.0, 6.2 Hz, 1H), 5.99-5.82 (m, 2H), 5.73 (d, J=7.6 Hz, 1H), 5.27 (d, J=5.1 Hz, 1H), 5.10 (dd, J=5.3, 4.7 Hz, 1H), 4.29 (ddq, J=9.8, 8.6, 7.0 Hz, 2H), 4.17 (ddd, J=6.2, 5.2, 1.0 Hz, 1H), 4.12-3.98 (m, 3H), 3.39 (s, 2H), 1.32 (td, J=6.9, 0.6 Hz, 6H). MS m/z: C15H24N2O8P,

[M+H]+, calculated: 391.13, measured: 391.38.

(1-3-4) Synthesis of VP-U-6

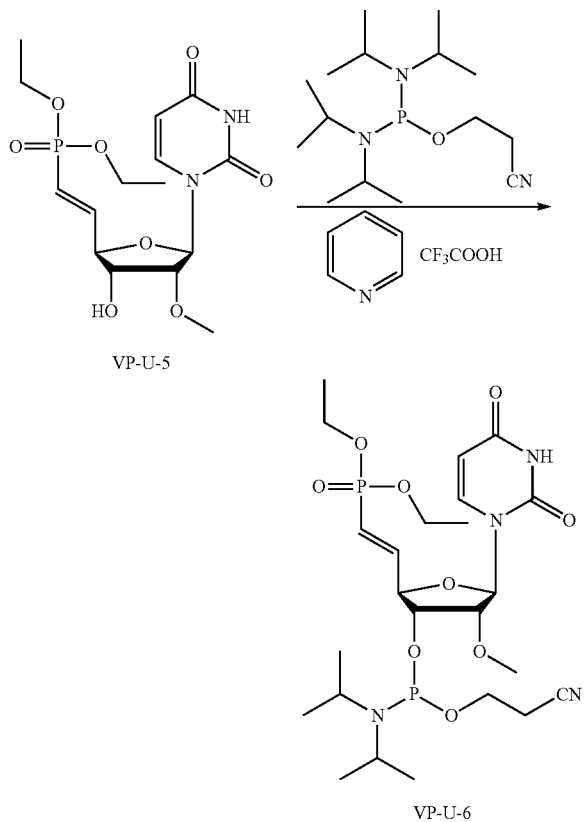

VP-U-5 (391 mg, 1.0 mmol), pyridine trifluoroacetate (0.232 g, 1.2 mmol), N-methylimidazole (0.099 g, 1.2 mmol), and bis(diisopropylamino)(2-cyanoethoxy)phosphine (0.452 g, 1.5 mmol) were added into 10 ml of anhydrous dichloromethane under argon atmosphere to react under stirring at room temperature for 5 hours. The solvent was evaporated to dryness, and then the residue was purified by column chromatography (200-300 mesh normal phase silica gel, with a gradient elution of dichloromethane:acetonitrile (containing 0.5 wt % triethylamine)=3:1-1:3). The eluate was collected and concentrated to remove the solvent to give a total of 508 mg of target product VP-U-6. 31P NMR (161 MHz, DMSO-d6) δ 150.34, 150.29, 17.07, 15.50. MS m/z: C24H41N4O9P2, [M+H]+, calculated: 591.23, measured: 591.55. The above data indicated that VP-U-6 was the target product VP-Um, which was involved in the synthesis of RNA strands as a nucleoside monomer.

(1-3B) Preparation of an Antisense Strand of Conjugate 2

The antisense strand of Conjugate 2 differs from that of Conjugate 1 only in the modification of the first nucleotide at 5'-terminal. During the preparation of an antisense strand according to the phosphoramidite solid phase synthesis method, after the linking of 2'-methoxy modified uridine monomer (Um) as the last nucleoside monomer, the monomer of Formula (CPR-I) (purchased by Suzhou GenePharma Inc. as Cat #13-2601-XX) was linked to 5' terminal of the antisense strand by a four-step reaction of deprotection, coupling, capping, and oxidation, so as to form a 5'-phosphate modification.

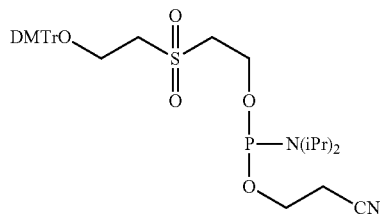

(CPR-I)

During the synthesis, the universal solid phase support, the conditions of deprotection, coupling, capping, oxidation or sulfurization reaction, cleavage and deprotection, purification and desalting used were the same as those used in the synthesis of the sense strand.

The purity was detected by ion exchange chromatography (IEX-HPLC), with a purity of 99.0%; and the molecular weight was analyzed by liquid chromatography-mass spectrometry (LC-MS), with a calculated value of 6924.43 and a measured value of 6924.0. The fact that the measured value is in conformity with the calculated value indicates that an antisense strand AS having the target sequence is synthesized.

(1-3C) Preparation of an Antisense Strand of Conjugate 3

The synthesis process is the same as that of the antisense strand of Conjugate 2, except that the above oxidation reaction condition is replaced with a sulfurization reaction condition in the linking of the CPR-I monomer. It is expected that an antisense strand of Conjugate 3 with a 5'-phosphorothioate modification can be prepared.

(1-4) Synthesis of Conjugates 1 and 2

For Conjugate 1, the S strand and AS strand were respectively dissolved in water for injection to get a solution of 40 mg/mL. They are mixed in an equimolar ratio, heated at 50° C. for 15 min, and then cooled at room temperature, such that they could form a double-stranded structure via hydrogen bonds. After the conjugate was diluted to a concentration of 0.2 mg/mL by using ultra-pure water (homemade by Milli-Q ultra-pure water instrument, with resistivity of 18.2MΩ*cm (25° C.)), the molecular weight was measured by a LC-MS instrument (purchased from Waters Corp., model: LCT Premier). As a result, the calculated values of the molecular weight for S and AS were respectively 7627.5 and 6920.17, and the measured values thereof were respectively 7626.9 and 6920.1. The fact that the measured values were in conformity with the calculated values indicated that the synthesized Conjugate 1 had the designed target double-stranded nucleic acid sequence with the L-9 conjugation molecule.

For Conjugate 2, it was prepared and assayed for molecular weight by the same methods. As a result, the calculated values of the molecular weight for S and AS were respectively 7627.5 and 6924.43, and the measured values thereof were respectively 7626.5 and 6923.4. The fact that the measured values were in conformity with the calculated values indicated that the synthesized Conjugate 2 was the designed target double-stranded nucleic acid sequence with the L-9 conjugation molecule, since the measured values were in conformity with the calculated values.

The structures of Conjugates 1 and 2 are as shown by Formula (403).

Preparation Example 2 Preparation of Conjugates 4-12 and Comparative Conjugate 1

It was expected that the subject conjugates can be prepared by using the same method as that in Preparation Example 1, except that: 1) the siRNAs respectively have the sequences as shown in Table 3 corresponding to Conjugates 4-12 and Comparative Conjugate 1; and 2) in the case where the target sequence comprises unmodified nucleotide, in the cleavage and deprotection conditions, after treatment with aqueous ammonia, the product is dissolved in N-methylpyrrolidone in an amount of 0.4 ml/μmol, followed by addition of 0.3 ml/μmol of triethylamine and 0.6 ml/μmol of triethylamine trihydrofluoride, with respect to the amount of the single strand nucleic acid, thereby removing the 2'-TBDMS protection on ribose.

The conjugated siRNA sequences in the subject conjugates are shown in Table 3. Therein, the siRNA comprised in the Comparative Conjugate 1 is the negative control siRNA which shows no inhibitory effect on HBV gene.

TABLE 3 siRNA conjugates

| SIRNA Conjugate | NO. | | Sequence Direction 5'-3' | SEQ ID NO |
|---|---|---|---|---|
| Conjugate 1 | L10-siHB3M1SVP | S | GmsAmsAmAmGmUmAfUfGfUmCmAmAmCmGmAmAmUm Am | 24 |
| | | AS | VP-UmsAfsUmUmCmGfUmUmGmAmCmAmUmAfCmUfUmUm CmsUmsUm | 67 |
| Conjugate 2 | L10-siHB3M1SP | S | GmsAmsAmAmGmUmAfUfGfUmCmAmAmCmGmAmAmUm Am | 24 |
| | | AS | P-UmsAfsUmUmCmGfUmUmGmAmCmAmUmAfCmUfUmUm CmsUmsUm | 68 |
| Conjugate 3 | L10-siHB3M1SPs | S | GmsAmsAmAmGmUmAfUfGfUmCmAmAmCmGmAmAmUm Am | 24 |
| | | AS | Ps-UmsAfsUmUmCmGfUmUmGmAmCmAmUmAfCmUfUmUm CmsUmsUm | 69 |
| Conjugate 4 | L10-siHB3M1VP | S | GmAmAmGmUmAfUfGfUmCmAmAmCmGmAmAmUmAm | 12 |
| | | AS | VP-UmAfUmUmCmGfUmUmGmAmCmAmUmAfCmUfUmUmCm UmUm | 70 |
| Conjugate 5 | L10-siHB3M1P | S | GmAmAmGmUmAfUfGfUmCmAmAmCmGmAmAmUmAm | 12 |
| | | AS | P-UmAfUmUmCmGfUmUmGmAmCmAmUmAfCmUfUmUmCm UmUm | 71 |
| Conjugate 6 | L10-siHB3M1 | S | GmAmAmGmUmAfUfGfUmCmAmAmCmGmAmAmUmAm | 12 |
| | | AS | UmAfUmUmCmGfUmUmGmAmCmAmUmAfCmUfUmUmCm UmUm | 15 |
| Conjugate 7 | L10-siHB3M1S | S | GmsAmsAmAmGmUmAfUfGfUmCmAmAmCmGmAmAmUm Am | 24 |
| | | AS | UmsAfsUmUmCmGfUmUmGmAmCmAmUmAfCmUfUmUm CmsUmsUm | 27 |
| Conjugate 8 | L10-siHB3M2SVP | S | GmsAmsAmAmGfUmAfUfGfUmCmAmAmCmGmAmAmUm Am | 30 |
| | | AS | VP-UmsAfsUmUmCmGfUmUfGfAmCmAmUmAfCmUfUmUmCms UmsUm | 72 |
| Conjugate 9 | L10-siHB3M3SP | S | GmsAmsAmAmGfUmAfUfGfUmCmAmAmCmGmAmAmUm Am | 30 |
| | | AS | P-UmsAfsUmUmCmGfUmUmGmAmCmAmUmAfCmUfUmUm CmsUmsUm | 68 |
| Conjugate 10 | L10-siHB2M1SP | S | GmsAmsAmAmGmUmAfUfGfUmCmAmAmCmGmAmAmUm Um | 23 |
| | | AS | P-AmsAfsUmUmCmGfUmUmGmAmCmAmUmAfCmUfUmUm CmsCmsAm | 73 |
| Conjugate 11 | L10-siHB5M1SVP | S | UmsGmsGmAmAmAmGmUmAfUfGfUmCmAmAmCmGmAm AmUmAm | 56 |
| | | AS | VP-UmsAfsUmUmCmGfUmUmGmAmCmAmUmAfCmUfUmUm CmCmAmsUmsUm | 74 |

TABLE 3-continued siRNA conjugates

| SIRNA Conjugate | NO. | | Sequence Direction 5'-3' | SEQ ID NO |
|---|---|---|---|---|
| Conjugate 12 | L10-siHB3 | S | GAAAGUAUGUCAACGAAUA | 75 |
| | | AS | UAUUCGUUGACAUACUUUCUU | 76 |
| Conjugate 13 | P10-siHB3M1SVP | S | GmsAmsAmAmGmUmAfUfGfUmCmAmAmCmGmAmAmUmAm | 24 |
| | | AS | VP-UmsAfsUmUmCmGfUmUmGmAmCmAmUmAfCmUfUmUmCmsUmsUm | 67 |
| Conjugate 14 | R5-siHB3M1SVP | S | GmsAmsAmAmGmUmAfUfGfUmCmAmAmCmGmAmAmUmAm | 24 |
| | | AS | VP-UmsAfsUmUmCmGfUmUmGmAmCmAmUmAfCmUfUmUmCmsUmsUm | 67 |
| Conjugate 15 | LA5-siHB3M1SVP | S | GmsAmsAmAmGmUmAfUfGfUmCmAmAmCmGmAmAmUmAm | 24 |
| | | AS | VP-UmsAfsUmUmCmGfUmUmGmAmCmAmUmAfCmUfUmUmCmsUmsUm | 67 |
| Conjugate 16 | LB5-siHB3M1SVP | S | GmsAmsAmAmGmUmAfUfGfUmCmAmAmCmGmAmAmUmAm | 24 |
| | | AS | VP-UmsAfsUmUmCmGfUmUmGmAmCmAmUmAfCmUfUmUmCmsUmsUm | 67 |
| Conjugate 17 | V8-siHB3M1SVP | S | GmsAmsAmAmGmUmAfUfGfUmCmAmAmCmGmAmAmUmAm | 24 |
| | | AS | VP-UmsAfsUmUmCmGfUmUmGmAmCmAmUmAfCmUfUmUmCmsUmsUm | 67 |
| Conjugate 18 | W8-siHB3M1SVP | S | GmsAmsAmAmGmUmAfUfGfUmCmAmAmCmGmAmAmUmAm | 24 |
| | | AS | VP-UmsAfsUmUmCmGfUmUmGmAmCmAmUmAfCmUfUmUmCmsUmsUm | 67 |
| Conjugate 19 | X8-siHB3M1SVP | S | GmsAmsAmAmGmUmAfUfGfUmCmAmAmCmGmAmAmUmAm | 24 |
| | | AS | VP-UmsAfsUmUmCmGfUmUmGmAmCmAmUmAfCmUfUmUmCmsUmsUm | 67 |
| Conjugate 20 | Z5-siHB3M1SVP | S | GmsAmsAmAmGmUmAfUfGfUmCmAmAmCmGmAmAmUmAm | 24 |
| | | AS | VP-UmsAfsUmUmCmGfUmUmGmAmCmAmUmAfCmUfUmUmCmsUmsUm | 67 |
| Comp. Conjugate 1 | L10-siNCM1SP | S | UmsUmsCmUmCmCmGfAfAfCmGmUmGmUmCmAmCmGmUm | 77 |
| | | AS | P-AmsCfsGmUmGmAfCmAmCmGmUmUmCmGfGmAfGmAmAmsCmsUm | 78 |
| Comp. Conjugate 2 | K4-siHB3M1SVP | S | GmsAmsAmAmGmUmAfUfGfUmCmAmAmCmGmAmAmUmAm | 24 |
| | | AS | VP-UmsAfsUmUmCmGfUmUmGmAmCmAmUmAfCmUfUmUmCmsUmsUm | 67 |

Preparation Example 3 Preparation of the Conjugate P10-siHB3M1SVP (Conjugate 13)
(3-1) Synthesis of Compound P-10
Compound P-10 was synthesized according to the following method.
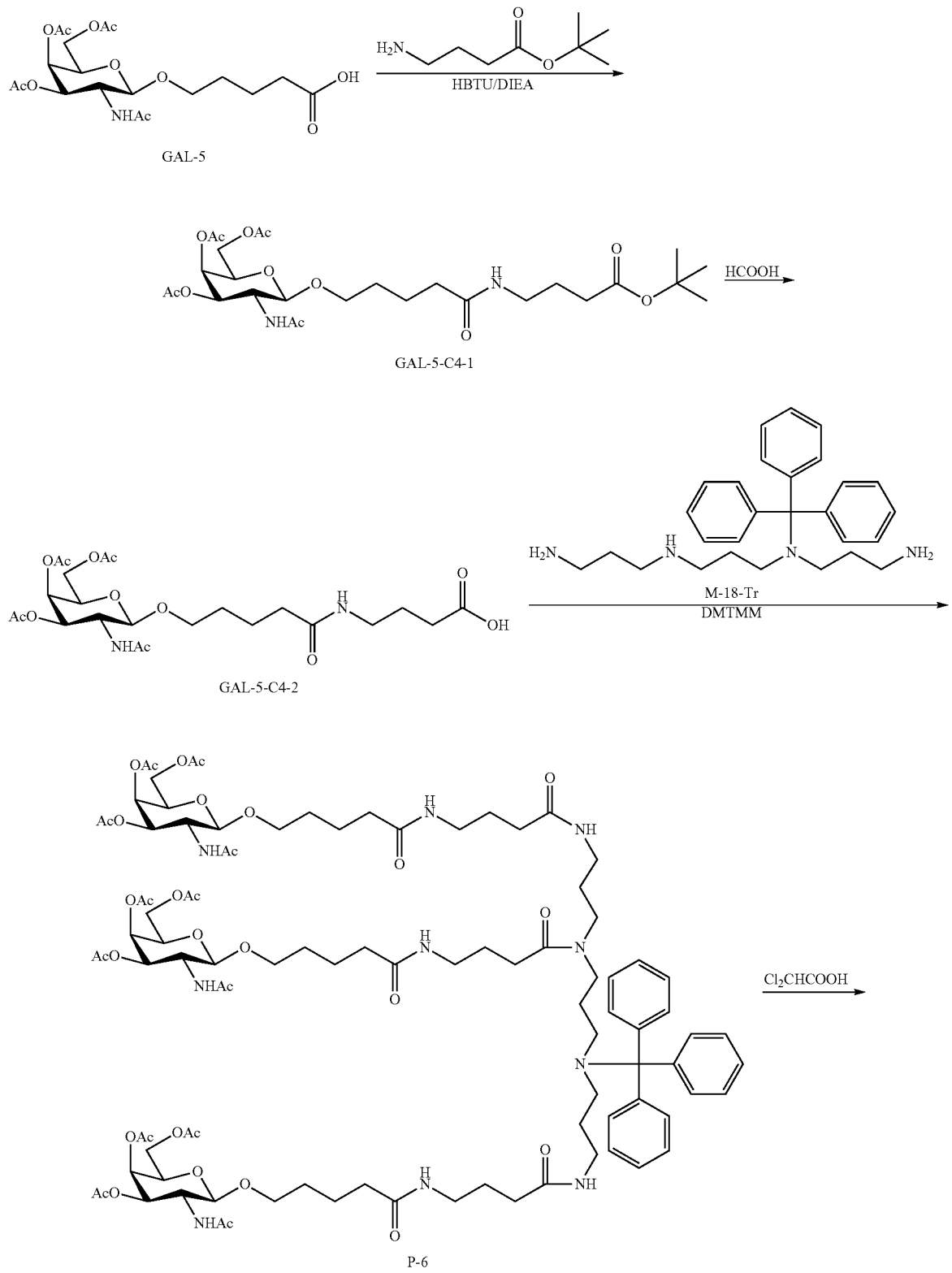

-continued
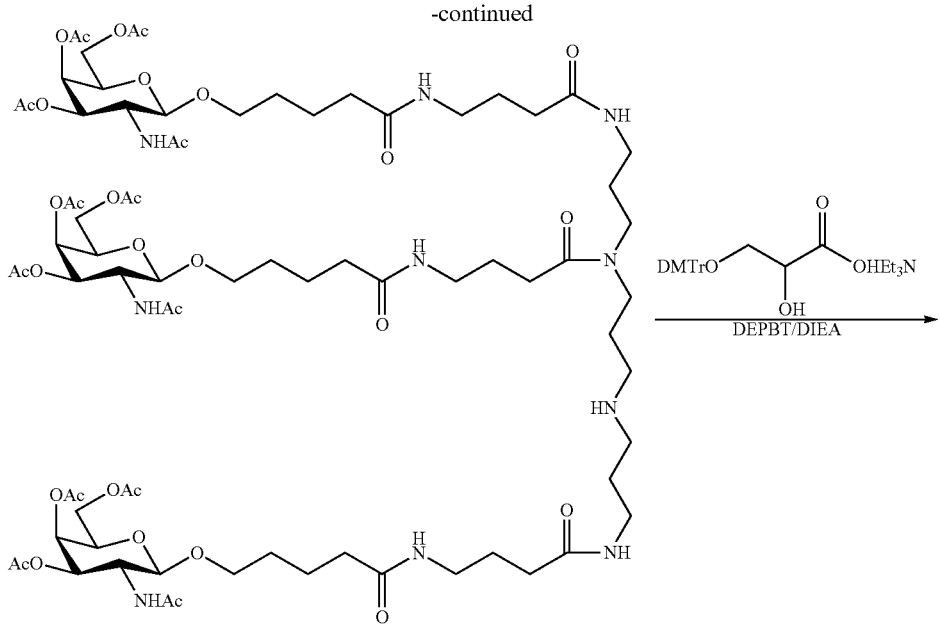
P-7
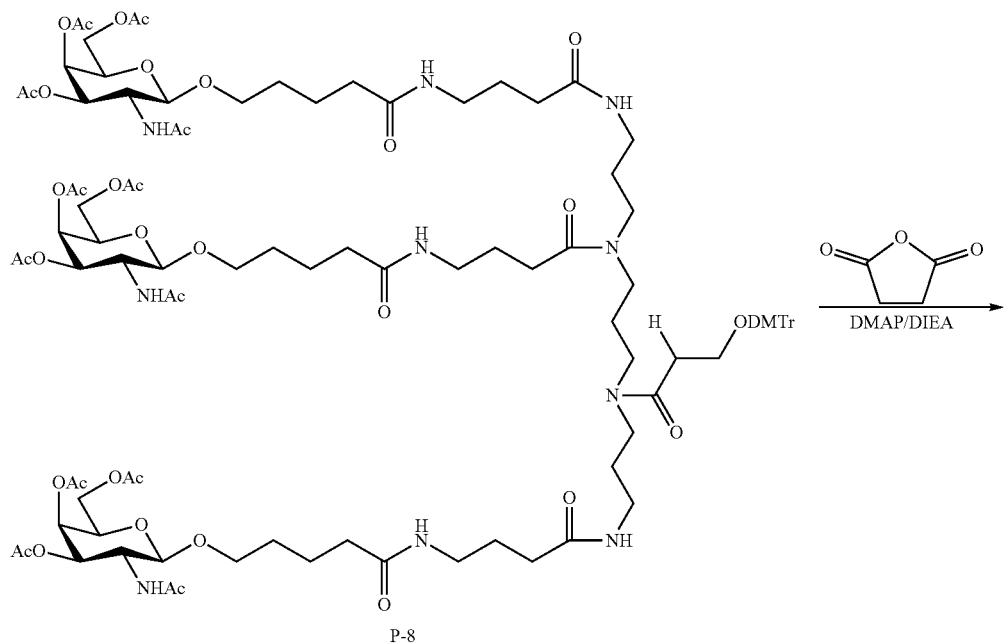
P-8

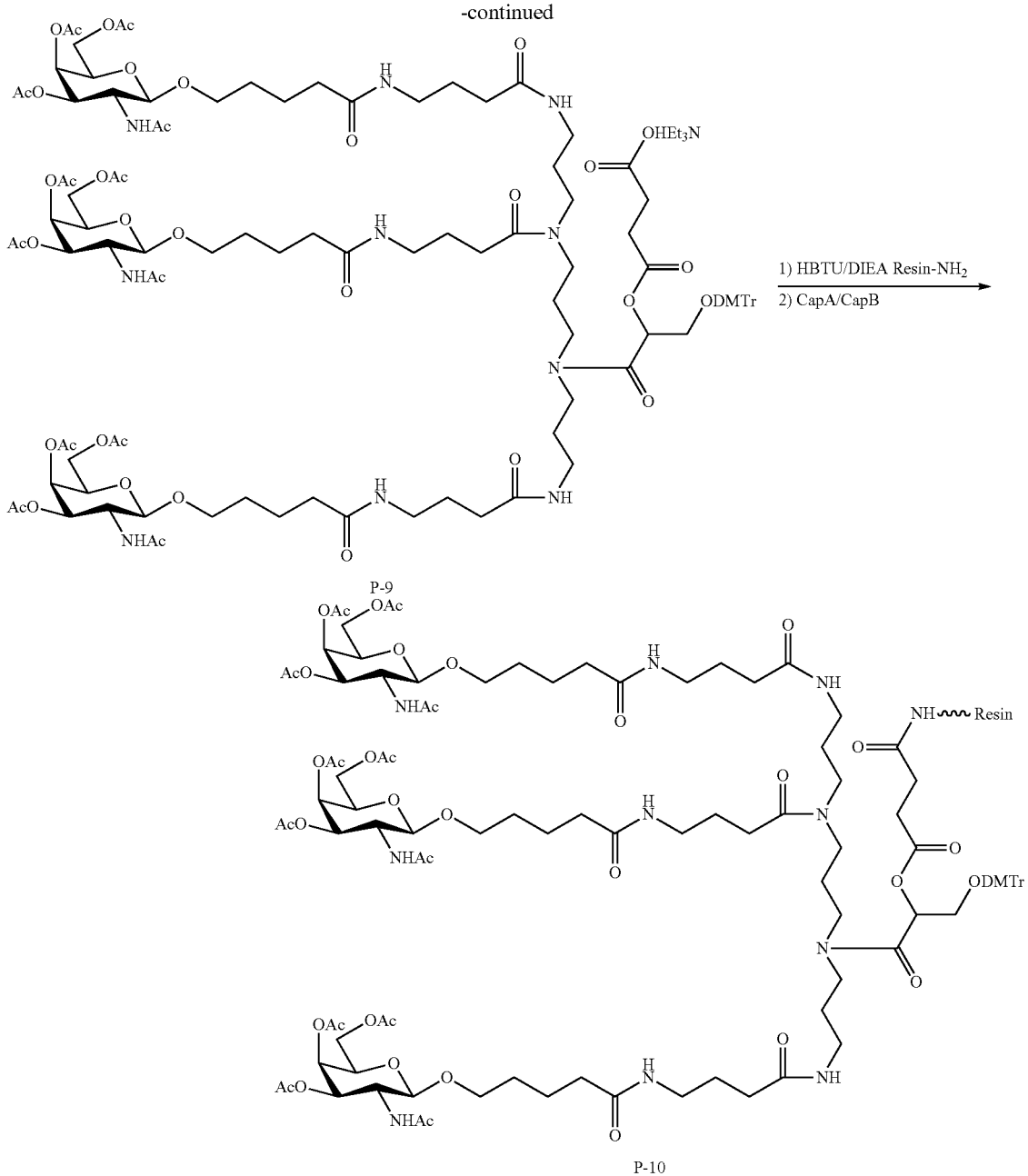

(3-1-1) Synthesis of GAL5-C4-1

GAL-5 (13.43 g, 30.0 mmol) obtained according to the method described in (1-1-1) above, t-butyl 4-aminobutyrate hydrochloride (5.87 g, 30.0 mmol), O-benzotriazol-tetramethyluronium hexafluorophosphate (13.65 g, 36.0 mmol) and diisopropylethylamine (11.63 g, 90.0 mmol) were added into 40 ml of N,N-dimethylformamide, dissolved uniformly and then stirred at room temperature to react for 5 hours. The resultant reaction solution was added with 300 ml of saturated aqueous sodium bicarbonate solution, extracted three times, each with 200 ml of ethyl acetate. The organic phases were combined and washed once with 200 ml of saturated brine. The organic phases were isolated and dried with anhydrous sodium sulfate. The solvent was removed by evaporation under reduced pressure, and the residue was subjected to suction filtration to dryness in a vacuum oil pump to give 30.3 g of crude product GAL5-C4-1 as oil, which was directly used in the next reaction.

(3-1-2) Synthesis of GAL5-C4-2

The crude product GAL5-C4-1 (30.3 g, 30 mmol) obtained in step (3-1-1) was dissolved in 180 ml of formic acid and stirred at room temperature to react for 16 hours. The solvent was evaporated to dryness. The residue was purified by column chromatography (200-300 mesh normal phase silica gel, with a gradient elution of dichloromethane:methanol=100:18-100:20). The reaction eluate was collected and concentrated to remove the solvents to give a total of 14.84 g of the target product GAL5-C4-2.

(3-1-3) Synthesis of P-6

M-18-Tr (2.02 g, 4.69 mmol) obtained according to the method described in step (1-1-4) and GAL5-C4-2 (8.24 g, 15.48 mmol, obtained by combining two batches of products) obtained in step (3-1-2) were mixed and dissolved in 47 ml of acetonitrile, added with N-methylmorpholine (3.13 g, 30.96 mmol) followed by 4-(4,6-dimethoxytriazin-2-yl)-4-methylmorpholine hydrochloride (DMTMM, 4.28 g, 15.48 mmol) to react under stirring at room temperature for 2 hours. The resultant reaction solution was diluted with 20 ml of dichloromethane. The organic phase was washed with 10 ml of saturated sodium bicarbonate solution and 10 ml of saturated brine, respectively. The organic phases were combined, dried with anhydrous sodium sulfate, and filtered. The solvent was removed by evaporation to dryness under reduced pressure to give a crude product, which was purified by using a normal phase silica gel column (200-300 mesh). The column was packed with petroleum ether, added with 1 wt % triethylamine for neutralizing the acidity of silica gel, and eluted with a gradient elution of dichloromethane:methanol=100:5-100:7. The eluate was collected, and the solvent was removed by evaporation to dryness under reduced pressure to give a total of 8.27 g of pure product P-6.

(3-1-4) Synthesis of P-7

P-6 (6.82 g, 3.456 mmol) obtained in (3-1-3) above was dissolved in 69 ml of dichloromethane, and added with dichloroacetic acid (13.367 g, 103.67 mmol) to react at room temperature for 2 hours. The resultant reaction solution was diluted by adding 100 ml of dichloromethane, washed and adjusted to pH 7-8 with saturated sodium bicarbonate solution.

The aqueous phase was extracted six times, each with 30 ml of dichloromethane. The organic phases were combined, dried with anhydrous sodium sulfate, and filtered. Then the solvent was removed by evaporation to dryness under reduced pressure to give a crude product. The crude product was purified by using a normal phase silica gel (200-300 mesh). The column was added with 10 wt % triethylamine for neutralizing the acidity of silica gel, equilibrated with 1 wt ‰ triethylamine and eluted with a gradient elution of dichloromethane:methanol=100:30-100:40. The eluate was collected, and the solvent was removed by evaporation to dryness under reduced pressure to give a total of 4.82 g of P-7. MS m/z: C78H127N10O33, [M+H]+, calculated: 1732.91, measured: 1735.73.

(3-1-5) Synthesis of P-8

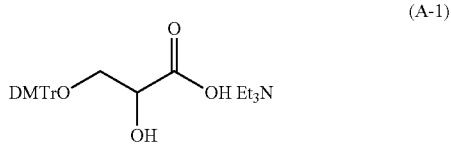

(A-1)

P-7 (2.653 g, 1.532 mmol) and A-1 (2.342 g, 4.596 mmol) were mixed and dissolved in 16 ml of dichloromethane, and added with 3-diethoxyphosphoryl-1,2,3-benzotrizin-4(3H)-one (DEPBT) (1.375 g, 4.596 mmol) followed by diisopropylethylamine (1.188 g, 9.191 mmol) to react under stirring at 25° C. for 2 hours. The organic phase was washed with 10 ml of saturated sodium bicarbonate. The aqueous phase was extracted three times, each with 10 ml of dichloromethane. The organic phase was washed with 10 ml of saturated brine. The aqueous phase was extracted twice, each with 10 ml of dichloromethane, and the organic phases were combined, dried with anhydrous sodium sulfate and filtered. The solvent was removed by evaporation to dryness under reduced pressure, and the residue was foam-dried in a vacuum oil pump overnight to give a crude product. The crude product was subjected to a column purification. The column was filled with 120 g normal phase silica gel (200-300 mesh), added with 20 ml triethylamine for neutralizing the acidity of silica gel, equilibrated with petroleum ether containing 1 wt % triethylamine and eluted with a gradient elution of petroleum ether:ethyl acetate:dichloromethane:N,N-dimethylformamide=1:1:1:0.5-1:1:1:0.6. The eluate was collected, and the solvent was removed by evaporation to dryness under reduced pressure to give a total of 2.793 g of pure product P-8.

(3-1-6) Synthesis of P-9

P-8 (490 mg, 0.231 mmol), succinic anhydride (69 mg, 0.693 mmol) and 4-dimethylaminopyridine (DMAP, 68 mg, 0.554 mmol) were mixed and dissolved in 2.3 ml of dichloromethane, and added with diisopropylethylamine (DIPEA, 149 mg, 1.155 mmol) to react under stirring at 25° C. for 21 hours. The resultant reaction solution was diluted with 50 ml dichloromethane, and then washed with 100 ml of 0.5 M triethylamine phosphate. The aqueous phase was extracted three times, each with 10 ml of dichloromethane. The organic phases were combined, and the solvent was removed by evaporation to dryness under reduced pressure to give a crude product. The crude product was subjected to a column purification. The column was filled with 80 g normal phase silica gel (200-300 mesh), added with 1 wt % triethylamine for neutralizing the acidity of silica gel, equilibrated with dichloromethane and eluted with a gradient elution of 1 wt ‰ triethylamine-containing dichloromethane:methanol=100:18-100:20. The eluate was collected, and the solvent was removed by evaporation to dryness under reduced pressure to give a total of 200 mg of pure product P-9 conjugation molecule. MS m/z: C106H153N10O41, [M-DMTr]+, calculated: 1921.05, measured: 1920.97.

(3-1-7) Synthesis of P-10

P-10 was prepared by using the same method as that in step (1-1-9) of Preparation Example 1, except that the P-9 conjugation molecule was used to replace the L-9 conjugation molecule, thereby obtaining the P-9 conjugation molecule linked to a solid phase support.

(3-2) Synthesis of the Conjugate P10-siHB3M1SVP

Conjugate 13 was prepared by using the same method as that in steps (1-2)-(1-4) of Preparation Example 1, except that Compound P-10 was used to replace Compound L-10 to start the synthesis of a sense strand. It was expected that the conjugate P10-siHB3M1SVP having a structure as shown by Formula (404) can be obtained.

Preparation Example 4 Preparation of the Conjugate R5-siHB3M1SVP (Conjugate 14)

(4-1) Synthesis of Compound R-5

Compound R-5 was synthesized according to the following method.

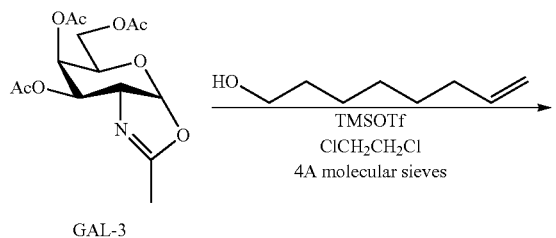
GAL-3
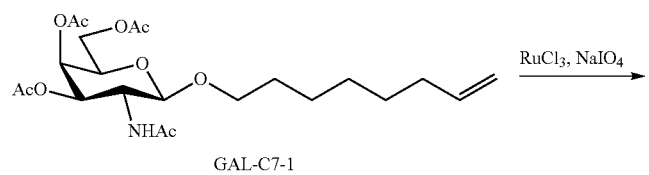
GAL-C7-1
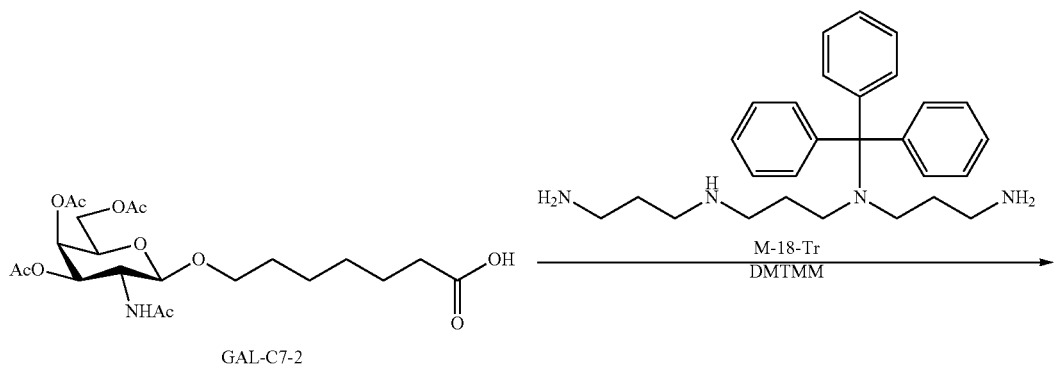
GAL-C7-2
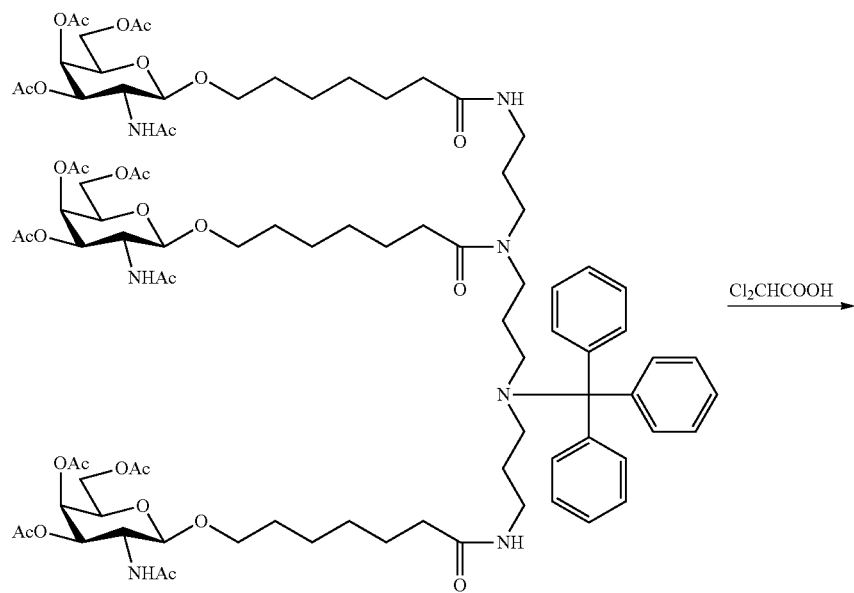
R-1

-continued
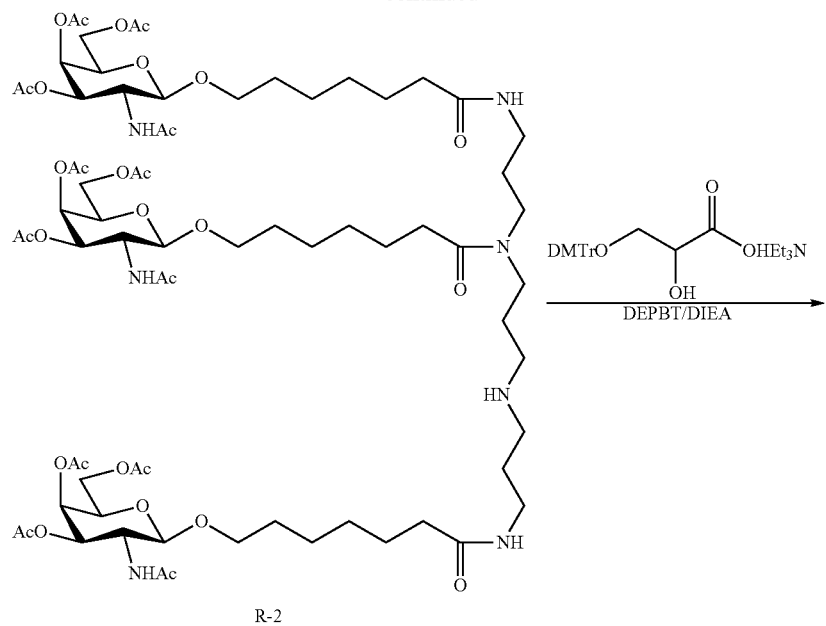
R-2
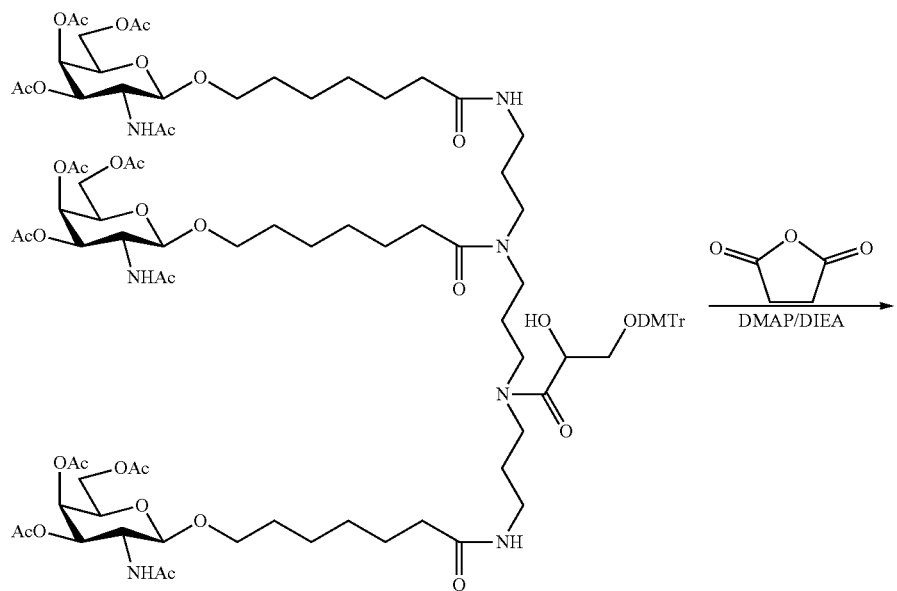
R-3

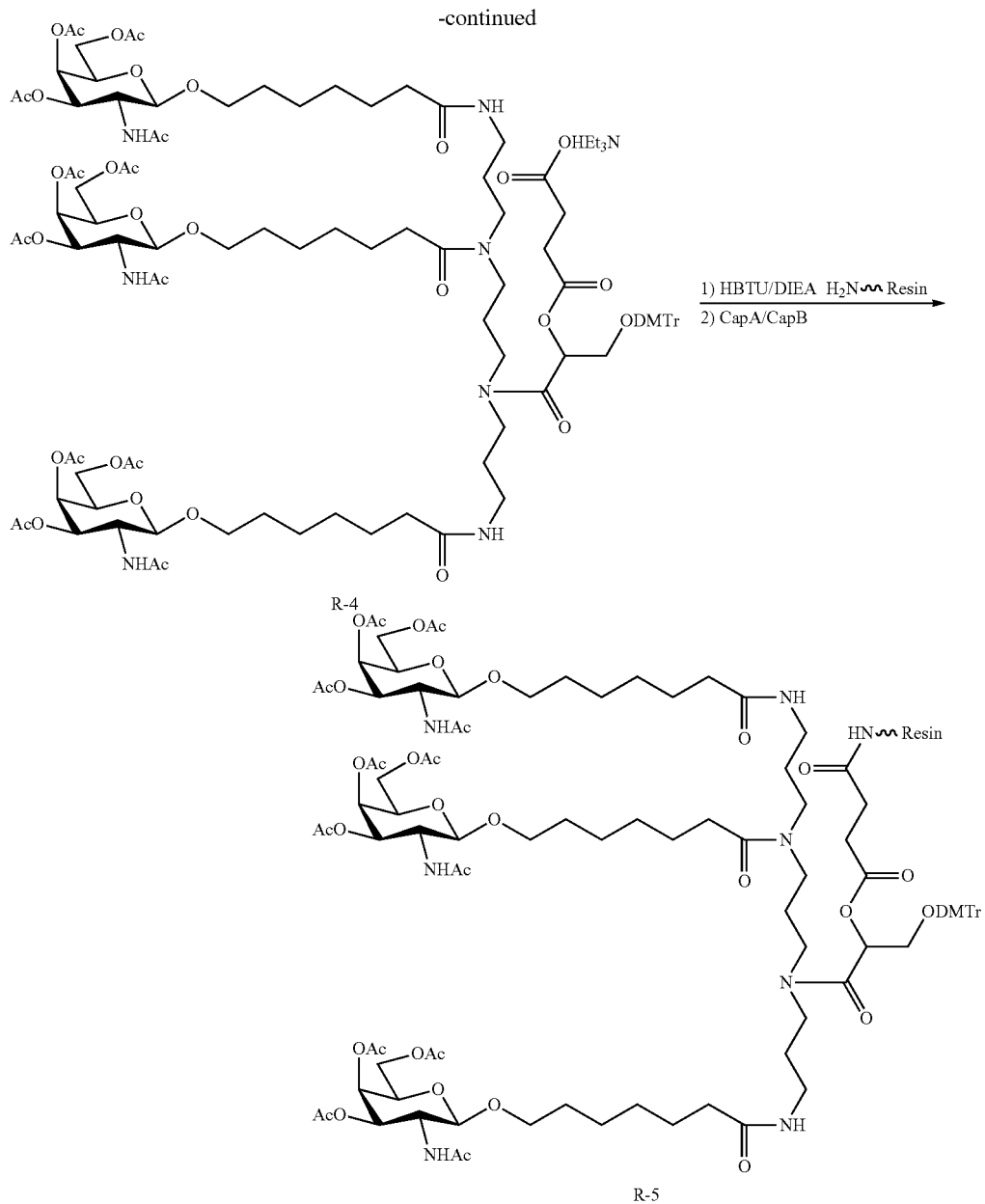

(4-1-1) Synthesis of GAL-C7-1

GAL-3 (26.4 g, 80.2 mmol) obtained according to the method described in step (1-1-1b) was dissolved in 134 ml of anhydrous 1,2-dichloroethane, and added with 60 g of 4 Å molecular sieve powder followed by 7-octen-1-ol (11.3 g, 88.2 mmol) to react under stirring at room temperature for 10 minutes. Trimethylsilyl trifluoromethanesulphonate (8.9 g, 40.1 mmol) was added in an ice bath and nitrogen atmosphere to react under stirring at room temperature for 24 hours. The 4 Å molecular sieve powder was removed by filtration. 500 ml of saturated aqueous sodium bicarbonate solution was added to the filtrate for washing. The organic phase was isolated. The aqueous phase was extracted once with 100 ml of dichloromethane. The organic phases were combined and washed once with 250 ml of saturated brine. The organic phase was isolated and dried with anhydrous sodium sulfate. The solvent was removed by evaporation under reduced pressure and the residue was subjected to suction filtration to dryness in a vacuum oil pump to give 33.3 g of product GAL-C7-1 as a yellow syrup, which was directly used in the next oxidation reaction without purification.

(4-1-2) Synthesis of GAL-C7-2

GAL-C7-1 (33.3 g, 72.8 mmol) obtained in step (4-1-1) was dissolved in a mixed solvent of 160 ml of dichloromethane and 160 ml of acetonitrile, added with 216 ml of water and solid sodium periodate (62.3 g, 291.2 mmol) respectively, stirred in an ice water bath for 10 minutes, and added with a catalyst ruthenium trichloride (498 mg, 2.4 mmol). The reaction was naturally warmed to room temperature and stirred for 23 hours. The resultant reaction solution was diluted by adding 200 ml of water under stirring, and adjusted to pH 7.5 by adding saturated sodium bicarbonate. The organic phase was isolated and discarded. The aqueous phase was extracted three times, each with dichloromethane. The organic phases were discarded. The aqueous phase was adjusted to a pH of about 3 with citric acid solid and extracted three times (each with 200 ml of dichloromethane), and the organic phases were combined and dried with anhydrous sodium sulfate. The solvent was removed by evaporation under reduced pressure, and then the residue was purified by column chromatography (200-300 mesh normal phase silica gel, with a gradient elution of dichloromethane:methanol=100:18-100:20) to give 22.4 g of product GAL-C7-2 as a white foamy solid. MS m/z: C21H32NO11, [M+H]+, calculated: 476.50, measured: 475.94.

(4-1-3) Synthesis of R-1

M-18-Tr (2.02 g, 4.69 mmol) obtained according to the method described in step (1-1-4) and GAL-C7-2 (7.36 g, 15.48 mmol) were mixed and dissolved in 47 ml of acetonitrile, added with N-methylmorpholine (3.13 g, 30.96 mmol) followed by 4-(4,6-dimethoxytriazin-2-yl)-4-methylmorpholine hydrochloride (DMTMM, 4.28 g, 15.48 mmol) to react under stirring at room temperature for 2 hours. The resultant reaction solution was diluted with 200 ml of dichloromethane. The organic phase was washed with 100 ml of saturated sodium bicarbonate solution and 100 ml of saturated brine, respectively. The organic phases were combined, dried with anhydrous sodium sulfate, and filtered. The solvent was removed by evaporation to dryness under reduced pressure to give a crude product, which was purified by a normal phase silica gel column (200-300 mesh). The column was packed with petroleum ether, added with 1 wt % triethylamine for neutralizing the acidity of silica gel, and eluted with a gradient elution of dichloromethane:methanol=100:5-100:7. The eluate was collected and the solvent was removed by evaporation to dryness under reduced pressure to give 7.82 g of pure product R-1.

(4-1-4) Synthesis of R-2

R-1 (6.23 g, 3.456 mmol) was dissolved in 69 ml of dichloromethane, and added with dichloroacetic acid (13.367 g, 103.67 mmol) to react at room temperature for 2 hours. The resultant reaction solution was diluted by adding 100 ml of dichloromethane, washed and adjust to pH 7-8 with saturated sodium bicarbonate solution. The aqueous phase was extracted six times, each with 30 ml of dichloromethane. The organic phases were combined, dried with anhydrous sodium sulfate, and filtered. Then the solvent was removed by evaporation to dryness under reduced pressure to give a crude product. The crude product was purified by a normal phase silica gel column (200-300 mesh). The column was added with 10 wt % triethylamine for neutralizing the acidity of silica gel, equilibrated with 1 wt ‰ triethylamine, and eluted with a gradient elution of dichloromethane:methanol=100:30-100:40. The solvent was removed by evaporation to dryness under reduced pressure to give 4.49 g of pure product R-2.

(4-1-5) Synthesis of R-3

R-2 (2.391 g, 1.532 mmol) and A-1 (2.342 g, 4.596 mmol) were mixed and dissolved in 16 ml of dichloromethane, and added with 3-(diethoxyphosphoryloxy)-1,2,3-benzotrizin-4 (3H)-one (DEPBT, 1.375 g, 4.596 mmol) followed by diisopropylethylamine (1.188 g, 9.191 mmol) to react under stirring at 25° C. for 2 hours. The organic phase was washed with 10 ml of saturated sodium bicarbonate. The aqueous phase was extracted three times, each with 10 ml of dichloromethane. The organic phase was washed with 10 ml of saturated brine. The aqueous phase was extracted twice, each with 10 ml of dichloromethane. The organic phases were combined, dried with anhydrous sodium sulfate and filtered. The solvent was removed by evaporation to dryness under reduced pressure, and the residue was foam-dried in a vacuum oil pump overnight to give a crude product. The crude product was subjected to a column purification. The column was filled with 120 g normal phase silica gel (200-300 mesh), added with 20 ml triethylamine for neutralizing the acidity of silica gel, equilibrated with petroleum ether containing 1 wt % triethylamine, and eluted with a gradient elution of petroleum ether:ethyl acetate:dichloromethane:N,N-dimethylformamide=1:1:1:0.5-1:1:1:0.6. The solvent was removed by evaporation to dryness under reduced pressure to give 2.642 g of pure product R-3.

(4-1-6) Synthesis of R-4

R-3 (795 mg, 0.4074 mmol), succinic anhydride (82 mg, 0.8148 mmol) and 4-dimethylaminopyridine (DMAP, 100 mg, 0.8148 mmol) were mixed and dissolved in 4 ml of dichloromethane, and added with diisopropylethylamine (DIEA, 100 mg, 0.8148 mmol) to react under stirring at 25° C. for 18 hours. The resultant reaction solution was washed with 5 ml of 0.5 M triethylamine phosphate. The aqueous phase was extracted three times, each with 5 ml of dichloromethane. The organic phases were combined, and the solvent was removed by evaporation to dryness under reduced pressure to give a crude product. The crude product was subjected to a column purification. The column was filled with 30 g normal phase silica gel (200-300 mesh), added with 1 wt % triethylamine for neutralizing the acidity of silica gel, equilibrated with dichloromethane, and eluted with a gradient elution of 1 wt ‰ triethylamine-containing dichloromethane:methanol=100:18-100:20. The eluate was collected, and the solvent was removed by evaporation to dryness under reduced pressure to give 505 mg of pure product of R-4 conjugation molecule.

(4-1-7) Synthesis of R-5

R-5 was prepared by using the same method as that in step (1-1-9) of Preparation Example 1, except that R-4 conjugation molecule was used to replace the L-9 conjugation molecule, thereby obtaining the R-4 conjugation molecule linked to a solid phase support.

(4-2) Synthesis of the Conjugate R5-siHB3M1SVP

Conjugate 14 was prepared by using the same method as that in steps (1-2)-(1-4) of Preparation Example 1, except that Compound R-5 was used to replace Compound L-10 to start the synthesis of a sense strand. It was expected that the conjugate R5-siHB3M1SVP with a structure as shown by Formula (407) can be obtained.

Preparation Example 5 Preparation of the Conjugate LA5-siHB3M1SVP (Conjugate 15)

It was expected that Compound LA-5 can be synthesized according to the following process route:

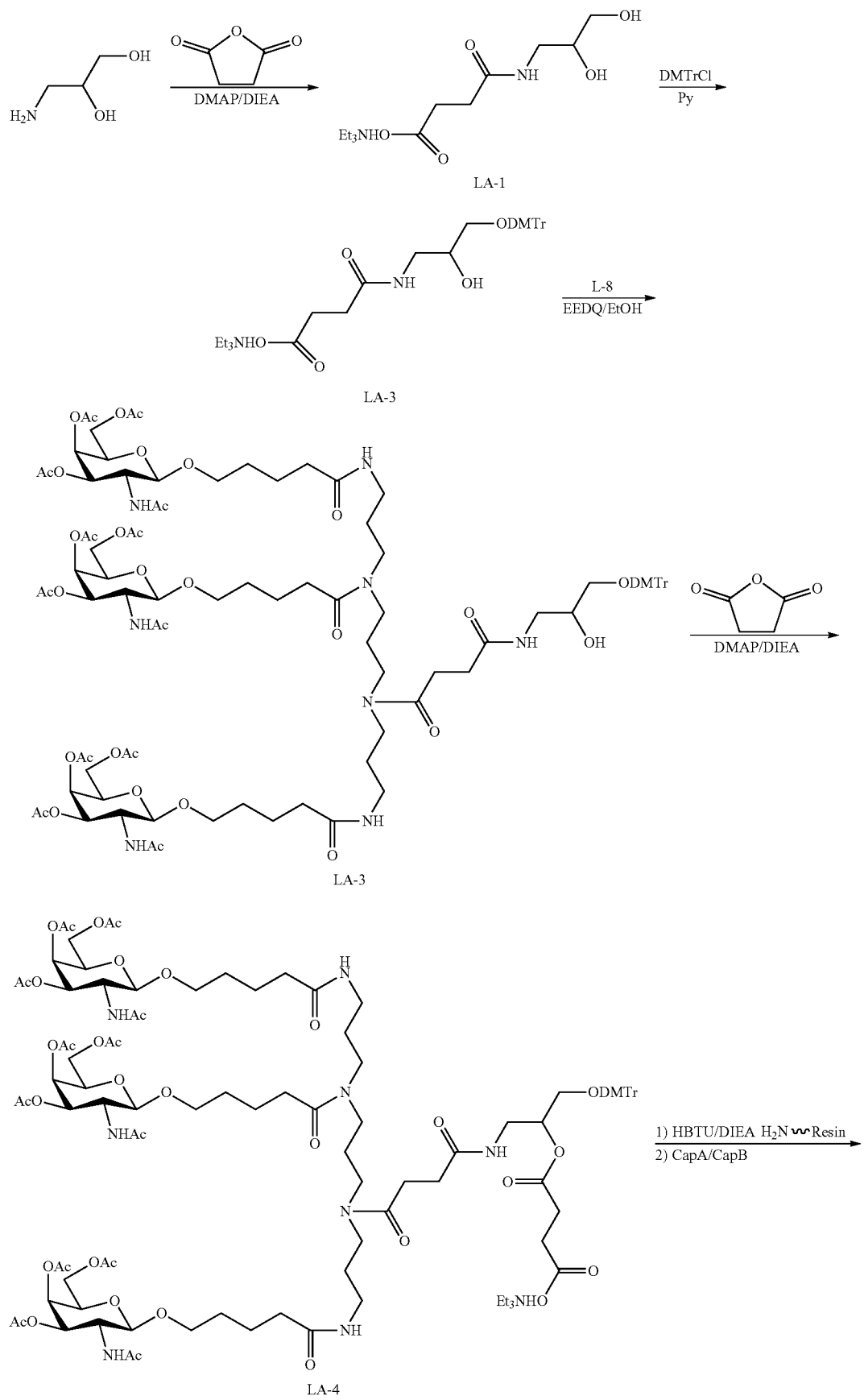

-continued

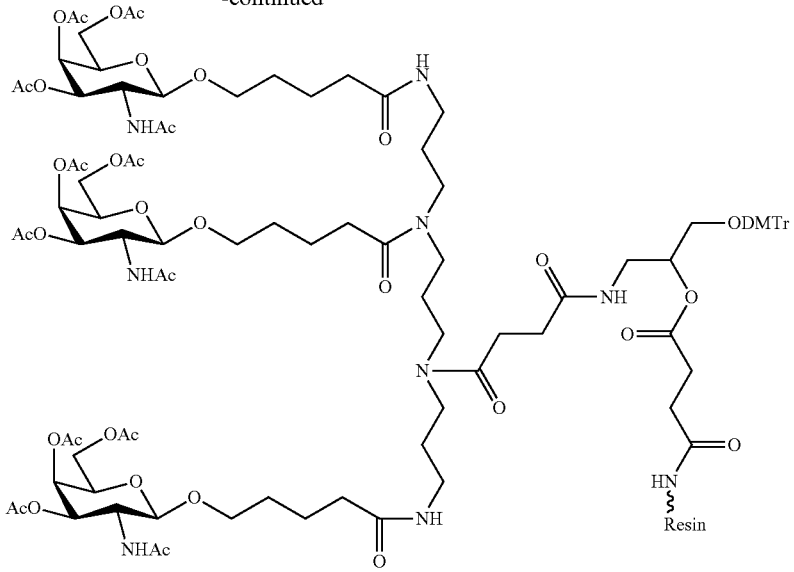

LA-5

Conjugate 15 was prepared by using the same method as that in steps (1-2)-(1-4) of Preparation Example 1, except that Compound LA-5 was used to replace Compound L-10 to start the synthesis of a sense strand. It was expected that the conjugate LA5-siHB3M1SVP with a structure as shown by Formula (412) can be obtained.

Preparation Example 6 Preparation of the Conjugate LB5-siHB3M1SVP (Conjugate 16)

(6-1) Synthesis of Compound LB-5

Compound LB-5 was synthesized according to the following process:

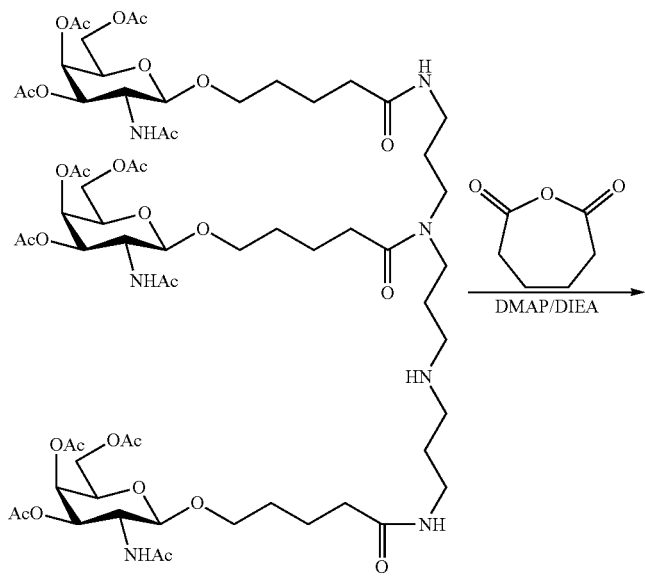

L-8

-continued
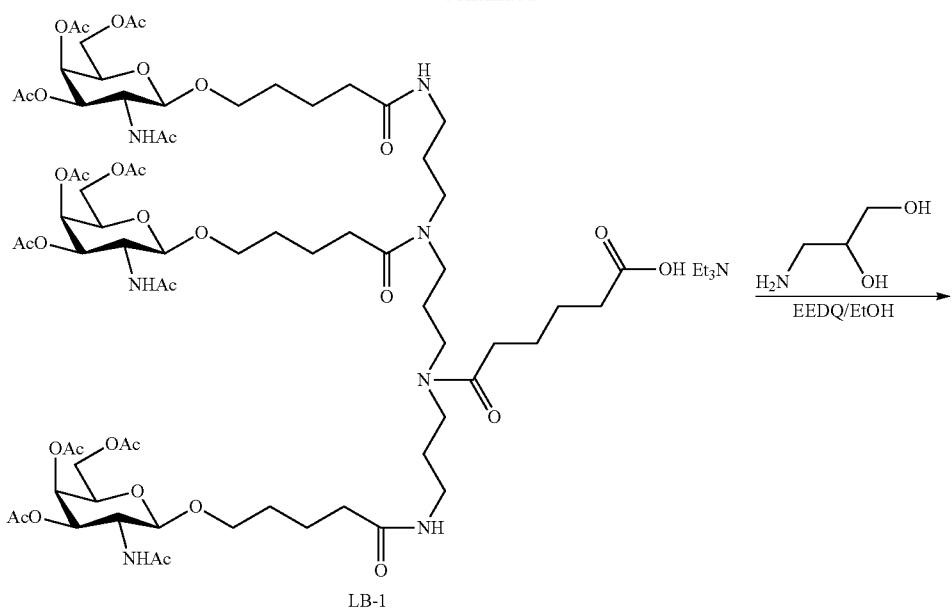
LB-1
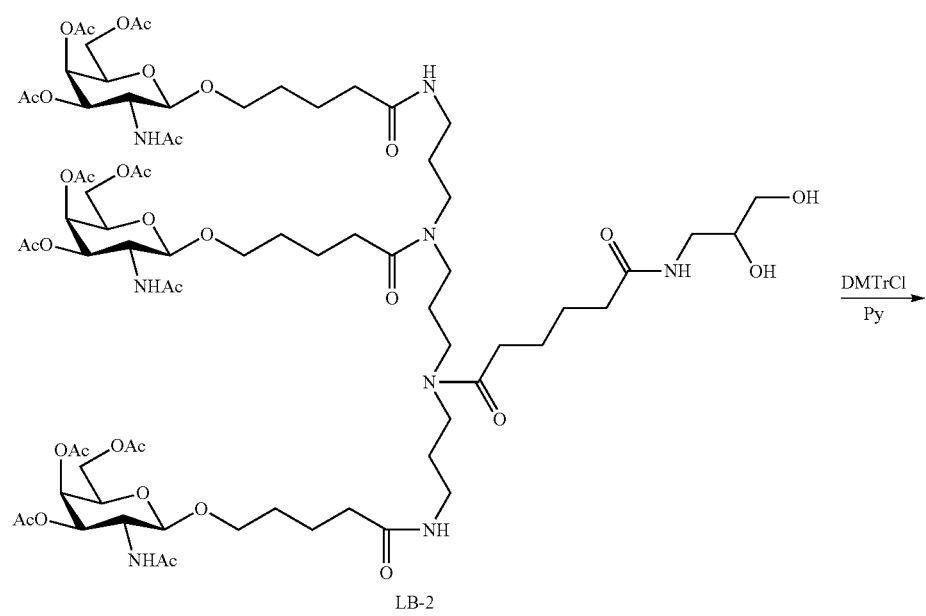
LB-2

-continued
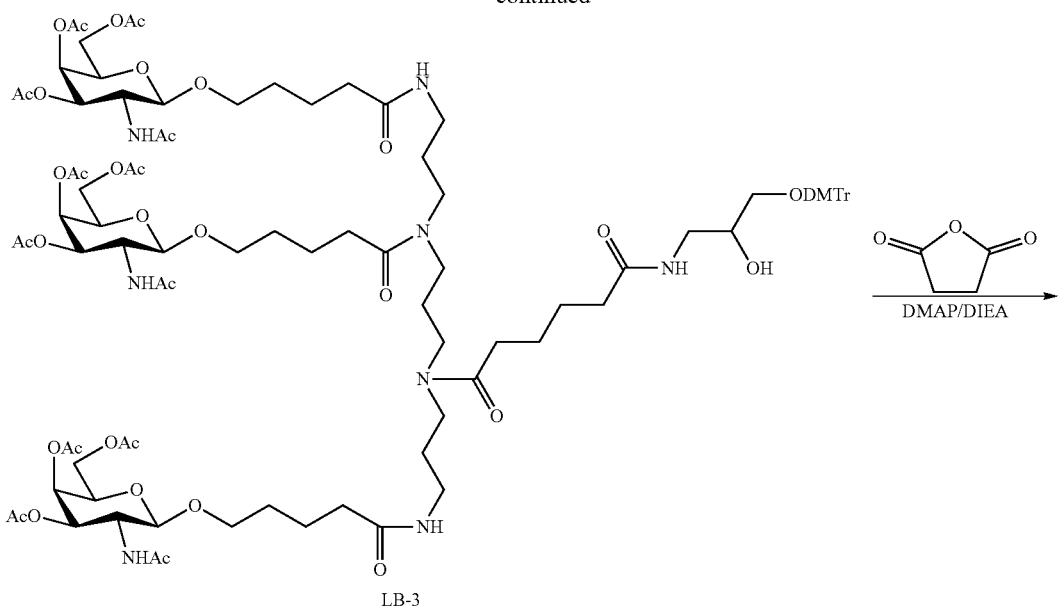
LB-3
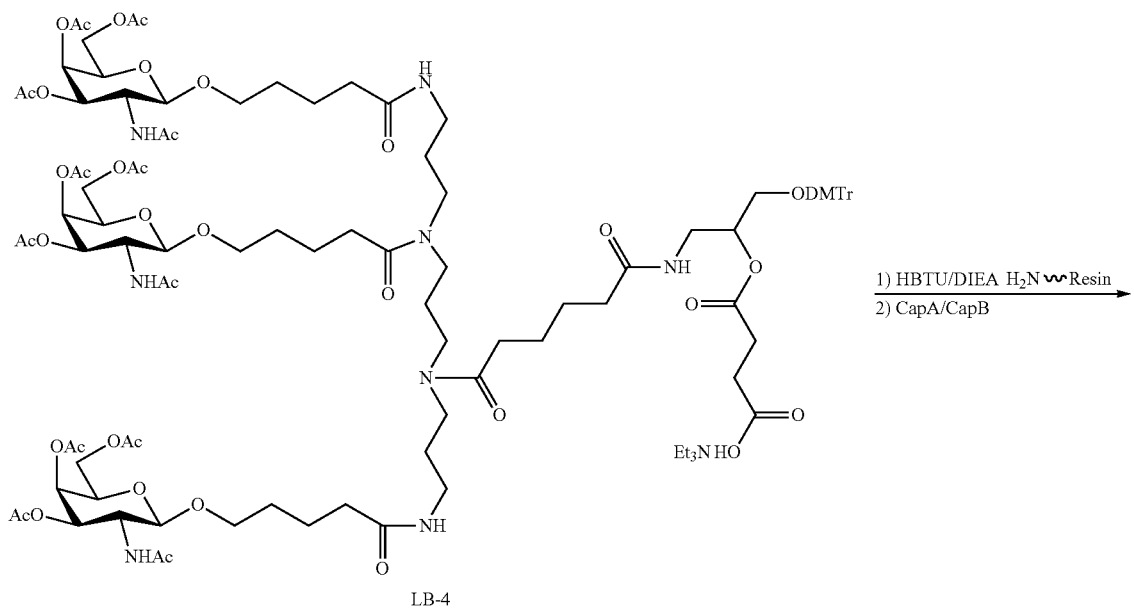
LB-4

-continued

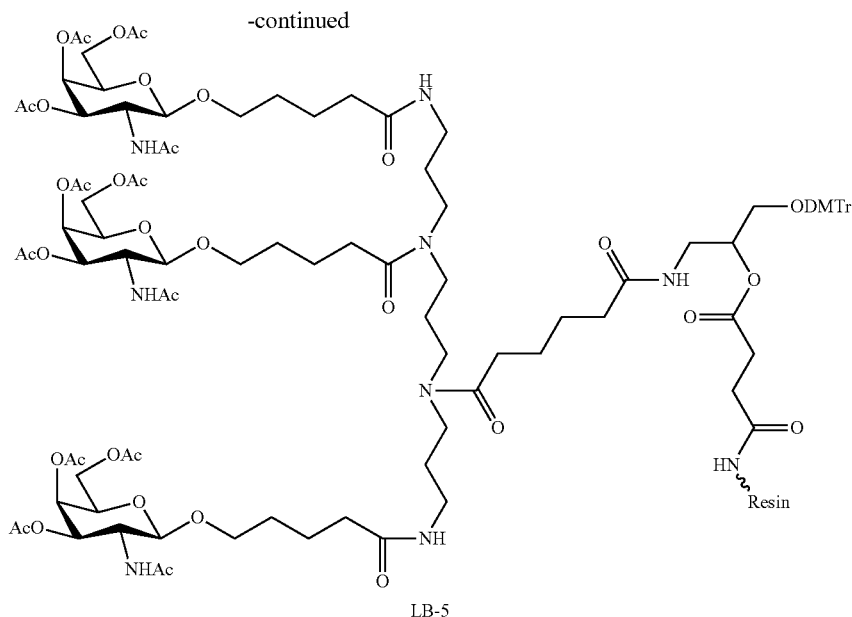

LB-5

(6-1-1) Synthesis of LB-1

L-8 (5.0 g, 3.386 mmol) obtained according to the method described in step (1-1-6), adipic anhydride (870 mg, 6.772 mmol) and 4-dimethylaminopyridine (DMAP, 827 mg, 6.772 mmol) were mixed, dissolved in 130 ml of dichloromethane, and added with diisopropylethylamine (DIEA, 2.2 g, 16.931 mmol) to react under stirring at 25° C. for 4 hours. The resultant reaction solution was added with 70 ml dichloromethane for dilution and then washed with 0.5 M triethylamine phosphate. The aqueous phase was extracted four times, each with 10 ml of dichloromethane. The organic phases were combined, and the solvent was removed by evaporation to dryness under reduced pressure to give a crude product. The crude product was subjected to a column purification. The column was filled with 120 g normal phase silica gel (200-300 mesh), added with 1 wt % triethylamine for neutralizing the acidity of silica gel, equilibrated with dichloromethane, and eluted with a gradient elution of petroleum ether:ethyl acetate:dichloromethane:methanol=1:1:1:0.2-1:1:1:1. The solvent was removed by evaporation to dryness under reduced pressure to give 4.267 g of pure product LB-1.

(6-1-2) Synthesis of LB-2

LB-1 (4.697 g, 2.753 mmol, combination of 2 batches of products) obtained according to the method described in step (6-1-1), 3-amino-1,2-propanediol (313 mg, 3.442 mmol), 4-(4,6-dimethoxytriazin-2-yl)-4-methylmorpholine hydrochloride (DMTMM, 953 mg, 3.442 mmol) and N-methylmorpholine (700 mg, 6.884 mmol) were sequentially added to the mixed solution of 30 ml of acetonitrile and 3 ml of methanol to react under stirring at room temperature overnight. The solvent was evaporated to dryness, and the residue was purified by column chromatography (200-300 mesh normal phase silica gel, with a gradient elution of dichloromethane:methanol=1:0.07-1:0.5). The eluate was collected and concentrated to remove the solvents to give 3.27 g of target product LB-2.

(6-1-3) Synthesis of LB-3

LB-2 (2.27 g, 1.353 mmol) was dissolved in 14 ml of anhydrous pyridine, and added with 4,4'-dimethoxytrityl chloride (688 mg, 2.03 mmol) to react under stirring at room temperature overnight. The reaction was quenched by addition of 150 ml of methanol. The solvent was evaporated to dryness, and the residue was purified by column chromatography (200-300 mesh normal phase silica gel, with a gradient elution of dichloromethane:methanol=1:0.05-1:0.2). The eluate was collected and concentrated to remove the solvent to give 1.647 g of target product LB-3.

(6-1-4) Synthesis of LB-4:

LB-3 (822 mg, 0.415 mmol), succinic anhydride (83 g, 0.83 mmol) and 4-dimethylaminopyridine (DMAP, 102 mg, 0.83 mmol) were mixed, dissolved in 4 ml of dichloromethane, added with DIPEA (270 mg, 2.075 mmol), and stirred at 25° C. to react overnight. The resultant reaction solution was washed with 0.5 M triethylamine phosphate three times. The aqueous phase was extracted three times, each with 2 ml of dichloromethane. The organic phases were combined, and the solvent was removed by evaporation to dryness under reduced pressure to give a crude product. The crude product was subjected to a column purification. The column was filled with normal phase silica gel (200-300 mesh), added with 5 wt % triethylamine for neutralizing the acidity of silica gel, equilibrated with petroleum ether, and eluted with a gradient elution of 1 wt ‰ triethylamine-containing dichloromethane:methanol=100:5-100:20. The solvent was removed by evaporation to dryness under reduced pressure to give 787 mg of pure product LB-4 conjugation molecule.

(6-1-5) Synthesis of LB-5

LB-5 was prepared by using the same method as that in step (1-1-9) of Preparation Example 1, except that the LB-4 conjugation molecule was used to replace the L-9 conjugation molecule, thereby obtaining the LB-4 conjugation molecule linked to a solid phase support.

(6-2) Synthesis of the Conjugate LB5-siHB3M1SVP

Conjugate 16 was prepared by using the same method as that in steps (1-2)-(1-4) of Preparation Example 1, except that Compound LB-5 was used to replace Compound L-10 to start the synthesis of a sense strand. It was expected that the conjugate LB5-siHB3M1SVP with a structure as shown by Formula (413) can be obtained.

Preparation Example 7 Synthesis of the Conjugate V8-siHB3M1SVP (Conjugate 17)

It was expected that Compound V-8 can be synthesized according to the following process route:

-continued
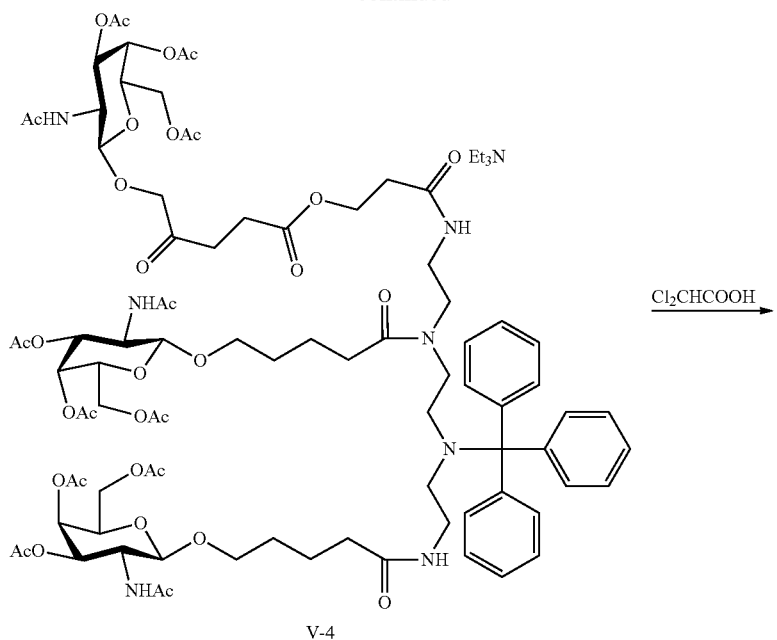
V-4
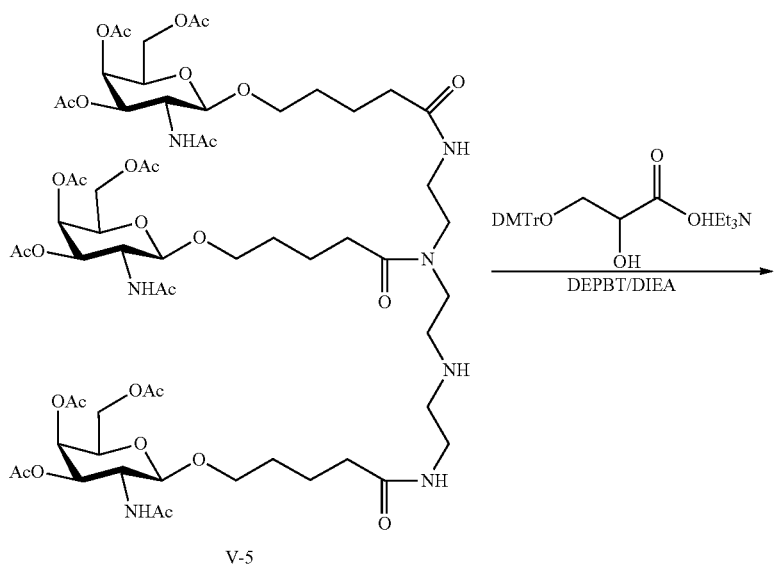
V-5

-continued
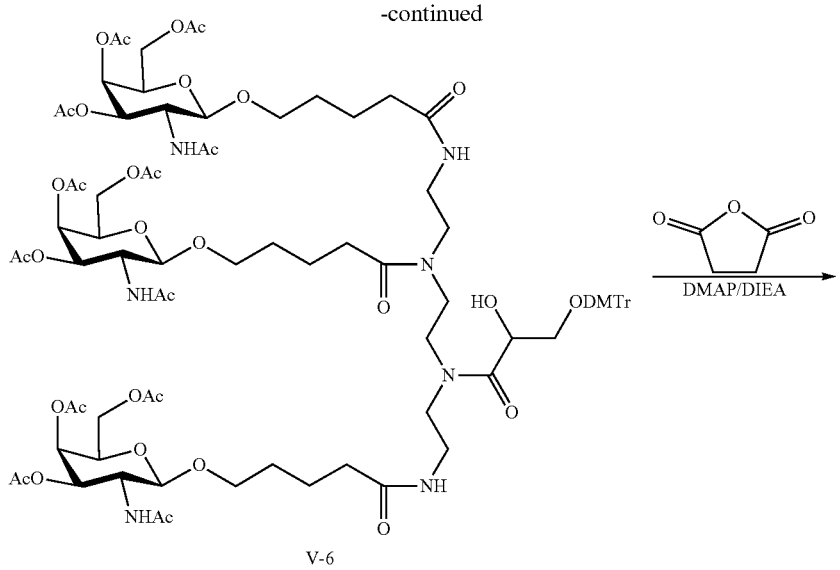
V-6
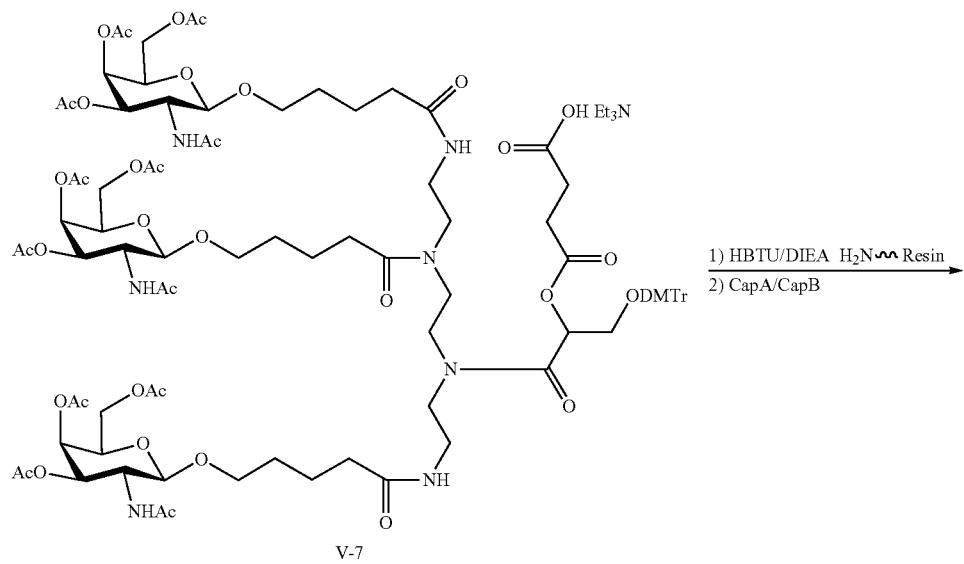
V-7
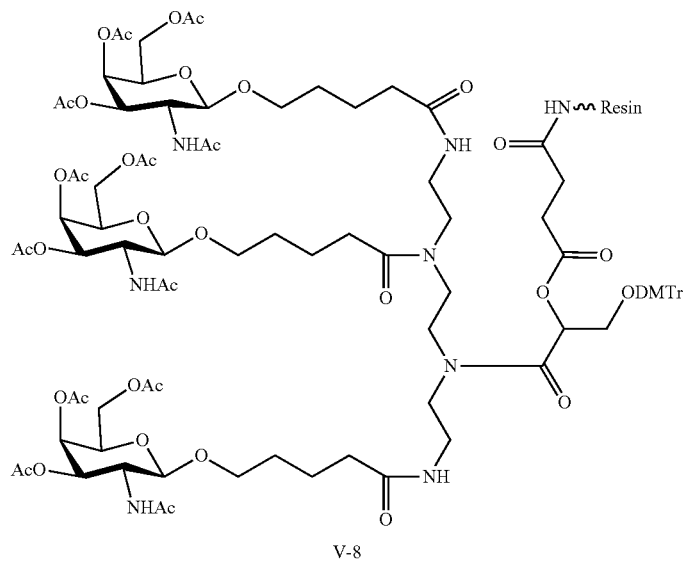
V-8

Conjugate 17 was prepared by using the same method as that in steps (1-2)-(1-4) of Preparation Example 1, except that Compound V-8 was used to replace Compound L-10 to start the synthesis of a sense strand. It was expected that the conjugate V8-siHB3M1SVP with a structure as shown by Formula (414) can be obtained.

Preparation Example 8 Preparation of the Conjugate W8-siHB3M1SVP (Conjugate 18)

(8-1) Synthesis of Compound W-8

Compound W-8 was synthesized according to the following process:

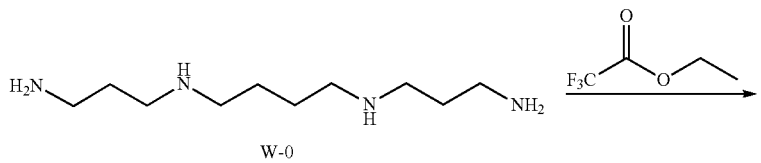

W-0

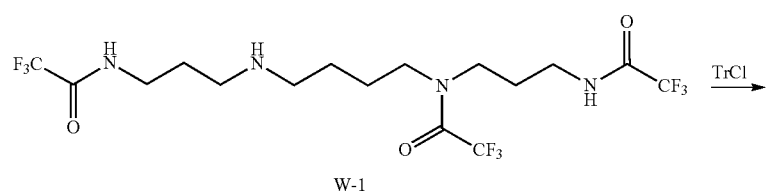

W-1

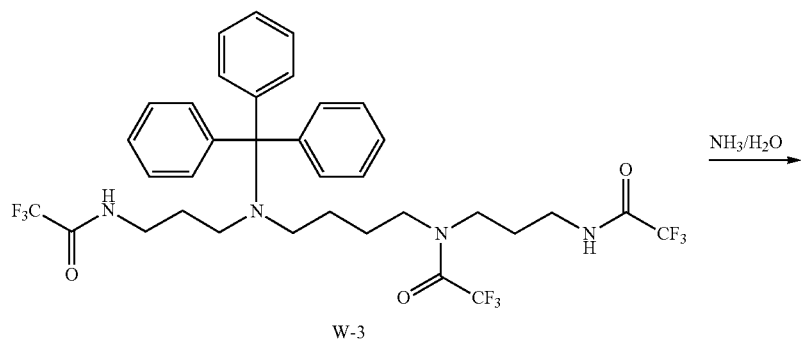

W-3

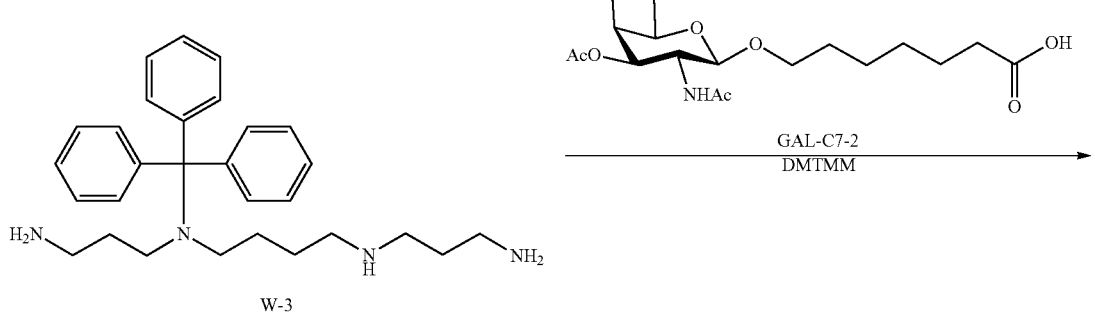

W-3

-continued
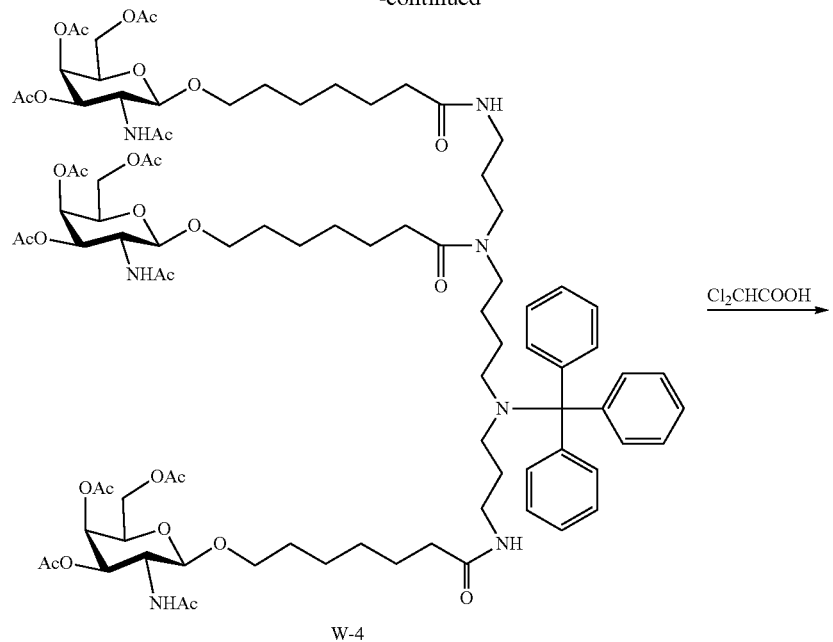
W-4
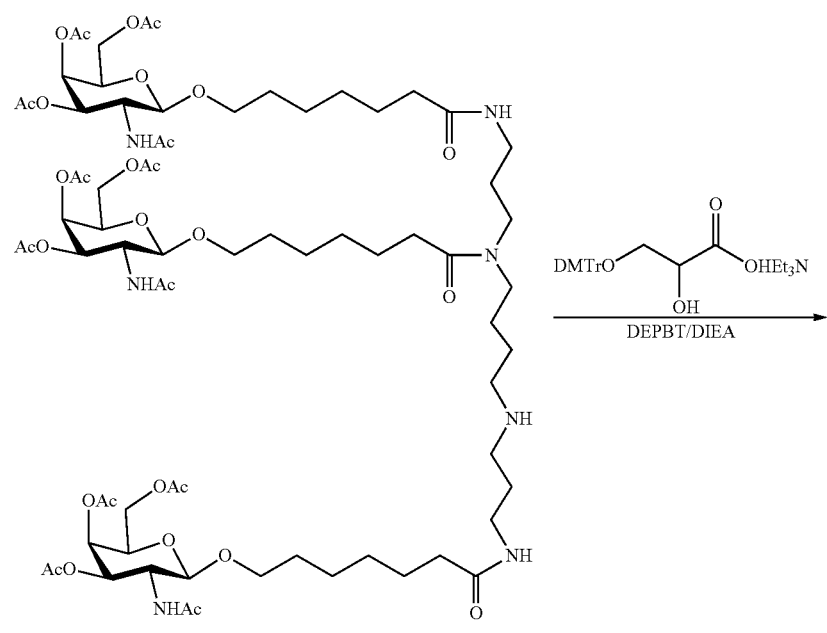
W-5

-continued
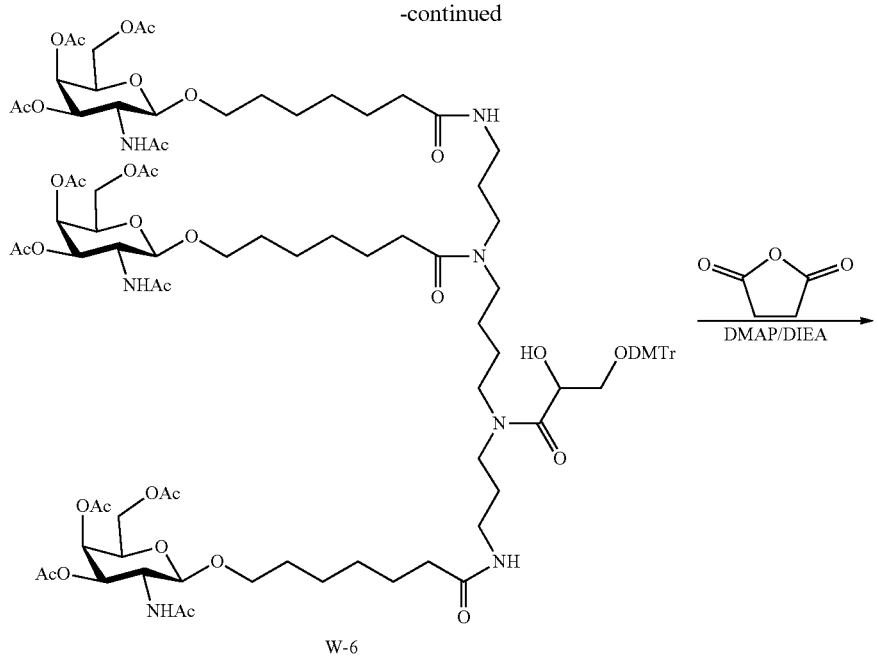
W-6
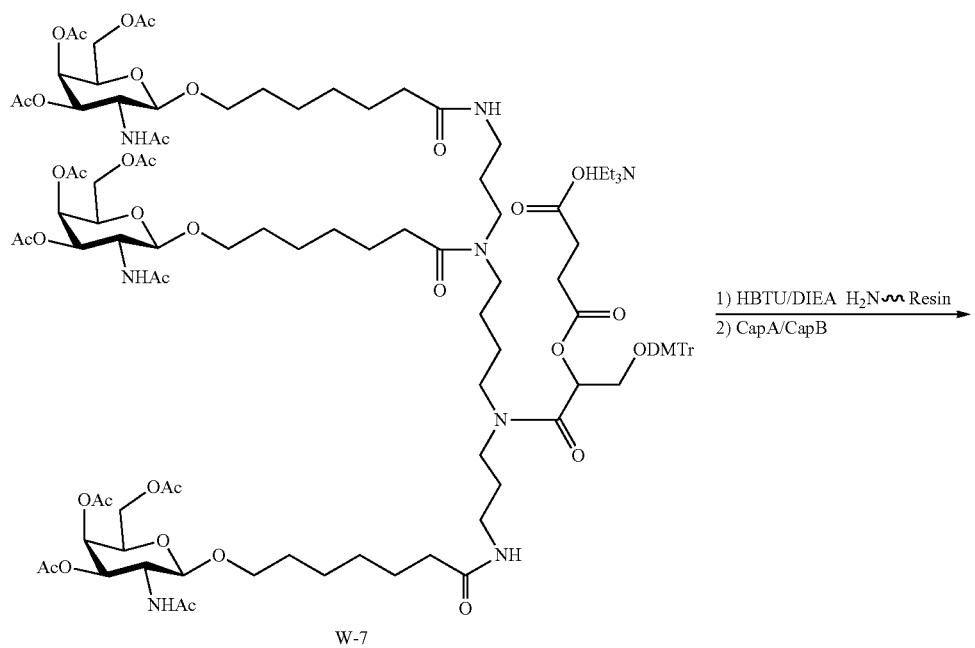
W-7

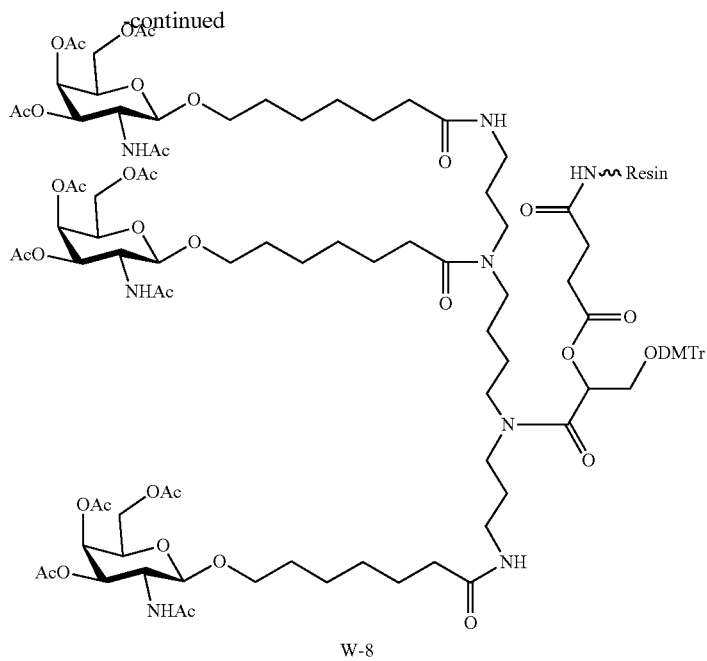

W-8

(8-1-1) Synthesis of W-1

W-0 (2.024 g, 10 mmol) was dissolved in 25 ml of acetonitrile, added with triethylamine (4.048 g, 40 mmol), and cooled to about 0° C. in an ice water bath. Ethyl trifluoroacetate (5.683 g, 40 mmol) was added to react at room temperature for 22 hours. The solvent was removed by evaporation to dryness under reduced pressure, and the residue was foam-dried in a vacuum oil pump for 18 hours to give 5.835 g of crude solid product W-1.

(8-1-2) Synthesis of W-2

The crude product W-1 (5.835 g, 10 mmol) was dissolved in 50 ml of dichloromethane. The resultant reaction solution was added with TrCl (3.345 g, 12 mmol) and triethylamine (1.518 g, 15 mmol) to react under stirring at room temperature for 20 hours. The resultant reaction solution was washed twice (each with 20 ml of saturated sodium bicarbonate) and once with 20 ml of saturated brine. The organic phases were combined, dried with anhydrous sodium sulfate and filtered. The organic solvent was removed by evaporation to dryness under reduced pressure, and the residue was foam-dried in a vacuum oil pump overnight to give 8.012 g of crude solid product W-2. The crude solid product W-2 was used in the next deprotection reaction without treatment.

(8-1-3) Synthesis of W-3

The crude product W-2 (8.012 g, 10 mmol) was dissolved in 100 ml of methanol, and added with 100 ml of aqueous methylamine solution (40 wt %) to react under stirring at 50° C. for 23 hours. Insoluble particles were removed by filtration. The solvent was removed by evaporation to dryness under reduced pressure. The residue was added with 200 ml of mixed solvent of DCM:methanol in a volume ratio of 1:1, and the resultant organic phase was washed with 50 ml of saturated sodium bicarbonate. The aqueous phase was extracted three times, each with 50 ml of dichloromethane. The organic phases were combined, dried with anhydrous sodium sulfate and filtered. The solvent was removed by evaporation to dryness under reduced pressure, and the residue was foam-dried in a vacuum oil pump overnight, and purified by using a normal phase silica gel column (200-300 mesh). The column was packed with petroleum ether, added with 1 wt % triethylamine for neutralizing the acidity of silica gel, and eluted with a gradient elution of dichloromethane:methanol:aqueous ammonia (25 wt %)=1:1:0.05-1:1:0.25. The eluate was collected. The solvent was removed by evaporation to dryness under reduced pressure, and the residue was foam-dried in a vacuum oil pump to give 3.062 g of pure product W-3.

(8-1-4) Synthesis of W-4

W-3 (0.675 g, 1.517 mmol) and GAL-C7-2 (2.60 g, 5.46 mmol) were mixed and dissolved in 47 ml of acetonitrile, added with diisopropylethylamine (1.57 g, 12.14 mmol) followed by 3-(diethoxyphosphoryloxy)-1,2,3-benzotrizin-4(3H)-one (DEPBT, 1.816 g, 6.04 mmol) to react under stirring at room temperature for 2.5 hours. The resultant reaction solution was diluted with 100 ml of dichloromethane. The organic phase was washed with 80 ml of saturated sodium bicarbonate solution and 80 ml of saturated brine, respectively. The organic phases were combined, dried with anhydrous sodium sulfate, and filtered. The solvent was removed by evaporation to dryness under reduced pressure to give a crude product, which was purified by using a normal phase silica gel column (200-300 mesh). The column was packed with petroleum ether, added with 1 wt % triethylamine for neutralizing the acidity of silica gel, and eluted with a gradient elution of dichloromethane:methanol=100:5-100:7. The eluate was collected, and the solvent was removed by evaporation to dryness under reduced pressure to give 1.610 g of pure product W-4.

(8-1-5) Synthesis of W-5

W-4 (1.61 g, 0.886 mmol) was dissolved in 125 ml of dichloromethane, and added with dichloroacetic acid (3.5 ml, 42.43 mmol) to react at room temperature for 1 hour. The resultant reaction solution was neutralized by adding 150 ml of pyridine. The solvent was removed by evaporation to dryness under reduced pressure to give a crude product. The crude product was purified by a normal phase silica gel column (200-300 mesh). The column was added with 10 wt % triethylamine for neutralizing the acidity of silica gel, equilibrated with 1 wt ‰ triethylamine and eluted with a gradient elution of dichloromethane:methanol=100:30-100:40. The eluate was collected, and the solvent was removed by evaporation to dryness under reduced pressure to give 1.26 g of pure product W-5.

(8-1-6) Synthesis of W-6

W-5 (1.25 g, 0.793 mmol) and A-1 (1.21 g, 2.38 mmol) obtained according to the method described in step (1-1-7a) were mixed and dissolved in 12 ml of dichloromethane, and added with 3-(diethoxyphosphoryloxy)-1,2,3-benzotrizin-4 (3H)-one (DEPBT, 0.712 g, 2.38 mmol) followed by diisopropylethylamine (0.615 g, 4.76 mmol) to react under stirring at 25° C. for 3 hours. The organic phase was washed with 80 ml of saturated sodium bicarbonate. The aqueous phase was extracted three times, each with 10 ml of dichloromethane. The organic phases were combined and washed with 10 ml of saturated brine. The organic phases were combined, dried with anhydrous sodium sulfate and filtered. The solvent was removed by evaporation to dryness under reduced pressure, and the residue was foam-dried in a vacuum oil pump overnight to give a crude product, which was subjected to a column purification. The column was filled with 185 g normal phase silica gel (200-300 mesh), added with 20 ml triethylamine for neutralizing the acidity of silica gel, equilibrated with petroleum ether containing 1 wt % triethylamine and eluted with a gradient elution of petroleum ether:ethyl acetate:dichloromethane:N,N-dimethylformamide=1:1:1:0.1-1:1:1:0.7. The eluate was collected, and the solvent was removed by evaporation to dryness under reduced pressure to give 1.57 g of pure product W-6.

(8-1-7) Synthesis of W-7

W-6 (1.238 g, 0.63 mmol), succinic anhydride (0.189 g, 1.89 mmol) and 4-dimethylaminopyridine (DMAP, 0.231 g, 1.89 mmol) were mixed and dissolved in 7 ml of dichloromethane, and added with DIEA (0.407 g, 3.15 mmol) to react under stirring at 25° C. for 24 hours. The reaction solution was washed with 5 ml of 0.5 M triethylamine phosphate. The aqueous phase was extracted three times, each with 5 ml of dichloromethane. The organic phases were combined, and the solvent was removed by evaporation to dryness under reduced pressure to give a crude product. The crude product was subjected to a column purification. The column was filled with 30 g normal phase silica gel (200-300 mesh), added with 1 wt % triethylamine for neutralizing the acidity of silica gel, equilibrated with dichloromethane and eluted with a gradient elution of 1 wt ‰ triethylamine-containing dichloromethane:methanol=100:18-100:20. The eluate was collected, and the solvent was removed by evaporation to dryness under reduced pressure to give 1.033 g of pure product W-7 conjugation molecule. MS m/z: C101H146N7O38, [M-DMTr]+, calculated: 1763.92, measured: 1763.21.

(8-1-8) Synthesis of W-8

W-8 was prepared by using the same method as that in step (1-1-9) of Preparation Example 1, except that the W-7 conjugation molecule was used to replace the L-9 conjugation molecule, thereby obtaining the W-7 conjugation molecule linked to a solid phase support.

(8-2) Synthesis of the conjugate W8-siHB3M1SVP

Conjugate 18 was prepared by using the same method as that in steps (1-2)-(1-4) of Preparation Example 1, except that Compound W-8 was used to replace Compound L-10 to start the synthesis of a sense strand. It was expected that the conjugate W8-siHB3M1SVP with a structure as shown by Formula (415) can be obtained.

Preparation Example 9 Preparation of the Conjugate X8-siHB3M1SVP (Conjugate 19)

It was expected that Compound X-8 can be synthesized according to the following process route:

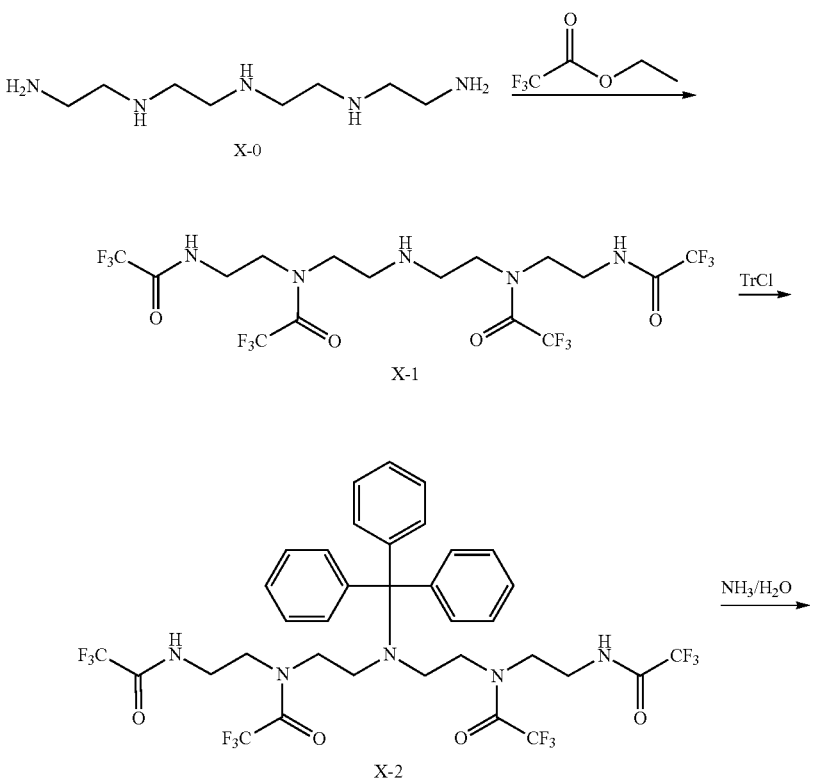

-continued
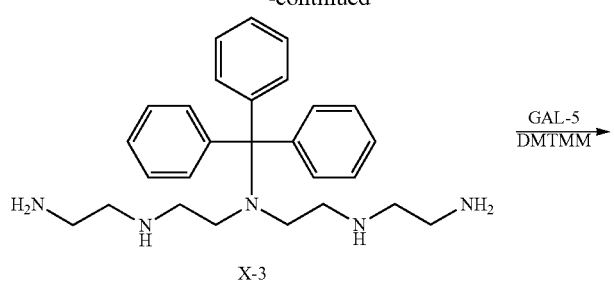
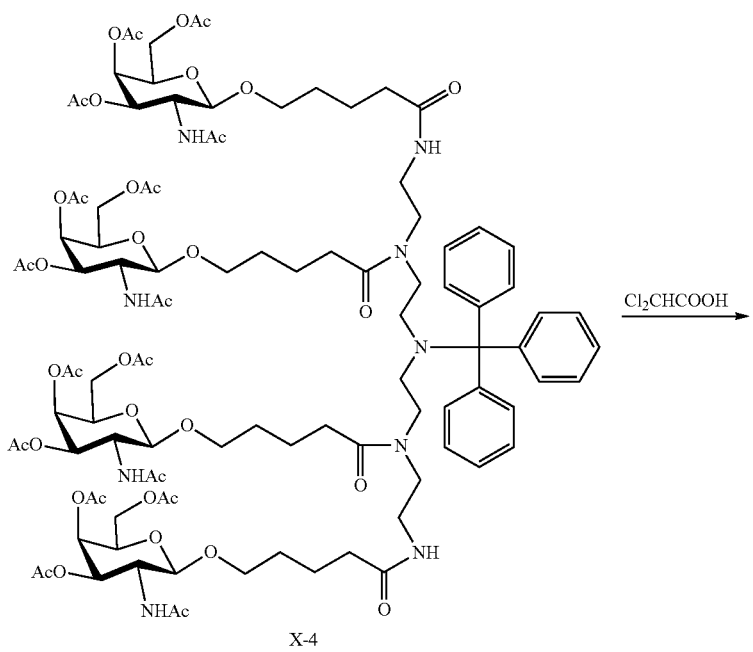
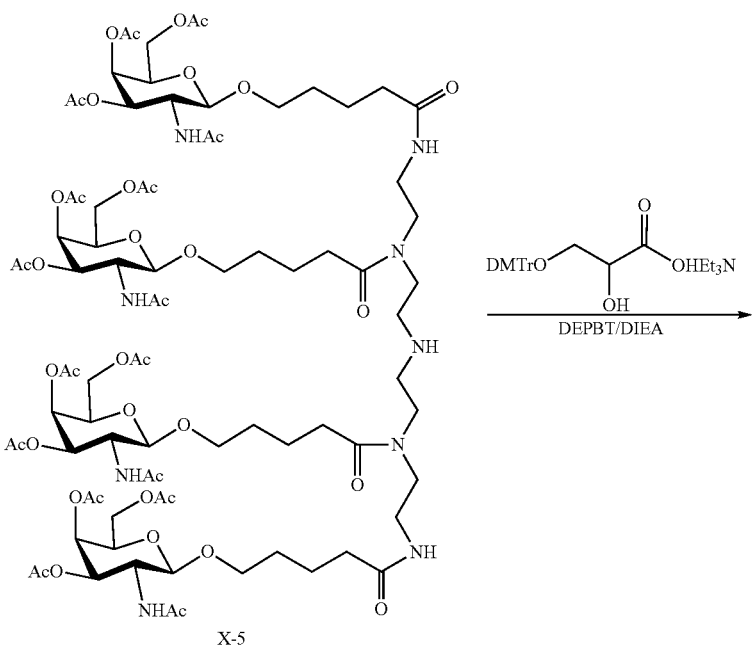

-continued
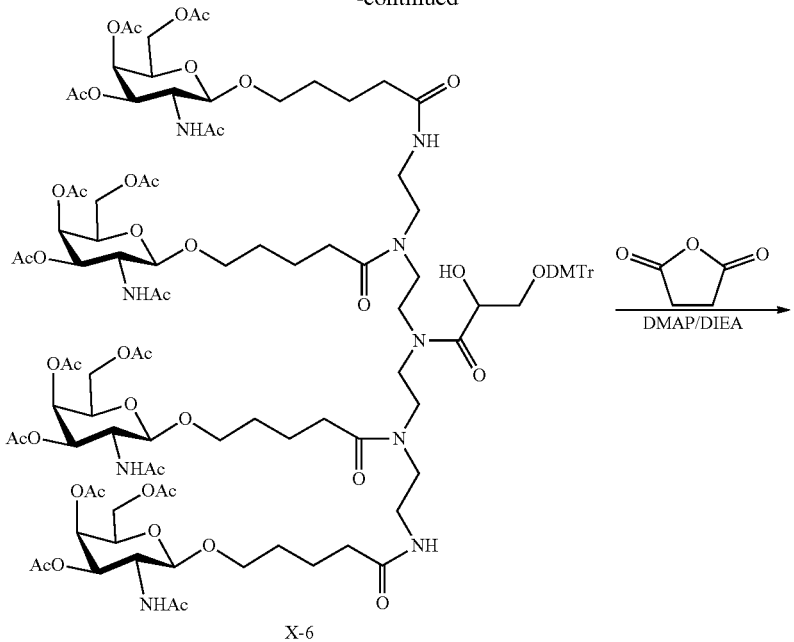
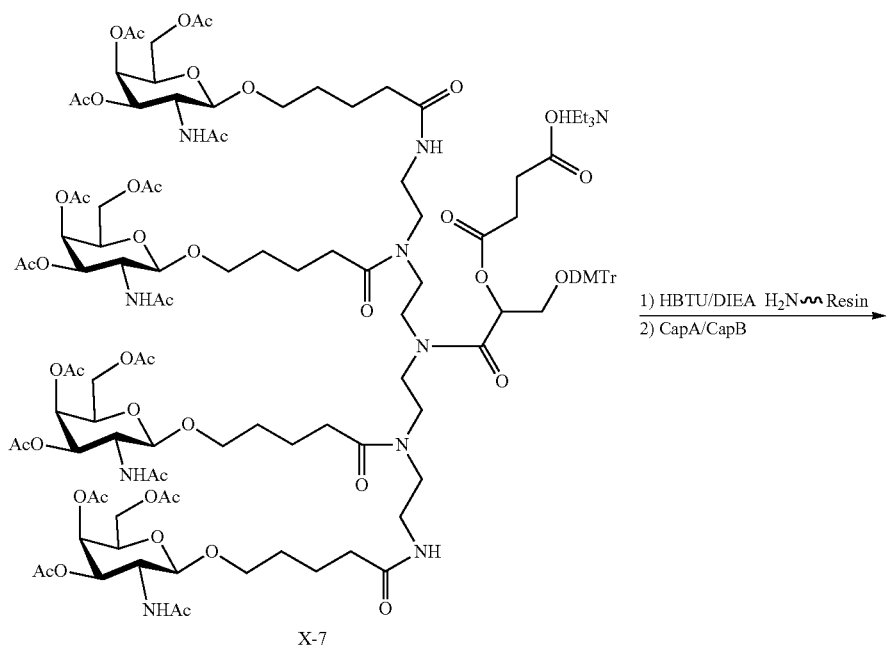

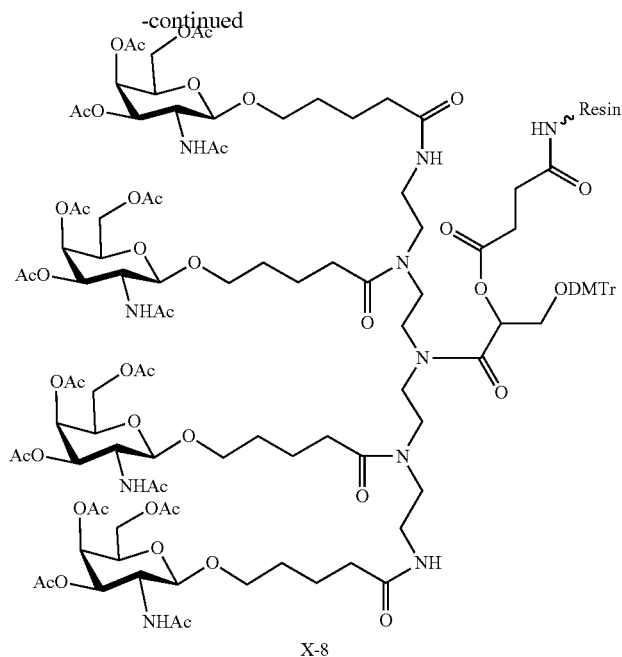

X-8

Conjugate 19 was prepared by using the same method as that in steps (1-2)-(1-4) of Preparation Example 1, except that Compound X-8 was used to replace Compound L-10 to start the synthesis of a sense strand. It was expected that the conjugate X8-siHB3M1SVP with a structure as shown by Formula (421) can be obtained.

Preparation Example 10 Preparation of the Conjugate Z5-siHB3M1SVP (Conjugate 20)

(10-1) Synthesis of Compound Z-5

Compound Z-5 was synthesized according to the following process:

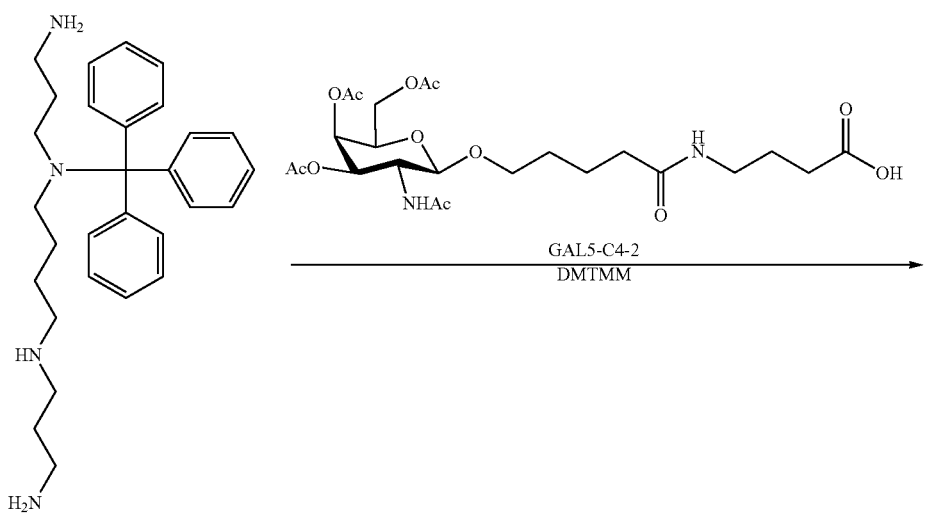

-continued
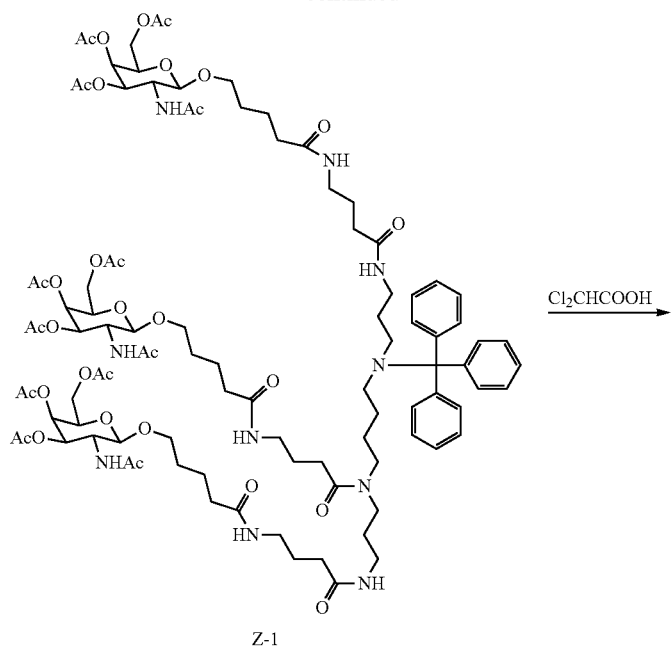
Z-1
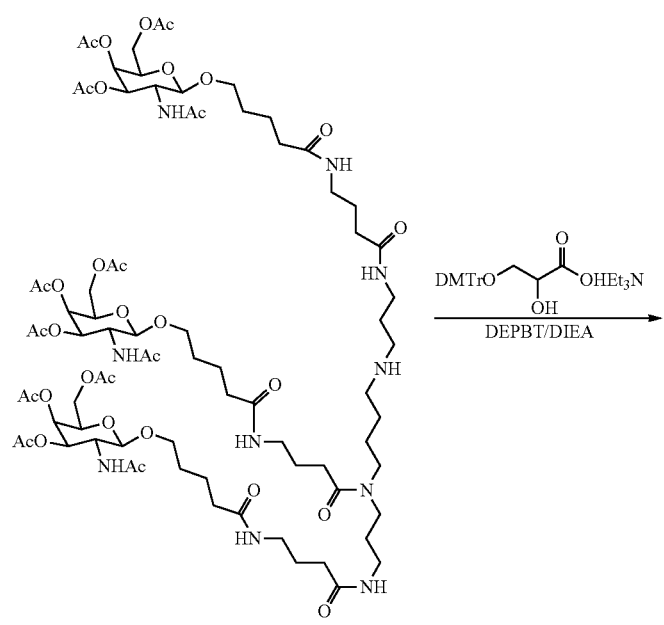
Z-2

-continued
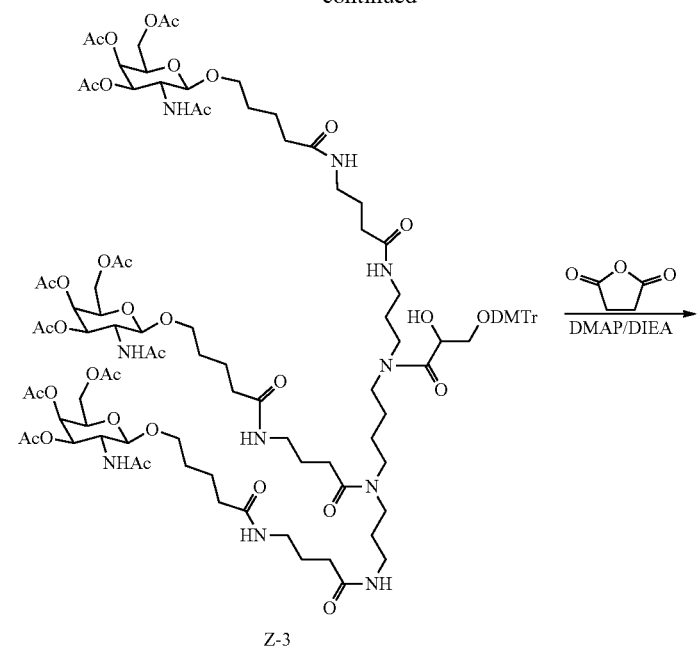
Z-3
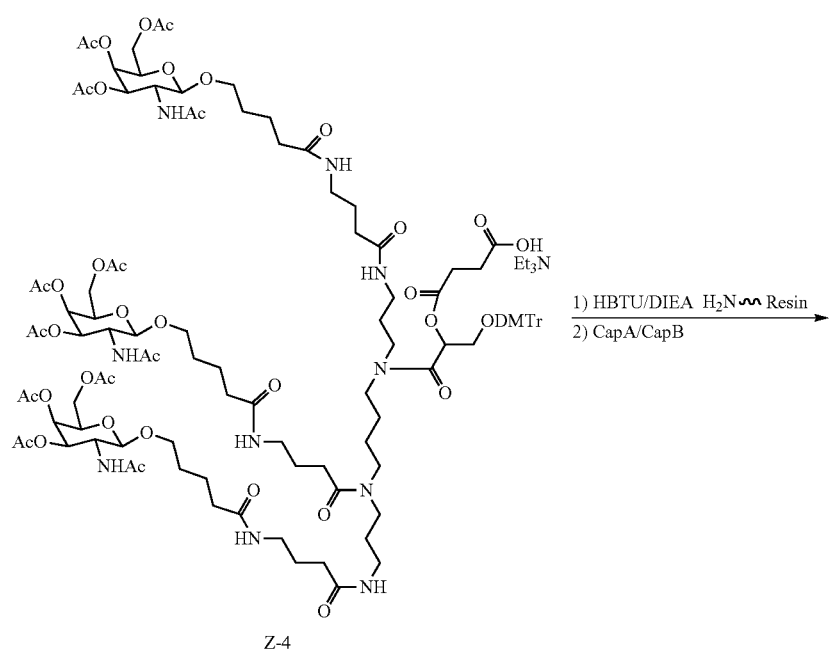
Z-4

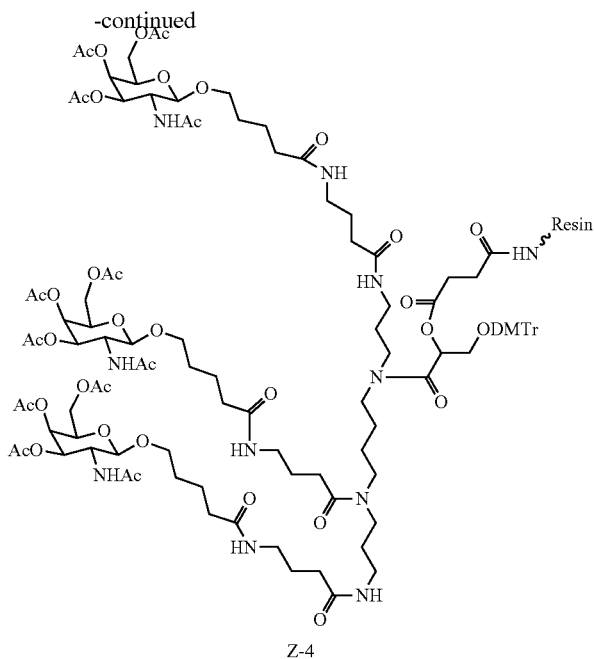

Z-4

(10-1-1) Synthesis of Z-1

W-3 (1.50 g, 3.37 mmol) obtained according to the method described in step (8-1-3) and GAL5-C4-2 (7.18 g, 13.48 mmol) obtained according to the method described in step (3-1-2) were mixed and dissolved in 34 ml of dichloromethane, and added with diisopropylethylamine (3.48 g, 26.96 mmol) followed by 3-(diethoxyphosphoryloxy)-1,2,3-benzotrizin-4(3H)-one (DEPBT, 4.04 g, 13.48 mmol) to react under stirring at room temperature for 4.5 hours. The resultant reaction solution was diluted with 100 ml of dichloromethane. The organic phase was washed with 80 ml of saturated sodium bicarbonate solution and 80 ml of saturated brine, respectively. The organic phases were combined, dried with anhydrous sodium sulfate, and filtered. The solvent was removed by evaporation to dryness under reduced pressure to give a crude product. The crude product was purified by using a normal phase silica gel column (200-300 mesh). The column was packed with petroleum ether, added with 1 wt % triethylamine for neutralizing the acidity of silica gel, and eluted with a gradient elution of dichloromethane:methanol=30:1-15:1. The eluate was collected, and the solvent was removed by evaporation to dryness under reduced pressure to give 3.97 g of pure product Z-1. MS m/z: C98H143N10O33, [M+H]+, calculated: 1987.98, measured: 1987.90.

(10-1-2) Synthesis of Z-2

Z-1 (3.97 g, 2.00 mmol) was dissolved in 250 ml of dichloromethane, and added with dichloroacetic acid (10.941 g, 84.85 mmol) to react at room temperature for 1 hour. Pyridine was added to neutralize the resultant reaction solution to be neutral. The solvent was removed by evaporation to dryness under reduced pressure to give a crude product. The column was filled with 220 g normal phase silica gel (200-300 mesh), and added with 10 wt % pyridine for neutralizing the acidity of silica gel, equilibrated with 1 wt ‰ pyridine and eluted with a gradient elution of dichloromethane:methanol=10:1-2:1. The eluate was collected, and the solvent was removed by evaporation to dryness under reduced pressure to give 3.49 g of pure product Z-2. MS m/z: C79H129N10O33, [M+H]+, calculated: 1746.94, measured: 1746.90.

(10-1-3) Synthesis of Z-3

Z-2 (3.49 g, 2.0 mmol) and A-1 (3.06 g, 6.0 mmol) obtained according to the method described in step (1-1-7a) were mixed and dissolved in 30 ml of dichloromethane, and added with 3-(diethoxyphosphoryloxy)-1,2,3-benzotrizin-4(3H)-one (DEPBT, 1.80 g, 6.0 mmol) followed by diisopropylethylamine (1.55 g, 12.0 mmol) to react under stirring at 25° C. for 3 hours. The resultant reaction solution was diluted with 100 ml dichloromethane. The organic phase was washed two times, each with 30 ml of saturated sodium bicarbonate. The aqueous phase was extracted with 10 ml of dichloromethane. The organic phases were combined and washed with 50 ml of saturated brine. The obtained organic phases were combined and dried with anhydrous sodium sulfate, and filtered. The solvent was removed by evaporation to dryness under reduced pressure, and the residue was foam-dried in a vacuum oil pump overnight to give a crude product. The crude product was subjected to a column purification. The column was filled with 200 g normal phase silica gel (200-300 mesh), added with 20 ml triethylamine for neutralizing the acidity of silica gel. The column was equilibrated with petroleum ether containing 1 wt % triethylamine and eluted with a gradient elution of dichloromethane:methanol=25:1-15:1. The eluate was collected, and the solvent was removed by evaporation to dryness under reduced pressure to give 2.2 g of pure product Z-3. MS m/z: C103H151N10O38, [M+H]+, calculated: 2136.02, measured: 2136.20.

(10-1-4) Synthesis of Z-4:

Z-3 (2.10 g, 0.983 mmol) was dissolved in 14.8 ml of dichloromethane containing DIEA (0.635 g, 4.915 mmol), 4-dimethylaminopyridin (DMAP, 240 mg, 1.966 mmol) was added to the resultant solution and stirred to clarity. Succinic anhydride (197 mg, 1.966 mmol) was added to react under stirring at 25° C. for 18 hours. The resultant reaction solution was diluted by adding 50 ml dichloromethane. The organic phase was washed with 80 ml of 0.5 M triethylamine phosphate. The aqueous phase was extracted two times, each with 50 ml of dichloromethane. The organic phases were combined, and the solvent was removed by evaporation to dryness under reduced pressure to give a crude product. The crude product was subjected to a column purification. The column was filled with 188 g normal phase silica gel (200-300 mesh), added with 1 wt % triethylamine for neutralizing the acidity of silica gel, equilibrated with dichloromethane and eluted with a gradient elution of 1 wt ‰ triethylamine-containing dichloromethane:methanol=10:1-3:1. The eluate was collected, and the solvent was removed by evaporation to dryness under reduced pressure to give 1.95 g of pure product Z-4 conjugation molecule. MS m/z: C107H155N10O41, [M+H]+, calculated: 1935.07, measured: 1935.29.

(10-2) Synthesis of Z-5

Z-5 was prepared by using the same method as that in step (1-1-9) of Preparation Example 1, except that the Z-4 conjugation molecule was used to replace the L-9 conjugation molecule, thereby obtaining the Z-4 conjugation molecule linked to a solid phase support.

(3-2) Synthesis of the Conjugate Z5-siHB3M1SVP

Conjugate 20 was prepared by using the same method as that in steps (1-2)-(1-4) of Preparation Example 1, except that Compound Z-5 was used to replace Compound L-10 to start the synthesis of a sense strand. It was expected that the conjugate Z5-siHB3M1SVP with a structure as shown by Formula (422) can be obtained.

Preparation Example 11 Preparation of the Conjugate K4-siHB3M1SVP (Comparative Conjugate 2)

(11-1) Synthesis of Compound K-4

Compound K-4 was synthesized according to the following process:

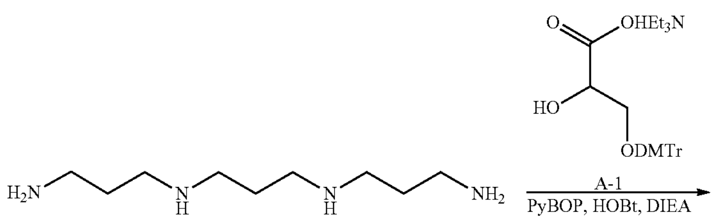

K-0

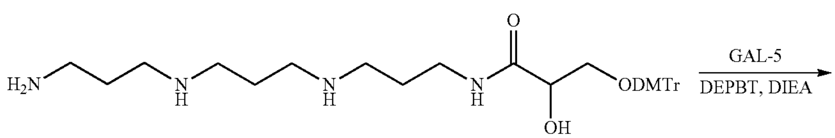

K-1

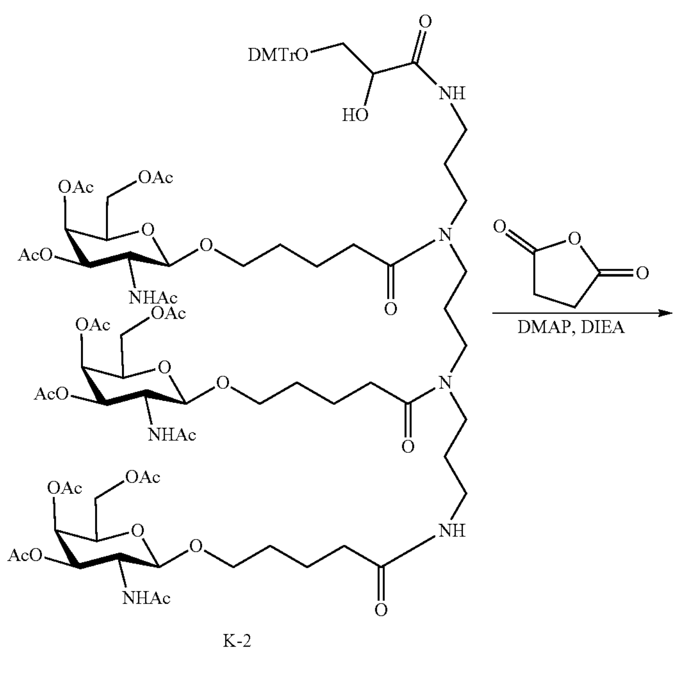

K-2

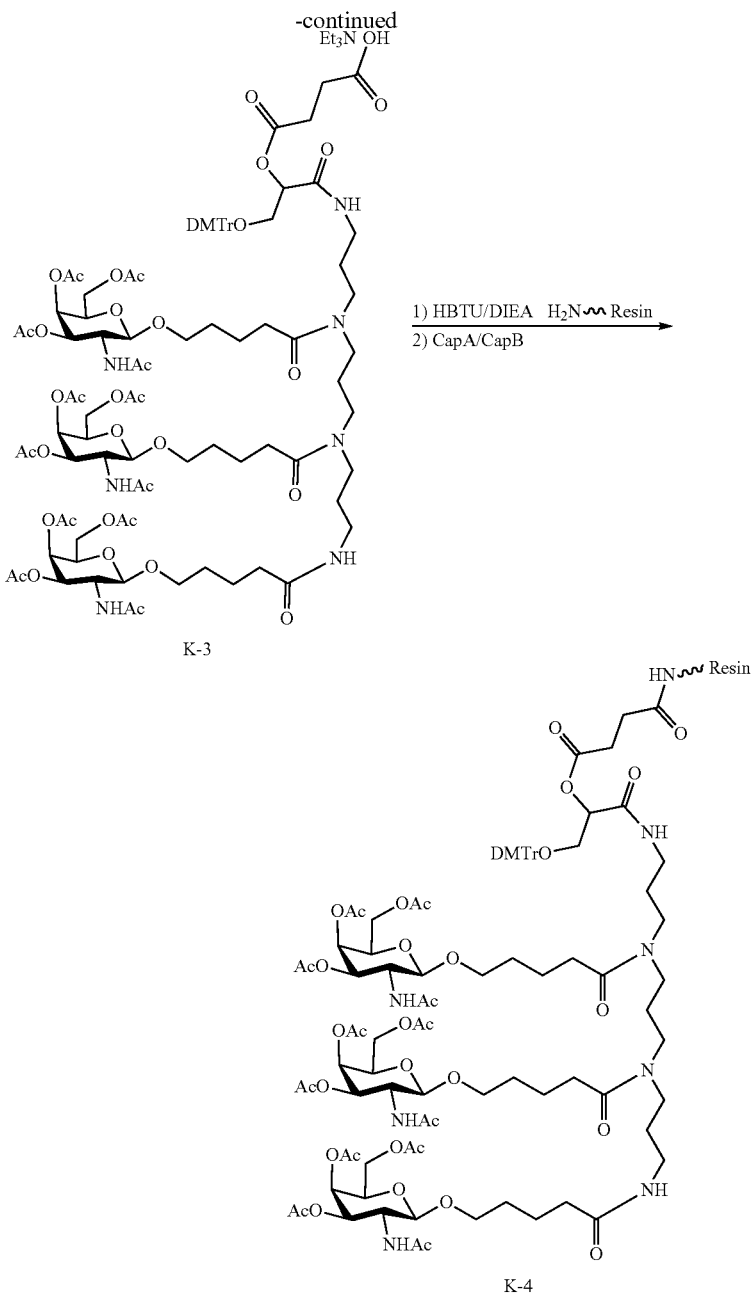

(11-1-1) Synthesis of K-1

A-1 (3.0 g, 6.0 mmol) obtained according to the method described in step (1-1-7a), PyBOP (6.2 g, 12.0 mmol), HOBt (1.6 g, 2.0 mmol) and diisopropylethylamine (DIEA, 3.9 g, 30.0 mmol) were added into 60 ml of dichloromethane to react under stirring at room temperature for 10 minutes. Then the solution was added into K-0 (5.6 g, 30.0 mmol) to react at room temperature for 1 hour and 50 minutes. The reaction solution was poured into 30 ml saturated sodium bicarbonate solution. The aqueous phase was extracted three times, each with 30 ml of dichloromethane. The organic phases were combined, washed with saturated sodium chloride solution, dried with anhydrous sodium sulfate, and filtered. The filtrate was concentrated and purified by a normal phase silica gel column (200-300 mesh). The column was eluted with a gradient elution of dichloromethane:methanol:aqueous ammonia (25 wt %)=10:2:0.1-4:4:1. The eluate was collected, the solvent was removed by concentration, and the residue was foam-dried in a vacuum oil pump to give 2.2 g of product K-1 as a white solid. $^1$H NMR (400 MHz, DMSO-d6) δ 8.02 (s, 1H), 7.43 (d, J=7.8 Hz, 2H), 7.34-7.17 (m, 7H), 6.87 (d, J=8.6 Hz, 4H), 4.05 (d, J=5.2 Hz, 1H), 3.74 (s, 6H), 3.20-3.01 (m, 5H), 2.60-2.38 (m, 12H), 1.60-1.39 (m, 8H), 1.24 (s, 1H). MS m/z: $C_{33}H_{47}N_4O_5$, [M+H]+, calculated: 579.35, measured: 579.26.

(11-1-2) Synthesis of K-2

GAL-5 (483 mg, 1.08 mmol) obtained according to the method described in step (1-1-1), 3-diethoxyphosphoryl-1,2,3-benzotrizin-4(3H)-one (359 mg, 1.2 mmol), diisopropylethylamine (DIEA, 310 mg, 2.4 mmol) were added into 3 ml of dichloromethane under stirring at room temperature for 30 minutes. The mixture was added with K-1 (174 mg, 0.3 mmol) to react at room temperature for 16 hours. The reaction solution was poured into 10 ml saturated sodium bicarbonate solution. The aqueous phase was extracted three times, each with 10 ml of dichloromethane. The organic phases were combined, washed with 10 ml of saturated sodium chloride solution, dried with anhydrous sodium sulfate and filtered. The obtained organic phase was concentrated, and the residue was purified by a normal phase silica gel column (200-300 mesh). The column was eluted with the elution of dichloromethane:methanol=20:1. The eluate was collected, the solvent was removed by concentration, and the residue was foam-dried in a vacuum oil pump to give 205 mg of product K-2 as a yellow solid.

(11-1-3) Synthesis of K-3

K-2 (205 mg, 0.11 mmol), succinic anhydride (22 mg, 0.22 mmol), 4-dimethylaminopyridine (DMAP, 27 mg, 0.22 mmol) and diisopropylethylamine (DIEA, 71 mg, 0.55 mmol) were added into 1.1 ml of dichloromethane to react under stirring at room temperature overnight. The reaction solution was washed three times, each with 0.5 ml of 0.5 M triethylamine phosphate. Each aqueous phase was reverse extracted once with 0.5 ml of dichloromethane. The organic phases were dried with anhydrous sodium sulfate, concentrated to remove the solvent. The residue was foam-dried in a vacuum oil pump to give 218 mg of K-3 conjugation molecule as a light yellow solid.

(11-1-4) Synthesis of K-4

K-4 was prepared by the same method as that in step (1-1-9) of Preparation Example 1, except that the K-3 conjugation molecule was used instead of the L-9 conjugation molecule to obtain the K-3 conjugation molecule linked to a solid phase support.

(11-2) Synthesis of the Conjugate K4-siHB3M1SVP

Comparative Conjugate 2 was prepared by using the same method as that in steps (1-2)-(1-4) of Preparation Example 1, except that Compound K-4 was used to replace Compound L-10 to start the synthesis of a sense strand. It was expected that the conjugate K4-siHB3M1SVP with a structure as shown by Formula (423) can be obtained:

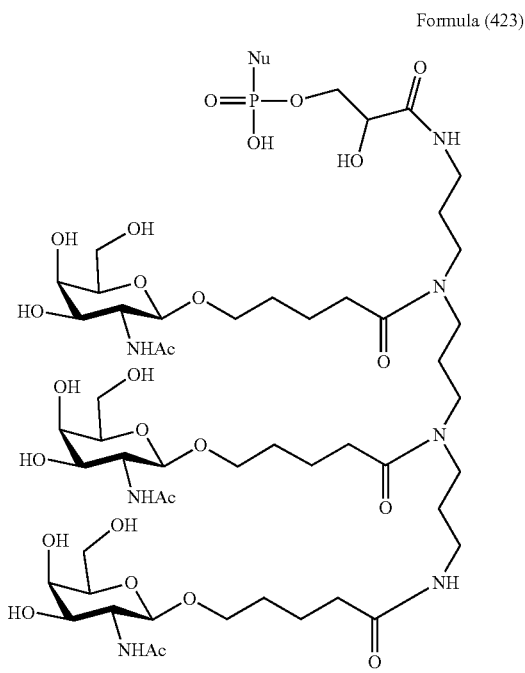

Formula (423)

wherein Nu is siRNA in the conjugate K4-siHB3M1SVP.

Preparation Example 12 Preparation of the siRNA

The siRNA sequences provided in the present disclosure as listed in Table 4 were obtained by conventional solid phase synthesis methods. A mixture of sense and antisense strands at equal moles was dissolved in DEPC water, and then conventionally annealed to form a double-stranded siRNA.

TABLE 4 siRNA sequences

| SiRNA | No. | | Sequence direction 5'-3' | SEQ ID NO |
|---|---|---|---|---|
| siRNA 1 | siHB3M1SVP | Sense strand | GmsAmsAmAmGmUmAfUfGfUmCmAmAmCmGmAmAmUmAm | 24 |
| | | Antisense strand | VP-UmsAfsUmUmCmGfUmUmGmAmCmAmUmAfCmUfUmUmCmsUmsUm | 67 |
| SIRNA 2 | siHB3M1S | Sense strand | GmsAmsAmAmGmUmAfUfGfUmCmAmAmCmGmAmAmUmAm | 24 |
| | | Antisense strand | UmsAfsUmUmCmGfUmUmGmAmCmAmUmAfCmUfUmUmCmsUmsUm | 27 |
| siRNA 3 | siHB3M1SPs | Sense strand | GmsAmsAmAmGmUmAfUfGfUmCmAmAmCmGmAmAmUmAm | 24 |
| | | Antisense strand | Ps-UmsAfsUmUmCmGfUmUmGmAmCmAmUmAfCmUfUmUmCmsUmsUm | 69 |
| siRNA 4 | siHB3M1SP | Sense strand | GmsAmsAmAmGmUmAfUfGfUmCmAmAmCmGmAmAmUmAm | 24 |
| | | Antisense strand | P-UmsAfsUmUmCmGfUmUmGmAmCmAmUmAfCmUfUmUmCmsUmsUm | 68 |

TABLE 4-continued siRNA sequences

| SiRNA | No. | | Sequence direction 5'-3' | SEQ ID NO |
|---|---|---|---|---|
| NC | siNCM1SP | Sense strand | UmsUmsCmUmCmCmGfAfAfCmGmUmGmUmCm AmCmGmUm | 77 |
| | | Antisense strand | P-AmsCfsGmUmGmAfCmAmCmGmUmUmCmGfGm AfGmAmAmsCmsUm | 78 |

In Table 4, siRNA 1-4 were the siRNAs of the present disclosure that specifically target the P gene region of THBV; NC was a negative control siRNA that had no inhibitory effect on HIBV gene.

After the preparation of the siRNAs or conjugates of the present disclosure above, they were lyophilized to solid powder via standard process and stored until used. When being use, they can be reconstituted to a solution at a desired concentration dissolved in, for example, water for injection, normal saline (NS), phosphate buffer (PB), or phosphate buffered solution (PBS).

Experimental Example 1 the On-Target Activity and Off-Target Activity of the siRNA Conjugates in In Vitro psiCHECK System HEK293A cells used in this experimental example were provided by Nucleic Acid Technology Laboratory, Institute of Molecular Medicine, Peking University and cultured in DMEM complete media (Hyclone company) containing 20% fetal bovine serum (FBS, Hyclone company), 0.2 v % Penicillin-Streptomycin (Gibco, Invitrogen company) at 37° C. in an incubator containing 5% $CO_2$/95% air.

In this experimental example, Conjugate 2 was investigated in in vitro psiCHECK system for the on-target activity and off-target effect.

According to the method described in Kumico Ui-Tei et. al., Functional dissection of siRNA sequence by systematic DNA substitution: modified siRNA with a DNA seed arm is a powerful tool for mammalian gene silencing with significantly reduced off-target effect. Nucleic Acids Research, 2008.36(7), 2136-2151, plasmids for detection were constructed and co-transfected with the siRNA conjugates to be detected into HEK293A cells; and the expression levels of the dual luciferase reporter gene reflect the on-target activity and off-target effect of the siRNA conjugates. Specific steps are as follows:

[1] Construction of Plasmids for Detection

Four recombinant plasmids were constructed using psiCHECK™-2 (Promega™) plasmid, in which GSCM represents the on-target plasmid; and PSCM, GSSM and PSSM represent the off-target plasmids:

(1) GSCM, containing a target sequence, wherein the target sequence is completely complementary to the nucleotide sequence at positions 2-19 from 5' terminal of the antisense strand in Conjugate 2, and is used to detect the on-target activity of the antisense strand.

(2) PSCM, containing a target sequence, wherein the target sequence is completely complementary to the nucleotide sequence at positions 1-18 from 5' terminal of the sense strand in Conjugate 2, and is used to detect the off-target activity of the sense strand.

(3) GSSM, containing a target sequence, wherein the target sequence is completely complementary to the nucleotide sequence at positions 2-8 from 5' terminal of the antisense strand in Conjugate 2, while the remaining part of the target sequence corresponds to but is completely mismatched with the nucleotide sequence at positions 9-21 from 5' terminal of the antisense strand in Conjugate 2; that is, when the nucleotide at any position in positions 9-21 from 5' terminal of the antisense strand in Conjugate 2 is G, C, A or U, the nucleotide at the corresponding position in the target sequence is T, A, C or G respectively. GSSM is used to detect the off-target activity of the seed region of the antisense strand.

(4) PSSM, containing a target sequence, wherein the target sequence is completely complementary to the nucleotide sequence at positions 1-8 from 5' terminal of the sense strand in Conjugate 2, while the remaining part of the target sequence corresponds to but is completely mismatched with the nucleotide sequence at positions 9-19 from 5' terminal of the sense strand in Conjugate 2; that is, when the nucleotide at any position in positions 9-21 from 5' terminal of the sense strand in Conjugate 2 is G, C, A or U, the nucleotide at the corresponding position in the target sequence is T, A, C or G respectively. PSSM is used to detect the off-target activity of the seed region of the sense strand.

Each of the above target sequences were synthesized by Suzhou GenePharma Inc. The sequence information is shown in Table 5.

TABLE 5

| target sequences | | | | |
|---|---|---|---|---|
| Plasmid name | No. | | Sequence direction 5'-3' | SEQ ID NO |
| GSCM | GSCM-s | Sense strand | TCGAGTGGAAAGTATGTCAACGAATTGC | 79 |
| | GSCM-as | Antisense strand | GGCCGCAATTCGTTGACATACTTTCCAC | 80 |
| PSCM | PSCM-s | Sense strand | TCGAGAATTCGTTGACATACTTTCCAGC | 81 |
| | PSCM-as | Antisense strand | GGCCGCTGGAAAGTATGTCAACGAATTC | 82 |

TABLE 5-continued target sequences

| Plasmid name | No. | | Sequence direction 5'-3' | SEQ ID NO |
|---|---|---|---|---|
| GSSM | GSSM-s | Sense strand | TCGAGGTTCCCTGCGTGAAACGAATTGC | 83 |
|  | GSSM-as | Antisense strand | GGCCGCAATTCGTTTCACGCAGGGAACC | 84 |
| PSSM | PSSM-s | Sense strand | TCGAGCCGGATGGTCACGACTTTCCAGC | 85 |
|  | PSSM-as | Antisense strand | GGCCGCTGGAAAGTCGTGACCATCCGGC | 86 |

The target sequence was inserted into the Xho I/Not I site of the psiCHECK™-2 plasmid.

[2] Transfection

In a 96-well plate, the siRNA conjugate and each of the above plasmids were co-transfected according to the instruction of Lipofectamine™ 2000 (Invitrogen), each plasmid corresponding to several specific concentrations of Conjugate 2. Specifically, 10 ng of plasmid was transfected per well, using 0.2 µL of Lipofectamine™ 2000 per well. For the on-target plasmid GSCM, the final concentration (based on the concentration of siRNA) of Conjugate 2 was from 1 nM to 0.000977 nM (fold serial dilutions of 11 concentrations). For the other three off-target plasmid, the final concentration of Conjugate 2 was from 10 nM to 0.000038 nM (4-fold serial dilutions of 10 concentrations). Those untreated with the conjugate in each group were used as control, with 3 replicate wells per group.

[3] Detection 24 hours after co-transfection, the HEK293A cells were lysed by using a dual luciferase reporter gene assay kit (Promega, cat. E2940) according to the instruction to detect the expression level of the dual luciferase reporter gene. The *Renilla* luciferase protein level was normalized to the firefly luciferase protein level. The dose-response curves were plotted by the activity results measured at different siRNA concentrations, and the curves were fitted using the function log(inhibitor) vs. response-Variable slope of Graphpad 5.0 software. The $IC_{50}$ of Conjugate 2 targeting GSCM was calculated based on the dose-response curve.

$$Y = Bot + \frac{Top - Bot}{1 + 10^{(LogIC50-X) \times HillSlope}}$$

wherein:

Y is the expression level of remaining mRNA,

X is the logarithm of the concentration of transfected siRNA conjugates,

Bot is the Y value at the bottom of the steady stage,

Top is the Y value at the top of the steady stage,

Log IC50 is the X value at which Y is the median value between the bottom and the top, and HillSlope is the slope of the curve.

The results show that for GSCM, the $IC_{50}$ value of Conjugate 2 is 0.0513 nM ($R^2$=0.9911); For PSCM, GSSM and PSSM, Conjugate 2 shows no significantly inhibitory effect at each siRNA concentration, indicating that the siRNA conjugate of the present disclosure not only has higher activity in vitro, but also exhibits low off-target effect.

Experimental Example 2 Stability of the siRNA Conjugates of the Present Disclosure in the Lysosome Lysate In Vitro The sequence of the negative control siRNA used in this experimental example is as follows:

```
Sense strand:
                                    (SEQ ID No: 9)
5'-CmCmUmUmGAGGCmAUmACmUmUmCmAAAdTsdT-3'

Antisense strand:
                                    (SEQ ID NO: 10)
5'-UfUmUfGAAGUfAUGCCUfCAAGGdTsdT-3'
```

This siRNA was synthesized by phosphoramidite solid phase synthesis method. The negative control and Conjugate 2 were formulated with 0.9% NaCl aqueous solution respectively into the solutions with a concentration of 20 µM (based on the concentration of siRNA), which were marked as negative control and Conjugate 2.

1) Detection of the Stability in Murine Lysosome Lysate

Preparation of test samples treated with the lysosome lysate: Conjugate 2 and the negative control (20 µM, each 6 µl) were individually mixed well with 27.2 µL of aqueous sodium citrate solution (pH 5.0), 4.08 µL of deionized water and 2.72 µL of murine lysosome lysate (Rat Liver Tritosomes, purchased from Xenotech Inc., Cat No. $R_{0610}$.LT, Lot No. 1610069), at a final concentration of acid phosphatase of 0.2 mU/µL, and incubated at a constant temperature of 37° C. 5 µL mixed solution was taken at each time point of 0 h, 1 h, 2 h, 4 h, 6 h, and 24 h, respectively, added to 15 µL of 9 M urea solution for denaturation, and added with 4 L of 6× loading buffer (purchased from Solarbio Inc., Cat No. 20160830), then immediately cryopreserved in a −80° C. freezer to quench the reaction. 0 h represents the moment when the sample was taken out immediately after the samples to be tested are mixed well with the lysosome lysate.

Preparation of reference samples untreated with the lysosome lysate: Conjugate 2 and the negative control (20 µM, each 1.5 µL) at equal moles were mixed well with 7.5 µL of aqueous sodium citrate solution (pH 5.0) and 1 µL of deionized water, added to 30 µL of 9 M urea solution for denaturation, and added with 8 µL of 6× loading buffer, then immediately cryopreserved in a −80° C. freezer to quench the reaction. The reference sample of the negative control was marked as M1, the reference sample of Conjugate 2 was marked as M2.

16 wt % of non-denatured polyacrylamide gel was prepared. 20 µL each of the test samples and the reference samples above was loaded onto the gel to perform electrophoresis under 20 mA constant current for 10 minutes and then under 40 mA constant current for 30 minutes. After finishing the electrophoresis, the gel was placed on a shaker and stained with Gelred dye (BioTium, Cat No. 13G1203) for 10 minutes. The gel was subjected to imaging, observation and photocopying. The results are shown in FIG. 1.

2) Detection of the Stability in Human Lysosome Lysate

Figure 2:
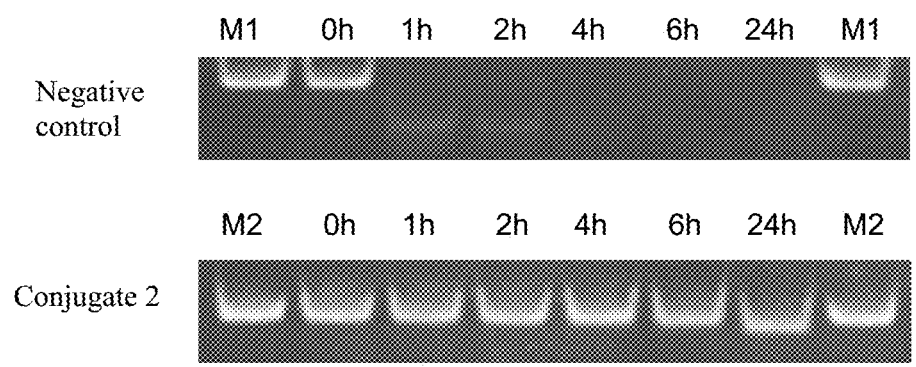
FIG. 2 shows PAGE electrophoretogram of Conjugate 2 after incubation with human lysosome lysate over different periods of time.

The stabilities of the negative control and Conjugate 2 in the human lysosome lysate were measured using the same method as that in 1), except that the murine lysosome lysate was replaced with the human lysosome lysate (Human Liver Lysosomes, purchased from Xenotech Inc., Cat No. $R_{0610}$.L, Lot No. 1610316). The results are shown in FIG. 2.

The results indicate that the siRNA conjugates of the present disclosure can remain undegraded for at least 24 hours both in human lysosome lysate and in murine lysosome lysate, showing satisfactory stability.

The expression level of HBV mRNA in liver tissue was detected by real-time fluorescent qPCR. Specifically, the extracted total RNA was reverse transcribed into the cDNA by using ImProm-II™ reverse transcription kit (Promega) according to the instruction, and then the inhibitory efficiency of siRNAs against the expression of HBV mRNA in liver tissue was detected by using the fluorescent qPCR kit (Beijing Cowin Biosicences Co., Ltd). In this fluorescent qPCR method, GAPDH gene was used as an internal control gene, the HBV and GAPDH were detected by using the primers for HBV and GAPDH, respectively.

Sequences of the primers for detection are shown in Table 6.

TABLE 6

Sequences of the primers for detection

| Genes | Upstream Primers | Downstream Primers |
|---|---|---|
| HBV | 5'-GTCTTTTGGGTTTTGCTGCC-3' (SEQ ID NO: 87) | 5'-GCAACGGGGTAAAGGTTCAG-3' (SEQ ID NO: 88) |
| GAPDH | 5'-GGTCGGAGTCAACGGATTT-3' (SEQ ID NO: 89) | 5'-CCAGCATCGCCCCACTTGA-3' (SEQ ID NO: 90) |

Experimental Example 3 Inhibitory Efficiency of the siRNA Conjugates Against the Expression of HBV mRNA in HBV Model Mice 1) In this experimental example, the inhibition efficiencies of Conjugates 1 and 2 against the expression of HBV mRNA in HBV model mice C57BL/6J-Tg (Alb1HBV) 44Bri/J were investigated.

The HBV model mice C57BL/6J-Tg (Alb1HBV) 44Bri/J used in this experimental example were purchased from Department of Laboratory Animal Science, Peking University Health Science Center. Conjugate 2 was formulated with 0.9% NaCl aqueous solution into a solution with a concentration of 0.2 mg/ml (based on the concentration of siRNA). Conjugate 1 was formulated with 0.9% NaCl aqueous solution into solutions with the concentration of 0.2 mg/ml and 0.06 mg/ml (based on the concentration of siRNA).

HBsAg content in mouse serum was measured using Hepatitis B Virus Surface Antigen Assay Kit (Enzyme-linked Immunosorbent Assay, ELISA) (Shanghai Kehua Bio-engineering Co., Ltd.). Mice with S/COV>10 were selected, randomly divided into two groups (all female, 6 mice in each group) and respectively recorded as the control group and the test group. Animals in each group were subcutaneously injected with various drugs on day 1 in the administration volume of 5 mL/kg. The drug dosages for all animals were calculated according to the body weight. Therein, the mice in the control group were injected with normal saline; the mice in the test group were injected with Conjugate 2 at an administration dosage of 1 mg/kg. All the animals were sacrificed on day 28 after administration, and were subjected to a gross anatomy to observe whether the internal organs were diseased. The diseased tissues discovered by visual observation were preserved with 10% formalin for further pathological observation. The liver was collected and kept with RNA later (Sigma Aldrich), and the liver tissue was homogenized with a tissue homogenizer. Then the total RNA was extracted and obtained by Trizol according to the standard procedures for total RNA extraction.

In this fluorescent qPCR method, the inhibitory activity of siRNA was expressed as the inhibition percentage against HBV mRNA and calculated by the following equation:

The inhibition percentage against HBV mRNA=(1−the remaining expression of HBV gene)×100%

The remaining expression of HBV gene=(the copy number of HBV gene in the test group/the copy number of GAPDH gene in the test group)/(the copy number of HBV gene in the control group/the copy number of GAPDH gene in the control group)×100%

The results are shown in Table 7.

Through the same method, the inhibition efficiencies in vivo of Conjugate 1 at different doses (n=5) against the expression of HBV mRNA were detected. The results are shown in Table 7.

TABLE 7

The inhibition of siRNA conjugates against the expression of HBV mRNA in mice liver

| siRNA conjugate | No. | Administration dose (mg/kg) | Inhibition efficiency against HBV mRNA in liver (%) |
|---|---|---|---|
| Conjugate 2 | L10-siHB3M1SP | 1 | 77.41 |
| Conjugate 1 | L10-siHB3M1SVP | 1 | 88.27 |
| Conjugate 1 | L10-siHB3M1SVP | 0.3 | 57.95 |

As can be seen from the above results, all conjugates of the present disclosure show high inhibitory activity against the expression of HBV mRNA in mice in vivo, indicating that the siRNA conjugates of the present disclosure have excellent delivery efficiency in vivo.

2) Through the same method as that in 1), the inhibition efficiency in vivo of Conjugate 3-Conjugate 20 against HBV mRNA was detected. It can be expected that Conjugate 3-Conjugate 20 containing the siRNAs with different lengths and similar modification schemes have higher inhibitory activity against mRNA; and that Conjugate 3-Conjugate 20 containing the same siRNA and similar conjugate molecules also have higher inhibitory activity against mRNA.

Experimental Example 4 the Time-Dependent Test of the Inhibitory Efficiency of the siRNA Conjugates Against the Expression Levels of HBsAg, HBeAg and HBV DNA in HBV Model Mice Serum HBV model mice C57B/6N-Tg (1.28 HBV)/Vst (genotype A) used in this experimental example were purchased from Beijing Vitalstar Biotechnology Co., Ltd. Conjugate 1 was formulated with 0.9% NaCl aqueous solution into solutions with the concentration of 0.6 mg/ml and 0.2 mg/ml (based on the concentration of siRNA).

The mice with a serum HBsAg content >10$^4$ COI were selected (half male and half female), randomly divided into three groups (6 mice in each group) and respectively recorded as the control group, the high-dose group and the low-dose group. Animals in each group were subcutaneously injected with various drugs on day 1 in the administration volume of 5 mL/kg. The drug dosages for all animals were calculated according to the body weight. All animals were administered in the morning. If the blood sampling was required, the administration would be performed after the blood sampling. Therein, the animals in the control group were injected with normal saline; the animals in the test groups were injected with Conjugates 1 at different concentrations (3 mg/kg for the high-dose group; 1 mg/kg for the low-dose group). The blood was taken from mouse orbital venous plexus before administration and on days 7, 13, 21, 28, 42, 56, 70, 84, 98, 112, 126, 140 and 154 after administration, and the levels of HBsAg, HBeAg and HBV DNA in serum was measured for each time point.

About 100 µl orbital blood was taken each time, and the serum was no less than 20 µl after centrifugation, resuspended with PBS to 500 µl, and delivered to Clinical Laboratory Center of Beijing Dian Diagnostics to measure the contents of HBsAg, HBeAg and HBV DNA in serum, which were expressed in COI, COI and IU/ml, respectively.

The normalized levels of the indicators to be measured (HBsAg, HBeAg and HBV DNA) were calculated according to the following equation:

The normalized level of the indicators to be measured=(the remaining content of the indicators to be measured after administration/the content of the indicators to be measured before administration)×100%

The inhibition percentage of the indicators to be measured=(1−the normalized level of the indicators to be measured)×100%

The experimental data are all expressed as $\overline{X}$±SEM, and the data are analyzed with Graphpad prism 5.0 statistical analysis software. The data are initially tested for normal distribution and homogeneity of variance. If the data meet normal distribution (p>0.20) and homogeneity of variance (p>0.10), then comparison among groups would be performed by LSD method using single-factor analysis of variance for multiple comparisons. P<0.05 is considered as being statistically significant. If the data fail to meet normal distribution and homogeneity of variance, then comparison among multiple groups would be performed by Krushkal-Wallis H method for Non-Parametric Test. If the result obtained by Kruskal-wallis H test are statistically significant (p<0.05), then after rank transformation of the data, pairwise comparisons among multiple groups would be conducted. P<0.05 is considered to be statistically significant.

Figure 3:
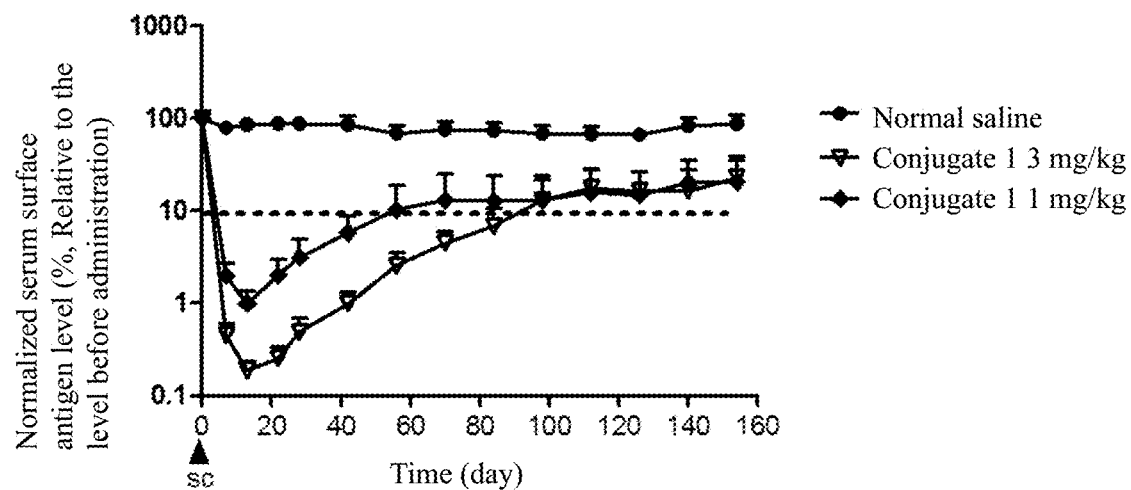
FIG. 3 is a diagram showing normalized serum surface antigen level over time after the subcutaneous administration of Conjugate 1 at a single dose of 3 mg/kg or 1 mg/kg (Y-axis is logarithmic axis).
Figure 4:
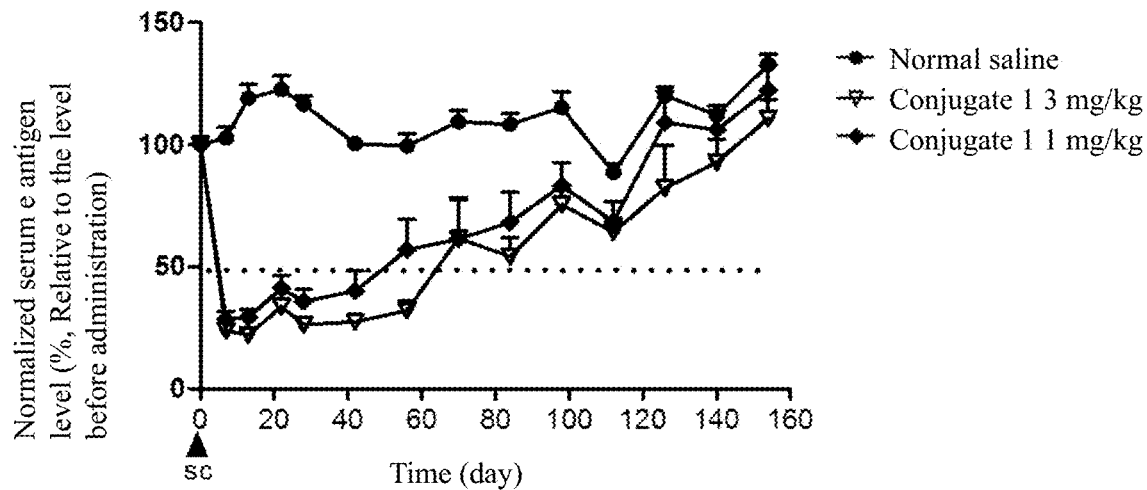
FIG. 4 is a diagram showing normalized serum e-antigen level over time after the subcutaneous administration of Conjugate 1 at a single dose of 3 mg/kg or 1 mg/kg.
Figure 5:
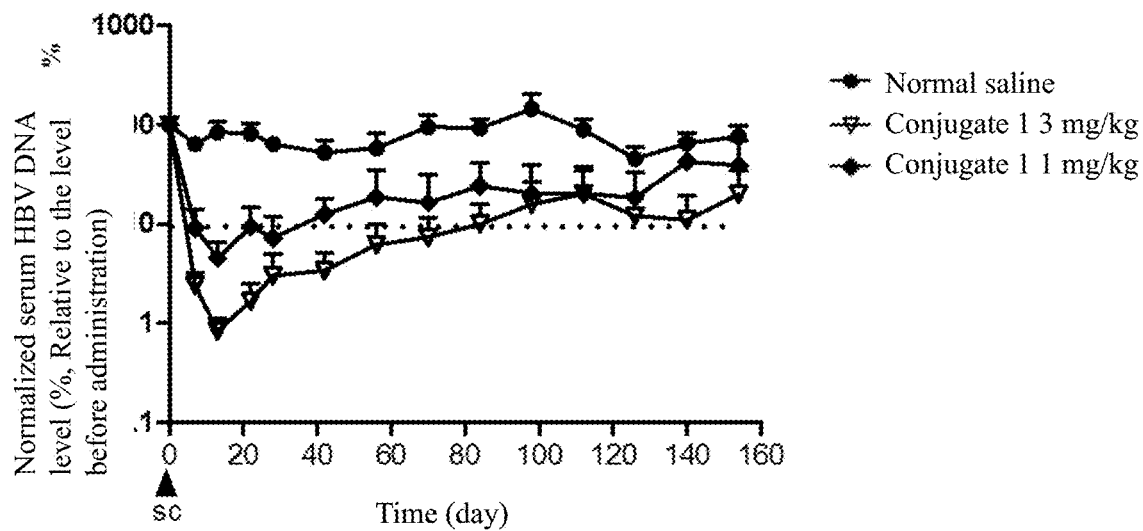
FIG. 5 is a diagram showing normalized serum HBV DNA level over time after the subcutaneous administration of Conjugate 1 at a single dose of 3 mg/kg or 1 mg/kg (Y-axis is logarithmic axis).

The results are shown in FIG. 3-5.

As can be seen from FIG. 3, the negative control group administered with normal saline shows no inhibitory effect on the serum surface antigen at different time points after administration. In contrast, Conjugate 1 at two doses shows excellent inhibitory effect on HBsAg at different time points after administration. For the high-dose group, the maximum inhibition percentage against HBsAg is up to 99.8% on day 13 after a single administration; and the inhibition percentage against HBsAg remains above 90% over a period of up to 84 days after administration. At the end of the observation, the inhibition percentage against HBsAg is still up to 77.0%. As to the low-dose group, the maximum inhibition percentage against HBsAg is 99.0% on day 13 after administration. At the end of the observation on day 154, the inhibition percentage against HBsAg is still up to 79.4%.

As can be seen from FIG. 4, Conjugate 1 can also inhibit the expression of HBeAg, wherein the high-dose group shows an inhibition percentage of about 50% against the expression of HBeAg in serum on day 70 after administration. Till the end of the observation on day 154, the inhibition percentage against HBsAg rebounds to the level before administration.

As can be seen from FIG. 5, Conjugate 1 can also efficiently inhibit the expression of HBV DNA, and maintains higher inhibition percentage over an observation period up to 154 days.

As to the high-dose group, the maximum inhibition percentage against HBV DNA is up to 99.2% on day 13 after a single administration. The inhibition percentage against HBV DNA remains above 90% over a period of up to 84 days after administration. At the end of the observation, the inhibition percentage against HBV DNA is still up to 80.1%. As to the low-dose group, the maximum inhibition percentage against HBV DNA is up to 95.4% on day 13 after administration. At the end of the observation on day 154, the inhibition percentage against HBV DNA is still up to 60.8%.

The above results show that the conjugates of the present disclosure show stable and efficient inhibition against the expression of HBV gene over an extended time period, and especially exhibit sustained inhibition against the surface antigens, showing excellent effects.

Experimental Example 5 Inhibitory Activity of the siRNA in In Vitro psiCHECK System The inhibitory activity of each siRNA in Preparation Example 12 in in vitro psiCHECK system was investigated in this experimental example.

The detection plasmid GSCM in Experiment Example 1 and the siRNA to be detected (siRNAs 1-4 and NC) were co-transfected into HEK293A cells; and the expression levels of the dual luciferase reporter gene reflect the inhibitory activity of the siRNA. Specific steps are as follows:

In a 96-well plate, the siRNA and GSCM plasmid were co-transfected according to the instruction of Lipofectamine™ 2000 (Invitrogen). Specifically, 10 ng of plasmid was transfected per well, using 0.2 µL of Lipofectamine™ 2000 per well. The final concentrations of the siRNA were 0.1 nM, 0.01 nM and 0.001 nM. Those untreated with the siRNA in each group were used as control, with 3 replicate wells per group.

Figure 6:
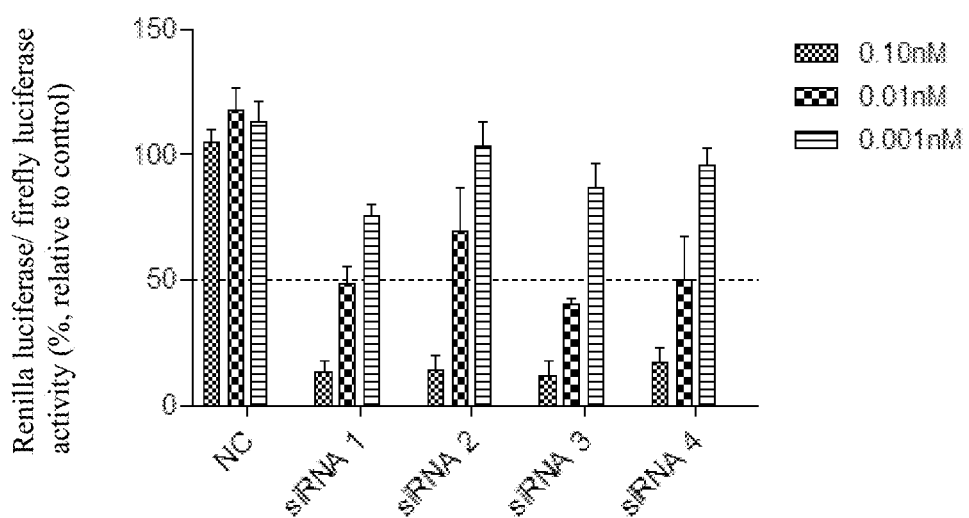
FIG. 6 shows inhibitory activities of siRNAs 1 to 4 in psiCHECK system.

24 hours after co-transfection, the HEK293A cells were lysed by using a dual luciferase reporter gene assay kit (Promega, Cat No. E2940) according to the instruction to detect the expression level of the dual luciferase reporter gene. The *Renilla* luciferase protein level was normalized to the firefly luciferase protein level. The results are shown in FIG. 6.

The results show that siRNAs 1-4 all have good inhibitory activity in vitro. At the concentration of 0.1 nM, the inhibition percentage of each siRNA is above 80%.

Figure 7:
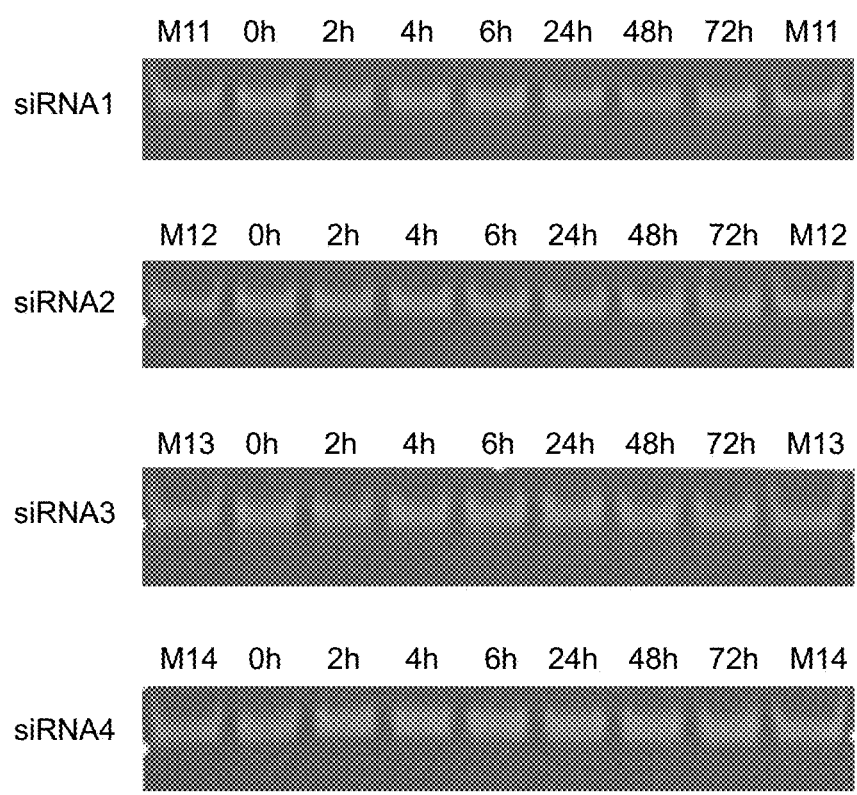
FIG. 7 shows PAGE electrophoretograms of siRNAs 1 to 4 after incubation with human plasma over different periods of time.

Experimental Example 6 Stability of the siRNA in Human Plasma In Vitro siRNAs 1-4 (20 µM, 12 µl) obtained in Preparation Example 12 were individually mixed well with 108 µL of 90% human plasma (diluted in PBS) and incubated at a constant temperature of 37° C. 10 µL samples were taken at each time point of 0 h, 2 h, 4 h, 6 h, 24 h, 48 h and 72 h, respectively, and immediately frozen in liquid nitrogen and cryopreserved in a −80° C. freezer. After sampling at each time point, each sample was diluted 5-fold with 1×PBS (pH 7.4) and then taken in a volume of 10 µL for use. Meanwhile, each of the siRNAs was taken at equal moles (20 µM, 1 µL) and mixed well with 49 µL of 1×PBS (pH 7.4), and 10 µL of the mixture was taken as the reference sample untreated with human plasma (respectively marked as "M11-M14"). 16 wt % of non-denatured polyacrylamide gel was prepared. Each sample above was mixed with 4 µL of loading buffer (aqueous solution of 20 mM EDTA, 36 wt % glycerol, and 0.06 wt % bromophenol blue) and then loaded onto the gel to perform electrophoresis under 20 mA constant current for 20 minutes and then under 40 mA constant current for about 60 minutes. After finishing the electrophoresis, the gel was placed on a shaker and stained with Gelred dye (BioTium, Cat No. 13G1203) for 15 minutes. The gel was subjected to imaging, observation and photocopying. The results are shown in FIG. 7.

The results show that there is no significant difference in band brightness between the siRNAs of the present disclosure and the reference sample at different time points, and the bands are clear without tailing, which indicates that the siRNAs do not degrade and have good stability.

The preferred embodiments of the present disclosure are described above in detail, but the present disclosure is not limited to the specific details of the above-described embodiments. Various simple variations of the technical solution of the present disclosure can be made within the scope of the technical concept of the present disclosure, and these simple variations are within the scope of the present disclosure.

It is to be noted that each of the specific technical features described in the above embodiments can be combined in any suitable manner as long as no contradiction is caused. In order to avoid unnecessary repetition, the various possible combination manners are no longer described in the present disclosure.

In addition, the various different embodiments of the present disclosure may also be carried out in any combination as long as it does not contravene the idea of the present disclosure, which should also be regarded as the disclosure of the present disclosure.

---

What is claimed is:

1. A siRNA capable of inhibiting the expression of an HBV gene, comprising a sense strand and an antisense strand, wherein each nucleotide in the sense strand and the antisense strand is a modified nucleotide, wherein the sense strand and the antisense strand both comprise fluoro modified nucleotides and non-fluoro modified nucleotides; a "fluoro modified nucleotide" refers to a nucleotide formed by substituting the 2'-hydroxy of the ribose group of the nucleotide with a fluoro group, and a "non-fluoro modified nucleotide" refers to a nucleotide formed by substituting the 2'-hydroxy of the ribose group of the nucleotide with a non-fluoro group, or a nucleotide analogue; the sense strand comprises a nucleotide sequence 1; the antisense strand comprises a nucleotide sequence 2; the nucleotide sequence 1 and the nucleotide sequence 2 are at least partly reverse complementary to form a double-stranded region; wherein the nucleotide sequence 1 and the nucleotide sequence shown in SEQ ID NO: 1 have an equal length and no more than 3 nucleotide differences; and the nucleotide sequence 2 and the nucleotide sequence shown in SEQ ID NO: 2 have an equal length and no more than 3 nucleotide differences:

5'-GAAAGUAUGUCAACGAAUZ-3'   (SEQ ID NO: 1),

5'-Z'AUUCGUUGACAUACUUUC-3'   (SEQ ID NO: 2), wherein Z is U, Z' is A;

the nucleotide sequence 1 comprises a nucleotide $Z_A$ at the position corresponding to Z; the nucleotide sequence 2 comprises a nucleotide $Z'_B$ at the position corresponding to Z'; the nucleotide $Z'_B$ is the first nucleotide from 5' terminal of the antisense strand; and the fluoro modified nucleotides are located within the nucleotide sequence 1 and the nucleotide sequence 2; wherein in the direction from 5' terminal to 3' terminal, the nucleotides at positions 7, 8 and 9 in the sense strand of the nucleotide sequence 1 are fluoro modified nucleotides; the nucleotides at positions 2, 6, 14 and 16 in the antisense strand of the nucleotide sequence 2 are fluoro modified nucleotides; and the nucleotides at the other positions in the antisense strand and sense strand are non-fluoro modified nucleotides.

2. The siRNA according to claim 1, wherein the sense strand further comprises a nucleotide sequence 3, and the antisense strand further comprises a nucleotide sequence 4; the nucleotide sequence 3 and the nucleotide sequence 4 have a length of 1-4 nucleotides, respectively; the nucleotide sequence 3 is linked to 5' terminal of the nucleotide sequence 1; and the nucleotide sequence 4 is linked to 3' terminal of the nucleotide sequence 2; the nucleotide sequence 3 and the nucleotide sequence 4 have equal length and are substantially reverse complementary or completely reverse complementary to each other; the "substantially reverse complementary" means that there is no more than 1 base mispairing between two nucleotide sequences; and the "completely reverse complementary" means that there is no mispairing between two nucleotide sequences.

3. The siRNA according to claim 2, wherein the nucleotide sequence 3 and the nucleotide sequence 4 both have a length of 1 nucleotide and the base of the nucleotide sequence 3 is G; or the nucleotide sequence 3 and the nucleotide sequence 4 both have a length of 2 nucleotides; in the direction from 5' terminal to 3' terminal, the bases of the nucleotide sequence 3 are U and G in succession; or the nucleotide sequence 3 and the nucleotide sequence 4 both have a length of 3 nucleotides; in the direction from 5' terminal to 3' terminal, the bases of the nucleotide sequence 3 are U, U and G in succession; or the nucleotide sequence 3 and the nucleotide sequence 4 both have a length of 4 nucleotides; in the direction from 5' terminal to 3' terminal, the bases of the nucleotide sequence 3 are A, U, U, and G in succession.

4. The siRNA according to claim 1, wherein the siRNA further comprises a nucleotide sequence 5, which has a length of 1-3 nucleotides and is linked to 3' terminal of the antisense strand, thereby constituting a 3' overhang of the antisense strand.

5. The siRNA according to claim 4, wherein the nucleotide sequence 5 has a length of 2 nucleotides; and in the direction from 5' terminal to 3' terminal, the nucleotide sequence 5 is 2 consecutive thymidine deoxyribonucleotides, 2 consecutive uridine ribonucleotides or 2 nucleotides complementary to the target mRNA.

6. The siRNA according to claim 5, wherein the nucleotide sequence 1 comprises the nucleotide sequence shown in SEQ ID NO: 3 or SEQ ID NO: 4; and the nucleotide sequence 2 comprises any one of the nucleotide sequences selected from the group consisting of the nucleotide sequences shown in SEQ ID NO: 5, SEQ ID NO: 6, SEQ ID NO: 7 and SEQ ID NO: 8:

5'-GAAAGUAUGUCAACGAAUU-3'   (SEQ ID NO: 3),

5'-GAAAGUAUGUCAACGAAUA-3'   (SEQ ID NO: 4),

5'-AAUUCGUUGACAUACUUUCUU-3'   (SEQ ID NO: 5),

5'-AAUUCGUUGACAUACUUUCCA-3'   (SEQ ID NO: 6),

5'-UAUUCGUUGACAUACUUUCUU-3'   (SEQ ID NO: 7),

5'-UAUUCGUUGACAUACUUUCCA-3'   (SEQ ID NO: 8).

7. The siRNA according to claim 6, wherein the siRNA is any one of the following siP1 to siP4:

siP1

Sense strand: 5'-GAAAGUAUGUCAAC-GAAUU -3' (SEQ ID NO: 3),

Antisense strand: 5'-AAUUCGUUGACAUAC-UUUCUU -3' (SEQ ID NO: 5), siP2

Sense strand: 5'-GAAAGUAUGUCAACG-AAUU -3' (SEQ ID NO: 3),

Antisense strand: 5'-AAUUCGUUGACAUAC-UUUCCA -3' (SEQ ID NO: 6), siP3

Sense strand: 5'-GAAAGUAUGUCAAC-GAAUA -3' (SEQ ID NO: 4),

Antisense strand: 5'-UAUUCGUUGACAUAC-UUUCUU -3' (SEQ ID NO: 7), siP4

Sense strand: 5'-GAAAGUAUGUCAA-CGAAUA -3' (SEQ ID NO: 4),

Antisense strand: 5'-UAUUCGUUGACAUAC-UUUCCA -3' (SEQ ID NO: 8).

8. The siRNA according to claim 1, wherein each non-fluoro modified nucleotide is independently selected from a nucleotide formed by substituting the 2'-hydroxy of the ribose group of the nucleotide with a non-fluoro group, or a nucleotide analogue.

9. The siRNA according to claim 8, wherein each non-fluoro modified nucleotide is a methoxy modified nucleotide which refers to a nucleotide formed by substituting the 2'-hydroxy of the ribose group with a methoxy group.

10. The siRNA according to claim 9, wherein the siRNA is any one of the following siRNAs:

siHB1M1

Sense strand: 5'-GmAmAmAmGmUmAfUfGfJmC-mAmAmCmGmAmAmUmUm-3' (SEQ ID NO: 11),

Antisense strand: 5'-AmAfUmUmCmGfUmUmG-mAmCmAmUmAfCmUfUmUmC-mUmUm-3' (SEQ ID NO: 13);

siHB2M1

Sense strand: 5'-GmAmAmAmGmUmAfUfGfJmC-mAmAmCmGmAmAmUmUm-3' (SEQ ID NO: 11),

Antisense strand: 5'-AmAfUmUmCmGfUmUmG-mAmCmAmUmAfCmUfUmUm-CmCmAm-3' (SEQ ID NO: 14);

siHB3M1

Sense strand: 5'-GmAmAmAmGmUmAfUfGfUmC-mAmCmGmAmAmUmAm-3' (SEQ ID NO: 12),

Antisense strand: 5'-UmAfUmUmCmGfUmUmG-mAmCmAmUmAfCmUfUmUm-CmUmUm-3' (SEQ ID NO: 15);

siHB4M1

Sense strand: 5'-GmAmAmAmGmUmAfUfGfUmC-mAmCmGmAmAmUmAm-3' (SEQ ID NO: 12),

Antisense strand: 5'-UmAfUmUmCmGfUmUmG-mAmCmAmUmAfCmUfUmUm-CmCmAm-3' (SEQ ID NO: 16);

siHB5M1

Sense strand: 5'-UmGmGmAmAmAmGmUmA-fUfGfUmCmAmAmCmGmAm-AmUmAm-3' (SEQ ID NO: 51), Antisense strand: 5'-UmAfUmUmCmGfUmUmG-mAmCmAmUmAfCmUfUmUmCmCmAmU-mUm-3' (SEQ ID NO: 52).

11. The siRNA according to claim 1, wherein at least one of the phosphate groups in the phosphate-ribose backbone of at least one single strand of the sense strand and the antisense strand is a phosphorothioate group, and at least one linkage selected from the group consisting of the following inter-nucleotide linkages is a phosphorothioate linkage:

the linkage between the first and second nucleotides at 5' terminal of the sense strand;

the linkage between the second and third nucleotides at 5' terminal of the sense strand;

the linkage between the first and second nucleotides at 3' terminal of the sense strand;

the linkage between the second and third nucleotides at 3' terminal of the sense strand;

the linkage between the first and second nucleotides at 5' terminal of the antisense strand;

the linkage between the second and third nucleotides at 5' terminal of the antisense strand;

the linkage between the first and second nucleotides at 3' terminal of the antisense strand; and the linkage between the second and third nucleotides at 3' terminal of the antisense strand.

12. The siRNA according to claim 11, wherein the siRNA is any one of the following siRNAs:

siHB1M1S

Sense strand: 5'-GmsAmsAmAmGmUmA-fUfGfUJmCmAmAmCmGmAm-AmUmUm-3' (SEQ ID NO: 23), Antisense strand: 5'-AmsAfsUmUmCmGfUmUmG-mAmCmAmUmAfCmUfUmUm-CmsUmsUm-3' (SEQ ID NO: 25);

siHB2M1S

Sense strand: 5'-GmsAmsAmAmGmUmA-fUfGfUmCmAmAmCmGmAm-AmUmUm-3' (SEQ ID NO: 23),

Antisense strand: 5'-AmsAfsUmUmCmGfUmUmG-mAmCmAmUmAfCmUfUmUm-CmsCmsAm-3' (SEQ ID NO: 26);

siHB3M1S

Sense strand: 5'-GmsAmsAmAmGmUmA-fUfGfUmCmAmAmCmGmAm-AmUmAm-3' (SEQ ID NO: 24),

Antisense strand: 5'-UmsAfsUmUmCmGfUmUmG-mAmCmAmUmAfCmUfUmUm-CmsUmsUm-3' (SEQ ID NO: 27);

siHB4M1S

Sense strand: 5'-GmsAmsAmAmGmUmA-fUfGfUmCmAmAmCmGmAm-AmUmAm-3' (SEQ ID NO: 24),

Antisense strand: 5'-UmsAfsUmUmCmGfUmUmG-mAmCmAmUmAfCmUfUmUm-CmsCmsAm-3' (SEQ ID NO: 28);

siHB5M1S

Sense strand: 5'-UmsGmsGmAmAmAmGmUmA-
fUfGfUmCmAmAmCmGmAmAm-
UmAm-3' (SEQ ID NO: 56), Antisense strand: 5'-UmsAfsUmUmCmGfUmUmG-
mAmCmAmUmAfCmUfUmUmCmCmAmUm-
sUm-3' (SEQ ID NO: 57).

13. The siRNA according to claim 1, wherein the nucleotide at 5'-terminal of the antisense strand of the siRNA is a 5'-phosphate nucleotide or a 5'-phosphate analogue modified nucleotide, wherein the 5'-phosphate nucleotide or 5'-phosphate analogue modified nucleotide has a structure as shown by one of Formula (202), (203), (204), (205) or (206):

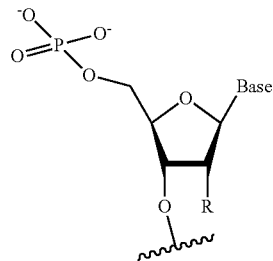

Formula (202)

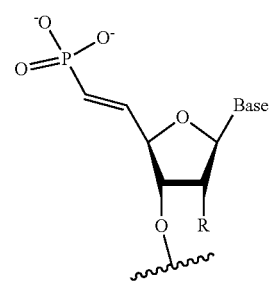

Formula (203)

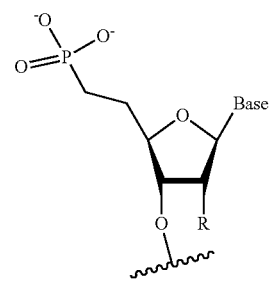

Formula (204)

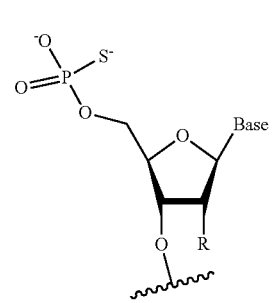

Formula (205)

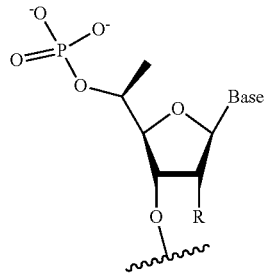

Formula (206)

wherein R represents a group selected from the group consisting of H, OH, F and methoxy: "Base" represents a base selected from A, U, C, G, and T.

14. The siRNA according to claim 13, wherein the siRNA is any one of the following siRNAs:

siHB1M1P

Sense strand: 5'-GmAmAmAmGmUmAfUfGfJmC-
mAmAmCmGmAmAmUmUm-3' (SEQ ID NO:11),

Antisense strand: 5'-P1-AmAfUmUmCmGfUmUmG-
mAmCmAmUmAfCmUfUmUmCm-
UmUm-3' (SEQ ID NO: 35);

siHB2M1P

Sense strand: 5'-GmAmAmAmGmUmAfUfGfUmC-
mAmAmCmGmAmAmUmUm-3' (SEQ ID NO:11),

Antisense strand: 5'-P1-AmAfUmUmCmGfUmUmG-
mAmCmAmUmAfCmUfUmUm-
CmCmAm-3' (SEQ ID NO: 35);

siHB3M1P

Sense strand: 5'-GmAmAmAmGmUmAfUfGfUmC-
mAmAmCmGmAmAmUmAm-3' (SEQ ID NO:12),

Antisense strand: 5'-P1-UmAfUmUmCmGfUmUmG-
mAmCmAmUmAfCmUfUmUm-
CmUmUm-3' (SEQ ID NO: 27);

siHB4M1P

Sense strand: 5'-GmAmAmAmGmUmAfUfGfJmC-
mAmAmCmGmAmAmUmAm-3' (SEQ ID NO:12),

Antisense strand: 5'-P1-UmAfUmUmCmGfUmUmG-
mAmCmAmUmAfCmUfUmUm-
CmCmAm-3' (SEQ ID NO:38);

siHB5M1P

Sense strand: 5'-UmGmGmAmAmAmGmUmA-
fUfGfUmCmAmAmCmGmAm-
AmUmAm-3' (SEQ ID NO:51), Antisense strand: 5'-P1-UmAfUmUmCmGfUmUmG-
mAmCmAmUmAfCmUfUmUmCmCmAmU-
mUm-3' (SEQ ID NO:61);

siHB1M1SP

Sense strand: 5'-GmsAmsAmAmGmUmA-
fUfGfUmCmAmAmCmGmAm-
AmUmUm-3' (SEQ ID NO:23), Antisense strand: 5'-P1-AmsAfsUmUmCmGfU-
mUmGmAmCmAmUmAfCmUfU-
mUmCmsUmsUm-3' (SEQ ID NO:43);

siHB2M1SP

Sense strand: 5'-GmsAmsAmAmGmUmA-
fUfGfUmCmAmAmCmGmAm-
AmUmUm-3'  (SEQ ID NO:23), Antisense strand: 5'-P1-AmsAfsUmUmCmGfU-
mUmGmAmCmAmUmAfCmUfU-
mUmCmsCmsAm-3'  (SEQ ID NO:44);

siHB3M1SP

Sense strand: 5'-GmsAmsAmAmGmUmA-
fUfGfUmCmAmAmCmGmAm-
AmUmAm-3'  (SEQ ID NO:24), Antisense strand: 5'-P1-UmsAfsUmUmCmGfU-
mUmGmAmCmAmUmAfCmUfU-
mUmCmsUmsUm-3'  (SEQ ID NO:45);

siHB4M1SP

Sense strand: 5'-GmsAmsAmAmGmUmA-
fUfGfUmCmAmAmCmGmAm-
AmUmAm-3'  (SEQ ID NO:24), Antisense strand: 5'-P1-UmsAfsUmUmCmGfU-
mUmGmAmCmAmUmAfCmUfU-
mUmCmsCmsAm-3'  (SEQ ID NO:46);

siHB5M1SP

Sense strand: 5'-UmsGmsGmAmAmAmGmUmA-
fUfGfUmCmAmAmCmGmAm-
AmUmAm-3'  (SEQ ID NO:56), Antisense strand: 5'-P1-UmsAfsUmUmCmGfU-
mUmGmAmCmAmUmAfCmUfU-
mUmCmsCmsAm-3'  (SEQ ID NO:64).

15. A pharmaceutical composition comprising the siRNA according to claim 1 and a pharmaceutically acceptable carrier, wherein the weight ratio of the siRNA and the pharmaceutically acceptable carrier is 1:(1-500).

16. The pharmaceutical composition according to claim 15, wherein the pharmaceutically acceptable carrier comprises an organic amine, a helper lipid and a PEGylated lipid; wherein the organic amine is a compound as shown by Formula (201) and/or a pharmaceutically acceptable salt thereof:

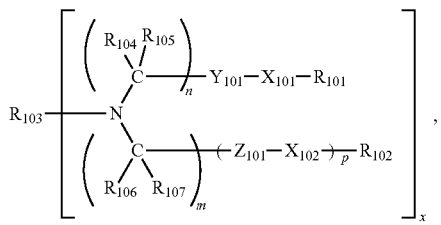

Formula (201)

wherein:

$X_{101}$ and $X_{102}$ independently of one another are selected from O, S, N-A and C-A, wherein A is hydrogen or a $C_1$-$C_{20}$ hydrocarbon chain;

$Y_{101}$ and $Z_{101}$ independently of one another are selected from C=O, C=S, S=O, CH—OH and $SO_2$;

$R_{101}$, $R_{102}$, $R_{103}$, $R_{104}$, $R_{105}$, $R_{106}$ and $R_{107}$ independently of one another are selected from hydrogen; a cyclic or an acyclic, substituted or unsubstituted, branched or unbranched aliphatic group; a cyclic or an acyclic, substituted or unsubstituted, branched or unbranched heteroaliphatic group; a substituted or unsubstituted, branched or unbranched acyl group; a substituted or unsubstituted, branched or unbranched aryl group; and a substituted or unsubstituted, branched or unbranched heteroaryl group;

x is an integer of 1-10;

n is an integer of 1-3, m is an integer of 0-20, p is an integer of 0 or 1, wherein if m and p are 0, then $R_{102}$ is hydrogen; and if at least one of n and m is 2, then $R_{103}$ and nitrogen in Formula (201) form a structure as shown by Formula (202) or (203):

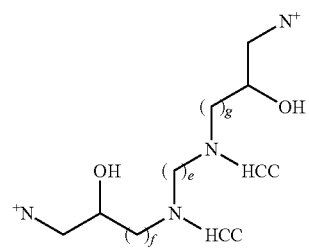

Formula (202)

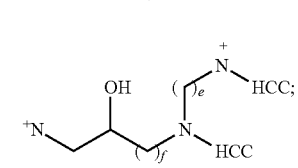

Formula (203)

wherein g, e and f independently of one another are an integer of 1-6; "HCC" represents a hydrocarbon chain; and each *N indicates a nitrogen atom shown in Formula (201).

17. The pharmaceutical composition according to claim 16, wherein the organic amine is an organic amine as shown by Formula (214) and/or an organic amine as shown by Formula (215):

Formula (214)
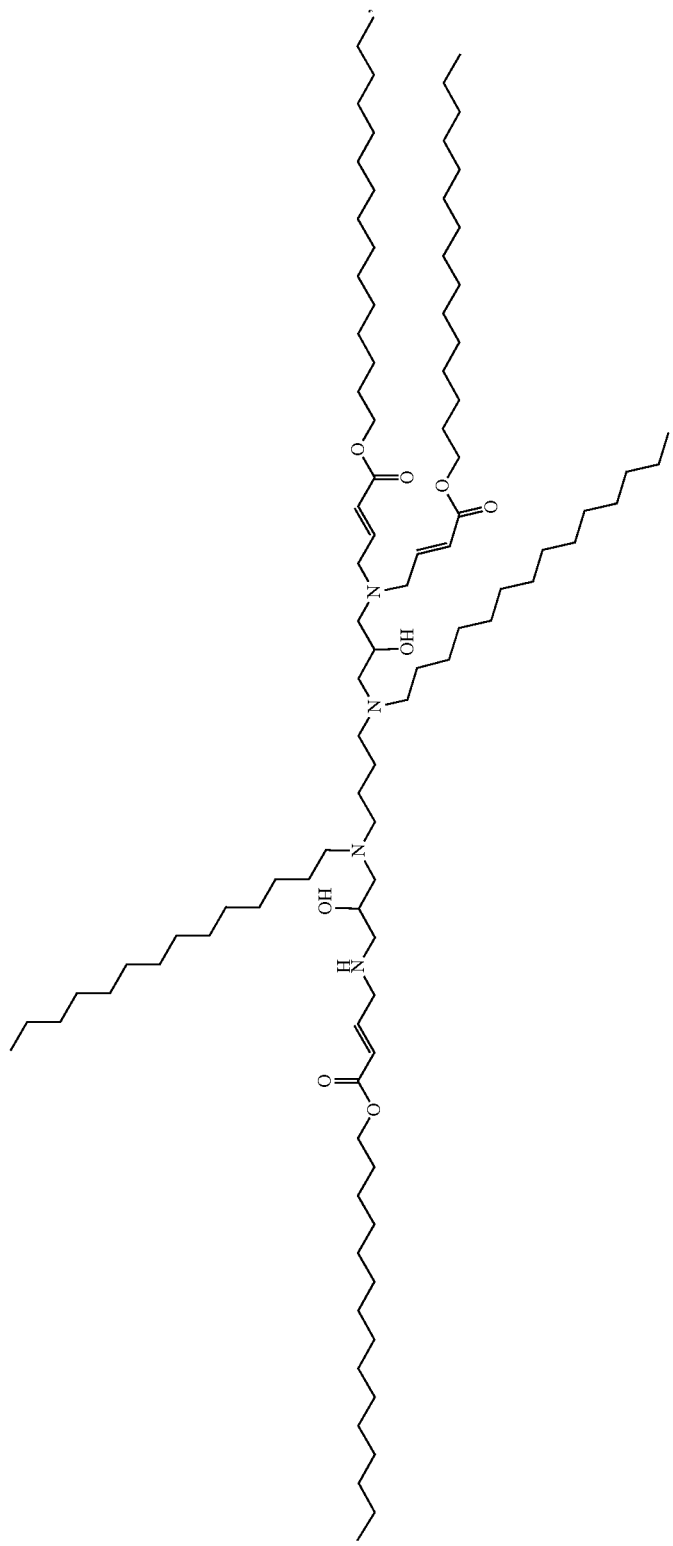

Formula (215)
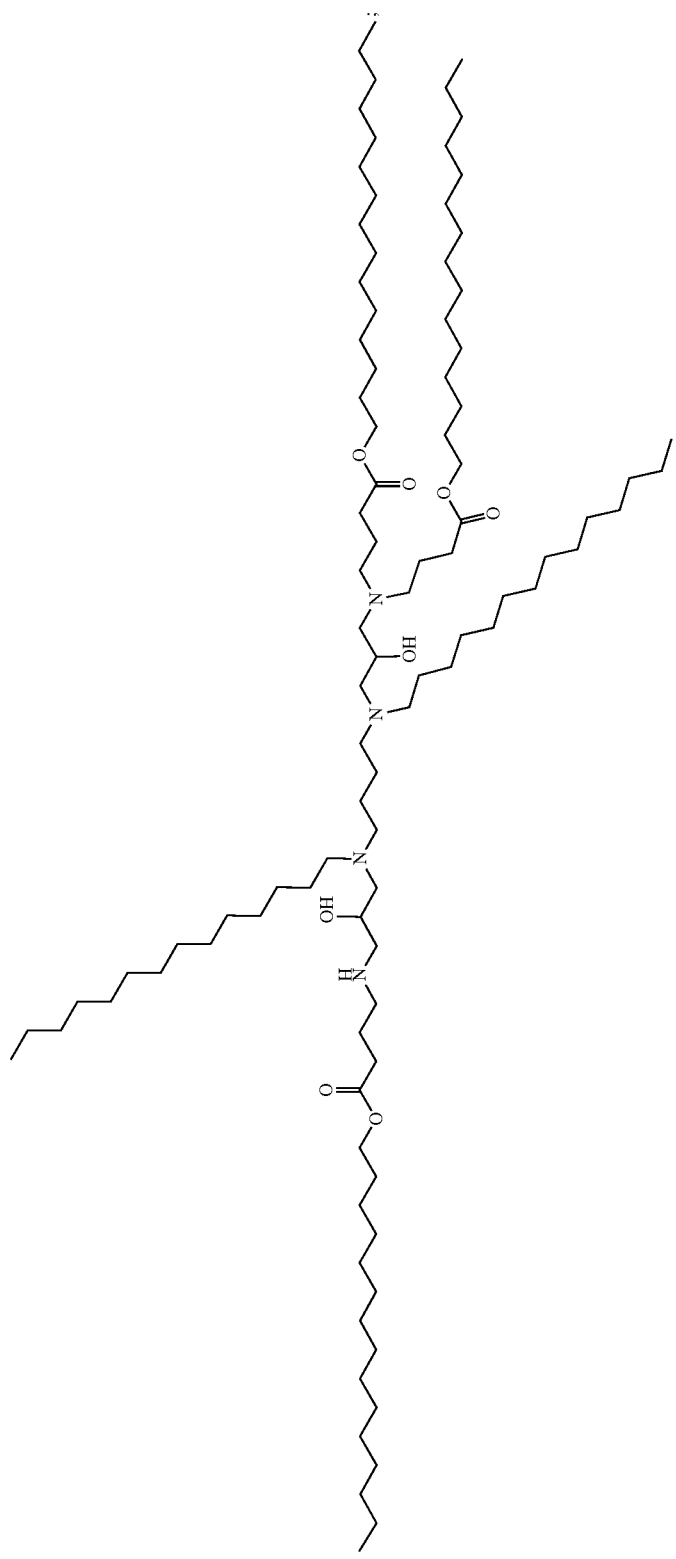

the helper lipid is cholesterol, cholesterol analogs and/or cholesterol derivatives; and the PEGylated lipid is 1,2-dipalmitoyl-sn-glycero-3-phosphoethanolamine-N-[methoxy(polyethylene glycol)]-2000.

18. The pharmaceutical composition according to claim 16, wherein the molar ratio among the organic amine, the helper lipid, and the PEGylated lipid is (19.7-80): (19.7-80): (0.3-50).

19. The siRNA conjugate comprising the siRNA according to claim 1 and a ligand conjugated to the siRNA.

20. The siRNA conjugate according to claim 16, wherein the ligand is a pharmaceutically acceptable conjugation group which comprises a pharmaceutically acceptable targeting group and a linker; and the siRNA, the linker and the targeting group are covalently linked in succession;

wherein the linker has a structure as shown by Formula (301):

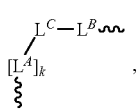

Formula (301)

wherein k is an integer of 1-3;

$L^A$ is an amide bond-comprising chain moiety that has a structure as shown by Formula (302), two terminals of which are respectively linked to the targeting group and the $L^C$ moiety each via an ether bond:

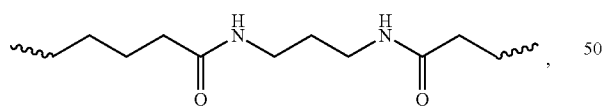

Formula (302)

$L^B$ is an N-acylpyrrolidine-comprising chain moiety that has a structure as shown by Formula (303), which has a carbonyl group and is linked to the $L^C$ moiety via an amide bond at one end, and has an oxygen atom and is linked to the siRNA via a phosphoester bond at the other end thereof:

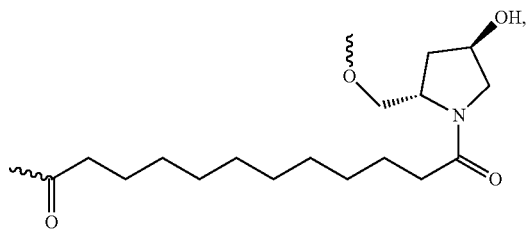

Formula (303)

$L^C$ is a bivalent to tetravalent linking group based on hydroxymethyl aminomethane, dihydroxymethyl aminomethane or trihydroxymethyl aminomethane, $L^C$ being linked to each of the LA moieties through an ether bond via an oxygen atom, and being linked to the LB moiety through an amide bond via the nitrogen atom; or wherein the linker has a structure as shown by Formula (306):

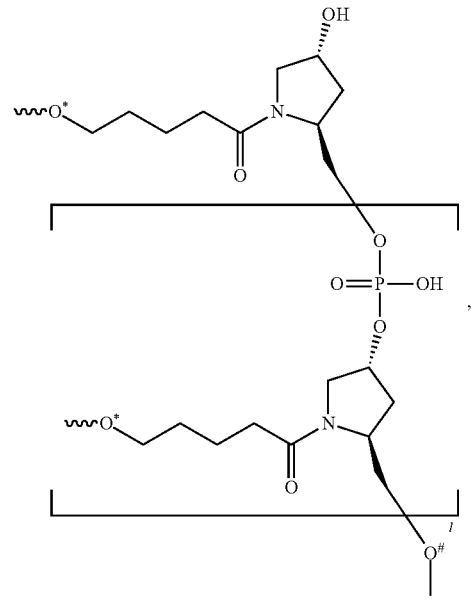

Formula (306)

wherein, l is an integer of 0-3;

* represents the site on the linker linked to the targeting group via ether bond; and represents the site on the linker linked to the siRNA via phosphoester bond.

21. The siRNA conjugate according to claim 20, wherein the siRNA conjugate has a structure as shown by Formula (305) or by Formula (307):

267 268
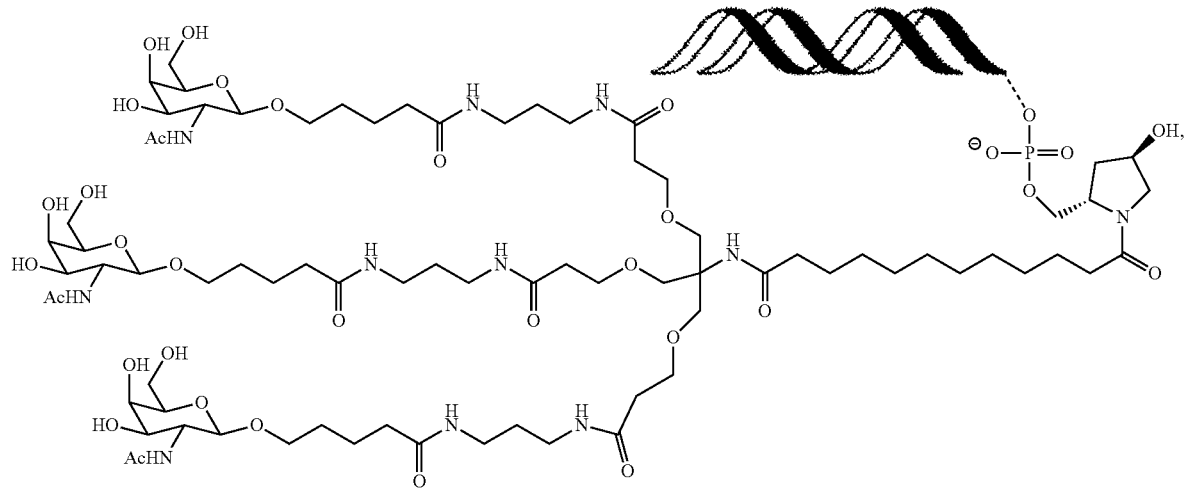
Formula (305)
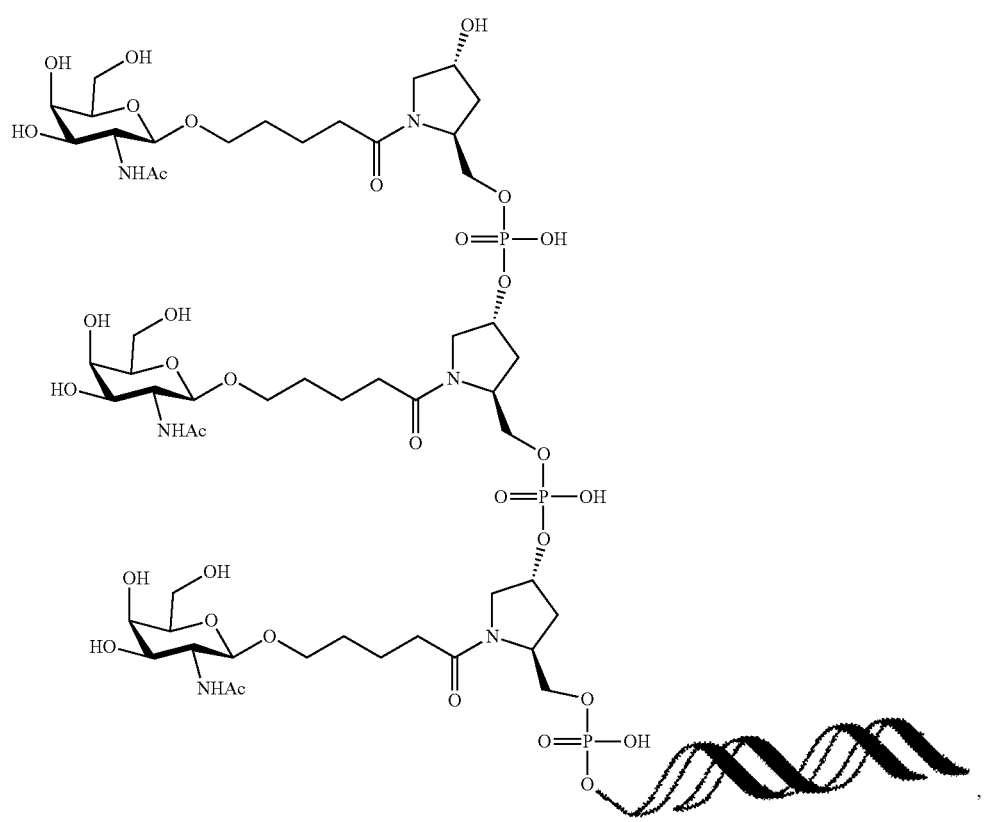
Formula (307)

wherein, the double helix structure represents the siRNA; and the linker is linked to 3'-terminal of the sense strand of the siRNA.

22. A siRNA conjugate having a structure as shown by Formula (401):

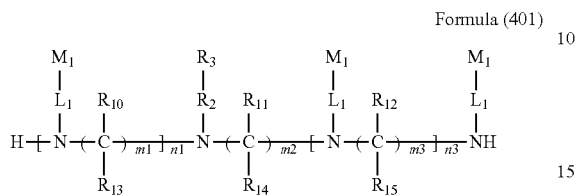

Formula (401)

wherein, n1 is an integer of 1-3, and n3 is an integer of 0-4;

m1, m2, and m3 independently of one another are an integer of 2-10;

$R_{10}$, $R_{11}$, $R_{12}$, $R_{13}$, $R_{14}$ and $R_{15}$ independently of one another are one of H, methyl or ethyl;

$R_3$ is a group having a structure as shown by Formula (A59):

Formula (A59)

wherein, $E_1$ is OH, SH or $BH_2$; Nu is the siRNA according to claim 1;

$R_2$ is any group capable of linking to the N atom on the nitrogenous backbone and linking to A59;

each $L_1$ is independently selected from the linkage combinations of one or more of Formulae A1-A26:

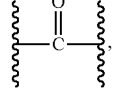 (A1)

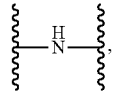 (A2)

(A3)

(A4)

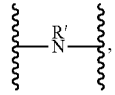 (A5)

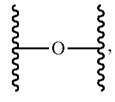

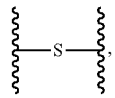

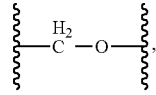 (A6)

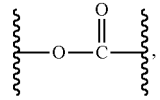 (A7)

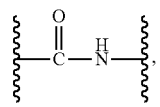 (A8)

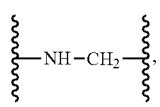 (A9)

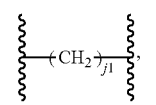 (A10)

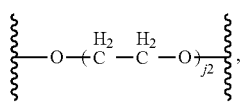 (A11)

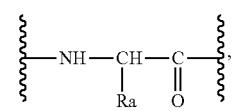 (A12)

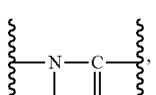 (A13)

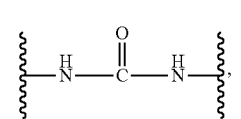 (A14)

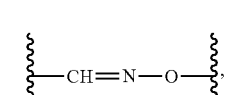 (A15)

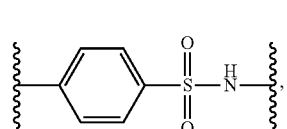 (A16)

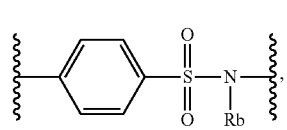 (A17)

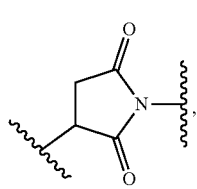 (A18)

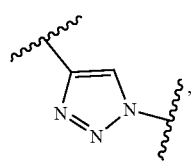 (A19)
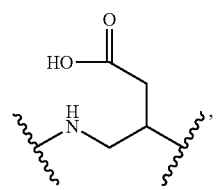 (A20)
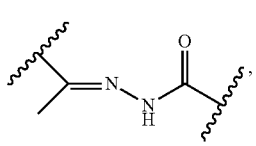 (A21)
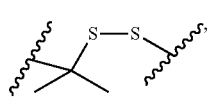 (A22)
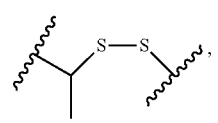 (A23)
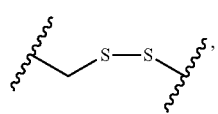 (A24)
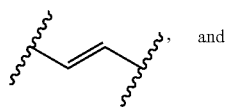 (A25) and
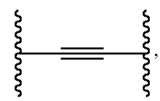 (A26)
wherein j1 is an integer of 1-20; j2 is an integer of 1-20; R' is a $C_1$-$C_{10}$ alkyl;
Ra is selected from one of Formulae A27-A45:
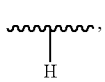 (A27)
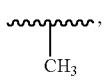 (A28)
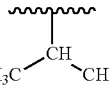 (A29)
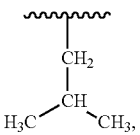 (A30)
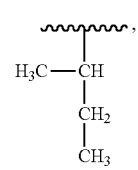 (A31)
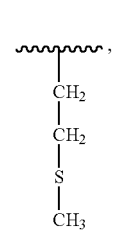 (A32)
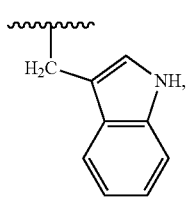 (A33)
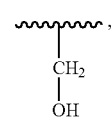 (A34)
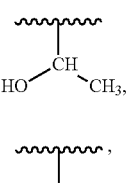 (A35)
(A36)
(A37)
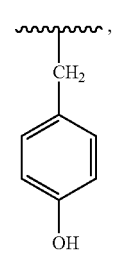
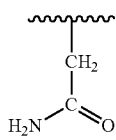 (A38)

(A39) 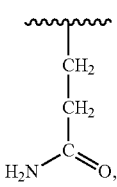

(A40) 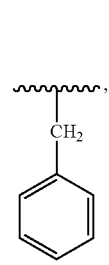

(A41) 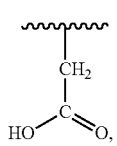

(A42) 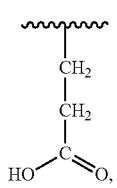

(A43) 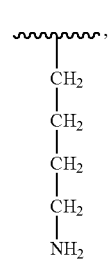

(A44) 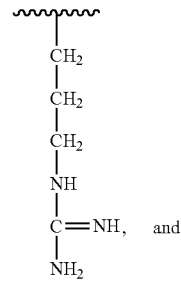

(A45) 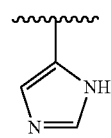

Rb is a $C_1$-$C_{10}$ alkyl; and

〰 represents the site where a group is covalently linked;

each $M_1$ is independently selected from one of the ligands that have affinity to the asialoglycoprotein receptors (ASGP-R) on the surface of mammalian hepatocytes.

23. The siRNA conjugate according to claim 22, wherein $L_1$ is selected from the linkage combinations of one or more of Formulae A1, A4, A5, A6, A8, A10, A11, and A13.

24. The siRNA conjugate according to claim 22, wherein $L_1$ has a length of 3 to 25 atoms.

25. The siRNA conjugate according to claim 22, wherein m1, m2 and m3 independently of one another are an integer of 2-5.

26. The siRNA conjugate according to claim 22, wherein each $M_1$ is independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose, and L-4-thioribose.

27. The siRNA conjugate according to claim 22, wherein $R_2$ comprises both a site linking to the N atom on the nitrogenous backbone and a site linking to the P atom in $R_3$; and wherein in $R_2$, the site linking to the N atom on the nitrogenous backbone forms an amide bond with the N atom, and the site linking to the P atom in $R_3$ forms a phosphoester bond with the P atom.

28. The siRNA conjugate according to claim 22, wherein the conjugate has a structure as shown by Formula (403), (404), (405), (406), (407), (408), (409), (410), (411), (412), (413), (414), (415), (416), (417), (418), (419), (420), (421), or (422):
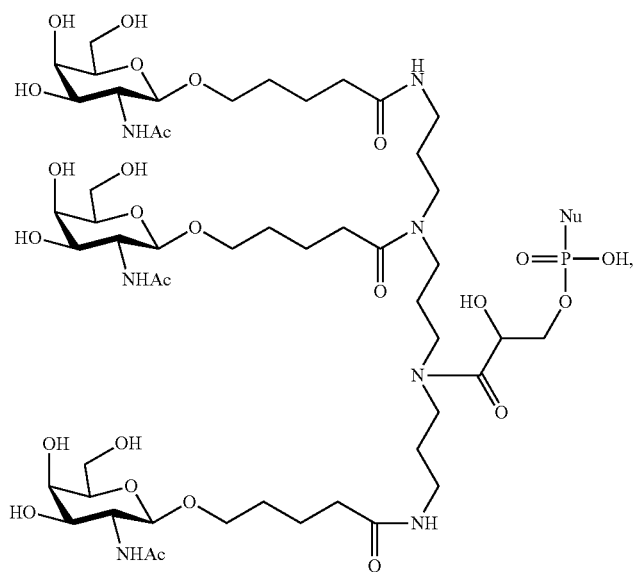
Formula (403)
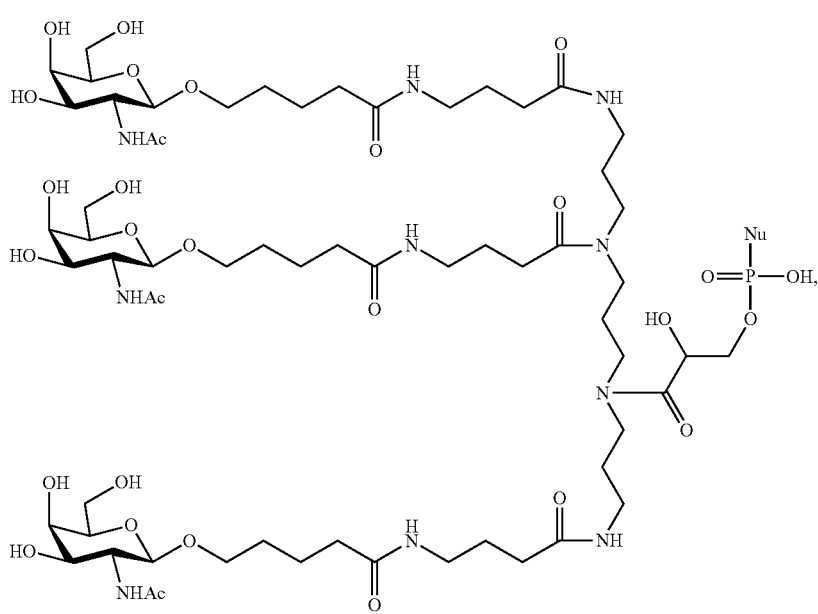
Formula (404)

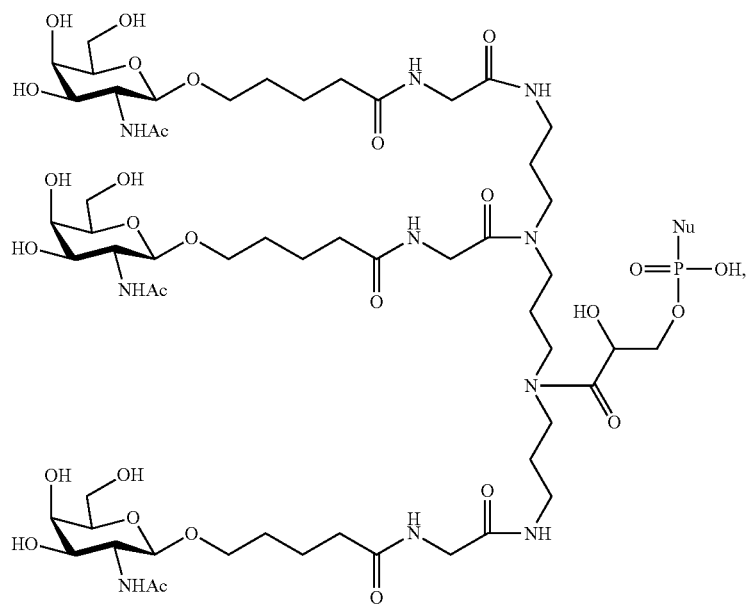
Formula (405)
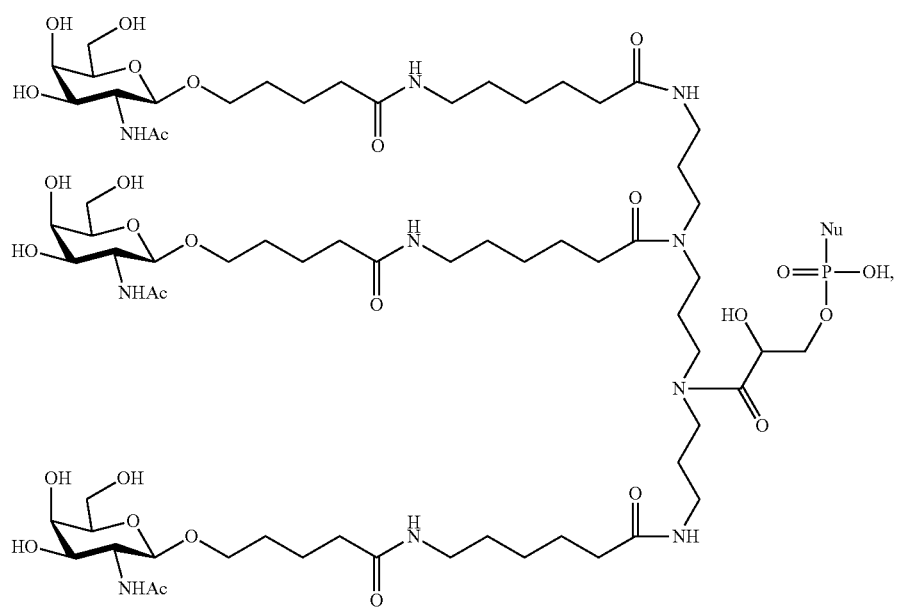
Formula (406)

-continued
Formula (407)
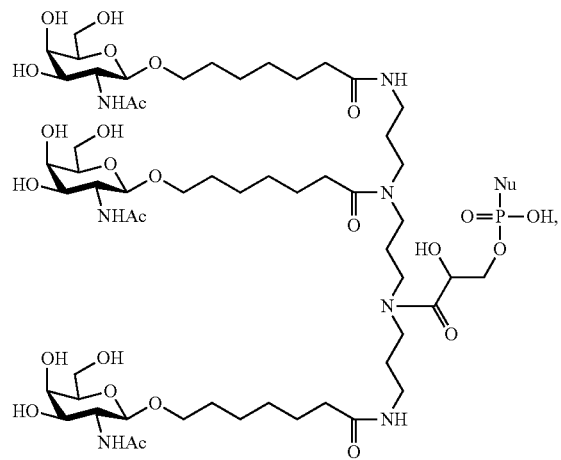
Formula (408)
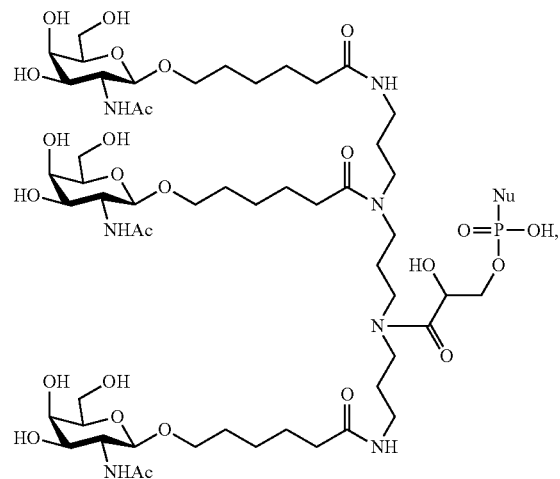
Formula (409)
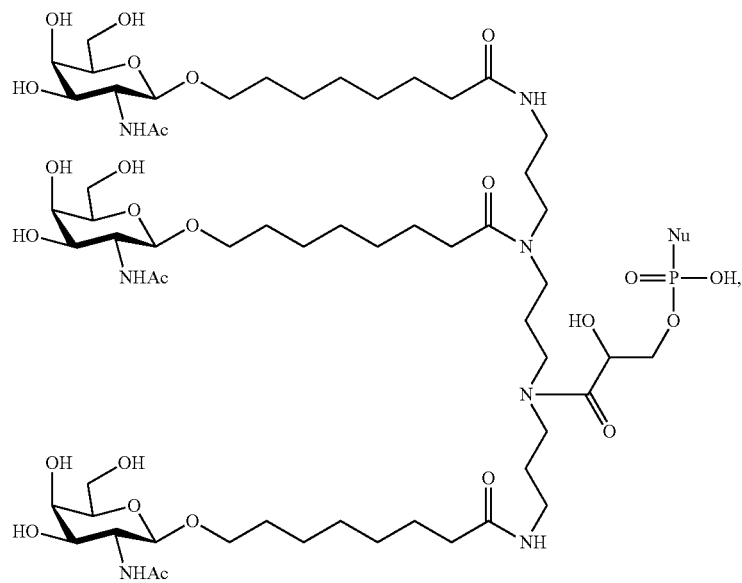
Formula (410)
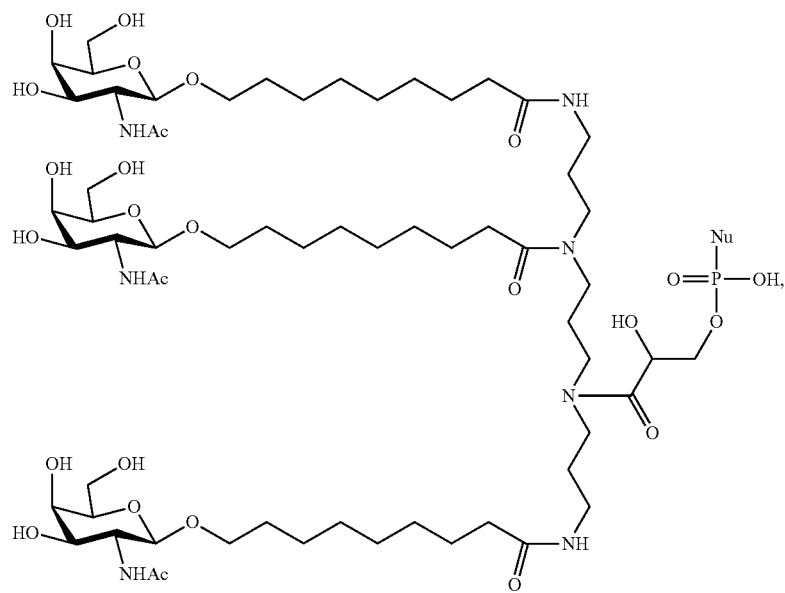

-continued
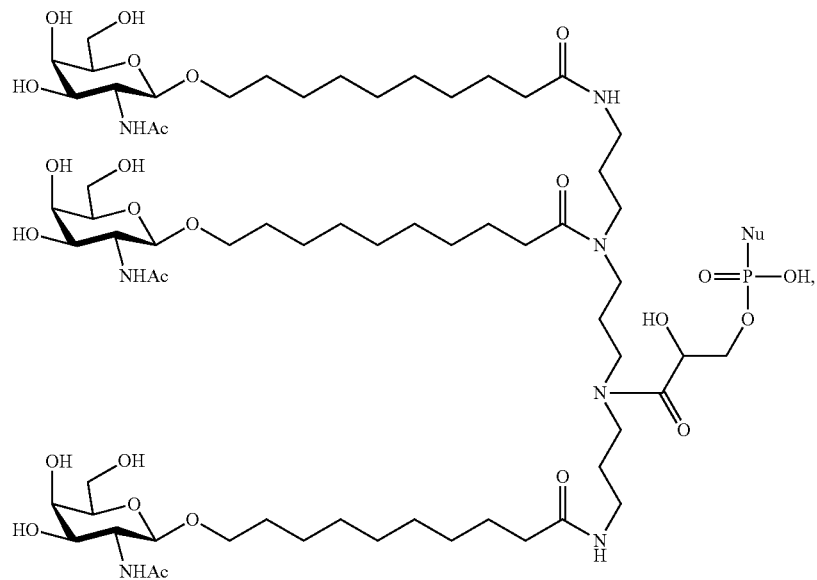
Formula (411)
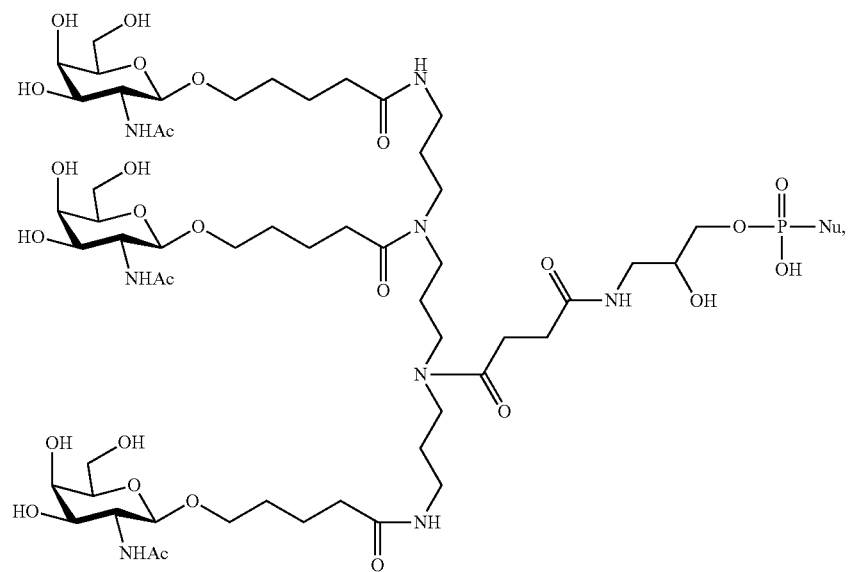
Formula (412)

Formula (413)
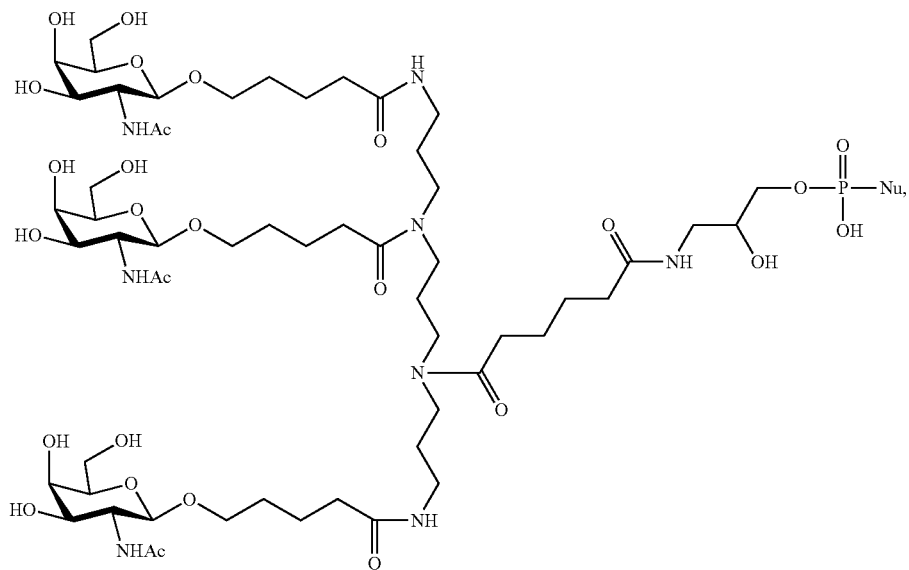
Formula (414)
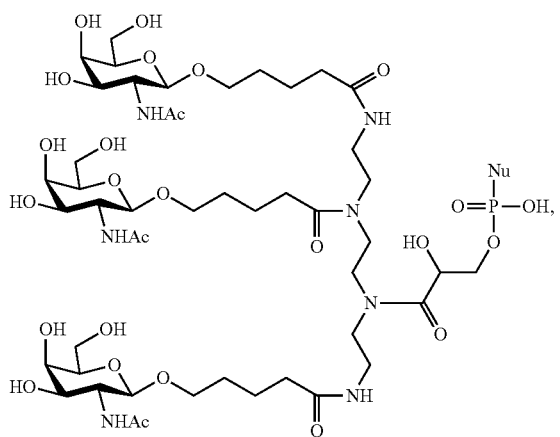
Formula (415)
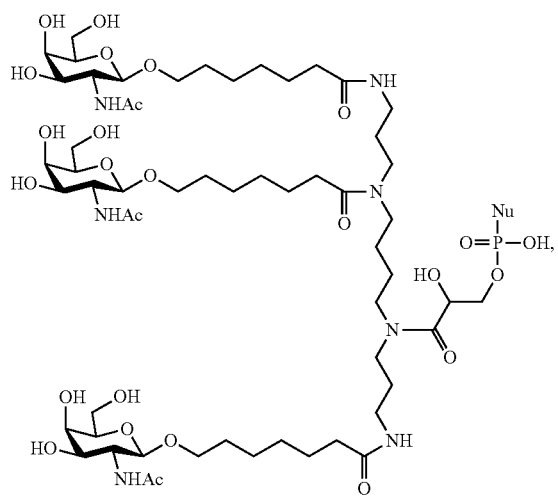
Formula (416)
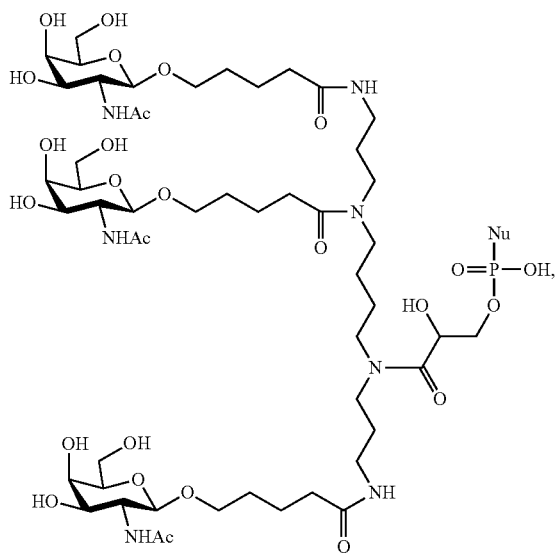
Formula (417)
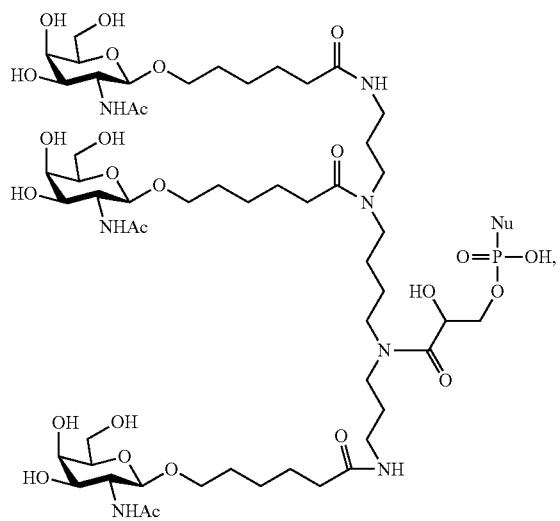

Formula (418)
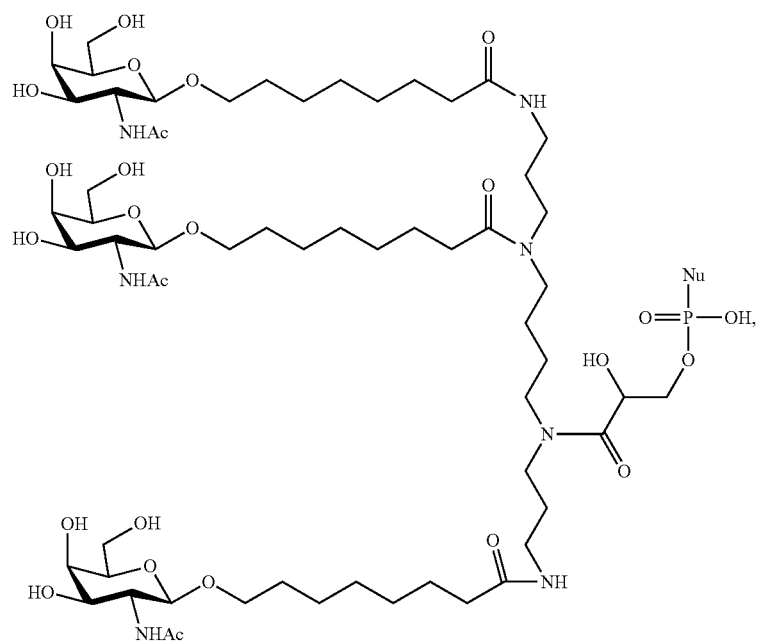
Formula (419)
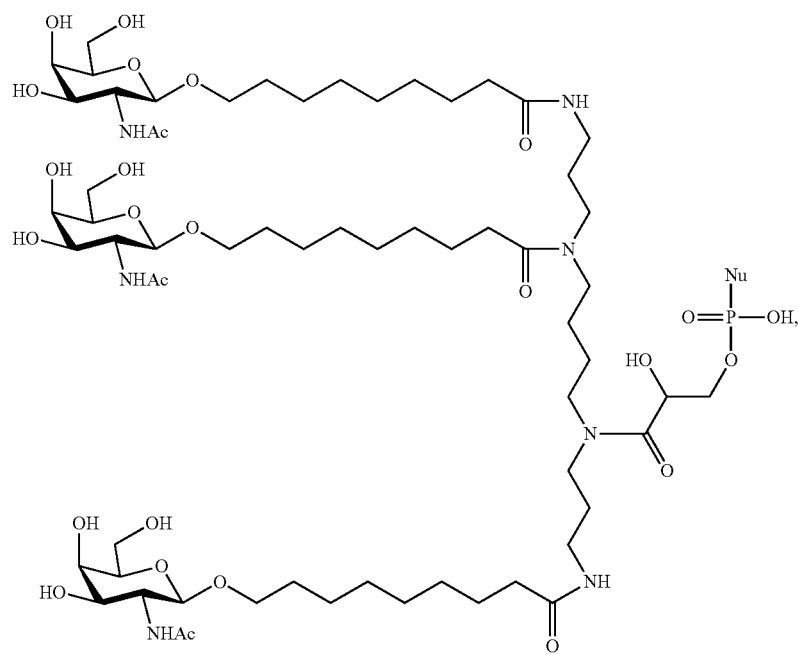

-continued

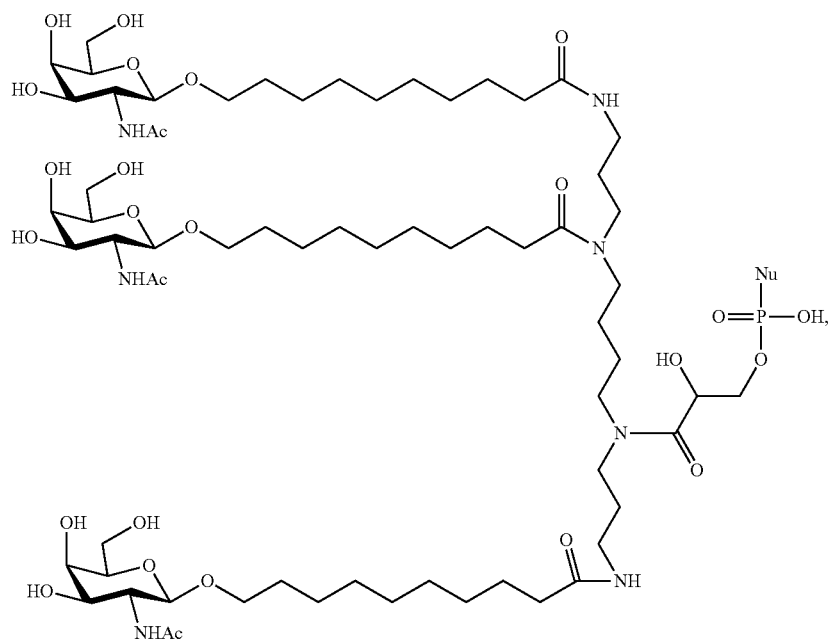

Formula (420)

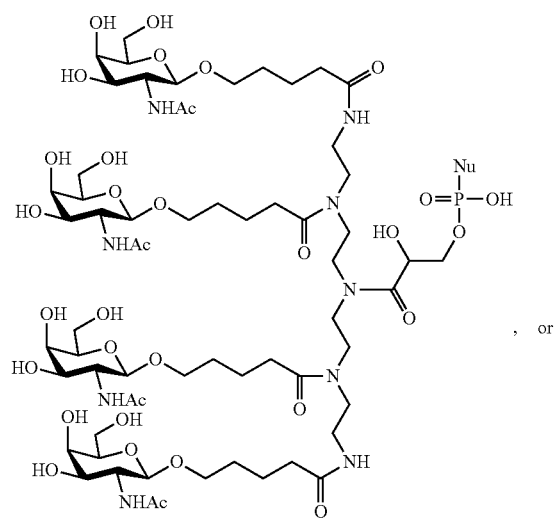

Formula (421)

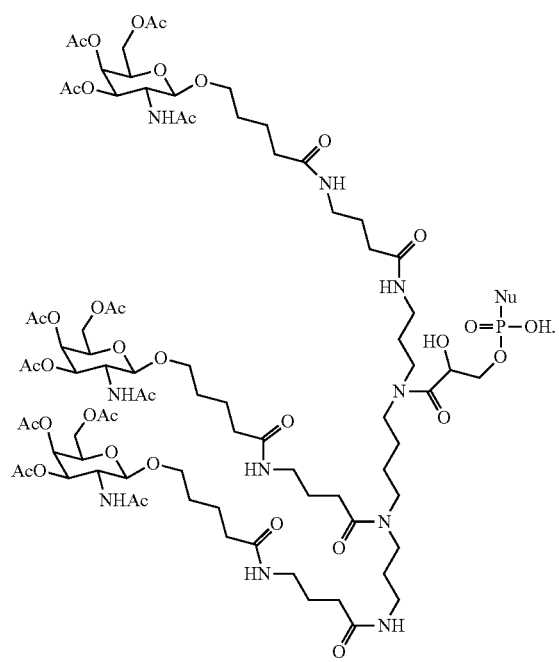

Formula (422)

29. The siRNA conjugate according to claim 28, wherein the P atom in Formula A59 is linked to 3' terminal of the sense strand.

30. A method for treating and/or preventing a pathological condition or disease caused by HBV infection, comprising administering to a patient an effective amount of the siRNA according to claim 1.

31. A method for inhibiting the expression of HBV genes, comprising contacting an effective amount of the siRNA according to claim 1.

32. The method of claim 30, wherein the pathological condition or disease caused by HBV infection is selected from chronic liver diseases, hepatitis, hepatic fibrosis, and liver proliferative diseases.

33. A method for treating and/or preventing a pathological condition or disease caused by HBV infection, comprising the pharmaceutical composition according to claim 15.

34. A method for treating and/or preventing a pathological condition or disease caused by HBV infection, comprising the siRNA conjugate according to claim 19.

35. A method for inhibiting the expression of HBV genes, comprising the pharmaceutical composition according to claim 15.

36. A method for inhibiting the expression of HBV genes, comprising the siRNA conjugate according to claim 19 with hepatitis cells infected with HBV.

37. The siRNA conjugate according to claim 23, wherein $L_1$ is selected from the linkage combinations of at least two of Formulae A1, A4, A8, A10, and A11.

38. The siRNA conjugate according to claim 23, wherein $L_1$ has a length of 4 to 15 atoms.

39. The siRNA conjugate according to claim 25, wherein m1=m2=m3.

40. The siRNA conjugate according to claim 27, wherein $R_2$ is selected from B5, B6, B5', or B6':

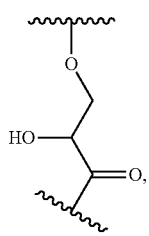
(B5)

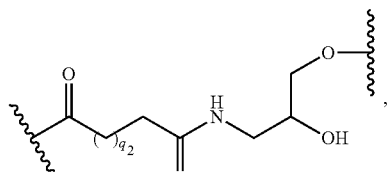
(B6)

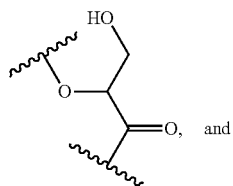
(B5')

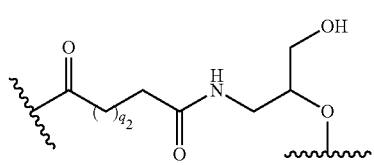
(B6')

wherein ∿∿∿ represents the site where a group is covalently linked; and $q_2$ is an integer of 1-10.

* * * * *

SEQUENCE LISTING

```
<160> NUMBER OF SEQ ID NOS: 90

<210> SEQ ID NO 1
<211> LENGTH: 19
<212> TYPE: RNA
<213> ORGANISM: Artificial Sequence
<220> FEATURE:
<223> OTHER INFORMATION: siRNA

<400> SEQUENCE: 1
gaaaguaugu caacgaauu                                                    19

<210> SEQ ID NO 2
<211> LENGTH: 19
<212> TYPE: RNA
<213> ORGANISM: Artificial Sequence
<220> FEATURE:
<223> OTHER INFORMATION: siRNA

<400> SEQUENCE: 2
aauucguuga cauacuuuc                                                    19

<210> SEQ ID NO 3
<211> LENGTH: 19
<212> TYPE: RNA
<213> ORGANISM: Artificial Sequence
<220> FEATURE:
<223> OTHER INFORMATION: siRNA

<400> SEQUENCE: 3
gaaaguaugu caacgaauu                                                    19

<210> SEQ ID NO 4
<211> LENGTH: 19
<212> TYPE: RNA
```

```
<213> ORGANISM: Artificial Sequence
<220> FEATURE:
<223> OTHER INFORMATION: siRNA

<400> SEQUENCE: 4
gaaaguaugu caacgaaua                                                   19

<210> SEQ ID NO 5
<211> LENGTH: 21
<212> TYPE: RNA
<213> ORGANISM: Artificial Sequence
<220> FEATURE:
<223> OTHER INFORMATION: siRNA

<400> SEQUENCE: 5
aauucguuga cauacuuucu u                                                21

<210> SEQ ID NO 6
<211> LENGTH: 21
<212> TYPE: RNA
<213> ORGANISM: Artificial Sequence
<220> FEATURE:
<223> OTHER INFORMATION: siRNA

<400> SEQUENCE: 6
aauucguuga cauacuuucc a                                                21

<210> SEQ ID NO 7
<211> LENGTH: 21
<212> TYPE: RNA
<213> ORGANISM: Artificial Sequence
<220> FEATURE:
<223> OTHER INFORMATION: siRNA

<400> SEQUENCE: 7
uauucguuga cauacuuucu u                                                21

<210> SEQ ID NO 8
<211> LENGTH: 21
<212> TYPE: RNA
<213> ORGANISM: Artificial Sequence
<220> FEATURE:
<223> OTHER INFORMATION: siRNA

<400> SEQUENCE: 8
uauucguuga cauacuuucc a                                                21

<210> SEQ ID NO 9
<211> LENGTH: 21
<212> TYPE: DNA
<213> ORGANISM: Artificial Sequence
<220> FEATURE:
<223> OTHER INFORMATION: siRNA

<400> SEQUENCE: 9
ccuugaggca uacuucaaat t                                                21

<210> SEQ ID NO 10
<211> LENGTH: 21
<212> TYPE: DNA
<213> ORGANISM: Artificial Sequence
<220> FEATURE:
<223> OTHER INFORMATION: siRNA

<400> SEQUENCE: 10
uuugaaguau gccucaaggt t                                                21
```

```
<210> SEQ ID NO 11
<211> LENGTH: 19
<212> TYPE: RNA
<213> ORGANISM: Artificial Sequence
<220> FEATURE:
<223> OTHER INFORMATION: siRNA

<400> SEQUENCE: 11
gaaaguaugu caacgaauu                                                  19

<210> SEQ ID NO 12
<211> LENGTH: 19
<212> TYPE: RNA
<213> ORGANISM: Artificial Sequence
<220> FEATURE:
<223> OTHER INFORMATION: siRNA

<400> SEQUENCE: 12
gaaaguaugu caacgaaua                                                  19

<210> SEQ ID NO 13
<211> LENGTH: 21
<212> TYPE: RNA
<213> ORGANISM: Artificial Sequence
<220> FEATURE:
<223> OTHER INFORMATION: siRNA

<400> SEQUENCE: 13
aauucguuga cauacuuucu u                                               21

<210> SEQ ID NO 14
<211> LENGTH: 21
<212> TYPE: RNA
<213> ORGANISM: Artificial Sequence
<220> FEATURE:
<223> OTHER INFORMATION: siRNA

<400> SEQUENCE: 14
aauucguuga cauacuuucc a                                               21

<210> SEQ ID NO 15
<211> LENGTH: 21
<212> TYPE: RNA
<213> ORGANISM: Artificial Sequence
<220> FEATURE:
<223> OTHER INFORMATION: siRNA

<400> SEQUENCE: 15
uauucguuga cauacuuucu u                                               21

<210> SEQ ID NO 16
<211> LENGTH: 21
<212> TYPE: RNA
<213> ORGANISM: Artificial Sequence
<220> FEATURE:
<223> OTHER INFORMATION: siRNA

<400> SEQUENCE: 16
uauucguuga cauacuuucc a                                               21

<210> SEQ ID NO 17
<211> LENGTH: 19
<212> TYPE: RNA
<213> ORGANISM: Artificial Sequence
<220> FEATURE:
```

```
<223> OTHER INFORMATION: siRNA

<400> SEQUENCE: 17
gaaaguaugu caacgaauu                                                 19

<210> SEQ ID NO 18
<211> LENGTH: 19
<212> TYPE: RNA
<213> ORGANISM: Artificial Sequence
<220> FEATURE:
<223> OTHER INFORMATION: siRNA

<400> SEQUENCE: 18
gaaaguaugu caacgaaua                                                 19

<210> SEQ ID NO 19
<211> LENGTH: 21
<212> TYPE: RNA
<213> ORGANISM: Artificial Sequence
<220> FEATURE:
<223> OTHER INFORMATION: siRNA

<400> SEQUENCE: 19
aauucguuga cauacuuucu u                                              21

<210> SEQ ID NO 20
<211> LENGTH: 21
<212> TYPE: RNA
<213> ORGANISM: Artificial Sequence
<220> FEATURE:
<223> OTHER INFORMATION: siRNA

<400> SEQUENCE: 20
aauucguuga cauacuuucc a                                              21

<210> SEQ ID NO 21
<211> LENGTH: 21
<212> TYPE: RNA
<213> ORGANISM: Artificial Sequence
<220> FEATURE:
<223> OTHER INFORMATION: siRNA

<400> SEQUENCE: 21
uauucguuga cauacuuucu u                                              21

<210> SEQ ID NO 22
<211> LENGTH: 21
<212> TYPE: RNA
<213> ORGANISM: Artificial Sequence
<220> FEATURE:
<223> OTHER INFORMATION: siRNA

<400> SEQUENCE: 22
uauucguuga cauacuuucc a                                              21

<210> SEQ ID NO 23
<211> LENGTH: 19
<212> TYPE: RNA
<213> ORGANISM: Artificial Sequence
<220> FEATURE:
<223> OTHER INFORMATION: siRNA

<400> SEQUENCE: 23
gaaaguaugu caacgaauu                                                 19
```

```
<210> SEQ ID NO 24
<211> LENGTH: 19
<212> TYPE: RNA
<213> ORGANISM: Artificial Sequence
<220> FEATURE:
<223> OTHER INFORMATION: siRNA

<400> SEQUENCE: 24
gaaaguaugu caacgaaua                                                    19

<210> SEQ ID NO 25
<211> LENGTH: 21
<212> TYPE: RNA
<213> ORGANISM: Artificial Sequence
<220> FEATURE:
<223> OTHER INFORMATION: siRNA

<400> SEQUENCE: 25
aauucguuga cauacuuucu u                                                 21

<210> SEQ ID NO 26
<211> LENGTH: 21
<212> TYPE: RNA
<213> ORGANISM: Artificial Sequence
<220> FEATURE:
<223> OTHER INFORMATION: siRNA

<400> SEQUENCE: 26
aauucguuga cauacuuucc a                                                 21

<210> SEQ ID NO 27
<211> LENGTH: 21
<212> TYPE: RNA
<213> ORGANISM: Artificial Sequence
<220> FEATURE:
<223> OTHER INFORMATION: siRNA

<400> SEQUENCE: 27
uauucguuga cauacuuucu u                                                 21

<210> SEQ ID NO 28
<211> LENGTH: 21
<212> TYPE: RNA
<213> ORGANISM: Artificial Sequence
<220> FEATURE:
<223> OTHER INFORMATION: siRNA

<400> SEQUENCE: 28
uauucguuga cauacuuucc a                                                 21

<210> SEQ ID NO 29
<211> LENGTH: 19
<212> TYPE: RNA
<213> ORGANISM: Artificial Sequence
<220> FEATURE:
<223> OTHER INFORMATION: siRNA

<400> SEQUENCE: 29
gaaaguaugu caacgaauu                                                    19

<210> SEQ ID NO 30
<211> LENGTH: 19
<212> TYPE: RNA
<213> ORGANISM: Artificial Sequence
<220> FEATURE:
<223> OTHER INFORMATION: siRNA
```

```
<400> SEQUENCE: 30
gaaaguaugu caacgaaua                                                    19

<210> SEQ ID NO 31
<211> LENGTH: 21
<212> TYPE: RNA
<213> ORGANISM: Artificial Sequence
<220> FEATURE:
<223> OTHER INFORMATION: siRNA

<400> SEQUENCE: 31
aauucguuga cauacuuucu u                                                 21

<210> SEQ ID NO 32
<211> LENGTH: 21
<212> TYPE: RNA
<213> ORGANISM: Artificial Sequence
<220> FEATURE:
<223> OTHER INFORMATION: siRNA

<400> SEQUENCE: 32
aauucguuga cauacuuucc a                                                 21

<210> SEQ ID NO 33
<211> LENGTH: 21
<212> TYPE: RNA
<213> ORGANISM: Artificial Sequence
<220> FEATURE:
<223> OTHER INFORMATION: siRNA

<400> SEQUENCE: 33
uauucguuga cauacuuucu u                                                 21

<210> SEQ ID NO 34
<211> LENGTH: 21
<212> TYPE: RNA
<213> ORGANISM: Artificial Sequence
<220> FEATURE:
<223> OTHER INFORMATION: siRNA

<400> SEQUENCE: 34
uauucguuga cauacuuucc a                                                 21

<210> SEQ ID NO 35
<211> LENGTH: 21
<212> TYPE: RNA
<213> ORGANISM: Artificial Sequence
<220> FEATURE:
<223> OTHER INFORMATION: siRNA

<400> SEQUENCE: 35
aauucguuga cauacuuucu u                                                 21

<210> SEQ ID NO 36
<211> LENGTH: 21
<212> TYPE: RNA
<213> ORGANISM: Artificial Sequence
<220> FEATURE:
<223> OTHER INFORMATION: siRNA

<400> SEQUENCE: 36
aauucguuga cauacuuucc a                                                 21

<210> SEQ ID NO 37
<211> LENGTH: 21
```

```
<212> TYPE: RNA
<213> ORGANISM: Artificial Sequence
<220> FEATURE:
<223> OTHER INFORMATION: siRNA

<400> SEQUENCE: 37
uauucguuga cauacuuucu u                                              21

<210> SEQ ID NO 38
<211> LENGTH: 21
<212> TYPE: RNA
<213> ORGANISM: Artificial Sequence
<220> FEATURE:
<223> OTHER INFORMATION: siRNA

<400> SEQUENCE: 38
uauucguuga cauacuuucc a                                              21

<210> SEQ ID NO 39
<211> LENGTH: 21
<212> TYPE: RNA
<213> ORGANISM: Artificial Sequence
<220> FEATURE:
<223> OTHER INFORMATION: siRNA

<400> SEQUENCE: 39
aauucguuga cauacuuucu u                                              21

<210> SEQ ID NO 40
<211> LENGTH: 21
<212> TYPE: RNA
<213> ORGANISM: Artificial Sequence
<220> FEATURE:
<223> OTHER INFORMATION: siRNA

<400> SEQUENCE: 40
aauucguuga cauacuuucc a                                              21

<210> SEQ ID NO 41
<211> LENGTH: 21
<212> TYPE: RNA
<213> ORGANISM: Artificial Sequence
<220> FEATURE:
<223> OTHER INFORMATION: siRNA

<400> SEQUENCE: 41
uauucguuga cauacuuucu u                                              21

<210> SEQ ID NO 42
<211> LENGTH: 21
<212> TYPE: RNA
<213> ORGANISM: Artificial Sequence
<220> FEATURE:
<223> OTHER INFORMATION: siRNA

<400> SEQUENCE: 42
uauucguuga cauacuuucc a                                              21

<210> SEQ ID NO 43
<211> LENGTH: 21
<212> TYPE: RNA
<213> ORGANISM: Artificial Sequence
<220> FEATURE:
<223> OTHER INFORMATION: siRNA

<400> SEQUENCE: 43
```
aauucguuga cauacuuucu u                                              21

<210> SEQ ID NO 44
<211> LENGTH: 21
<212> TYPE: RNA
<213> ORGANISM: Artificial Sequence
<220> FEATURE:
<223> OTHER INFORMATION: siRNA

<400> SEQUENCE: 44
aauucguuga cauacuuucc a                                              21

<210> SEQ ID NO 45
<211> LENGTH: 21
<212> TYPE: RNA
<213> ORGANISM: Artificial Sequence
<220> FEATURE:
<223> OTHER INFORMATION: siRNA

<400> SEQUENCE: 45
uauucguuga cauacuuucu u                                              21

<210> SEQ ID NO 46
<211> LENGTH: 21
<212> TYPE: RNA
<213> ORGANISM: Artificial Sequence
<220> FEATURE:
<223> OTHER INFORMATION: siRNA

<400> SEQUENCE: 46
uauucguuga cauacuuucc a                                              21

<210> SEQ ID NO 47
<211> LENGTH: 21
<212> TYPE: RNA
<213> ORGANISM: Artificial Sequence
<220> FEATURE:
<223> OTHER INFORMATION: siRNA

<400> SEQUENCE: 47
aauucguuga cauacuuucu u                                              21

<210> SEQ ID NO 48
<211> LENGTH: 21
<212> TYPE: RNA
<213> ORGANISM: Artificial Sequence
<220> FEATURE:
<223> OTHER INFORMATION: siRNA

<400> SEQUENCE: 48
aauucguuga cauacuuucc a                                              21

<210> SEQ ID NO 49
<211> LENGTH: 21
<212> TYPE: RNA
<213> ORGANISM: Artificial Sequence
<220> FEATURE:
<223> OTHER INFORMATION: siRNA

<400> SEQUENCE: 49
uauucguuga cauacuuucu u                                              21

<210> SEQ ID NO 50
<211> LENGTH: 21
<212> TYPE: RNA

```
<213> ORGANISM: Artificial Sequence
<220> FEATURE:
<223> OTHER INFORMATION: siRNA

<400> SEQUENCE: 50
uauucguuga cauacuuucc a                                              21

<210> SEQ ID NO 51
<211> LENGTH: 21
<212> TYPE: RNA
<213> ORGANISM: Artificial Sequence
<220> FEATURE:
<223> OTHER INFORMATION: siRNA

<400> SEQUENCE: 51
uggaaaguau gucaacgaau a                                              21

<210> SEQ ID NO 52
<211> LENGTH: 23
<212> TYPE: RNA
<213> ORGANISM: Artificial Sequence
<220> FEATURE:
<223> OTHER INFORMATION: siRNA

<400> SEQUENCE: 52
uauucguuga cauacuuucc auu                                            23

<210> SEQ ID NO 53
<211> LENGTH: 23
<212> TYPE: RNA
<213> ORGANISM: Artificial Sequence
<220> FEATURE:
<223> OTHER INFORMATION: siRNA

<400> SEQUENCE: 53
uauucguuga cauacuuucc aau                                            23

<210> SEQ ID NO 54
<211> LENGTH: 21
<212> TYPE: RNA
<213> ORGANISM: Artificial Sequence
<220> FEATURE:
<223> OTHER INFORMATION: siRNA

<400> SEQUENCE: 54
uggaaaguau gucaacgaau u                                              21

<210> SEQ ID NO 55
<211> LENGTH: 23
<212> TYPE: RNA
<213> ORGANISM: Artificial Sequence
<220> FEATURE:
<223> OTHER INFORMATION: siRNA

<400> SEQUENCE: 55
aauucguuga cauacuuucc auu                                            23

<210> SEQ ID NO 56
<211> LENGTH: 21
<212> TYPE: RNA
<213> ORGANISM: Artificial Sequence
<220> FEATURE:
<223> OTHER INFORMATION: siRNA

<400> SEQUENCE: 56
uggaaaguau gucaacgaau a                                              21
```

```
<210> SEQ ID NO 57
<211> LENGTH: 23
<212> TYPE: RNA
<213> ORGANISM: Artificial Sequence
<220> FEATURE:
<223> OTHER INFORMATION: siRNA

<400> SEQUENCE: 57
uauucguuga cauacuuucc auu                                              23

<210> SEQ ID NO 58
<211> LENGTH: 23
<212> TYPE: RNA
<213> ORGANISM: Artificial Sequence
<220> FEATURE:
<223> OTHER INFORMATION: siRNA

<400> SEQUENCE: 58
uauucguuga cauacuuucc aau                                              23

<210> SEQ ID NO 59
<211> LENGTH: 21
<212> TYPE: RNA
<213> ORGANISM: Artificial Sequence
<220> FEATURE:
<223> OTHER INFORMATION: siRNA

<400> SEQUENCE: 59
uggaaaguau gucaacgaau u                                                21

<210> SEQ ID NO 60
<211> LENGTH: 23
<212> TYPE: RNA
<213> ORGANISM: Artificial Sequence
<220> FEATURE:
<223> OTHER INFORMATION: siRNA

<400> SEQUENCE: 60
aauucguuga cauacuuucc auu                                              23

<210> SEQ ID NO 61
<211> LENGTH: 23
<212> TYPE: RNA
<213> ORGANISM: Artificial Sequence
<220> FEATURE:
<223> OTHER INFORMATION: siRNA

<400> SEQUENCE: 61
uauucguuga cauacuuucc auu                                              23

<210> SEQ ID NO 62
<211> LENGTH: 23
<212> TYPE: RNA
<213> ORGANISM: Artificial Sequence
<220> FEATURE:
<223> OTHER INFORMATION: siRNA

<400> SEQUENCE: 62
uauucguuga cauacuuucc aau                                              23

<210> SEQ ID NO 63
<211> LENGTH: 23
<212> TYPE: RNA
<213> ORGANISM: Artificial Sequence
<220> FEATURE:
```

```
<223> OTHER INFORMATION: siRNA

<400> SEQUENCE: 63
aauucguuga cauacuuucc auu                                         23

<210> SEQ ID NO 64
<211> LENGTH: 23
<212> TYPE: RNA
<213> ORGANISM: Artificial Sequence
<220> FEATURE:
<223> OTHER INFORMATION: siRNA

<400> SEQUENCE: 64
uauucguuga cauacuuucc auu                                         23

<210> SEQ ID NO 65
<211> LENGTH: 23
<212> TYPE: RNA
<213> ORGANISM: Artificial Sequence
<220> FEATURE:
<223> OTHER INFORMATION: siRNA

<400> SEQUENCE: 65
uauucguuga cauacuuucc aau                                         23

<210> SEQ ID NO 66
<211> LENGTH: 23
<212> TYPE: RNA
<213> ORGANISM: Artificial Sequence
<220> FEATURE:
<223> OTHER INFORMATION: siRNA

<400> SEQUENCE: 66
aauucguuga cauacuuucc auu                                         23

<210> SEQ ID NO 67
<211> LENGTH: 21
<212> TYPE: RNA
<213> ORGANISM: Artificial Sequence
<220> FEATURE:
<223> OTHER INFORMATION: siRNA

<400> SEQUENCE: 67
uauucguuga cauacuuucu u                                           21

<210> SEQ ID NO 68
<211> LENGTH: 21
<212> TYPE: RNA
<213> ORGANISM: Artificial Sequence
<220> FEATURE:
<223> OTHER INFORMATION: siRNA

<400> SEQUENCE: 68
uauucguuga cauacuuucu u                                           21

<210> SEQ ID NO 69
<211> LENGTH: 21
<212> TYPE: RNA
<213> ORGANISM: Artificial Sequence
<220> FEATURE:
<223> OTHER INFORMATION: siRNA

<400> SEQUENCE: 69
uauucguuga cauacuuucu u                                           21
```

```
<210> SEQ ID NO 70
<211> LENGTH: 21
<212> TYPE: RNA
<213> ORGANISM: Artificial Sequence
<220> FEATURE:
<223> OTHER INFORMATION: siRNA

<400> SEQUENCE: 70
uauucguuga cauacuuucu u                                          21

<210> SEQ ID NO 71
<211> LENGTH: 21
<212> TYPE: RNA
<213> ORGANISM: Artificial Sequence
<220> FEATURE:
<223> OTHER INFORMATION: siRNA

<400> SEQUENCE: 71
uauucguuga cauacuuucu u                                          21

<210> SEQ ID NO 72
<211> LENGTH: 21
<212> TYPE: RNA
<213> ORGANISM: Artificial Sequence
<220> FEATURE:
<223> OTHER INFORMATION: siRNA

<400> SEQUENCE: 72
uauucguuga cauacuuucu u                                          21

<210> SEQ ID NO 73
<211> LENGTH: 21
<212> TYPE: RNA
<213> ORGANISM: Artificial Sequence
<220> FEATURE:
<223> OTHER INFORMATION: siRNA

<400> SEQUENCE: 73
aauucguuga cauacuuucc a                                          21

<210> SEQ ID NO 74
<211> LENGTH: 23
<212> TYPE: RNA
<213> ORGANISM: Artificial Sequence
<220> FEATURE:
<223> OTHER INFORMATION: siRNA

<400> SEQUENCE: 74
uauucguuga cauacuuucc auu                                        23

<210> SEQ ID NO 75
<211> LENGTH: 19
<212> TYPE: RNA
<213> ORGANISM: Artificial Sequence
<220> FEATURE:
<223> OTHER INFORMATION: siRNA

<400> SEQUENCE: 75
gaaaguaugu caacgaaua                                             19

<210> SEQ ID NO 76
<211> LENGTH: 21
<212> TYPE: RNA
<213> ORGANISM: Artificial Sequence
<220> FEATURE:
<223> OTHER INFORMATION: siRNA
```

```
<400> SEQUENCE: 76
uauucguuga cauacuuucu u                                          21

<210> SEQ ID NO 77
<211> LENGTH: 19
<212> TYPE: RNA
<213> ORGANISM: Artificial Sequence
<220> FEATURE:
<223> OTHER INFORMATION: siRNA

<400> SEQUENCE: 77
uucuccgaac gugucacgu                                             19

<210> SEQ ID NO 78
<211> LENGTH: 21
<212> TYPE: RNA
<213> ORGANISM: Artificial Sequence
<220> FEATURE:
<223> OTHER INFORMATION: siRNA

<400> SEQUENCE: 78
acgugacacg uucggagaac u                                          21

<210> SEQ ID NO 79
<211> LENGTH: 28
<212> TYPE: DNA
<213> ORGANISM: Artificial Sequence
<220> FEATURE:
<223> OTHER INFORMATION: siRNA

<400> SEQUENCE: 79
tcgagtggaa agtatgtcaa cgaattgc                                   28

<210> SEQ ID NO 80
<211> LENGTH: 28
<212> TYPE: DNA
<213> ORGANISM: Artificial Sequence
<220> FEATURE:
<223> OTHER INFORMATION: siRNA

<400> SEQUENCE: 80
ggccgcaatt cgttgacata ctttccac                                   28

<210> SEQ ID NO 81
<211> LENGTH: 28
<212> TYPE: DNA
<213> ORGANISM: Artificial Sequence
<220> FEATURE:
<223> OTHER INFORMATION: siRNA

<400> SEQUENCE: 81
tcgagaattc gttgacatac tttccagc                                   28

<210> SEQ ID NO 82
<211> LENGTH: 28
<212> TYPE: DNA
<213> ORGANISM: Artificial Sequence
<220> FEATURE:
<223> OTHER INFORMATION: siRNA

<400> SEQUENCE: 82
ggccgctgga aagtatgtca acgaattc                                   28

<210> SEQ ID NO 83
<211> LENGTH: 28
```

```
<212> TYPE: DNA
<213> ORGANISM: Artificial Sequence
<220> FEATURE:
<223> OTHER INFORMATION: siRNA

<400> SEQUENCE: 83
tcgaggttcc ctgcgtgaaa cgaattgc                                         28

<210> SEQ ID NO 84
<211> LENGTH: 28
<212> TYPE: DNA
<213> ORGANISM: Artificial Sequence
<220> FEATURE:
<223> OTHER INFORMATION: siRNA

<400> SEQUENCE: 84
ggccgcaatt cgtttcacgc agggaacc                                         28

<210> SEQ ID NO 85
<211> LENGTH: 28
<212> TYPE: DNA
<213> ORGANISM: Artificial Sequence
<220> FEATURE:
<223> OTHER INFORMATION: siRNA

<400> SEQUENCE: 85
tcgagccgga tggtcacgac tttccagc                                         28

<210> SEQ ID NO 86
<211> LENGTH: 28
<212> TYPE: DNA
<213> ORGANISM: Artificial Sequence
<220> FEATURE:
<223> OTHER INFORMATION: siRNA

<400> SEQUENCE: 86
ggccgctgga aagtcgtgac catccggc                                         28

<210> SEQ ID NO 87
<211> LENGTH: 20
<212> TYPE: DNA
<213> ORGANISM: Artificial Sequence
<220> FEATURE:
<223> OTHER INFORMATION: primer

<400> SEQUENCE: 87
gtcttttggg ttttgctgcc                                                  20

<210> SEQ ID NO 88
<211> LENGTH: 20
<212> TYPE: DNA
<213> ORGANISM: Artificial Sequence
<220> FEATURE:
<223> OTHER INFORMATION: primer

<400> SEQUENCE: 88
gcaacggggt aaaggttcag                                                  20

<210> SEQ ID NO 89
<211> LENGTH: 19
<212> TYPE: DNA
<213> ORGANISM: Artificial Sequence
<220> FEATURE:
<223> OTHER INFORMATION: primer
```

```
<400> SEQUENCE: 89
ggtcggagtc aacggattt                                                19

<210> SEQ ID NO 90
<211> LENGTH: 19
<212> TYPE: DNA
<213> ORGANISM: Artificial Sequence
<220> FEATURE:
<223> OTHER INFORMATION: primer

<400> SEQUENCE: 90
ccagcatcgc cccacttga                                                19
```